(12) United States Patent
Stadtmueller et al.

(10) Patent No.: US 7,521,457 B2
(45) Date of Patent: *Apr. 21, 2009

(54) PYRIMIDINES AS PLK INHIBITORS

(75) Inventors: Heinz Stadtmueller, Gaweinstal (AT); Harald Engelhardt, Ebreichsdorf (AT); Martin Steegmaier, Vienna (AT); Anke Baum, Vienna (AT); Ulrich Guertler, Vienna (AT); Andreas Schoop, Vienna (AT); Jens Juergen Quant, Guntramsdorf (AT); Flavio Solca, Vienna (AT); Rudolf Hauptmann, Ebreichsdorf (AT); Ulrich Reiser, Vienna (AT); Stephan Karl Zahn, Vienna (AT); Lars Herfurth, Vienna (AT)

(73) Assignee: Boehringer Ingelheim International GmbH, Ingelheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/206,703

(22) Filed: Aug. 17, 2005

(65) Prior Publication Data

US 2006/0148800 A1 Jul. 6, 2006

(30) Foreign Application Priority Data

Aug. 20, 2004 (EP) .................. 04019775

(51) Int. Cl.
C07D 239/42 (2006.01)
C07D 239/46 (2006.01)
A61K 31/505 (2006.01)
A61K 31/506 (2006.01)
A61P 35/00 (2006.01)

(52) U.S. Cl. .............. 514/269; 514/275; 544/320; 544/323; 544/324

(58) Field of Classification Search ............ 544/323, 544/324, 320; 514/275, 269
See application file for complete search history.

(56) References Cited

FOREIGN PATENT DOCUMENTS

| WO | 0012485 | 3/2000 |
|---|---|---|
| WO | 0204429 A1 | 1/2002 |
| WO | 2004074244 A2 | 9/2004 |
| WO | WO 2004080980 A1 * | 9/2004 |

OTHER PUBLICATIONS

Cecil Textbook of Medicine, edited by Bennet, J.C., and Plum F., 20th edition, vol. 1, 1004-1010, 1996.*
Ahmed FASEB Journal 18, 5-7, 2004.*
Turner et al., Current Pharmaceutical Design. 2, 209-224, 1996.*
Sugar et al., Diagn. Microbiol. Infect. Dis. 21:129-133, 1995.*
Snyder et al., J. Med. Liban 48(4): 208-214, 2000.*
International Preliminary Report on Patentability (Form PCT/IB/373) for corresponding PCT/EP2005/054089.
Written Opinion of the International Searching Authority (Form PCT/ISA/237) for corresponding PCT/EP2005/054089.

* cited by examiner

*Primary Examiner*—Venkataraman Balasubramanian
(74) *Attorney, Agent, or Firm*—Michael P. Morris; Mary-Ellen M. Devlin; Philip I. Datlow

(57) ABSTRACT

The present invention encompasses compounds of general formula (1),

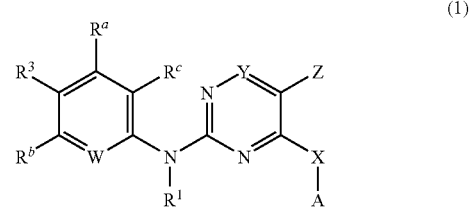

wherein
A, W, X, Y, Z, Ra, Rb, Rc, R1 and R3 are defined as in claim 1, which are suitable for the treatment of diseases characterised by excessive or abnormal cell proliferation, and the use thereof for preparing a pharmaceutical composition having the above-mentioned properties.

11 Claims, No Drawings

PYRIMIDINES AS PLK INHIBITORS

The present invention relates to new pyrimidines of general formula (1),

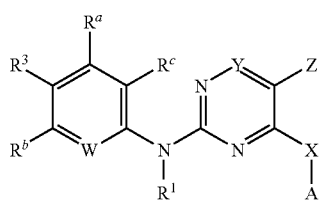

(1)

wherein the groups A, W, X, Y, Z, $R^a$, $R^b$, $R^c$, $R^1$ and $R^3$ have the meanings given in the claims and description, the isomers thereof, processes for preparing these pyrimidines and their use as pharmaceutical compositions.

BACKGROUND TO THE INVENTION

Tumour cells wholly or partly elude regulation and control by the body and are characterised by uncontrolled growth. This is due on the one hand to the loss of control proteins such as for example Rb, p16, p21 and p53 and also to the activation of so-called accelerators of the cell cycle, the cyclin-dependent kinases.

Studies in model organisms such as *Schizosaccharomyces pombe, Drosophila melanogaster* or *Xenopus laevis* as well as investigations in human cells have shown that the transition from the G2 phase to mitosis is regulated by the CDK1/cyclin B kinase (Nurse 1990, *Nature* 344: 503-508). This kinase, which is also known as "mitosis promoting factor" (MPF), phosphorylates and regulates a plurality of proteins, such as e.g. nuclear lamina, kinesin-like motor proteins, condensins and Golgi Matrix Proteins, which play an important part in the breakdown of the nuclear coat, in centrosome separation, the structure of the mitotic spindle apparatus, chromosome condensation and breakdown of the Golgi apparatus (Nigg. E. 2001, *Nat Rev Mol Cell Biol.* 2(1):21-32). A murine cell line with a temperature-sensitive CDK-1 kinase mutant shows a rapid breakdown in CDK-1 kinase after temperature increase and a subsequent arrest in the G2/M phase (Th ng et al. 1990, *Cell.* 63(2):313-24). The treatment of human tumour cells with inhibitors against CDK1/cyclin B, such as e.g. butyrolactone, leads to an arrest in the G2/M phase and subsequent apoptosis (Nishio, et al. 1996, *Anticancer Res.* 16(6B):3387-95).

Moreover, the protein kinase Aurora B has also been described as having an essential function during entry into mitosis. Aurora B phosphorylates histone H3 on Ser10 and thereby initiates chromosome condensation (Hsu et al. 2000, *Cell* 102:279-91). A specific cell cycle arrest in the G2/M phase may, however, also be initiated e.g. by inhibition of specific phosphatases such as e.g. Cdc25C (Russell and Nurse 1986, *Cell* 45:145-53). Yeasts with a defective Cdc25 gene arrest in the G2 phase, whereas overexpression of Cdc25 leads to premature entry into the mitosis phase (Russell and Nurse, 1987, *Cell* 49:559-67). Moreover, an arrest in the G2/M phase may also be initiated by inhibition of specific motor proteins, the so-called kinesins such as for example Eg5 (Mayer et al. 1999, *Science* 286:971-4), or by microtubuli stabilising or destabilising agents (e.g. colchicin, taxol, etoposide, vinblastine, vincristine) (Schiff and Horwitz 1980, *Proc Natl Acad Sci* USA 77:1561-5).

In addition to the cyclin-dependent and Aurora kinases the so-called polo-like kinases, a small family of serine/threonine kinases, also play an important role in the regulation of the eukaryotic cell cycle. Up till now the polo-like kinases PLK-1, PLK-2, PLK-3 and PLK-4 have been described in the literature. PLK-1 in particular has been found to play a central role in the regulation of the mitosis phase. PLK-1 is responsible for the maturation of the centrosomes, for the activation of phosphatase Cdc25C, as well as for the activation of the Anaphase Promoting Complex (Glover et al. 1998, *Genes Dev.* 12:3777-87; Qian et al. 2001, *Mol Biol Cell.* 12:1791-9). The injection of PLK-1 antibodies leads to a G2 arrest in untransformed cells, whereas tumour cells arrest during the mitosis phase (Lane and Nigg 1996, *J. Cell Biol.* 135:1701-13). Overexpression of PLK-1 has been demonstrated in various types of tumour, such as non-small-cell carcinoma of the lung, plate epithelial carcinoma, breast and colorectal carcinoma (Wolf et al. 1997, *Oncogene* 14:543-549; Knecht et al. 1999, *Cancer Res.* 59:2794-2797; Wolf et al. 2000, *Pathol. Res. Pract.* 196:753-759; Takahashi et al. 2003, *Cancer Sci.* 94:148-52). Therefore, this category of proteins also presents an interesting point of attack for therapeutic intervention in proliferative diseases (Liu and Erikson 2003, *Proc Natl Acad Sci USA* 100:5789-5794).

Pyrimidines are generally known as inhibitors of kinases. Thus, for example, pyrimidines are described as an active component with an anticancer activity in International Patent Application WO 00/53595, which describes the use of 2,4,5-substituted pyrimidines with a heterocyclic group in the 4-position and an anilino group in the 2 position, which in turn comprises a side chain with the length of at least one n-propyl group.

Moreover, International Patent Application WO 00/39101 describes the use of 2,4,5-substituted pyrimidines as compounds with an anticancer activity which are linked in the 2- and 4-position with an aromatic or heteroaromatic ring, at least one of which comprises a side chain with the length of at least one n-propyl group.

International Patent Application WO 97/19065 further proposes the use of 2,4,5-substituted pyrimidines with a 3,4-dialkoxyanilino group in position 2 as kinase inhibitors.

International Patent Application WO 02/04429 describes 2,4,5-substituted pyrimidines with a cyano group in position 5 and their cell cycle inhibiting effect.

International Patent Application WO 03/063794 describes the use of 2,4-pyrimidinediamines as inhibitors of the IgE and/or IgG receptor signal cascade.

Antiviral 2,4,5-substituted pyrimidines, wherein the groups $R^c$ and $R^d$ form a heteroaromatic five-membered ring at the nitrogen of the 4-position, are known from International Patent Application WO 99/41253.

2,4,5-substituted pyrimidines which carry (hetero)aryls in position 2 and 4 (WO00/27825) and also 2,4,5-substituted pyrimidines which carry a (hetero)aryl group functionalised with a nitrile group in position 2 or 4 (EP 0 945 443 A1) are described as having an antiviral activity.

The resistance of many types of tumour demands that new drugs be developed to fight the tumours. The aim of the present invention is therefore to indicate new active substances which may be used for the prevention and/or treatment of diseases characterised by excessive or anomalous cell proliferation.

DETAILED DESCRIPTION OF THE INVENTION

It has now been found that, surprisingly, compounds of general formula (1), wherein the groups A, W, X, Y, $R^a$, $R^b$, $R^c$, $R^1$, $R^2$ and $R^3$ are defined as hereinafter, act as inhibitors of specific cell cycle kinases. Thus, the compounds according to the invention may be used for example for the treatment of diseases associated with the activity of specific cell cycle kinases and characterised by excessive or anomalous cell proliferation.

The present invention relates to compounds of general formula (1)

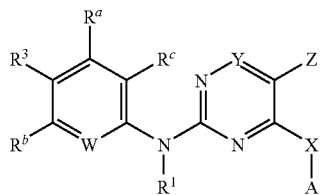

(1)

wherein
W denotes N or C—$R^2$,
X denotes —$NR^{1a}$, O or S,
Y denotes CH or N,
Z denotes hydrogen, halogen, —$NO_2$, $C_{1-3}$alkyl, $C_{2-3}$alkenyl, $C_{2-3}$alkynyl, halogen-$C_{1-3}$alkyl, —COH, —C(=O)—$C_{1-3}$alkyl, —C(=O)—$C_{2-3}$alkenyl, —C(=O)—$C_{2-3}$alkynyl, —C(=O)$C_{1-3}$alkyl-halogen or pseudohalogen;
A is selected from the formulae (i), (ii) or (iii)

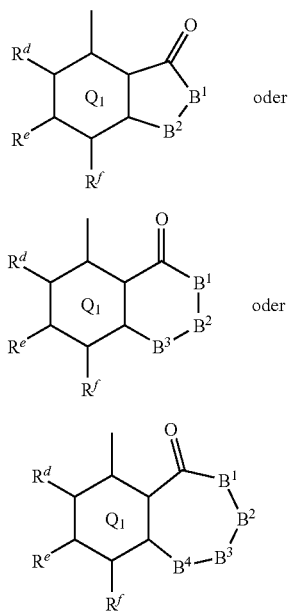

$Q_1$ denotes mono- or bicyclic aryl compounds,
$B^1$, $B^2$, $B^3$ and $B^4$ in each case independently of one another denote C—$R^gR^h$, N—$R^i$, O or S, while adjacent $B^1$-$B^4$ in each case do not represent —O—;
$R^1$ and $R^{1a}$ each independently of one another denote hydrogen or methyl,
$R^2$ denotes a group selected from among hydrogen, halogen, —$OR^4$, —C(=O)$R^4$, —C(=O)$NR^4R^5$, —$NR^4R^5$, —$NR^4C(=O)R^5$, —$NR^4SO_2R^5$, —N=$CR^4R^5$, —C=$NR^i$, —$SR^4$, —$SOR^4$, —$SO_2R^4$, —$SO_2NR^4R^5$ and pseudohalogen, or an optionally mono- or polysubstituted group selected from among $C_{1-6}$alkyl, $C_{2-6}$alkenyl, $C_{2-6}$alkynyl, $C_{3-6}$-cycloalkyl, aryl, heterocyclyl and heteroaryl, while the substituent(s) may be identical or different and are selected from among halogen, —$NO_2$, —$OR^4$, —C(=O)$R^4$, —C(=O)$OR^4$, —C(=O)$NR^4R^5$, —$NR^4R^5$, —$NR^4C(=O)R^5$, —$NR^4C(=O)OR^5$, —$NR^4C(=O)NR^5R^6$, —$NR^4SO_2R^5$, —N=$CR^4R^5$, —$SR^4$, —$SOR^4$, —$SO_2R^4$, —$SO_2NR^4R^5$, —$NR^4SO_2NR^5R^6$, —$OSO_2NR^5R^6$ and pseudohalogen;

$R^a$, $R^b$, $R^c$, $R^d$, $R^e$, $R^f$, $R^g$ and $R^h$ in each case independently of one another denote a group selected from among hydrogen, halogen, =O, —$NO_2$, —$OR^4$, —C(=O)$R^4$, —C(=O)$OR^4$, —C(=O)$NR^4R^5$, —$NR^4R^5$, —$NR^4C(=O)R^5$, —$NR^4C(=O)OR^5$, —$NR^4C(=O)NR^5R^6$, —$NR^4SO_2R^5$, —N=$CR^4R^5$, —C=$NR^i$, —$SR^4$, —$SOR^4$, —$SO_2R^4$, —$SO_2NR^4R^5$, —$NR^4SO_2NR^5R^6$, —$OSO_2NR^5R^6$ and pseudohalogen; or an optionally mono- or polysubstituted group selected from among $C_{1-6}$-alkyl, $C_{2-6}$-alkenyl, $C_{2-6}$-alkynyl, $C_{3-6}$-cycloalkyl, aryl, heterocyclyl and heteroaryl, while the substituent(s) may be identical or different and are selected from among halogen, $R^8$, —$NO_2$, —$OR^4$, —C(=O)$R^4$, —C(=O)$OR^4$, —C(=O)$NR^4R^5$, —$NR^4R^5$, —$NR^4C(=O)R^5$, —$NR^4C(=O)OR^5$, —$NR^4C(=O)NR^5R^6$, —$NR^4SO_2R^5$, —N=$CR^4R^5$, —$SR^4$, —$SOR^4$, —$SO_2R^4$, —$SO_2NR^4R^5$, —$NR^4SO_2NR^5R^6$, —$OSO_2NR^5R^6$ and pseudohalogen; and optionally the $R^g$ and $R^h$ located at the same or at adjacent C atoms may be attached in any combination to a common saturated or partially unsaturated 3-5-membered alkyl bridge which may contain one to two heteroatoms;

$R^i$ denotes a group selected from among hydrogen, =O, —$OR^4$, —C(=O)$R^4$, —C(=O)$OR^4$, —C(=O)$NR^4R^5$, —$NR^4R^5$, —$NR^4C(=O)R^5$, —$NR^4C(=O)OR^5$, —$NR^4C(=O)NR^5R^6$, —$NR^4SO_2R^5$, —N=$CR^4R^5$, —$SR^4$, —$SOR^4$, —$SO_2R^4$, —$SO_2NR^4R^5$, —$NR^4SO_2NR^5R^6$, —$OSO_2NR^5R^6$ and pseudohalogen; or an optionally mono- or polysubstituted group selected from among $C_{1-6}$alkyl, $C_{2-6}$alkenyl, $C_{2-6}$alkynyl, $C_{3-6}$cycloalkyl, aryl, heterocyclyl and heteroaryl, while the substituent(s) may be identical or different and are selected from among halogen, $R^8$, —$NO_2$, —$OR^4$, —C(=O)$R^4$, —C(=O)$OR^4$, —C(=O)$NR^4R^5$, —$NR^4R^5$, —$NR^4C(=O)R^5$, —$NR^4C(=O)OR^5$, —NR4C(=O)$NR^5R^6$, —$NR^4SO_2R^5$, —N=$CR^4R^5$, —$SR^4$, —$SOR^4$, —$SO_2R^4$, —$SO_2NR^4R^5$, —$NR^4SO_2NR^5R^6$, —$OSO_2NR^5R^6$ and pseudohalogen; and optionally the $R^i$ groups located at adjacent N atoms may be joined together or $R^i$ with $R^g$ or $R^h$ located at adjacent C atoms may be attached in any combination to a common saturated or partially unsaturated 3-5-membered alkyl bridge which may contain one to two heteroatoms;

$R^3$ is selected from the formulae (iv)-(x),

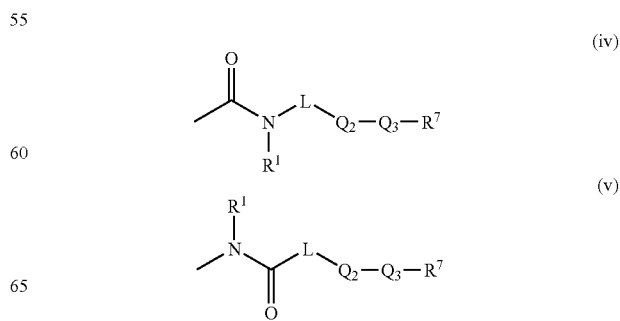

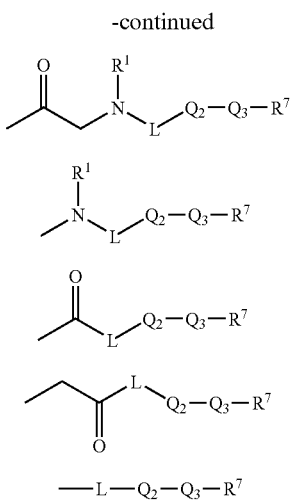

(vi)

(vii)

(viii)

(ix)

—L—$Q_2$—$Q_3$—$R^7$ (x)

$R^4$, $R^5$ and $R^6$ each independently of one another denote hydrogen or a group selected from among optionally mono- or polysubstituted $C_{1-5}$-alkyl, $C_{2-5}$alkenyl, $C_{2-5}$alkynyl, $C_{3-10}$cycloalkyl, aryl, heterocyclyl and heteroaryl, while the substituent(s) may be identical or different and are selected from among $C_{3-10}$-cycloalkyl, aryl, heterocyclyl, heteroaryl, halogen, —$NO_2$, —$OR^8$, —C(=O)$R^8$, —C(=O)$OR^8$, —C(=O)$NR^8R^9$, —$NR^8R^9$, —$NR^8C$(=O)$R^9$, —$NR^8C$(=O)$OR^9$, —$NR^8C$(=O)$NR^9R^{10}$, —$NR^8C$(=O)$ONR^9R^{10}$, —$NR^8SO_2R^9$, —N=$CR^8R^9$, —$SR^8$, —$SOR^8$, —$SO_2R^8$, —$SO_2NR^8R^9$, —$NR^8SO_2NR^9R^{10}$, —$OSO_2NR^8R^9$ and pseudohalogen;

L denotes a bond or a group selected from among optionally mono- or polysubstituted $C_{1-16}$-alkyl, $C_{2-16}$-alkenyl, $C_{2-16}$-alkynyl, $C_{3-10}$cycloalkyl, aryl, heterocyclyl and heteroaryl, while the substituent(s) may be identical or different and are selected from among halogen, —$NO_2$, —$OR^8$, —C(=O)$R^8$, —C(=O)$OR^8$, —C(=O)$NR^8R^9$, —$NR^8R^9$, —$NR^8C$(=O)$R^9$, —$NR^8C$(=O)$OR^9$, —$NR^8C$(=O)$NR^9R^{10}$, —$NR^8C$(=O)$ONR^9R^{10}$, —$NR^8SO_2R^9$, —N=$CR^8R^9$, —$SR^8$, —$SOR^8$, —$SO_2R^8$, —$SO_2NR^8R^9$, —$NR^8SO_2NR^9R^{10}$, —$OSO_2NR^8R^9$ and pseudohalogen;

$Q_2$ and $Q_3$ independently of one another denote a bond or a group selected from among optionally mono- or polysubstituted $C_{1-16}$-alkyl, $C_{2-16}$-alkenyl, $C_{2-16}$-alkynyl, $C_{3-10}$cycloalkyl, aryl, heterocyclyl and heteroaryl while the substituent(s) may be identical or different and are selected from among halogen, —$NO_2$, —$OR^8$, —C(=O)$R^8$, —C(=O)$OR^8$, —C(=O)$NR^8R^9$, —$NR^8R^9$, —$NR^8C$(=O)$R^9$, —$NR^8C$(=O)$OR^9$, —$NR^8C$(=O)$NR^9R^{10}$, —$NR^8C$(=O)$ONR^9R^{10}$, —$NR^8SO_2R^9$, —N=$CR^8R^9$, —$SR^8$, —$SOR^8$, —$SO_2R^8$, —$SO_2NR^8R^9$, —$NR^8SO_2NR^9R^{10}$, —$OSO_2NR^8R^9$ and pseudohalogen;

$R^7$ denotes hydrogen or a group selected from among optionally mono- or polysubstituted $C_{1-16}$-alkyl, $C_{2-6}$-alkenyl, $C_{2-6}$-alkynyl, $C_{3-10}$cycloalkyl, aryl, heterocyclyl and heteroaryl, while the substituent(s) may be identical or different and are selected from among halogen, $NO_2$, —$OR^8$, —C(=O)$R^8$, —C(=O)$OR^8$, —C(=O)$NR^8R^9$, —$NR^8R^9$, —$NR^8COR^9$, —$NR^8C$(=O)$OR^9$, —$NR^8C$(=O)$NR^9R^{10}$, —$NR^8C$(=O)$ONR^9R^{10}$, —$NR^8SO_2R^9$, —N=$CR^8R^9$, —$SR^8$, —$SOR^8$, —$SO_2R^8$, —$SO_2NR^8R^9$, —$NR^8SO_2NR^9R^{10}$, —$OSO_2NR^8R^9$ and pseudohalogen;

$R^8$, $R^9$ and $R^{10}$ each independently of one another denote hydrogen or a group selected from among optionally substituted $C_{1-8}$-alkyl, $C_{2-8}$-alkenyl, $C_{2-8}$-alkynyl, $C_{3-10}$-cycloalkyl, aryl, heterocyclyl and heteroaryl, while the substituent(s) may be identical or different and are selected from among halogen, methyl, ethyl, amino, methylamino, dimethylamino, —OH and pseudohalogen;

optionally in the form of the tautomers, racemates, enantiomners, diastereomers and mixtures thereof, and optionally the pharmacologically acceptable acid addition salts thereof.

In one aspect the invention relates to compounds of general formula (1) wherein
W denotes C—$R^2$ and the other groups are as hereinbefore defined.

In another aspect the invention relates to compounds of general formula (1), wherein
X denotes —$NR^{1a}$ or oxygen,
$R^1$ and $R^{1a}$ denote hydrogen;
$R^3$ denotes formula (iv) or (x),

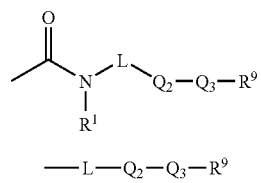

(iv)

—L—$Q_2$—$Q_3$—$R^9$ (x)

and the other groups are as hereinbefore defined.

In another aspect the invention relates to compounds of general formula (1), wherein
Y denotes CH and
$Q_1$ denotes monocyclic aryl compounds and the other groups are as hereinbefore defined.

In one aspect the invention relates to compounds of general formula (1), wherein
$R^c$ denotes a group selected from among hydrogen, —F, —Cl, methyl and ethyl and the other groups are as hereinbefore defined.

In another aspect the invention relates to compounds of general formula (1), wherein
$R^a$ and $R^b$ each independently of one another denote hydrogen or fluorine; or an optionally mono- or polysubstituted group selected from among $C_{1-2}$-alkyl, $C_2$-alkenyl, $C_2$-alkynyl, $C_{3-6}$-cycloalkyl, aryl, heterocyclyl and heteroaryl, while the substituent(s) may be identical or different and are selected from among hydrogen, halogen, —$NO_2$, —$OR^4$, —C(=O)$R^4$, —C(=O)$OR^4$, —C(=O)$NR^4R^5$, —$NR^4R^5$, —$NR^4C$(=O)$R^5$, —$NR^4C$(=O)$OR^5$, —$NR^4C$(=O)$NR^5R^6$, —$NR^4SO_2R^5$, —N=$CR^4R^5$, —$SR^4$, —$SOR^5$, —$SO_2R^4$, —$SO_2NR^4R^5$, —$NR^4$, —$SO_2NR^4R^5$, —$OSO_2NR^4R^5$ and pseudohalogen and the other groups are as hereinbefore defined.

In another aspect the invention also relates to compounds of general formula (1), wherein $R^a$ and $R^b$ denote hydrogen or fluorine and the other groups are as hereinbefore defined.

The invention also includes compounds of general formula (1), wherein
Z denotes halogen-$C_{1-3}$-alkyl, —COH, —C(=O)—$C_{1-3}$-alkyl, —C(=O)—$C_{2-3}$-alkenyl, —C(=O)—$C_{2-3}$-alkynyl, —C(=O)$C_{1-3}$-alkyl-halogen and pseudohalogen and the other groups are as hereinbefore defined.

In one aspect the invention relates to compounds of general formula (1), or the pharmaceutically active salts thereof, as pharmaceutical compositions.

In an essential aspect the invention relates to compounds of general formula (1), or the pharmaceutically active salts thereof, for use as pharmaceutical compositions with an antiproliferative activity.

Moreover the invention includes compounds of general formula (1), or the pharmaceutically active salts thereof, for use as pharmaceutical compositions with an antiproliferative activity with a selective kinase-inhibiting mechanism of activity.

In one aspect the invention relates to the use of compounds of general formula (1), or the pharmaceutically active salts thereof, for preparing a pharmaceutical composition with an antiproliferative activity with a PLK inhibiting mechanism of activity.

In another aspect the invention relates to pharmaceutical preparations, containing as active substance one or more compounds of general formula (I), or the physiologically acceptable salts thereof, optionally in conjunction with conventional excipients and/or carriers.

In another aspect the invention relates to the use of one or more compounds of general formula (1) for preparing a pharmaceutical composition for the treatment and/or prevention of cancer, infections, inflammatory and autoimmune diseases.

In another aspect the invention relates to a pharmaceutical preparation containing at least one compound of general formula (1)

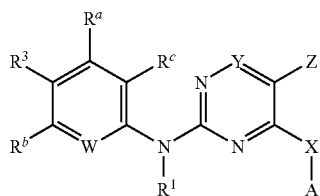

(1)

wherein

W denotes N or C—$R^2$,

X denotes —$NR^{1a}$, O or S,

Y denotes CH or N,

Z denotes hydrogen, halogen, —$NO_2$, $C_{1-3}$-alkyl, $C_{2-3}$-alkenyl, $C_{2-3}$-alkynyl, halogen-$C_{1-3}$-alkyl, —COH, —C(=O)—$C_{1-3}$-alkyl, —C(=O)—$C_{2-3}$-alkenyl, —C(=O)—$C_{2-3}$-alkynyl, —C(=O)$C_{1-3}$-alkyl-halogen and pseudohalogen;

A is selected from the formulae (i), (ii) or (iii)

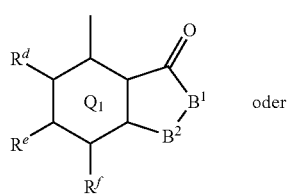

(i)

oder

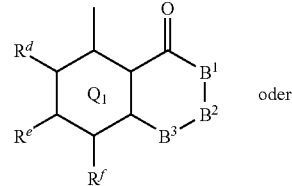

(ii)

oder

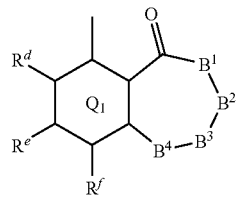

(iii)

$Q_1$ denotes mono- or bicyclic aryl compounds;

$B^1$, $B^2$, $B^3$ and $B^4$ in each case independently of one another represent C—$R^g R^h$, N—$R^i$, O or S, while adjacent $B^1$-$B^4$ in each case do not denote —O—;

$R^1$ and $R^{1a}$ each independently of one another denote hydrogen or methyl, $R^2$ denotes a group selected from among hydrogen, halogen, —$OR^4$, —C(=O)$R^4$, —C(=O)$NR^4R^5$, —$NR^4R^5$, —$NR^4C$(=O)$R^5$, —$NR^4SO_2R^5$, —N=$CR^4R^5$, —C=$NR^i$, —$SR^4$, —$SOR^4$, —$SO_2R^4$, —$SO_2NR^4R^5$ and pseudohalogen, or an optionally mono- or polysubstituted group selected from among $C_{1-6}$-alkyl, $C_{2-6}$-alkenyl, $C_{2-6}$-alkynyl, $C_{3-6}$-cycloalkyl, aryl, heterocyclyl and heteroaryl, while the substituent(s) may be identical or different and are selected from among halogen, —$NO_2$, —$OR^4$, —C(=O)$R^4$, —C(=O)$OR^4$, —C(=O)$NR^4R^5$, —$NR^4R^5$, —$NR^4C$(=O)$R^5$, —$NR^4C$(=O)$OR^5$, —$NR^4C$(=O)$NR^5R^6$, —$NR^4SO_2R^5$, —N=$CR^4R^5$, —$SR^4$, —$SOR^4$, —$SO_2R^4$, —$SO_2NR^4R^5$, —$NR^4SO_2NR^5R^6$, —$OSO_2NR^5R^6$ and pseudohalogen;

$R^a$, $R^b$, $R^c$, $R^d$, $R^e$, $R^f$, $R^g$ and $R^h$ in each case independently of one another denote a group selected from among hydrogen, halogen, =O, —$NO_2$, —$OR^4$, —C(=O)$R^4$, —C(=O)$OR^4$, —C(=O)$NR^4R^5$, —$NR^4R^5$, —$NR^4C$(=O)$R^5$, —$NR^4C$(=O)$OR^5$, —$NR^4C$(=O)$NR^5R^6$, —$NR^4SO_2R^5$, —N=$CR^4R^5$, —C=$NR^i$, —$SR^4$, —$SOR^4$, —$SO_2R^4$, —$SO_2NR^4R^5$, —$NR^4SO_2NR^5R^6$, —$OSO_2NR^5R^6$ and pseudohalogen; or an optionally mono- or polysubstituted group selected from among $C_{1-6}$-alkyl, $C_{2-6}$-alkenyl, $C_{2-6}$-alkynyl, $C_{3-6}$-cycloalkyl, aryl, heterocyclyl and heteroaryl, while the substituent(s) may be identical or different and are selected from among halogen, $R^8$, —$NO_2$, —$OR^4$, —C(=O)$R^4$, —C(=O)$OR^4$, —C(=O)$NR^4R^5$, —$NR^4R^5$, —$NR^4C$(=O)$R^5$, —$NR^4C$(=O)$OR^5$, —$NR^4C$(=O)$NR^5R^6$, —$NR^4SO_2R^5$, —N=$CR^4R^5$, —$SR^4$, —$SOR^4$, —$SO_2R^4$, —$SO_2NR^4R^5$, —$NR^4SO_2NR^5R^6$, —$OSO_2NR^5R^6$ and pseudohalogen; and optionally the $R^g$ and $R^h$ located at the same or at adjacent C atoms may be attached in any combination to a common saturated or partially unsaturated 3-5-membered alkyl bridge which may contain one to two heteroatoms;

$R^i$ denotes a group selected from among hydrogen, =O)—$OR^4$, —C(=O)$R^4$, —C(=O)$OR^4$, —C(=O)$NR^4R^5$, —$NR^4R^5$, —$NR^4C$(=O)$R^5$, —$NR^4C$(=O)$OR^5$, —$NR^4C$(=O)$NR^5R^6$, —$NR^4SO_2R^5$, —N=$CR^4R^5$, —$SR^4$, —$SOR^4$, —$SO_2R^4$, —$SO_2NR^4R^5$, —$NR^4SO_2NR^5R^6$, —$OSO_2NR^5R^6$ or an optionally mono- or polysubstituted group selected from among $C_{1-6}$-alkyl, $C_{2-6}$-alkenyl, $C_{2-6}$-alkynyl, $C_{3-6}$-cycloalkyl, aryl, heterocyclyl and heteroaryl, while the substituent(s) may be identical or different and are selected from among halogen, $R^8$, —$NO_2$, —$OR^4$, —$C(=O)R^4$, —$C(=O)OR^4$, —$C(=O)NR^4R^5$, —$NR^4R^5$, —$NR^4C(=O)R^5$, —$NR^4C(=O)OR^5$, —$NR4C(=O)NR^5R^6$, —$NR^4SO_2R^5$, —$N=CR^4R^5$, —$SR^4$, —$SOR^4$, —$SO_2R^4$, —$SO_2NR^4R^5$, —$NR^4SO_2NR^5R^6$, —$OSO_2NR^5R^6$ and pseudohalogen; and optionally the Ri groups located at adjacent N atoms may be joined together or to $R^g$ and $R^h$ located at adjacent C atoms in any combination with a common saturated or partially unsaturated 3-5-membered alkyl bridge which may contain one to two heteroatoms;

$R^3$ is selected from the formulae (iv)-(x),

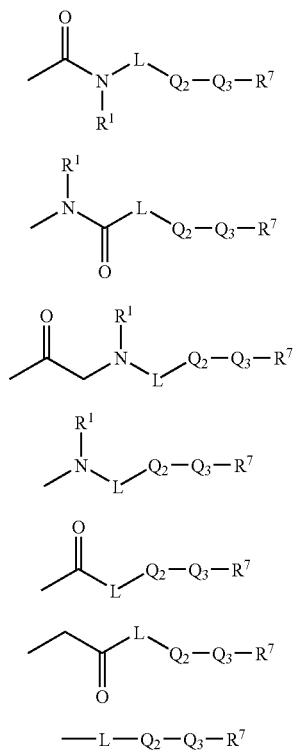

(iv)
(v)
(vi)
(vii)
(viii)
(ix)
(x)

$R^4$, $R^5$ and $R^6$ each independently of one another denote hydrogen or a group selected from among optionally mono- or polysubstituted $C_{1-5}$-alkyl, $C_{2-5}$-alkenyl, $C_{2-5}$-alkynyl, $C_{3-10}$-cycloalkyl, aryl, heterocyclyl and heteroaryl, while the substituent(s) may be identical or different and are selected from among $C_{3-10}$-cycloalkyl, aryl, heterocyclyl, heteroaryl, halogen, —$NO_2$, —$OR^8$, —$C(=O)R^8$, —$C(=O)OR^8$, —$C(=O)NR^8R^9$, —$NR^8R^9$, —$NR^8C(=O)R^9$, —$NR^8C(=O)OR^9$, —$NR^8C(=O)NR^9R^{10}$, —$NR^8C(=O)ONR^9R^{10}$, —$NR^8SO_2R^9$, —$N=CR^8R^9$, —$SR^8$, —$SOR^8$, —$SO_2R^8$, —$SO_2NR^8R^9$, —$NR^8SO_2NR^9R^{10}$, —$OSO_2NR^8R^9$ and pseudohalogen;

L denotes a bond or a group selected from among optionally mono- or polysubstituted $C_{1-16}$-alkyl, $C_{2-16}$-alkenyl, $C_{2-16}$-alkynyl, $C_{3-10}$-cycloalkyl, aryl, heterocyclyl and heteroaryl, while the substituent(s) may be identical or different and are selected from among halogen, —$NO_2$, —$OR^8$, —$C(=O)R^8$, —$C(=O)OR^8$, —$C(=O)NR^8R^9$, —$NR^8R^9$, —$NR^8C(=O)R^9$, —$NR^8C(=O)OR^9$, —$NR^8C$ $(=O)NR^9R^{10}$, —$NR^8C(=O)ONR^9R^{10}$, —$NR^8SO_2R^9$, —$N=CR^8R^9$, —$SR^8$, —$SOR^8$, —$SO_2R^8$, —$SO_2NR^8R^9$, —$NR^8SO_2NR^9R^{10}$, —$OSO_2NR^8R^9$ and pseudohalogen;

$Q_2$ and $Q_3$ independently of one another denote a bond or a group selected from among optionally mono- or polysubstituted $C_{1-16}$-alkyl, $C_{2-16}$-alkenyl, $C_{2-16}$-alkynyl, $C_{3-10}$-cycloalkyl, aryl, heterocyclyl and heteroaryl, while the substituent(s) may be identical or different and are selected from among halogen, —$NO_2$, —$OR^8$, —$C(=O)R^8$, —$C(=O)OR^8$, —$C(=O)NR^8R^9$, —$NR^8R^9$, —$NR^8C(=O)R^9$, —$NR^8C(=O)OR^9$, —$NR^8C(=O)NR^9R^{10}$, —$NR^8C(=O)ONR^9R^{10}$, —$NR^8SO_2R^9$, —$N=CR^8R^9$, —$SR^8$, —$SOR^8$, —$SO_2R^8$, —$SO_2NR^8R^9$, —$NR^8SO_2NR^9R^{10}$, —$OSO_2NR^8R^9$ and pseudohalogen;

$R^7$ denotes hydrogen or a group selected from among optionally mono- or polysubstituted $C_{1-16}$-alkyl, $C_{2-16}$-alkenyl, $C_{2-16}$-alkynyl, $C_{3-10}$-cycloalkyl, aryl, heterocyclyl and heteroaryl, while the substituent(s) may be identical or different and are selected from among halogen, $NO_2$, —$OR^8$, —$C(=O)R^8$, —$C(=O)OR^8$, —$C(=O)NR^8R^9$, —$NR^8R^9$, —$NR^8COR^9$, —$NR^8C(=O)OR^9$, —$NR^8C(=O)NR^9R^{10}$, —$NR^8C(=O)ONR^9R^{10}$, —$NR^8SO_2R^9$, —$N=CR^8R^9$, —$SR^8$, —$SOR^8$, —$SO_2R^8$, —$SO_2NR^8R^9$, —$NR^8SO_2NR^9R^{10}$, —$OSO_2NR^8R^9$ and pseudohalogen;

$R^8$, $R^9$ and $R^{10}$ each independently of one another denote hydrogen or a group selected from among optionally substituted $C_{1-8}$-alkyl, $C_{2-8}$-alkenyl, $C_{2-8}$-alkynyl, $C_{3-10}$-cycloalkyl, aryl, heterocyclyl and heteroaryl, while the substituent(s) may be identical or different and are selected from among halogen, —$NH_2$, —$OH$ and pseudohalogen;

optionally in the form of the tautomers, racemates, enantiomers, diastereomers and mixtures thereof, and optionally the pharmacologically acceptable acid addition salts thereof, and at least one other cytostatic or cytotoxic active substance, optionally in the form of the tautomers, racemates, enantiomers, diastereomers and mixtures thereof, and optionally the pharmacologically acceptable acid addition salts thereof.

Definitions

As used herein, the following definitions apply, unless stated otherwise.

By alkyl substituents are meant in each case saturated, straight-chain or branched aliphatic hydrocarbon groups (alkyl group).

The alkenyl substituents are in each case straight-chain or branched, unsaturated alkyl groups which have at least one double bond.

By alkynyl substituents are meant in each case straight-chain or branched, unsaturated alkyl groups which have at least one triple bond.

Haloalkyl refers to alkyl groups wherein one or more hydrogen atoms are replaced by halogen atoms. Haloalkyl includes both saturated alkyl groups and unsaturated alkenyl and alkynyl groups, such as for example —$CF_3$, —$CHF_2$, —$CH_2F$, —$CF_2CF_3$, —$CHFCF_3$, —$CH_2CF_3$, —$CF_2CH_3$, —$CHFCH_3$, —$CF_2CF_2CF_3$, —$CF_2CH_2CH_3$, —$CHFCH_2CH_3$ and —$CHFCH_2CF_3$.

Halogen relates to fluorine, chlorine, bromine and/or iodine atoms.

By pseudohalogen are meant the following groups: —OCN, —SCN, —$CF_3$ and —CN.

By cycloalkyl is meant a mono- or bicyclic ring, while the ring system may be a saturated ring or an unsaturated, non-aromatic ring, which may optionally also contain double bonds, such as for example cyclopropyl, cyclopropenyl, cyclobutyl, cyclobutenyl, cyclopentyl, cyclopentenyl, cyclohexyl, cyclohexenyl, norbornyl, norbornenyl, spiro[5.5]undecane, spiro[5.4]decane and spiro[4.4]nonane.

Aryl relates to monocyclic or bicyclic rings with 6-12 carbon atoms such as for example phenyl and naphthyl.

By heteroaryl are meant mono- or bicyclic rings which contain instead of one or more carbon atoms one or more identical or different heteroatoms, such as e.g. nitrogen, sulphur or oxygen atoms. Examples include furyl, thienyl, pyrrolyl, oxazolyl, thiazolyl, isoxazolyl, isothiazolyl, pyrazolyl, imidazolyl, triazolyl, tetrazolyl, oxadiazolyl, thiadiazolyl, pyridyl, pyrimidyl, pyridazinyl, pyrazinyl and triazinyl. Examples of bicyclic heteroaryl groups are indolyl, isoindolyl, benzofuranyl, benzothienyl, benzoxazolyl, benzothiazolyl, benzisoxazolyl, benzisothiazolyl, benzimidazolyl, indazolyl, isoquinolinyl, quinolinyl, quinoxalinyl, cinnolinyl, phthalazinyl, quinazolinyl and benzotriazinyl, indolizinyl, oxazolopyridinyl, imidazopyridinyl, naphthyridinyl, indolinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, cumarinyl, isocumarinyl, chromonyl, chromanonyl, pyridinyl-N-oxid, tetrahydroquinolinyl, dihydroquinolinyl, dihydroquinolinonyl, dihydroisoquinolinonyl, dihydrocumarinyl, dihydroisocumarinyl, isoindolinonyl, benzodioxanyl, benzoxazolinonyl, pyrrolyl-N-oxide, pyrimidinyl-N-oxide, pyridazinyl-N-oxide, pyrazinyl-N-oxide, quinolinyl-N-oxide, indolyl-N-oxide, indolinyl-N-oxide, isoquinolyl-N-oxide, quinazolinyl-N-oxide, quinoxalinyl-N-oxide, phthalazinyl-N-oxide, imidazolyl-N-oxide, isoxazolyl-N-oxide, oxazolyl-N-oxide, thiazolyl-N-oxide, indolizinyl-N-oxide, indazolyl-N-oxide, benzothiazolyl-N-oxide, benzimidazolyl-N-oxide, pyrrolyl-N-oxide, oxadiazolyl-N-oxide, thiadiazolyl-N-oxide, triazolyl-N-oxide, tetrazolyl-N-oxide, benzothiopyranyl-S-oxide and benzothiopyranyl-S,S-dioxide.

Heterocyclyl relates to saturated or unsaturated, non-aromatic mono-, bicyclic or bridged bicyclic rings comprising 5-12 carbon atoms, which carry heteroatoms, such as nitrogen, oxygen or sulphur, instead of one or more carbon atoms. Examples of such heterocylyl groups are tetrahydrofuranyl, pyrrolidinyl, pyrrolinyl, imidazolidinyl, imidazolinyl, pyrazolidinyl, pyrazolinyl, piperidyl, piperazinyl, indolinyl, isoindoliny, morpholinyl, thiomorpholinyl, homomorpholinyl, homopiperidyl, homopiperazinyl, thiomorpholinyl-S-oxide, thiomorpholinyl-S,S-dioxide, tetrahydropyranyl, piperidinyl, tetrahydrothienyl, homopiperidinyl, homothiomorpholinyl-S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, tetrahydrothienyl-S-oxide, tetrahydrothienyl-S,S-dioxide, homothiomorpholinyl-S-oxide, 2-oxa-5-azabicyclo[2.2.1]heptane, 8-oxa-3-aza-bicyclo[3.2.1]octane, 3,8-diaza-bicyclo[3.2.1]octane, 2,5-diaza-bicyclo[2.2.1]heptane, 3,8-diaza-bicyclo[3.2.1]octane, 3,9-diaza-bicyclo[4.2.1]nonane, 2,6-diaza-bicyclo[3.2.2]nonane, 2,7-diaza-spiro[3.5]nonane, 2,7-diaza-spiro[4.4]nonane, 2,8-diaza-spiro[4.5]decane, 3,9-diaza-spiro[5.5]undecane.

The Examples that follow illustrate the present invention without restricting its scope:

Preparation of the Compounds According to the Invention:

The compounds according to the invention may be prepared according to methods of synthesis A to C described hereinafter, wherein the substituents of general formulae (I to XVI) have the meanings given hereinbefore.

Method A

Step 1A

The intermediate compound III is prepared by substitution of a leaving group LG, for example halogen, SCN or methoxy, preferably chlorine, in a heteroaromatic system I by a nucleophile II.

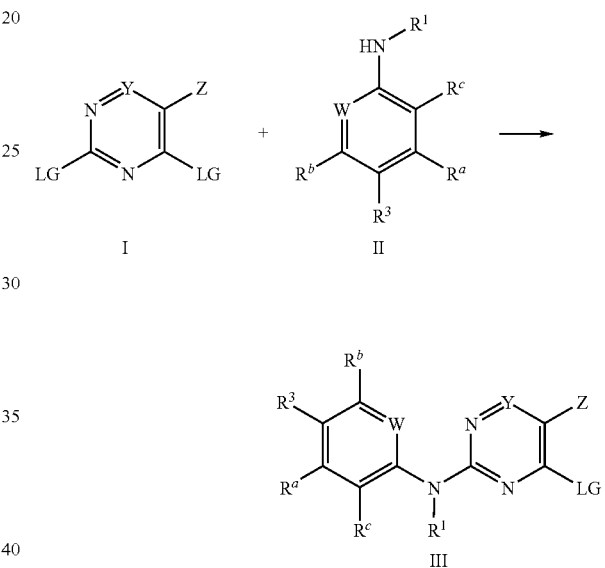

Diagram 1A 1 equivalent of compound I and 1 to 1.5 equivalents of compound II are stirred in a solvent, for example 1,4-dioxane, tetrahydrofuran, ethanol, isopropanal, N,N-dimethylformamide or N,N-dimethylacetamide. At a temperature of 15 to 25° C., 2 to 2.5 equivalents of a base, for example potassium carbonate, sodium carbonate, caesium carbonate, N-ethyl-N,N-diisopropylamine or triethylamine, are added. The reaction mixture is stirred for 6 to 72 h at a temperature of 20 to 100° C. Then the solvent is distilled off and the residue is combined with water which has been adjusted to a pH of between 1-4 with an inorganic acid, for example hydrochloric acid or sulphuric acid. This mixture is extracted two to three times with an organic solvent, for example diethyl ether, ethyl acetate or dichloromethane. The combined organic extracts are dried and the solvent is distilled off. The residue is purified by chromatography.

Step 2A

The end compound V is prepared by substitution of a leaving group LG, for example halogen, SCN or methoxy, preferably chlorine, in a heteroaromatic system III by a nucleophile IV.

Diagram 2A

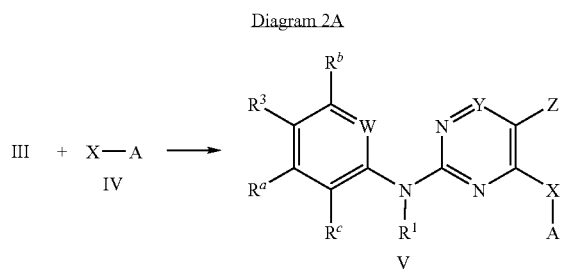

1 equivalent of the compound III and 1 to 3 equivalents of the compound IV are stirred in a solvent, for example 1,4-dioxane, N,N-dimethylformamide, N,N-dimethylacetamide or N-methyl-2-pyrrolidinone. At a temperature of 15 to 40° C., 1 to 2 equivalents of an inorganic acid, for example sulphuric acid or hydrochloric acid, are added. The reaction mixture is stirred for another 12 to 72 h at a temperature of 20 to 100° C. Then the solvent is distilled off and the residue is purified by chromatography.

Method B

Step 1B

The intermediate compound VII is prepared by substitution of a leaving group LG, for example halogen, SCN, methoxy, preferably chlorine, in a heteroaromatic system I by a nucleophile VI.

Diagram 1B

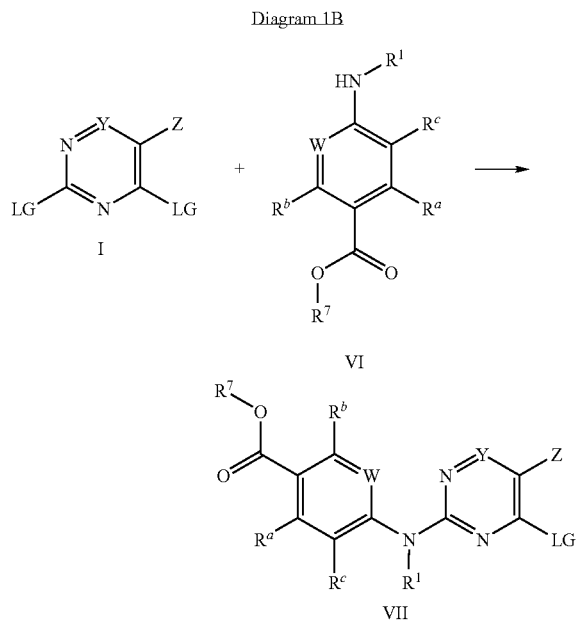

1 equivalent of the compound I and 1 to 1.5 equivalents of the compound VI are stirred in a solvent, for example 1,4-dioxane, tetrahydrofuran, ethanol, isopropanol, N,N-dimethylformamide or N,N-dimethylacetamide.

At a temperature of 15 to 25° C., 2 to 2.5 equivalents of a base, for example potassium carbonate, sodium carbonate, caesium carbonate, potassium hydrogen phosphate, N-ethyl-N,N-diisopropylamine or triethylamine are added. The reaction mixture is stirred for 6 to 72 h more at a temperature of 20 to 120° C. The reaction mixture is combined with water, which has been adjusted to a pH of 8 to 9 with an inorganic base, for example sodium hydrogen carbonate or potassium carbonate. This mixture is extracted two to three times with an organic solvent, for example diethyl ether or ethyl acetate.

The combined organic extracts are dried and the solvent is distilled off. The residue is purified by chromatography or repeated crystallisation.

Step 2B

The intermediate compound VIII is prepared by substituting a leaving group LG, for example halogen, SCN, methoxy, preferably chlorine, in a heteroaromatic system VII by a nucleophile IV.

Diagram 2B

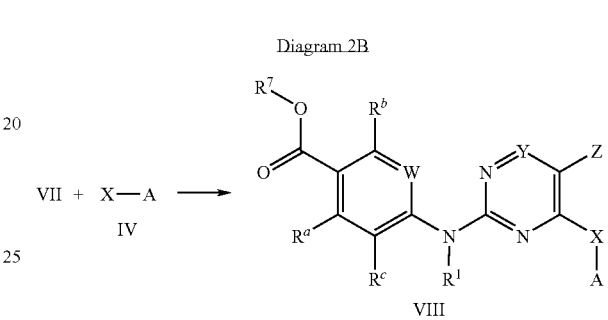

1 equivalent of the compound VII and 1 to 1.5 equivalents of the compound IV are stirred in a solvent, for example 1,4-dioxane, N,N-dimethylformamide, N,N-dimethylacetamide or N-methyl-2-pyrrolidinone. At a temperature of 15 to 40° C., 0.2 to 1 equivalent of an acid, for example sulphuric acid or hydrochloric acid, is added. The reaction mixture is stirred for another 12 to 72 h at a temperature of 20 to 100° C. The reaction mixture is stirred into water and the resulting precipitate is filtered off and dried. The precipitate may be purified by chromatography or crystallisation or used as the crude product in the next step.

Step 3B

Compounds VIII whose group $R^7$ denotes hydrogen may be used directly for preparing the end compounds X, while a compound VIII is reacted with a compound IX.

Compounds VIII whose group $R^7$ does not denote hydrogen are converted beforehand by hydrolysis or similar methods known to the skilled man into the compounds wherein the group $R^7$ denotes hydrogen.

Diagram 3B

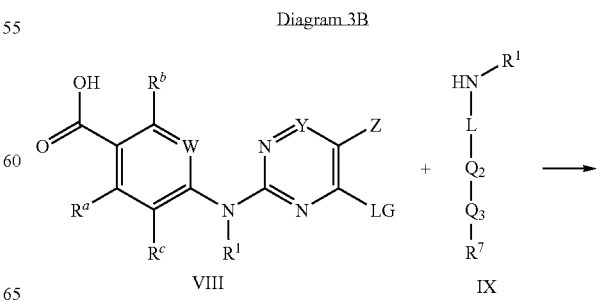

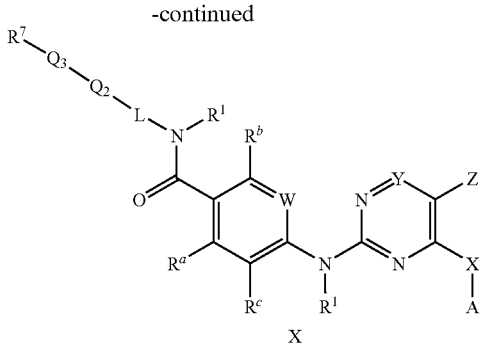

-continued

X 1 equivalent of the compound VIII, 1 to 1.5 equivalents of the compound IX and 1 to 3 equivalents of a base, for example triethylamine or ethyldiisopropylamine, are stirred in a solvent, for example 1,4-dioxane, N,N-dimethylformamide, N,N-dimethylacetamide or N-methyl-2-pyrrolidinone. At a temperature of 15 to 25° C., 1 to 1.5 equivalents of a coupling reagent, for example N,N-dicyclohexylcarbodiimide, N,N-diisopropyl-carbodiimide, O-(benzotriazol-1-yl)-N,N,N',N'-tetramethyluronium-tetrafluoroborate or 1-(3-N,N-dimethylaminopropyl)-3-ethylcarbodiimide are added. The reaction mixture is stirred for another 4 to 24 h at a temperature of 15 to 25° C. Then the solvent is distilled off and the residue is purified by chromatography.

Method C

Step 1C

The intermediate compound XI is prepared by substituting a leaving group LG, for example halogen, SCN, methoxy, preferably chlorine, at a heteroaromatic system I with a nucleophilic group IV.

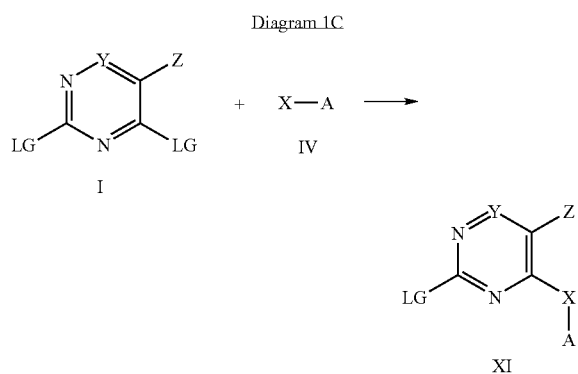

1 equivalent of the compound I and 1 to 3 equivalents of a base, for example triethylamine or ethyldiisopropylamine, are stirred in a solvent, for example 1,4-dioxane, tetrahydrofuran, N,N-dimethylformamide or N,N-dimethylacetamide. At a temperature of −60 to 0° C., 0.8 to 1.5 equivalents of a compound IV are added. The reaction mixture is stirred for 6 to 72 h at a temperature of 15 to 75° C. Then the solvent is distilled off and the residue is purified by chromatography.

Step 2C

The end compound V is prepared by substitution of a leaving group LG, for example halogen, SCN, methoxy, preferably chlorine, at a heteroaromatic system XI by a nucleophile II.

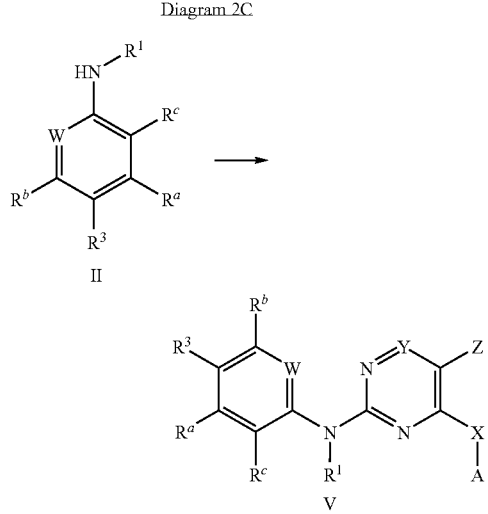

1 equivalent of the compound XI and 1 to 1.5 equivalents of the compound II are stirred in a solvent, for example 1,4-dioxane, N,N-dimethyl-formamide, N,N-dimethylacetamide or N-methyl-2-pyrrolidinone. At a temperature of 15 to 40° C. 1 to 2 equivalents of an acid, for example sulphuric acid or hydrochloric acid, are added. The reaction mixture is stirred for another 6 to 72 h at a temperature of 20 to 100° C. Then the solvent is distilled off and the residue is purified by chromatography.

Chromatography:

For medium pressure chromatography (MPLC) silica gel made by Millipore (name: Granula Silica Si-60A 35-70 µm) or C-18 RP-silica gel made by Macherey Nagel (name: Polygoprep 100-50 C18) is used.

For high pressure chromatography columns made by Waters (name: XTerra Prep. MS C18, 5 µM, 30*100 mm or Symmetrie C18, 5 µm, 19*100) are used.

Nuclear Magnetic Resonance (NMR) Spectroscopy:

The measurement is carried out in deuterised dimethylsulphoxide-d6. If other solvents are used they are explicitly mentioned in the Examples or in the methods. The measurements are given on a delta scale in ppm. Tetramethylsilane is taken as the standard. The measurements are carried out on an Avance 400 (400 MHz NMR spectrometer) made by Messrs Bruker Biospin GmbH.

The NMR spectra are given purely in a descriptive capacity. Basically, only the visible molecular signals are listed. If for example molecular signals are partly or completely masked by foreign signals such as for example water signals, DMSO signals or CDCl$_3$ signals they are not mentioned.

Mass Spectroscopy/UV Spectrometer:

These data are generated using an HPLC-MS apparatus (high performance liquid chromatography with mass detector) made by Agilent.

The apparatus is constructed so that a diode array detector (G1315B made by Agilent) and a mass detector (1100 LS-MSD SL; G1946D; Agilent) are connected in series downstream of the chromatography apparatus (column: Zorbax SB-C8, 3.5 µm, 2,1*50, Messrs. Agilent). The apparatus is operated with a flow of 0.6 ml/min. For a separation process a gradient is run through within 3.5 min (start of gradient:

95% water and 5% acetonitrile; end of gradient: 5% water and 95% acetonitrile; in each case 0.1% formic acid is added to the two solvents).

Method 1
2-(2-methoxy-4-propylcarbamoyl-phenylamino)-4-chloro-5-trifluoromethyl-pyrimidine

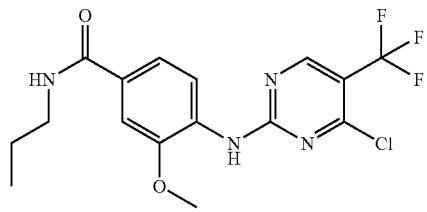

5 g (21.9 mmol) 2,4-dichloro-5-trifluoromethyl-pyrimidine are dissolved in 50 ml 1,4-dioxane and combined with 5.5 g (21.9 mmol) 4-amino-3-methoxybenzoic acid-propylamide hydrochloride (Zhuangyu Zhang, et al. 1989, *J Pharml Sci.* 78(10):829-32). 7.5 ml (43.8 mmol) ethyldiisopropylamine are added to this reaction mixture and the mixture is stirred for 2 days at ambient temperature. Then the reaction mixture is diluted with 250 ml of ethyl acetate and washed first with 300 ml aqueous 10% $KHSO_4$ solution, then with 300 ml saturated aqueous NaCl solution. The organic phase is dried with $MgSO_4$ and the solvent is eliminated in vacuo. The crude product is purified by column chromatography. The carrier used is silica gel and the eluant is a mixture of cyclohexane:ethyl acetate (75:25).

Yield: 2.30 g (5.9 mmol; 27%) $^1$H-NMR: 0.91 (t, 3H), 1.50-1.61 (m, 2H), 3.20-3.28 (m, 2H), 3.87 (s, 3H), 7.46-7.51 (m, 1H), 7.52-7.56 (m, 1H), 7.70-7.75 (m, 1H), 8.44 (t, 1H), 8.75 (s, 1H), 9.73 (s, 1H)

Method 2
7-amino-2,3-dihydro-isoindol-1-one

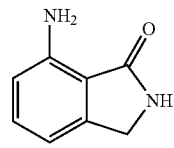

a) 7-nitro-2,3-dihydro-isoindol-1-one 1.5 g (5.473 mmol) methyl 2-bromomethyl-6-nitro-benzoate are dissolved in 20 ml N,N-dimethylformamide and combined with 15 ml of methanolic ammonia (7 mmol/ml). After 20 h at 25° C. the mixture is diluted with 100 ml of ethyl acetate and extracted 3 times with saturated sodium hydrogen carbonate solution. The organic phase is dried with magnesium sulphate and the solvent is eliminated in vacuo.

Yield: 960 mg (5.389 mmol, 99%) MS-ESI+: m/z=179 $[M+H]^+$ b) 7-amino-2,3-dihydro-isoindol-1-one 960 mg (5.389 mmol) 7-nitro-2,3-dihydro-isoindol-1-one are dissolved in 100 ml of tetrahydrofuran and combined with 100 mg palladium on charcoal. Then the mixture is stirred for 20 h at 25° C. and 4 bar hydrogen pressure ($H_2$ pressure). The catalyst is filtered off and the solvent is eliminated in vacuo.

Yield: 734 mg (4.958 mmol, 92%) MS-ESI+: m/z=149 $[M+H]^+$

The following 7-amino-2,3-dihydro-isoindol-1-one derivatives are prepared analogously to this method. A corresponding amine is used instead of ammonia:

-continued

| Structure | MS (ESI) (M + H)+ | Structure | MS (ESI) (M + H)+ |
|---|---|---|---|
| 7-amino-2-cyclohexyl-isoindolin-1-one | 231 | 7-amino-2-(4-hydroxybutyl)-isoindolin-1-one | 221 |
| 7-amino-2-isopentyl-isoindolin-1-one | 219 | 7-amino-2-(4-hydroxybenzyl)-isoindolin-1-one | 255 |
| 7-amino-2-(tetrahydropyran-4-yl)-isoindolin-1-one | 233 | 7-amino-2-(2-aminoethyl)-isoindolin-1-one | 192 |
| 7-amino-2-(3-hydroxypropyl)-isoindolin-1-one | 207 | 7-amino-2-(3-hydroxybenzyl)-isoindolin-1-one | 255 |
| 7-amino-2-(2-acetamidoethyl)-isoindolin-1-one | 234 | 8-amino-3-methyl-3,4-dihydrophthalazin-1(2H)-one | 178 |
| 7-amino-2-(3-(2-oxopyrrolidin-1-yl)propyl)-isoindolin-1-one | 274 | 8-amino-3-ethyl-3,4-dihydrophthalazin-1(2H)-one | 192 |
| 7-amino-2-(2-fluoroethyl)-isoindolin-1-one | 195 | 7-amino-2-(2-chloroethyl)-isoindolin-1-one | 211/213 |
| 7-amino-2-(2,2-difluoroethyl)-isoindolin-1-one | 213 | 7-amino-2-((1S,2S)-2-hydroxycyclohexyl)-isoindolin-1-one | 247 |

-continued
| | MS (ESI) (M + H)+ | | MS (ESI) (M + H)+ |
|---|---|---|---|
| 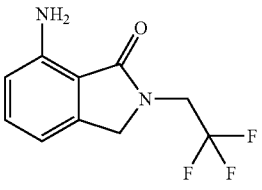 | 231 | 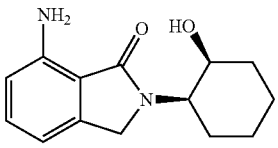 | 247 |
| 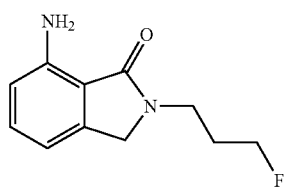 | 209 | 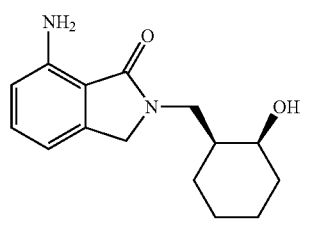 | 261 |
| 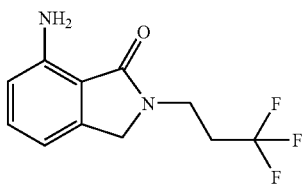 | 245 | 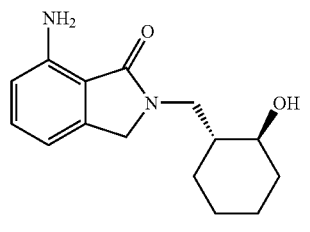 | 261 |
| 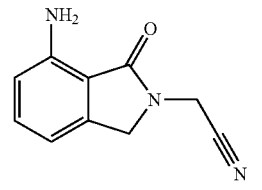 | 188 | 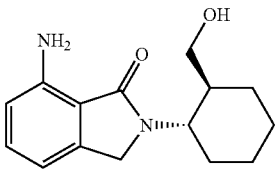 | 261 |
| 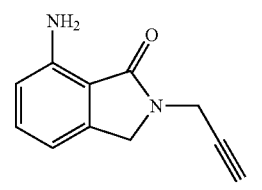 | 187 | 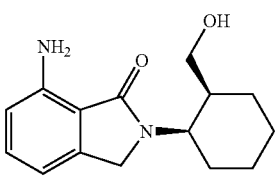 | 261 |
| 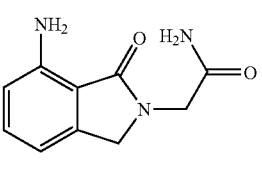 | 206 | 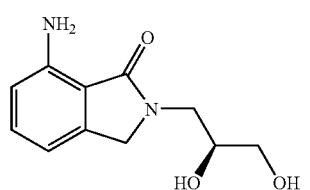 | 223 |
| 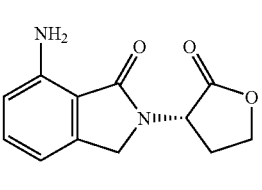 | 233 | 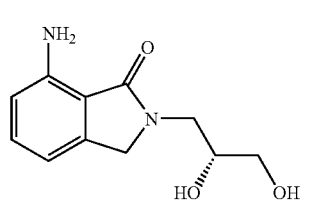 | 223 |

| Structure | MS (ESI) (M + H)⁺ | Structure | MS (ESI) (M + H)⁺ |
|---|---|---|---|
| 7-amino-2-(2-oxotetrahydrofuran-3-yl)isoindolin-1-one | 233 | 7-amino-2-(1-hydroxy-2-methylpropan-2-yl)isoindolin-1-one | 221 |
| 3-(7-aminoisoindolin-2-yl)propanenitrile | 202 | 7-amino-2-(trans-4-hydroxycyclohexyl)isoindolin-1-one | 247 |
| 7-amino-2-(3-aminopropyl)isoindolin-1-one | 206 | 7-amino-2-(1-methylpiperidin-4-yl)isoindolin-1-one | 246 |
| 7-amino-2-propylisoindolin-1-one | 191 | 7-amino-2-(3-hydroxy-2,2-dimethylpropyl)isoindolin-1-one | 235 |
| 7-amino-2-isobutylisoindolin-1-one | 205 | 8-amino-2-(2-fluoroethyl)-3-methyl-3,4-dihydrophthalazin-1(2H)-one | 224 |
| 7-amino-2-(2,2-difluoropropyl)isoindolin-1-one | 227 | N-(7-amino-1-oxoisoindolin-2-yl)-2-hydroxyacetamide | 222 |
| 7-amino-2-(2-fluoro-2-methylpropyl)isoindolin-1-one | 223 | | |

Method 3
Ethyl (4-amino-3-oxo-1,3-dihydro-isobenzofuran-1-yl)-acetate

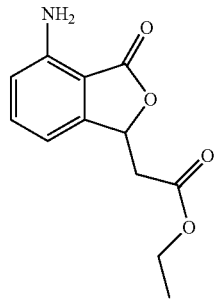

a) ethyl (4-amino-3-oxo-3H-isobenzofuran-1-ylidene)-acetate 500 mg (3.1 mmol) 4-amino-isobenzofuran-1,3-dione and 1.13 g (3.1 mmol) (ethoxy-carbonylmethylene)-triphenylphosphorane are dissolved in 5 ml of tetrahydrofuran (THF) and refluxed for 3 h. Then the solvent is eliminated in vacuo. The crude product is purified by column chromatography. The carrier used is silica gel and the eluant used is a mixture of cyclohexane:ethyl acetate (75:25).

Yield: 221 mg (0.95 mmol, 31%) MS-ESI+: m/z=234 [M+H]$^+$ b) ethyl (4-amino-3-oxo-1,3-dihydro-isobenzofuran-1-yl)-acetate 120 mg (0.51 mmol) ethyl (4-amino-3-oxo-3H-isobenzofuran-1-ylidene)-acetate are dissolved in 50 ml of methanol and combined with 50 mg palladium on activated charcoal (10% Pd). The reaction mixture is hydrogenated for 3 h at 2 bar H$_2$ pressure and 25° C. Then the catalyst is filtered off and the solvent is eliminated in vacuo.

Yield: 116 mg (0.49 mmol, 97%) MS (ESI): m/z=236 (M+H)$^+$ $^1$H-NMR: 1.17 (t, 3H), 2.68-2.78 (m, 1H), 3.08-3.16 (m, 1H), 4.10 (q, 2H), 5.67-5.74 (m, 1H), 6.28 (bs, 2H), 6.61-6.70 (m, 2H), 7.30-7.38 (m, 1H)

Method 4
5-amino-3H-quinazolin-4-one

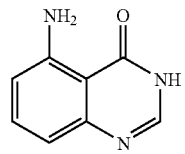

a) 2,6-diaminobenzamide 5 g (25.373 mmol) 2,6-dinitro-benzonitrile is combined with 20 ml of an aqueous 80% sulphuric acid and stirred for 2 h at 80° C. The reaction mixture is combined with 100 ml of tetrahydrofuran and neutralised with 10% aqueous sodium hydroxide solution. The organic phase is separated off, combined with another 100 ml of tetrahydrofuran and 200 mg palladium on charcoal and stirred for 20 h at 8 bar H$_2$ pressure and 25° C. The solids are filtered off. The filtrate is combined with 300 ml of ethyl acetate and extracted with saturated potassium hydrogen carbonate solution. The organic phase is separated off, dried and the solvent is eliminated in vacuo. The residue is purified by chromatography. The carrier used is silica gel and the eluant used is dichloromethane, to which 7% of a mixture of 90% methanol and 10% saturated aqueous ammonia solution are added.

Yield: 900 mg (5.958 mmol; 23%) MS (ESI): 152 (M+H)+ b) 5-amino-3H-quinazolin-4-one 900 mg (5.958 mmol) 2,6-diaminobenzamide are dissolved in 3.6 ml N,N-dimethylacetamide and combined with 6.3 ml (57.01 mmol) trimethylorthoformate and 792 µl (8.865 mmol) 98% sulphuric acid. After 16 h at 25° C. the reaction mixture is taken up with 20 ml of methanol and the solvent is eliminated in vacuo. The residue is again taken up in 20 ml of methanol, neutralised with concentrated ammonia. The solvent is eliminated in vacuo and the residue purified by chromatography. The carrier used is silica gel and the eluant used is dichloromethane, to which 7% of a mixture of 90% methanol and 10% saturated aqueous ammonia solution are added.

Yield: 782 mg (4.852 mmol; 81%) MS (ESI): 162 (M+H)$^+$

Method 5
9-amino-2,3,4,5-tetrahydro-2-benzazepin-1-one

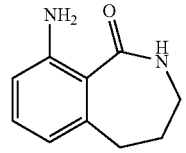

500 mg (1.825 mmol) 2-bromomethyl-6-nitro-methylbenzoate are heated to 100° C. in 2 ml trimethyl phosphate for 5 h. 2-(dimethylphosphonomethyl)-6-nitromethylbenzoate is obtained by evaporation under a high vacuum and used further directly. The crude product is dissolved in 24 ml of tetrahydrofuran at −70° C. under N$_2$, 2.7 ml (2.7 mmol) of a 1 M lithium hexamethyldisilazide solution in tetrahydrofuran is added dropwise and then 430 mg (2.70 mmol) tert.-butyl-N-(2-oxoethyl)-carbamate in 5 ml of tetrahydrofuran are added. The reaction mixture is slowly heated to ambient temperature, combined with 5 ml of 1 M HCl and extracted with ethyl acetate. The combined organic phases are concentrated by evaporation and, by chromatography on silica gel with a mixture of cyclohexane-ethyl acetate in the ratio 95:5 to 75:25, 338 mg (1.006 mmol, 55%) of the E-/Z mixture of 2-(3-tert.-butoxycarbonylamino-prop-1-en-1-yl)-6-nitro-methylbenzoate are obtained. This E-/Z-mixture is treated for 12 h with 10 ml of a saturated methanolic potassium hydroxide solution. After acidification with aqueous 1 M HCl and extraction with ethyl acetate 302 mg (0.938 mmol, 93%) of the E-/Z mixture of 2-(3-tert.-butoxycarbonylamino-prop-1-en-1-yl)-6-nitro-methylbenzoic acid are obtained. To this are added 20 mg Raney nickel in 100 ml of methanol and the mixture is hydrogenated at 5 bar H$_2$ pressure. The catalyst is filtered off, the filtrate concentrated by evaporation and stirred overnight with a 1:1 mixture of trifluoroacetic acid and dichloromethane at ambient temperature. After elimination of the solvent 133 mg (0.686 mmol, 73%) 2-amino-6-(3-amino-propyl)-benzoic acid are obtained. The further reaction is carried out by dissolving in 10 ml THF and 10 ml DCM with the addition of 300 mg (1.570 mmol) N-(3-dimethylaminopropyl)-N-4-ethylcarbodiimide hydrochloride and 134 µl (0.830 mmol) N,N-diisopropyl-ethylamine and 48 h stirring at ambient temperature. The solvent is eliminated in vacuo and the crude product is purified by chromatography with C18-RP silica gel and an eluant mixture of acetonitrile and water in the ratio 5:95 to 95:5, to which 0.1% formic acid has been added.

Yield: 28 mg (0.160 mmol, 23%) MS (ESI): m/z=177 (M+H)+

Method 6

4-amino-1-methyl-1,2-dihydro-indazol-3-one

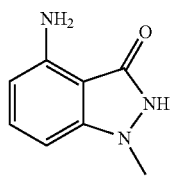

a) 4-nitro-1,2-dihydro-indazol-3-one 5 g (27.5 mmol) 2-amino-6-nitro-benzoic acid are combined with 22.2 ml (225.3 mmol) concentrated HCl and 45 ml (30.0 mmol) 5% aqueous sodium nitrite solution and stirred for 1 h at ambient temperature. Then the suspension is diluted with 150 ml dist. H₂O and added dropwise to 350 ml destilliertes water which has been saturated with sulphur dioxide. Sulphur dioxide is piped through the reaction mixture for a further 30 min. Then the reaction mixture is refluxed for 30 min and then left to cool slowly to 20° C. The resulting precipitate is filtered off.

Yield: 1.7 g (9.5 mmol, 35%) MS (ESI): m/z=180 (M+H)+ b) 1-methyl-4-nitro-1,2-dihydro-indazol-3-one 306 mg (1.7 mmol) 4-nitro-1,2-dihydro-indazol-3-one are dissolved in 1 ml N,N-dimethyl-acetamide, combined with 150 µl (2.4 mmol) methyl iodide and 500 µl (2.32 mmol) of N-ethyldiisopropylamide and stirred for 2 h at ambient temperature. Then the reaction mixture is combined with 40 ml of a 1 N aqueous hydrochloric acid and extracted twice with 50 ml dichloromethane. Then the organic phase is dried with MgSO₄, the solvent is eliminated in vacuo and the crude product is purified by chromatography. The carrier used is C18-RP-silica gel and a gradient is run through which consists of 95% water and 5% acetonitrile at the starting point and 5% water and 95% acetonitrile at the finishing point.

Yield: 144 mg (0.7 mmol, 44%) MS (ESI): m/z=194 (M+H)+ ¹H-NMR: 3.90 (s, 3H), 7.47-7.52 (m, 1H), 7.68-7.73 (m, 1H), 7.88-7.93 (m, 1H), 10.53 (s, 1H)

c) 4-amino-1-methyl-1,2-dihydro-indazol-3-one 140 mg (0.7 mmol) 1-methyl-4-nitro-1,2-dihydro-indazol-3-one are suspended in 6 ml of ethanol and combined with 600 mg (4.4 eq, 2.9 mmol) sodium dithionite, dissolved in 2 ml distilled water, and stirred for 15 min at 25° C. Then the reaction mixture is combined with distilled water and extracted twice with ethyl acetate. Then the organic phase is dried with MgSO₄ and the solvent is eliminated in vacuo.

Yield: 33 mg (0.2 mmol, 28%) MS (ESI): m/z=164 (M+H)+

4-amino-1,2-dihydro-indazol-3-one and the following compounds are prepared analogously to this method.

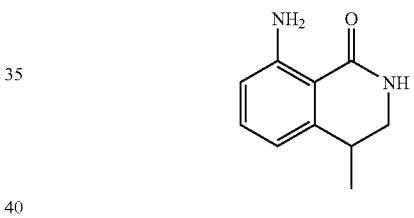

| | MS (ESI) (M+H)+ | | MS (ESI) (M+H)+ |
|---|---|---|---|
| | 178 | | 178 |
| | 194 | | |

Method 7

8-amino-4-methyl-3,4-dihydro-2H-isoquinolin-1-one a) methyl 2-(cyanomethyl-2-methyl)-6-nitro-benzoate 400 mg (1.8 mmol) methyl 2-cyanomethyl-6-nitro-benzoate are dissolved in 13 ml THF, combined with 114 µl (1.8 mmol) methyl iodide and the mixture is cooled to −20° C. under a nitrogen atmosphere. Then at this temperature 250 mg (2.2 mmol) potassium-tert-butoxide are added. After 1 h the solvent is eliminated in vacuo and the crude product is purified by chromatography. The carrier used is C18-RP-silica gel and a gradient is run through which consists of 95% water and 5% acetonitrile at the starting point and 5% water and 95% acetonitrile at the finishing point.

Yield: 289 mg (1.2 mmol, 68%) MS (ESI): 233 (M−H)− b) 8-amino-4-methyl-3,4-dihydro-2H-isoquinolin-1-one 400 mg (1.8 mmol) methyl 2-(cyanomethyl-2-methyl)-6-nitro-benzoate are dissolved in 13 ml of methanol and combined with 50 mg Raney nickel. The reaction mixture is hydrogenated for 16 h at 4 bar H₂ pressure and 25° C. Then the catalyst is filtered off and the solvent is eliminated in vacuo.

Yield: 170 mg (0.8 mmol, 46%) MS (ESI): 177 (M+H)+

8-amino-3,4-dihydro-2H-isoquinolin-1-one and 8-amino-4,4-dimethyl-3,4-dihydro-2H-isoquinolin-1-one and the following compounds are prepared analogously to this method.

| Structure | MS (ESI) (M+H)+ | Structure | MS (ESI) (M+H)+ |
|---|---|---|---|
| (8-amino-4-(3-hydroxypropyl)-3,4-dihydro-2H-isoquinolin-1-one) | 221 | (8-amino-4-isopropyl-3,4-dihydro-2H-isoquinolin-1-one) | 205 |
| (8-amino-4-benzyl-3,4-dihydro-2H-isoquinolin-1-one) | 253 | | |

Method 8
7-amino-indan-1-one

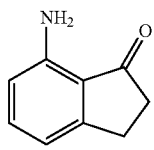

a) indan-4-ylamine 24 ml (349 mmol) 65% nitric acid are cooled to 0-5° C. 28 ml (518.5 mmol) of concentrated sulphuric acid are slowly added dropwise while cooling with ice. This solution is cooled to 5° C. and slowly added dropwise to 30 ml (232 mmol) indane cooled to 0-5° C., with vigorous stirring and further cooling with ice. The reaction mixture is stirred for 30 min at 0-5° C., and then heated to 25° C. for 1 h with stirring. Then the solution is added dropwise to 150 ml ice/water and stirred for 30 min. The aqueous phase is extracted three times with 200 ml diethyl ether. The combined organic phases are washed twice with 200 ml saturated sodium hydrogen carbonate solution and once with 150 ml distilled water. Then the organic phase is dried with MgSO$_4$ and the solvent is eliminated in vacuo. The crude product is dissolved in 250 ml of methanol and combined with 4.5 g Raney nickel. The reaction mixture is hydrogenated for 16 h at 3 bar H$_2$ pressure and 25° C. Then the catalyst is filtered off and the solvent is eliminated in vacuo. The crude product is purified by column chromatography. The carrier used is silica gel and the eluant used is a mixture of cyclohexane:ethyl acetate (75:25).

Yield: 3.81 g (28.6 mmol, 12%) MS (ESI): 134 (M+H)+
1H-NMR: 1.90-2.00 (m, 2H), 2.61 (t, 2H), 2.76 (t, 2H), 4.73 (s, 2H), 6.33-6.38 (m, 1H), 6.39-6.45 (m, 1H), 6.76-6.83 (m, 1H)

b) N-indan-4-yl-acetamide 226 mg (1.7 mmol) indan-4-ylamine are combined with 5 ml acetic anhydride. The suspension is stirred for 16 h at 70° C. The resulting solution is stirred into 40 ml distilled water, adjusted to pH 7 with sodium carbonate and extracted three times with 30 ml of ethyl acetate. Then the organic phase is dried with MgSO$_4$, the solvent is eliminated in vacuo and the crude product is purified by chromatography. The carrier used is silica gel and the eluant used is a mixture of cyclohexane:ethyl acetate (70:30).

Yield: 152 mg (0.9 mmol, 51%) MS (ESI): 176 (M+H)+
1H-NMR: 1.93-2.03 (m, 2H), 2.04 (s, 3H), 2.79 (t, 2H), 2.86 (t, 2H), 6.94-7.01 (m, 1H), 7.02-7.10 (m, 1H), 7.36-7.44 (m, 1H), 9.25 (s, 1H)

c) N-(3-oxo-indan-4-yl)-acetamide 147 mg (0.84 mmol) N-indan-4-yl-acetamide are dissolved in 10 ml acetone and combined with 770 µl of a 15% aqueous magnesium sulphate solution. The solution is cooled to 0° C. and 397 mg (2.490 mmol) potassium permanganate are added batchwise. After 2 h the mixture is diluted with 50 ml of water, and extracted three times with 20 ml chloroform. The organic phase is dried with magnesium sulphate and the solvent is eliminated in vacuo and the crude product is purified by chromatography. The carrier used is silica gel and the eluant used is a mixture of cyclohexane:ethyl acetate (85:15).

Yield: 95 mg (0.500 mmol, 60%) MS (ESI): 190 (M+H)+ d) 7-amino-indan-1-on 500 mg (2.6 mmol) N-(3-oxo-indan-4-yl)-acetamide are dissolved in 5 ml of ethanol, combined with 5 ml 18% hydrochloric acid and stirred for 3 h at 70° C. Then the reaction mixture is stirred into 100 ml distilled water, adjusted to pH 7 with sodium carbonate and extracted three times with 30 ml of ethyl acetate. Then the organic phase is dried with magnesium sulphate and the solvent is eliminated in vacuo.

Yield: 388 mg (2.6 mmol, 100%)

8-amino-3,4-dihydro-2H-naphthalen-1-one is prepared analogously to this method. 1,2,3,4-tetrahydronaphthalene is used as starting material instead of indane.

Method 9
N-(7-amino-1-oxo-1,3-dihydro-isoindol-2-yl)-acetamide

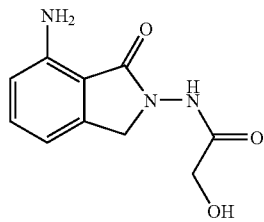

a) 2-benzyloxy-N-(7-nitro-1-oxo-1,3-dihydro-isoindol-2-yl)-acetamide 870 mg (4.5 mmol) 2-amino-7-nitro-2,3-dihydro-isoindol-1-one (prepared analogously to method 2) are dissolved in 82 ml dichloromethane and 64 ml THF. The solution is combined with 2.8 ml (3.3 eq, 20 mmol) benzyloxyacetyl chloride, 4.8 ml (28.0 mmol) N-ethyldiisopropyl-amine and 10 mg N,N-dimethylaminopyridine and stirred for 3 h at 25° C. Then the reaction mixture is combined with 100 ml aqueous 0.1 N hydrochloric acid and extracted three times with 50 ml of ethyl acetate. The organic phase is dried with magnesium sulphate, the solvent is eliminated in vacuo and the crude product is purified by chromatography. The carrier used is silica gel and the eluant used is a mixture of dichloromethane:methanol (95:5).

Yield: 910 mg (2.7 mmol, 59%)

b) N-(7-amino-1-oxo-1,3-dihydro-isoindol-2-yl)-acetamide 790 mg (2.3 mmol) 2-benzyloxy-N-(7-nitro-1-oxo-1,3-dihydro-isoindol-2-yl)-acetamide are dissolved in 100 ml of methanol and combined with 80 mg palladium hydroxide. The reaction mixture is hydrogenated for 48 h at 4 bar $H_2$ pressure and 25° C. Then the catalyst is filtered off and the solvent is eliminated in vacuo. The crude product is purified by chromatography. The carrier used is silica gel and the eluant used is a mixture of dichloromethane:methanol (90:10).

Yield: 210 mg (0.1 mmol, 41%) MS (ESI): 222 (M+H)$^+$

Method 10

6-amino-2-ethyl-3,4-dihydro-2H-benzo[f][1,4]oxazepin-5-one

a) 2-amino-6-(1-aminomethyl-propoxy)-benzonitrile 2.01 g (22 mmol) 1-amino-2-butanol are dissolved in 6.5 ml 1,4-dioxane, combined with 880 mg (7.8 mmol) sodium hydride and stirred for 30 min at ambient temperature. 2 g (14.7 mmol) of 2-amino-6-fluorobenzonitrile are added to this reaction mixture and it is stirred for 24 h at 50° C. Then the solvent is eliminated in vacuo and the crude product is purified by chromatography. The carrier used is silica gel and the eluant used is dichloromethane, to which 5% of a mixture of 90% methanol and 10% saturated aqueous ammonia solution has been added.

Yield: 1.15 g (5.6 mmol, 38%) MS (ESI): 206 (M+H)$^+$ b) 2-amino-6-(1-aminomethyl-propoxy)-benzoic acid 1.15 g (5.6 mmol) 2-amino-6-(1-aminomethyl-propoxy)-benzonitrile are dissolved in 10 ml 20% ethanolic KOH and stirred for 24 h at 80° C. Then the solvent is eliminated in vacuo and the crude product is purified by chromatography. The carrier used is silica gel and the eluant used is dichloromethane, to which 12% of a mixture of 90% methanol and 10% saturated aqueous ammonia solution have been added.

Yield: 262 mg (1.2 mmol, 21%) MS (ESI): 225 (M+H)$^+$ c) 6-amino-2-ethyl-3,4-dihydro-2H-benzo[f][1,4]oxazepin-5-one 262 mg (1.2 mmol) 2-amino-6-(1-aminomethyl-propoxy)-benzoic acid are dissolved in 26 ml THF, combined with 680 mg (3.5 mmol) 1-(3-dimethyl-aminopropyl)-3-ethylcarbodiimide hydrochloride and 0.6 ml (3.5 mmol) diisopropyl-ethylamine and stirred for 3 h at 50° C. Then the solvent is eliminated in vacuo and the crude product is purified by chromatography. The carrier used is silica gel and the eluant used is dichloromethane, to which 4% of a mixture of 90% methanol and 10% saturated aqueous ammonia solution have been added.

Yield: 50 mg (0.2 mmol, 21%) MS (ESI): 207 (M+H)$^+$

The following compounds are prepared analogously to this method. 1-amino-2-butanol was replaced by a corresponding aminoalcohol or by a corresponding 1,2-diaminoethylene.

| Structure | MS (ESI) (M + H)$^+$ | Structure | MS (ESI) (M + H)$^+$ |
|---|---|---|---|
| | 207 | | 251 |
| | 193 | | 179 |
| | 235 | | 221 |

|  | MS (ESI) (M + H)+ |  | MS (ESI) (M + H)+ |
|---|---|---|---|
| [structure] | 219 | [structure] | 206 |
| [structure] | 233 | [structure] | 235 |
| [structure] | 207 | [structure] | 227 |
| [structure] | 207 | [structure] | 219 |
| [structure] | 193 | [structure] | 207 |
| [structure] | 221 | [structure] | 269 |
| [structure] | 299 | [structure] | 225 |

| | MS (ESI) (M + H)⁺ | | MS (ESI) (M + H)⁺ |
|---|---|---|---|
| structure | 219 | structure | 253 |
| structure | 209 | structure | 241 |
| structure | 269 | structure | 233 |

Method 11
6-amino-3-benzyl-3,4-dihydro-1H-benzo[e][1,4]diazepine-2,5-dione

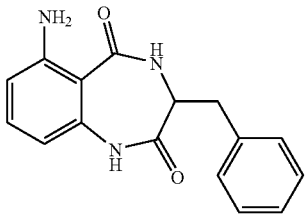

a) methyl 2-(2-amino-6-nitro-benzoylamino)-3-phenyl-propionate 1.18 g (6.5 mmol) 2-amino-6-nitrobenzoic acid, 1.0 g (4.6 mmol) D,L-phenylalanine-methylester hydrochloride, 4.05 ml (23.2 mmol) N-ethyldiisopropylamine are combined with 2.5 ml of tetrahydrofuran. 1.71 g (5.1 mmol) O-(benzotriazol-1-yl)-N,N,N',N'-tetramethyluronium-tetrafluoroborate are added to this reaction mixture and it is heated for 12 h to 50° C. Then the solvent is eliminated in vacuo and the crude product is purified by chromatography. The carrier used is silica gel and the eluant used is a mixture of cyclohexane:ethyl acetate (50:50).

Yield: 1.04 g (3.03 mmol, 65%) MS (ESI): 344 (M+H)⁺ b) 2-(2-amino-6-nitro-benzoylamino)-3-phenyl-propionic acid 1.04 g (3.03 mmol) methyl 2-(2-amino-6-nitro-benzoylamino)-3-phenyl-propionate are dissolved in 3 ml 20% ethanolic KOH and stirred for 1.5 h at 50° C. Then the solvent is eliminated in vacuo and the crude product is purified by chromatography. The carrier used is silica gel and the eluant used is dichloromethane, to which 15% of a mixture of 90% methanol and 10% saturated aqueous ammonia solution has been added.

Yield: 636 mg (1.9 mmol, 64%)

MS(ESI): 329 (M+H)⁺ ¹H-NMR: 2.86-2.94 (m, 1H), 3.17 (s, 1H), 3.22-3.29 (m, 1H), 4.30-4.38 (m, 1H), 6.63 (s, 2H), 6.89-6.96 (m, 1H), 6.97-7.02 (m, 1H), 7.12-7.21 (m, 2H), 7.21-7.27 (m, 2H), 7.28-7.35 (m, 2H), 8.33-8.43 (m, 1H)

c) 2-(2,6-diamino-benzoylamino)-3-phenyl-propionic acid 410 mg (1.25 mmol) 2-(2-amino-6-nitro-benzoylamino)-3-phenyl-propionic acid are dissolved in 50 ml of methanol and combined with 40 mg palladium on charcoal (10% Pd). The reaction mixture is hydrogenated for 9 h at 5 bar H₂ pressure and 25° C. Then the catalyst is filtered off, the solvent is eliminated in vacuo and the crude product is purified by chromatography. The carrier used is C18-RP-silica gel and a gradient is run through which consists of 95% water and 5% acetonitrile at the starting point and consists of 5% water and 95% acetonitrile at the finishing point.

Yield: 88 mg (0.29 mmol, 24%) MS (ESI): 300 (M+H)⁺ d) 6-amino-3-benzyl-3,4-dihydro-1H-benzo[e][1,4]diazepine-2,5-dione 88 mg (0.3 mmol) 2-(2,6-diamino-benzoylamino)-3-phenyl-propionic acid are dissolved in 2 ml THF, combined with 143 mg (0.9 mmol) 1-(3-dimethyl-aminopropyl)-3-ethylcarbodiimide hydrochloride and 103 µl (0.6 mmol) diisopropylethylamine and stirred for 17 h at 50° C. Then the solvent is eliminated in vacuo and the crude product is purified by chromatography. The carrier used is silica gel and the eluant used is dichloromethane, to which 5% of a mixture of 90% methanol and 10% saturated aqueous ammonia solution have been added.

Yield: 22 mg (0.08 mmol, 27%) MS (ESI): 282 (M+H)⁺

The following compounds are prepared analogously to method 11.

| | MS (ESI) (M + H)+ | | MS (ESI) (M + H)+ |
|---|---|---|---|
| 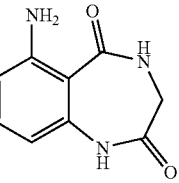 | 192 | 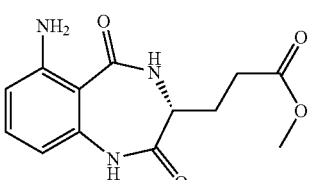 | 268 |
| 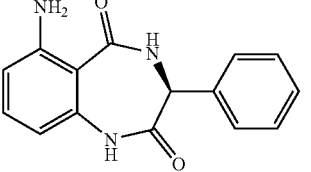 | 206 | 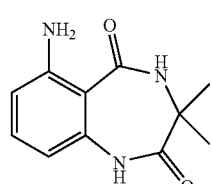 | 277 |
| 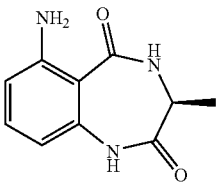 | 206 | 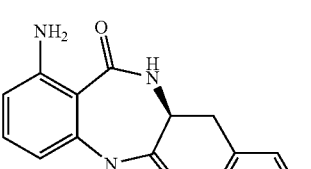 | 278 |
| 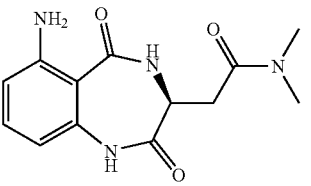 | 218 | 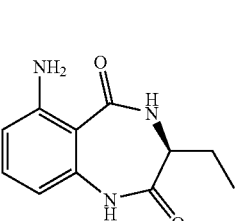 | 278 |
| 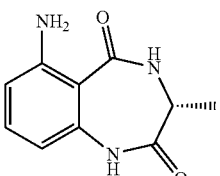 | 220 | 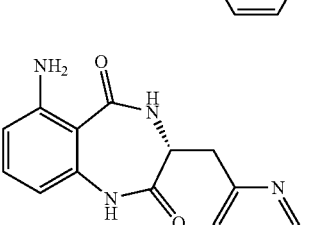 | 282 |
| 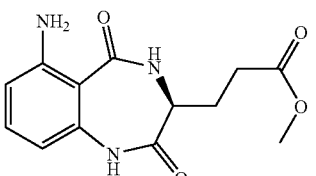 | 220 | 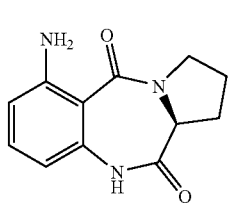 | 283 |
| 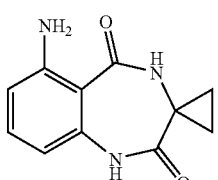 | 232 | 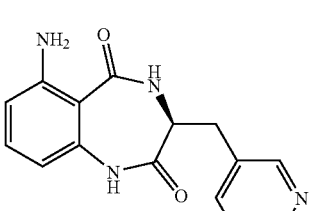 | 283 |

-continued
| | MS (ESI) (M + H)+ | | MS (ESI) (M + H)+ |
|---|---|---|---|
| 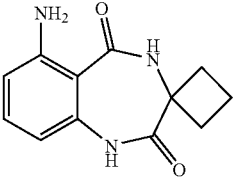 | 232 | 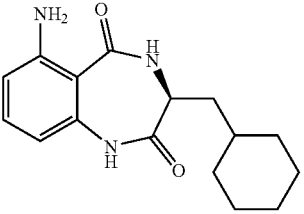 | 288 |
| 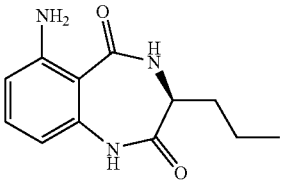 | 234 | 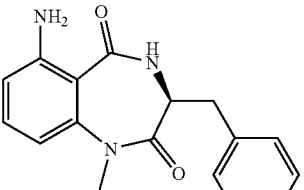 | 296 |
| 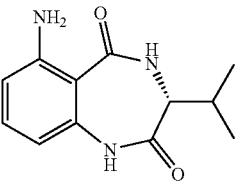 | 234 | 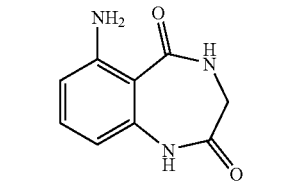 | 192 |
| 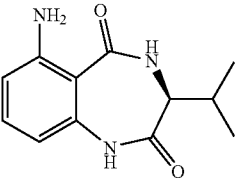 | 234 | 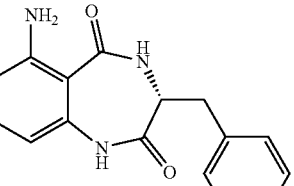 | 298 |
| 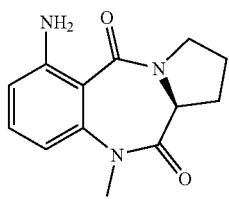 | 246 | 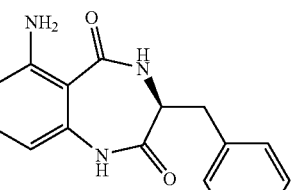 | 298 |
| 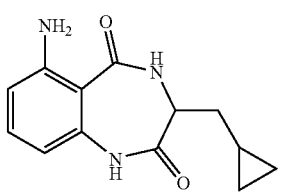 | 246 | 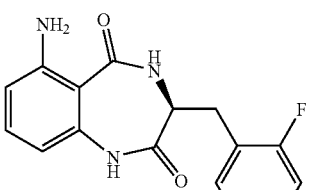 | 300 |

-continued

| Structure | MS (ESI) (M + H)+ | Structure | MS (ESI) (M + H)+ |
|---|---|---|---|
| | 246 | | 300 |
| | 248 | | 300 |
| | 248 | | 307 |
| | 248 | | 316/318 |
| | 250 | | 321 |
| | 265 | | 321 |

| MS (ESI) (M + H)+ | MS (ESI) (M + H)+ |
|---|---|
| 265 | 346 |

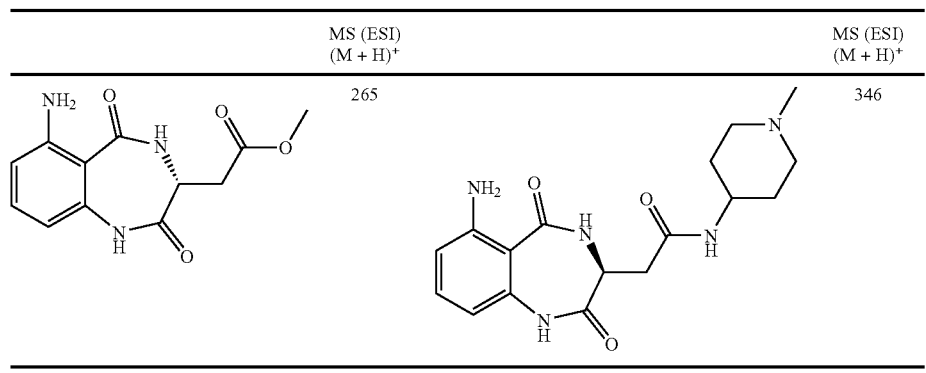

Method 12

2-(4-carboxy-2-methoxy-phenylamino)-4-chloro-5-trifluoromethyl-pyrimidine

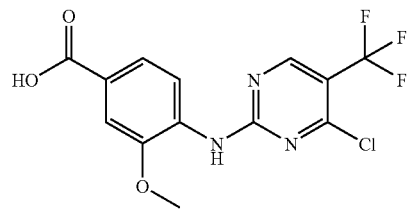

7.36 g (44 mmol) 4-amino-3-methoxybenzoic acid are suspended in 80 ml of an aqueous phosphate buffer solution (pH 6.3) and combined with 9.5 g (44 mmol) 2,4-dichloro-5-trifluoro-methyl-pyrimidine, which is dissolved in 240 ml 1,4-dioxane. After 4 h at 100° C. the reaction mixture is crystallised at 0° C. The precipitate is filtered off, the filtrate is combined with 150 ml of ethyl acetate and washed twice with 200 ml of a saturated aqueous sodium hydrogen carbonate solution. The organic phase is dried with $MgSO_4$ and the solvent is eliminated in vacuo. The crude product is suspended in 10 ml n-hexane and refluxed. The precipitate is filtered off, suspended in 48 ml of a saturated aqueous sodium hydrogen carbonate solution and heated to 65° C. for 1 h. Then the solution is crystallised at 0° C. The precipitate is filtered off, the filtrate is acidified with 1 N aqueous hydrochloric acid and combined with 100 ml of ethyl acetate. The organic phase is separated off, dried with magnesium sulphate and the solvent is eliminated in vacuo. The residue is recrystallised from ethyl acetate.

Yield: 330 mg (0.95 mmol, 2%) MS (ESI): 348 (M+H)+
1H-NMR: 1.55 (s, 1H), 4.01 (s, 3H), 7.61-7.64 (m, 1H), 7.79-7.85 (m, 1H), 8.34 (s, 1H), 8.59-8.63 (m, 1H), 8.66 (s, 1H)

Method 13

4-(4-amino-cyclohexyl)-morpholine

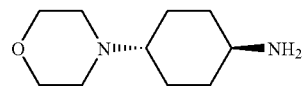

a) dibenzyl-(4-morpholino-4-yl-cyclohexyl)-amine 3.9 g (30 mmol) 4-dibenzylamino-cyclohexanone are dissolved in 100 ml dichloromethane and stirred with 3.9 g (45 mmol) morpholine and 9.5 g (45 mmol) sodium triacetoxyborohydride for 12 h at ambient temperature. Then water and potassium carbonate are added, the organic phase is separated off, dried and the solvent is eliminated in vacuo. The crude product is purified by column chromatography. The carrier used is silica gel and the eluant used is ethyl acetate, to which 10% of a mixture of 90% methanol and 10% saturated aqueous ammonia solution have been added. The suitable fractions are evaporated down in vacuo.

Yield: 6.6 g (18 mmol, 60%) cis-isomer 2 g (5.4 mmol, 18%) trans-isomer.

b) trans-4-morpholino-4-yl-cyclohexylamine 7.2 g (16.4 mmol) trans-dibenzyl-4-morpholino-cyclohexylamine are dissolved in 100 ml of methanol and hydrogenated on 1.4 g palladium on charcoal (10% Pd) at 30-50° C. The solvent is eliminated in vacuo and the residue is crystallised from ethanol and concentrated hydrochloric acid.

Yield: 3.9 g (15.2 mmol, 93%)

melting point: 312° C.

The following compounds are prepared analogously to Method 13:

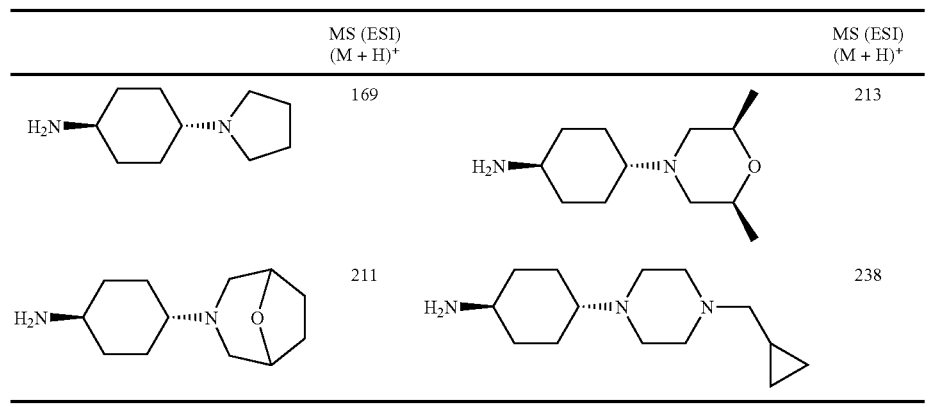

Method 14
2-(4-carboxy-2-methoxy-phenylamino)-4-chloro-5-trifluoromethyl-pyrimidine

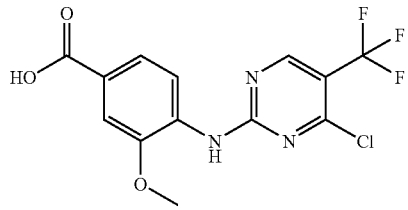

a) 2-(4-benzyloxycarbonyl-2-methoxy-phenylamino)-4-chloro-5-trifluoromethyl-pyrimidine 2 g (9.217 mmol) 2,4-dichloro-5-trifluoromethylpyrimidine are dissolved in 4 ml dioxane and combined with 6.01 g (18.430 mmol) caesium carbonate and 2.16 g (7.363 mmol) benzyl 4-amino-3-methoxybenzoate (WO 9825901). This suspension is stirred for 30 h at 100° C. The suspension is combined with 50 ml dichloromethane and methanol and filtered to remove the insoluble constituents. The solvent is eliminated in vacuo and the residue is purified by column chromatography. The carrier used is silica gel and the eluant used is a mixture of 85% cyclohexane and 15% ethyl acetate.

Yield: 1.03 g (2.360 mmol; 26%) UV max: 320 nm MS (ESI): 438/440 (M+H)$^+$Cl distribution 436/438 (M−H)$^-$Cl distribution b) 2-(4-carboxy-2-methoxy-phenylamino)-4-chloro-5-trifluoromethyl-pyrimidine 1 g (2.284 mmol) 2-(4-benzyloxycarbonyl-2-methoxy-phenylamino)-4-chloro-5-trifluoromethyl-pyrimidine are dissolved in 50 ml THF and combined with 100 mg palladium hydroxide. The reaction mixture is stirred for 16 h at ambient temperature and 4 bar hydrogen pressure. Then the catalyst is filtered off and the solvent is eliminated in vacuo.

Yield: 0.76 g (2.192 mmol; 96%) UV max: 288 nm MS (ESI): 346/348 (M−H)$^-$Cl distribution The following compounds are prepared analogously to this process:

2-(4-carboxy-phenylamino)-4-chloro-5-trifluoromethyl-pyrimidine
MS (ESI): 316/318 (M−H)$^-$Cl distribution 2-[4-(4-benzyloxycarbonyl-piperazin-1-yl)-phenylamino]-4-chloro-5-trifluoromethyl-pyrimidine
MS (ESI): 492/494 (M+H)$^+$Cl distribution 2-[4-(4-benzyloxycarbonyl-piperazin-1-yl)-2-methoxy-phenylamino]-4-chloro-5-trifluoromethyl-pyrimidine
MS (ESI): 522/524, (M+H)$^+$Cl distribution Method 15
3-pyrrolidin-1-yl-cyclobutylamine

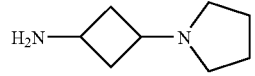

a) tert.butyl (3-benzyloxy-cyclobutyl)-carbamate 9.28 g (45 mmol) 3-benzyloxy-cyclobutancarboxylic acid (Org. Lett. 6(11), 1853-1856, 2004) are suspended in 80 ml dry tert-butanol and combined with 5.1 g (50 mmol) triethylamine and 13.8 g (50 mmol) phosphoric acid diphenylester azide. The reaction mixture is stirred for 20 h under reflux conditions. The solvent is eliminated in vacuo and the residue is taken up in dichloromethane. The organic phase is washed three times with 2 N sodium hydroxide solution, dried with sodium sulphate and the dichloromethane is eliminated in vacuo. The crude product is recrystallised from acetonitrile (1 g crude product: 5 ml acetonitrile).

Yield: 5.98 g (22 mmol; 48%) MS (ESI): 178 (M+H−boc)$^+$
Boc cleaving in the mass detector b) tert.butyl (3-hydroxy-cyclobutyl)-carbamate 2.77 g (10 mmol) tert.butyl (3-benzyloxy-cyclobutyl)-carbamate are suspended in 100 ml of methanol and combined with 200 mg palladium hydroxide. The reaction mixture is stirred for 5 h at 45° C. and 45 bar H$_2$ pressure. Then the catalyst is filtered off and the solvent is eliminated in vacuo. The residue is taken up in chloroform and washed three times with aqueous sodium hydrogen carbonate solution. The organic phase is dried with magnesium sulphate and the solvent is eliminated in vacuo.

Yield: 1.53 g (8.2 mmol; 82%) MS (ESI): 188 (M+H)$^+$ c) tert.butyl (3-tosyl-cyclobutyl)-carbamate 18.7 g (100 mmol) tert.butyl (3-hydroxy-cyclobutyl)-carbamate and 12.1 g (120 mmol) triethylamine are placed in 500 ml chloroform. 20.5 g (105 mmol) tosyl chloride, dissolved in 150 ml chloroform, is added dropwise to this solution at 0° C. with stirring. Then the mixture is left to come up to ambient temperature and stirred for 2 h. The organic phase is washed successively with water, dilute hydrochloric acid, sodium hydrogen carbonate solution and water. The organic phase is dried with magnesium sulphate and the solvent is eliminated in vacuo.

Yield: 28.30 g (83 mmol; 83%) MS (ESI): 342 (M+H)$^+$ d) tert.butyl (3-pyrrolidine-cyclobutyl)-carbamate 34.1 g (100 mmol) tert.butyl (3-tosyl-cyclobutyl)-carbamate are dissolved in 750 ml pyrrolidine, and combined with a catalytic amount of DMAP. The reaction mixture is refluxed for 20 h with stirring. The pyrrolidine is eliminated in vacuo, the residue is taken up in 500 ml of ethyl acetate and washed twice with saturated sodium hydrogen carbonate solution. The organic phase is dried with magnesium sulphate and the solvent is eliminated in vacuo. The crude product consists—as in all the analogous reactions—of a mixture of 2 isomeric compounds which are separated by column chromatography. The stationary phase used is silica gel and the eluant used is dichloromethane, to which 9% of a mixture of 90% methanol and 10% saturated aqueous ammonia solution have been added.

The substances that elute first are designated as follows:

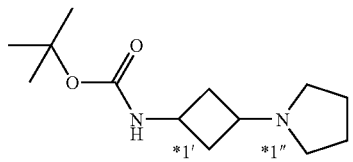

Yield product A: 1 g (4.17 mmol; 4%)
RF value (silica gel; dichloromethane:methanol:conc. aqueous ammonia=90:9:1)=0.62

The substances that elute second are designated as follows:

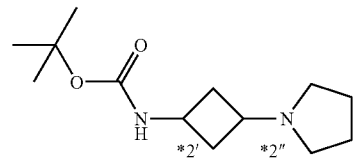

Yield product C: 2.00 g (8.33 mmol; 8%)
RF value (silica gel; dichloromethane:methanol:conc. aqueous ammonia=90:9:1)=0.53 e) (*1',*1")-3-pyrrolidin-1-yl-cyclobutylamine

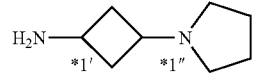

1 g (4.17 mmol) tert.butyl (3-pyrrolidine-cyclobutyl)-carbamate (product A from precursor) are stirred in 20 ml of a 2 N aqueous hydrochloric acid solution for 2 h at 40° C. Then the solvent is eliminated in vacuo and the residue is recrystallised from ethanol.

Yield: 0.43 g (2.786 mmol; 67%) MS (ESI): 141 (M+H)$^+$

The following compounds are prepared analogously to this process:

| | MS (ESI) (M + H)$^+$ | | MS (ESI) (M + H)$^+$ |
|---|---|---|---|
| H$_2$N–⬧–N(piperazine)N–CH$_3$ | 170 | H$_2$N–⬧–N(CH$_3$)(iPr) | 143 |
| H$_2$N–⬧–N(piperazine)N–CH$_2$-cyclopropyl | 210 | H$_2$N–⬧–N(N-methylpiperidinyl) | 198 |
| H$_2$N–⬧–N(homopiperazine)N–CH$_3$ | 184 | H$_2$N–⬧–N(piperazine)N–CH$_2$CH=CH$_2$ | 196 |
| H$_2$N–⬧–N(piperidinyl)–pyrrolidine | 224 | H$_2$N–⬧–N(piperazine)N–CH$_2$C≡CH | 194 |

-continued

| Structure | MS (ESI) (M + H)+ | Structure | MS (ESI) (M + H)+ |
|---|---|---|---|
| H₂N–[cyclobutyl]–N(piperidin-4-ol) *1' *1'' | 171 | H₂N–[cyclobutyl]–N(Me)(cyclohexyl) *1' *1'' | 183 |
| H₂N–[cyclobutyl]–N(Me)–CH₂–(1-methylpiperidin-4-yl) *1' *1'' | 212 | | |

(*2',*2'')-3-pyrrolidin-1-yl-cyclobutylamine

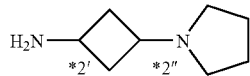

1 g (4.17 mmol) tert.butyl (3-pyrrolidine-cyclobutyl)-carbamate (product C from precursor) are stirred in 20 ml of a 2 N aqueous hydrochloric acid solution for 2 h at 40° C. Then the solvent is eliminated in vacuo and the residue is recrystallised from ethanol.

Yield: 0.43 g (3.09 mmol; 74%) MS (ESI): 141 (M+H)+

The following compounds are prepared analogously to this method:

| Structure | MS (ESI) (M + H)+ | Structure | MS (ESI) (M + H)+ |
|---|---|---|---|
| H₂N–[cyclobutyl]–N(piperidine) *2' *2'' | 155 | H₂N–[cyclobutyl]–N(Me)–CH₂–(1-methylpiperidin-4-yl) *2' *2'' | 212 |
| H₂N–[cyclobutyl]–N(morpholine) *2' *2'' | 157 | H₂N–[cyclobutyl]–N(Me)(iPr) *2' *2'' | 143 |
| H₂N–[cyclobutyl]–N(homomorpholine) *2' *2'' | 171 | H₂N–[cyclobutyl]–N(Me)(cyclopropyl) *2' *2'' | 141 |
| H₂N–[cyclobutyl]–N(N-methylhomopiperazine) *2' *2'' | 184 | H₂N–[cyclobutyl]–N(Me)(1-methylpiperidin-4-yl) *1' *1'' | 198 |
| H₂N–[cyclobutyl]–N(N-methylpiperazine) *2' *2'' | 170 | H₂N–[cyclobutyl]–N(piperazine-N-CH₂CH₂CF₃) *2' *2'' | 251 |

| Structure | MS (ESI) (M + H)+ | Structure | MS (ESI) (M + H)+ |
|---|---|---|---|
| H2N-[cyclobutyl]-N[piperazine]N-CH2-cyclopropyl  *2' *2" | 210 | H2N-[cyclobutyl]-N[piperazine]N-CH2-C≡CH  *2' *2" | 194 |
| H2N-[cyclobutyl]-N[piperazine]N-CH2CH2-pyrrolidinyl  *2' *2" | 253 | H2N-[cyclobutyl]-N[piperazine]N-CH2-CH=CH2  *2' *2" | 196 |
| H2N-[cyclobutyl]-N[piperidine]-N-pyrrolidinyl  *2' *2" | 224 | H2N-[cyclobutyl]-N[piperidine]-OH  *2' *2" | 171 |
| H2N-[cyclobutyl]-N(CH3)(cyclohexyl)  *2' *2" | 183 | | |

Method 16

2-(4-carboxy-2-bromo-phenylamino)-4-chloro-5-trifluoromethyl-pyrimidine

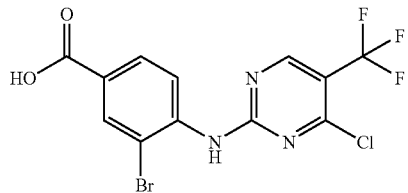

1 g (3.15 mmol) 2-(4-carboxy-phenylamino)-4-chloro-5-trifluoromethyl-pyrimidine are dissolved in 5 ml DMF and combined batchwise with 3.36 g (18.89 mmol) N-bromosuccinimide. The reaction mixture is stirred for 16 h at ambient temperature. The solvent is eliminated in vacuo and the residue is purified by column chromatography. The carrier used is C18-RP-silica gel and a gradient is ran through which consists of 95% water and 5% acetonitrile at the starting point and consists of 2% water and 98% acetonitrile at the finishing point. 0.1% formic acid is added in each case to both the water and to the acetonitrile.

Yield: 0.57 g (1.44 mmol; 46%) MS (ESI): 396/398 (M–H)+ Cl/Br distribution

Method 17

5-amino-3-(2-fluoro-ethyl)-3H-quinazolin-4-one

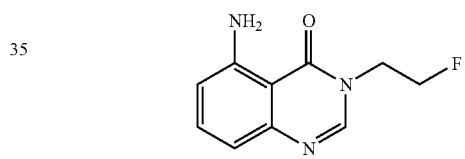

500 mg (3.102 mmol) 5-amino-3H-quinazolin-4-one are combined with 2 ml (15.596 mmol) 1-bromo-2-fluoroethane. 125 mg (3.125 mmol) sodium hydride are added thereto and the mixture is stirred for 5 days at ambient temperature. The reaction mixture is diluted with 100 ml of ethyl acetate and washed with 100 ml saturated aqueous sodium chloride solution. The aqueous phase is combined with 50 ml 1 N sodium hydroxide solution and extracted 5 times with ethyl acetate. The combined organic phases are dried and the solvent is eliminated in vacuo. The residue is purified by column chromatography. The carrier used is C18-RP-silica gel and a gradient is run through which consists of 95% water and 5% acetonitrile at the starting point and consists of 5% water and 95% acetonitrile at the finishing point. 0.1% formic acid is added in each case to both the water and to the acetonitrile.

Yield: 67 mg (0.323 mmol; 10%) MS (ESI): 208 (M+H)+

Method 18

8-amino-2-(2-fluoro-ethyl)-3,4-dihydro-2H-isoquinolin-1-one

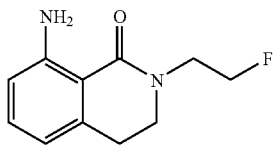

a) 8-dibenzylamino-3,4-dihydro-2H-isoquinolin-1-one 1.466 g (9.039 mmol) 8-amino-3,4-dihydro-2H-isoquinolin-1-one are dissolved in 15 ml DMF and combined with 3.226 g (23.340 mmol) potassium carbonate and with 3.808 ml (31.420 mmol) benzylbromide. This reaction mixture is stirred for 16 h at 50° C. The reaction mixture is diluted with ethyl acetate and extracted with sodium hydrogen carbonate solution. The organic phases are dried and the solvent is eliminated in vacuo.

Yield: 1.670 g (4.877 mmol; 54%) MS (ESI): 343 (M+H)$^+$ b) 8-dibenzylamino-2-(2-fluoro-ethyl)-3,4-dihydro-2H-isoquinolin-1-one 1.06 g (3.095 mmol) 8-dibenzylamino-3,4-dihydro-2H-isoquinolin-1-one are combined with 1.5 ml (12 mmol) 1-bromo-2-fluoro-ethane and at ambient temperature 780 mg (19.50 mmol) sodium hydride are added batchwise over a period of 30 h. The reaction mixture is diluted with ethyl acetate and extracted with sodium hydrogen carbonate solution. The organic phases are dried and the solvent is eliminated in vacuo. The crude product is purified by column chromatography. The carrier used is silica gel and the eluant used is dichloromethane, to which 5% of a mixture of 90% methanol and 10% saturated aqueous ammonia solution have been added.

Yield: 0.83 g (2.136 mmol; 69%) MS (ESI): 389 (M+H)$^+$ c) 8-amino-2-(2-fluoro-ethyl)-3,4-dihydro-2H-isoquinolin-1-one 830 mg (2.136 mmol) 8-dibenzylamino-2-(2-fluoro-ethyl)-3,4-dihydro-2H-isoquinolin-1-one are dissolved in 50 ml of methanol and combined with 80 mg palladium hydroxide. The reaction mixture is stirred for 48 h at ambient temperature and 4.5 bar $H_2$ pressure. Then the catalyst is filtered off and the solvent is eliminated in vacuo.

Yield: 0.403 g (1.935 mmol; 91%) MS (ESI): 209 (M+H)$^+$

The following compounds are prepared analogously to this process:

Method 19

7-amino-5H-phenanthridin-6-one

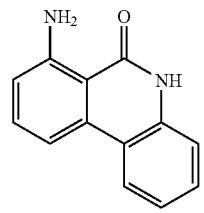

250 mg (1.16 mmol) methyl 2-chloro-6-nitro-benzoate, 458 mg (1.392 mmol) caesium carbonate, 211 mg (1.218 mmol) 2-nitrophenylboric acid and 18 mg (0.035 mmol) bis(tri-tert-butylphosphin)palladium(0) are placed under argon and combined with 0.8 ml dioxane. This reaction mixture is stirred for 48 h at 80° C. The reaction mixture is diluted with ethyl acetate and extracted with 1 N hydrochloric acid. The organic phase is dried and the solvent is eliminated in vacuo. The crude product is purified by column chromatography. The carrier used is C18-RP-silica gel and a gradient is run through which consists of 95% water and 5% acetonitrile at the starting point and consists of 5% water and 95% acetonitrile at the finishing point. 0.1% formic acid is added to both the water and the acetonitrile. The suitable fractions are freeze-dried. 71 mg of the intermediate product thus obtained are dissolved in 50 ml of methanol and combined with 10 mg palladium on charcoal. The reaction mixture is stirred for 48 h at ambient temperature and 4.5 bar $H_2$ pressure. 50 ml dichloromethane are added to the reaction solution, the mixture is treated for 5 min in the ultrasound bath and then the catalyst is filtered off. The solvent is eliminated in vacuo.

Yield: 46 mg (0.221 mmol; 94%) MS (ESI): 211 (M+H)$^+$

|  | MS (ESI) (M + H)$^+$ |  | MS (ESI) (M + H)$^+$ |
|---|---|---|---|
| ![structure] | 177 | ![structure] | 223 |
| ![structure] | 191 | | |

Method 20
C-(5-morpholin-4-ylmethyl-1H-[1,2,3]triazol-4-yl)-methylamine

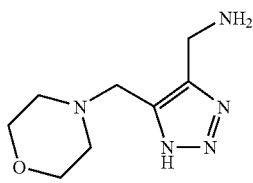

18.021 g (100 mmol) 1-azido-4-morpholino-2-butyne and 19.728 g (100 mmol) dibenzylamine are dissolved in 100 ml dioxane and heated to 80° C. with stirring. After stirring for 20 h at this temperature the solvent is eliminated in vacuo and the residue is purified by column chromatography. The carrier used is silica gel and the eluant used is dichloromethane, to which 5% of a mixture of 90% methanol and 10% saturated aqueous ammonia solution have been added. The suitable fractions are combined and the solvent is eliminated in vacuo. The residue is dissolved in 480 ml of methanol and combined with 30 ml concentrated aqueous hydrochloric acid and 1 g palladium on charcoal. This reaction mixture is stirred for 5 h at 50° C. and 50 bar $H_2$ pressure. Then the catalyst is filtered off and the solvent is eliminated in vacuo.

Yield: 8.588 g (28.00 mmol; 28%) MS (ESI): 198 (M+H)+

Method 21
4-morpholin-4-ylmethyl-cyclohexylamine

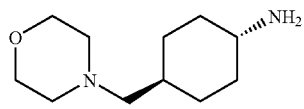

2.5 g (11 mmol) tert.butyl trans-(4-formyl-cyclohexyl)-carbamate dissolved in 25 ml dimethylacetamide are combined with 1 ml (11 mmol) morpholine and 0.7 ml acetic acid. 2.4 g (11.3 mmol) sodium triacetoxyborohydride dissolved in 12.5 ml dimethylacetamide is added to this mixture. The reaction mixture is stirred for 16 h at ambient temperature. Then the reaction mixture is added to 250 ml 10% potassium hydrogen carbonate solution and this mixture is extracted three times with 100 ml of ethyl acetate. The organic phases are combined, dried and then the solvent is eliminated in vacuo. The residue is taken up in 20 ml dichloromethane and 20 ml trifluoroacetic acid and stirred for 1 h at ambient temperature. The solvents are eliminated in vacuo.

Yield: 4.22 g (9.9 mmol; 90%) (double trifluoroacetic acid salt) MS (ESI): 199 (M+H)+

The following compounds are prepared analogously to this process:

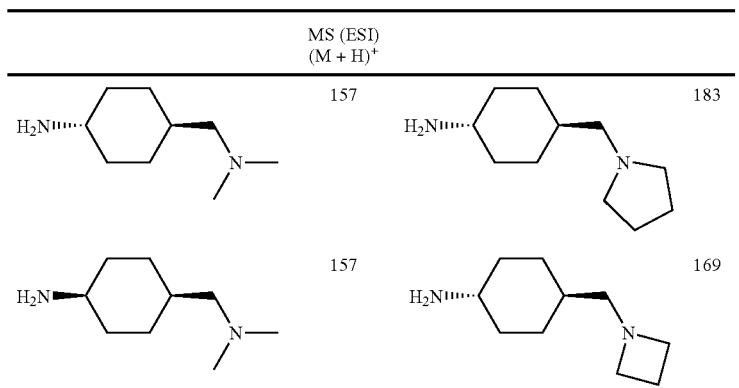

Method 22
7-amino-2-(2-fluoro-ethyl)-3-methyl-2,3-dihydro-isoindol-1-one

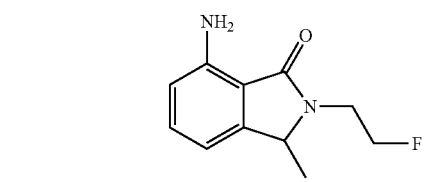

10 g (42.157 mmol) methyl 2-acetyl-6-nitro-benzoate (J. Org. Chem. (1952), 17, 164-76), 6.06 g (54.804 mmol) 2-fluoroethylamine and 9.32 ml (54.804 mmol) N-ethyldiisopropylamine are suspended in 25 ml of toluene and refluxed for 40 h with stirring. The reaction mixture is diluted with 400 ml of methanol and combined with 2.5 g palladium on charcoal. Then the mixture is stirred for 48 h at ambient temperature and 5 bar $H_2$ pressure. The catalyst is filtered off and the solvent is eliminated in vacuo. The residue is taken up in dichloromethane and washed with water. The organic phase is dried with magnesium sulphate, the solvent is eliminated in vacuo and the crude product is purified by chromatography. The carrier used is silica gel and the eluant used is a mixture of cyclohexane:ethyl acetate (70:30).

Yield: 3.83 g (18.404 mmol, 43%) MS (ESI): 209 (M+H)+
UV max: 318 nm

The following compounds are prepared analogously to this process, using the corresponding methyl 6-nitro-benzoate derivative:
| | MS (ESI) (M + H)+ | | MS (ESI) (M + H)+ |
|---|---|---|---|
| 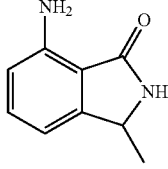 | 163 | 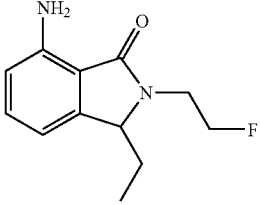 | 223 |
| 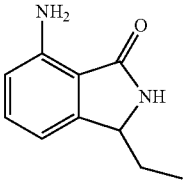 | 177 | 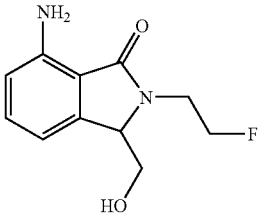 | 225 |
| 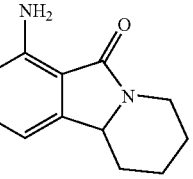 | 203 | 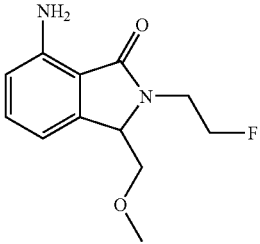 | 239 |
| 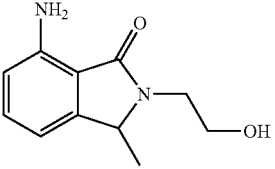 | 207 | 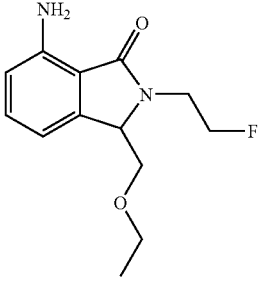 | 253 |
| 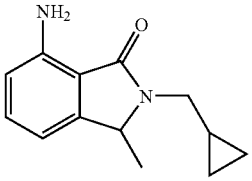 | 217 | 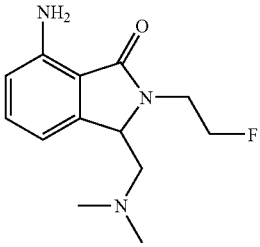 | 252 |

| MS (ESI) (M + H)⁺ | | MS (ESI) (M + H)⁺ |
|---|---|---|
| 221 | | 278 |
| 227 | | 237 |
| 241 | | 245 |

Method 23

2-azetidin-1-yl-ethylamine

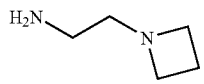

500 µl (7.49 mmol) azetidin are dissolved in 15 ml acetonitrile, combined with 4.831 g (34.822 mmol) potassium carbonate and 445 µl (7.038 mmol) chloroacetonitrile. This reaction mixture is stirred for 20 h at ambient temperature. To this reaction mixture are added 20 ml diethyl ether, the suspension is stirred for 10 min and filtered to separate the solid constituents. The filtrate is freed from solvents in vacuo. 463 mg (4.816 mmol) of this intermediate product are dissolved in 50 ml 7 N methanolic ammonia and Raney nickel is added. The reaction mixture is stirred for 2 h at 60° C. and 20 bar H₂ pressure. The catalyst is filtered off and the solvent is eliminated in vacuo.

Yield: 365 mg (3.664 mmol, 48%) MS (ESI): 101 (M+H)⁺

The following compounds are prepared analogously to this process:

| MS (ESI) (M + H)⁺ | | MS (ESI) (M + H)⁺ |
|---|---|---|
| 129 | | 156 |
| 131 | | 157 |

| MS (ESI) (M + H)+ | | MS (ESI) (M + H)+ |
|---|---|---|
| 158 | | 143 |
| 159 | | 145 |
| 159 | | 145 |
| 141 | | 158 |
| 165 | | 198 |
| 172 | | 145 |

Method 24
((S)-3-amino-pyrrolidin-1-yl)-acetonitrile

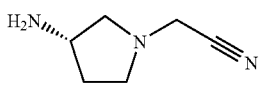

1 g (5.369 mmol) (S)-3-(Boc-amino)-pyrrolidine are dissolved in 20 ml acetonitrile and combined with 4.831 g (34.822 mmol) potassium carbonate and 322 μl (5.101 mmol) chloroacetonitrile. This reaction mixture is stirred for 20 h at ambient temperature. 20 ml diethyl ether are added to this reaction mixture, the suspension is stirred for 10 min and filtered to separate off the solid constituents. The filtrate is freed from the solvents in vacuo. The intermediate product is dissolved in 2 ml dioxane and combined with 13 ml of 4 N dioxanic hydrochloric acid and stirred overnight at RT. Then the solvent is eliminated in vacuo.

Yield: 500 mg (3.995 mmol, 74%) MS (ESI): 126 (M+H)+

Method 25
(R)-2-pyrrolidin-1-yl-propylamine

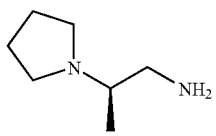

a) (R)-2-pyrrolidin-1-yl-propionamide 2 g (16.055 mmol) R-alaninamide hydrochloride, 6.67 g (16.083 mmol) potassium carbonate and 8 mg (0.048 mmol) potassium iodide are suspended in 50 ml acetonitrile and then combined with 1.921 ml (16.083 mmol) 1,4-dibromobutane. This reaction mixture is refluxed for 14 h with stirring. 100 ml 1 N hydrochloric acid and 100 ml dichloromethane are added to the reaction mixture. The organic phase is separated off and discarded. The aqueous phase is made basic with sodium hydroxide solution and extracted three times with dichloromethane. The organic phases are combined, dried and freed from the solvent in vacuo.

200 mbar and a sump temperature of approx. 50° C. The product is distilled at 69-71° C. and 10 mbar.

Yield: 160 mg (1.248 mmol, 18%) MS (ESI): 129 (M+H)$^+$

The following compounds are prepared analogously to this process:

| MS (ESI) (M + H)$^+$ | MS (ESI) (M + H)$^+$ |
|---|---|
| 129 | 157 |
| 129 | 169 |
| 129 | 183 |
| 143 | 183 |
| 157 | 197 |

Yield: 1.305 g (9.177 mmol, 57%) MS (ESI): 143 (M+H)$^+$ b) (R)-2-pyrrolidin-1-yl-propylamine Under a nitrogen atmosphere 31.65 ml 1 M Lithiumaluminiumhydrid solution (THF) are taken and combined with 1 g (7.032 mmol) (R)-2-pyrrolidin-1-yl-propionamide, dissolved in 2 ml THF, at 0° C. The reaction mixture is stirred for 48 h at 50° C. The reaction mixture is combined with 100 ml of methanol and then with the same amount of dichloromethane while cooling with ice. Approx. 25 g silica gel are added to this mixture and the solvent is eliminated in vacuo. This silica gel applied to a suction filter which has previously been charged with approx. 75 g silica gel. The suction filter is washed batchwise with a total of 500 ml of a mixture of dichloromethane, methanol and aqueous conc. ammonia (90: 9:1). The majority of the solvent is eliminated at a vacuum of Method 26

2-chloro-4-(2-(2-fluoro-ethyl-1-methyl-3-oxo-2,3-dihydro-1H-isoindol-4-ylamino)-5-trifluoromethyl-pyrimidine

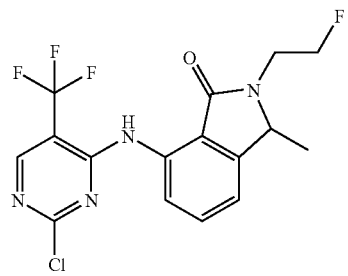

1.1 g (5.07 mmol) 2,4-dichloro-5-trifluoromethylpyrimidin are dissolved in 1 ml dioxane and combined with 0.9 g (4.322 mmol) 7-amino-2-(2-fluoro-ethyl)-3-methyl-2,3-dihydro-isoindol-1-one (method 22) and 0.9 ml (5.257 mmol) diisopropyethylamine. This mixture is stirred for 1 h at 80° C. Then the solvent is eliminated in vacuo. The crude product is purified by column chromatography. The carrier used is C18-RP-silica gel and a gradient is run through which consists of 95% water and 5% acetonitrile at the starting point and consists of 20% water and 80% acetonitrile at the finishing point. 0.1% formic acid are added to both the water and to the acetonitrile. The suitable fractions are combined with dichloromethane, the organic phase is separated off, dried and the solvent is eliminated in vacuo.

Yield: 485 mg (1.250 mmol, 25%) MS (ESI): 389/391 (M+H)$^+$; Cl distribution

The following compounds are prepared analogously to this process. The aniline derivatives used are described in the supplements to method 2, in method 10 and in the supplements to method 10. The preparation of the 2,4-dichloropyrimidine derivatives is known from the literature or may be carried out by methods known from the literature.

| | MS (ESI) (M + H)$^+$ | | MS (ESI) (M + H)$^+$ |
|---|---|---|---|
| 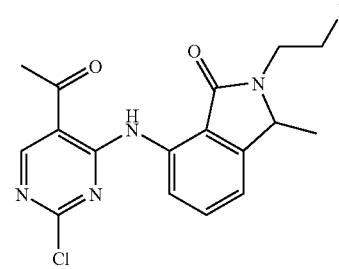 | 363/365 | 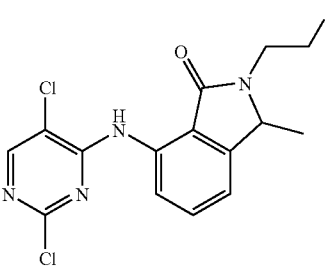 | 355/357 |
| 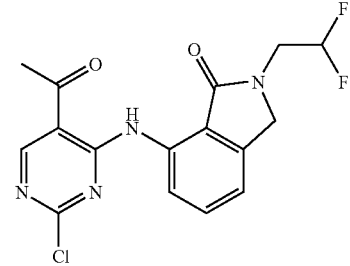 | 367/369 | 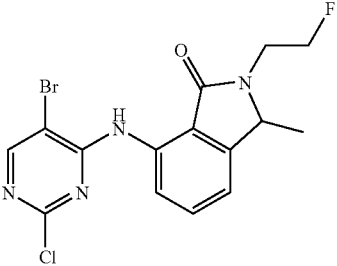 | 399/401 |
| 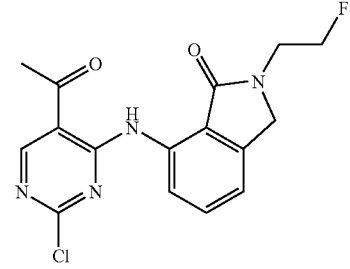 | 349/351 | 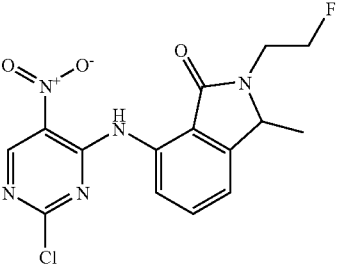 | 366/368 |
| 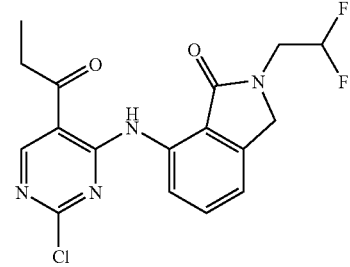 | 381/383 | 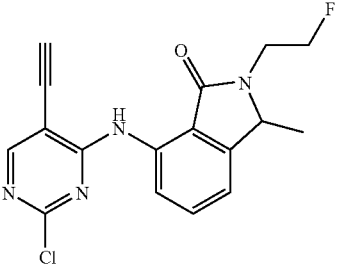 | 345/347 |

| MS (ESI) (M + H)+ | | MS (ESI) (M + H)+ | |
|---|---|---|---|
| 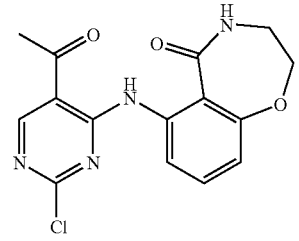 | 333/335 | 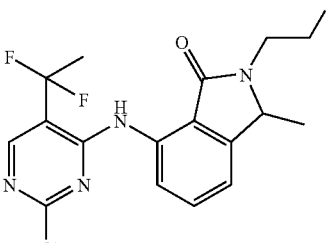 | 385/387 |
| 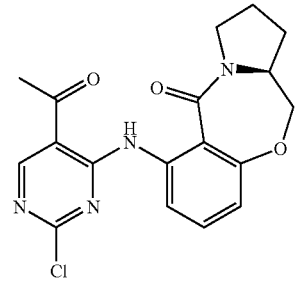 | 373/375 | 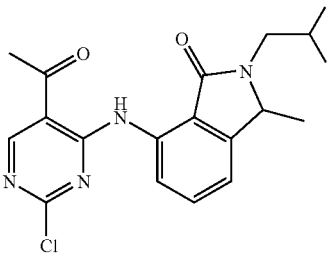 | 381/383 |
| 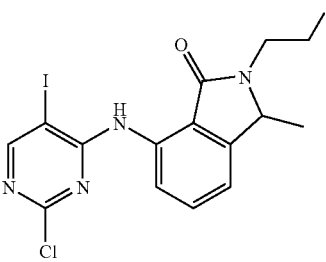 | 447/449 | | |

Method 27

2-[2-(4-amino-3-methoxy-phenyl)-1H-imidazol-4-yl]-ethanol

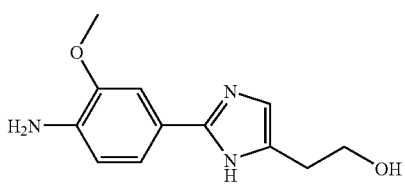

a) 3-methoxy-4-nitro-benzonitrile 25 g (150.504 mmol) 3-fluoro-4-nitrobenzonitrile and 25 g (462.757 mmol) sodium methoxide are dissolved in 125 ml THF at 0° C. This reaction mixture is stirred for 30 min. The reaction mixture is extracted with ethyl acetate and 1 N hydrochloric acid. The organic phase is dried with magnesium sulphate and the solvent is eliminated in vacuo.

Yield: 25.092 g (140.852 mmol, 94%) UV max: 334 nm b) 3-methoxy-4-nitro-benzamidine 99 ml (99 mmol) lithium-bis-trimethylsilylamide solution (1 mol/l in THF) are diluted with 640 ml THF, cooled to 10° C. and combined with 8.3 g (46.591 mmol) 3-methoxy-4-nitro-benzonitrile. The reaction mixture is stirred for 10 min at 20° C. The mixture is cooled to 0° C. and combined with 80 ml 3 N hydrochloric acid. The reaction mixture is evaporated down in vacuo and extracted with water and ethyl acetate. The aqueous phase is adjusted to pH 14 with 3 N sodium hydroxide solution. The product is then suction filtered.

Yield: 14.30 g (crude product: 60% purity) MS (ESI): 196 (M+H)+ $^{UV\ max:}$ 334 nm c) [2-(3-methoxy-4-nitro-phenyl)-1H-imidazol-4-yl]-acetic acid 7 g (60% purity, 21.519 mmol) 3-methoxy-4-nitro-benzamidine are dissolved in methanol and combined with 11 ml (44 mmol) 4 N dioxanic hydrochloric acid, the solvents are eliminated in vacuo. The residue and 6.13 g (44.384 mmol) potassium carbonate are suspended in 350 ml acetonitrile and combined with 3.24 ml (22.764 mmol) ethyl 4-chloracetoacetate and 880 mg (5.301 mmol) potassium iodide. The reaction mixture is stirred for 16 h at 45° C. The reaction mixture is diluted with water and combined with 1 N sodium hydroxide solution, and extracted with ethyl acetate. The aqueous phase is adjusted to pH 1 with 1 N HCL and saturated with sodium chloride. The product is then suction filtered.

Yield: 1.45 g (5.230 mmol, 24%) MS (ESI): 278 (M+H)+ UV max: 294 nm d) 2-[2-(3-methoxy-4-nitro-phenyl)-1H-imidazol-4-yl]-ethanol 1.45 g (5.23 mmol) [2-(3-methoxy-4-nitro-phenyl)-1H-imidazol-4-yl]-acetic acid are dissolved in 36 ml THF and cooled to 0° C. and combined with 10 ml (18 mmol) borane-THF complex (1.8 mol/V). After 1 h the mixture is heated to 20° C. and stirred for 16 h. Water is added until the development of gas has ended. Then the mixture is extracted twice with saturated aqueous sodium hydrogen carbonate solution and ethyl acetate. The organic phases are combined, dried and freed from the solvent in vacuo.

Yield: 0.65 g (2.465 mmol, 47%) MS (ESI): 264 (M+H)$^+$
$UV_{max}$: 298 nm e) 2-[2-(4-amino-3-methoxy-phenyl)-1H-imidazol-4-yl]-ethanol 0.144 g (0.547 mmol) 2-[2-(3-methoxy-4-nitro-phenyl)-1H-imidazol-4-yl]-ethanol are dissolved in 100 ml of methanol and combined with 0.08 g (5%) palladium on charcoal. The reaction mixture is hydrogenated for 16 h at 20° C. and 4 bar H$_2$ pressure. The palladium on charcoal is suction filtered and the methanol is eliminated in vacuo.

Yield: 87 mg (0.373 mmol, 68%) MS (APCI): 234 (M+H)$^+$
$UV_{max}$: 314 nm

The following compounds are prepared analogously to this process:

Method 28
2-methoxy-N$^4$-(3-pyrrolidin-1-yl-propyl)-benzene-1,4-diamine

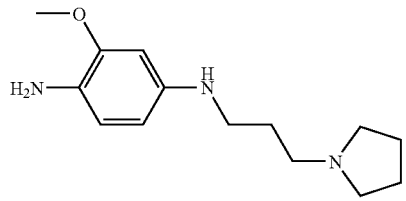

a) (3-methoxy-4-nitro-phenyl)-(3-pyrrolidin-1-yl-propyl)-amine 1 g (5.884 mmol) 4-fluoro-2-methoxy-1-nitro-benzene, 975 mg (7.369 mmol) 1-(3-aminopropyl)pyrrolidine and 1.5 ml (8.765 mmol) diisopropyethylamine are dissolved in 5 ml dioxane and stirred for 24 h at 95° C. The solvents are eliminated in vacuo and the crude product is purified by column chromatography. The carrier used is silica gel and the eluant used is dichloromethane, to which 15% of a mixture of 90% methanol and 10% saturated aqueous ammonia solution has been added.

Yield: 1.07 g (3.827 mmol; 65%) MS (ESI): 280 (M+H)$^+$

| | MS (ESI) (M + H)$^+$ | | MS (ESI) (M + H)$^+$ |
|---|---|---|---|
| H$_2$N—⌬(OMe)—imidazole-CH$_2$OH | 220 | H$_2$N—⌬(OMe)—imidazole-H | 190 |
| H$_2$N—⌬(OMe)—thiazole-CH$_2$CH$_2$OH | 251 | | |

2-[2-(4-amino-3-methoxy-phenyl)-thiazole-5-yl]-ethanol is prepared analogously to the processes described above. For the cyclisation, 4-amino-3-methoxy-thiobenzamide is used (analogously to J. Am. Soc. 82, 2656, 1960) instead of 3-methoxy-4-nitro-benzamidine.

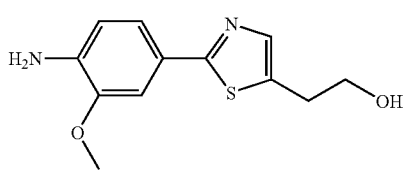

MS (ESI): 251 (M+H)$^+$ b) 2-methoxy-N$^4$-(3-pyrrolidin-1-yl-propyl)-benzene-1,4-diamine 200 mg (0.716 mmol) (3-methoxy-4-nitro-phenyl)-(3-pyrrolidin-1-yl-propyl)-amine are dissolved in 10 ml of methanol and combined with 537 µl (2.148 mmol) dioxanic hydrochloric acid and 20 mg palladium on charcoal. The reaction mixture is stirred for 1 h at ambient temperature and 5 bar H$_2$ pressure. The catalyst is filtered off and the solvent is eliminated in vacuo.

Yield: 213 mg (0.661 mmol, 92%) MS (ESI): 250 (M+H)$^+$
The following compounds are prepared analogously to this process:

| | MS (ESI) (M + H)+ | | MS (ESI) (M + H)+ |
|---|---|---|---|
| 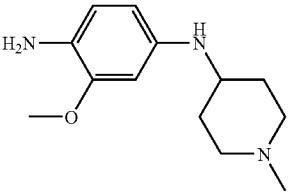 | 236 | 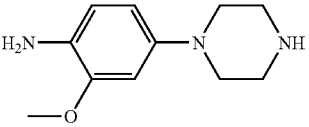 | 208 |
| 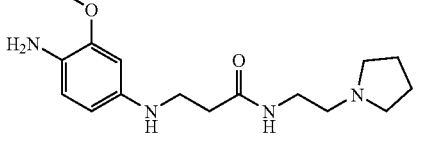 | 307 | 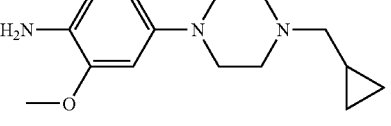 | 262 |
| 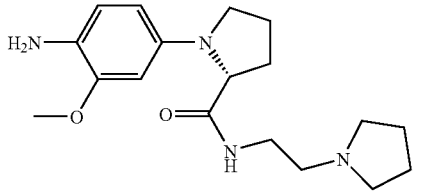 | 333 | 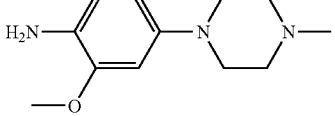 | 222 |
| 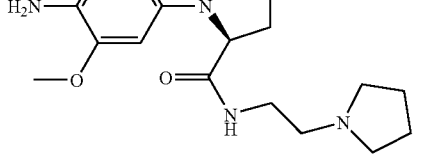 | 333 | 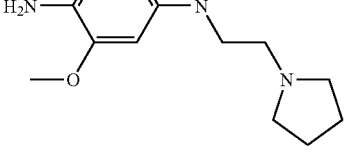 | 236 |
| 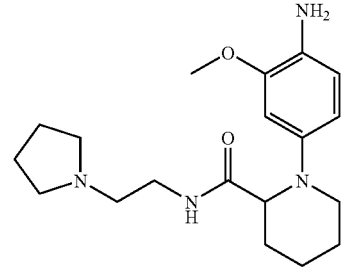 | 347 | 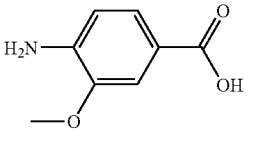 | 168 |
| 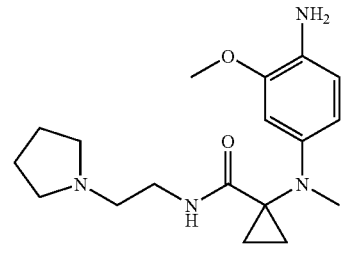 | 333 | 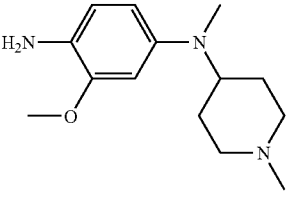 | 250 |
| 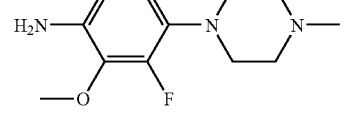 | 240 | 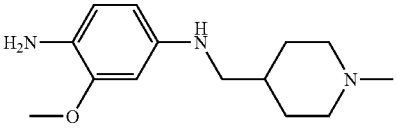 | 250 |

-continued

| | MS (ESI) (M + H)+ | | MS (ESI) (M + H)+ |
|---|---|---|---|
| 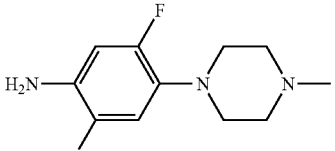 | 240 | 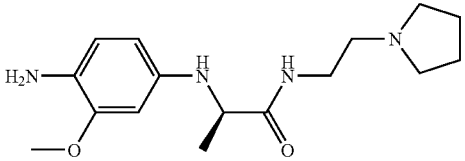 | 307 |
| 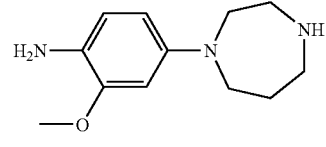 | 222 | 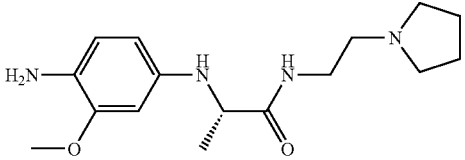 | 307 |

Method 29
2-(4-carboxy-2-bromo-phenylamino)-4-chloro-5-trifluoromethyl-pyrimidine

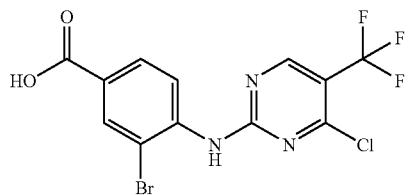

1 g (3.148 mmol) 2-(4-carboxy-2-methoxy-phenylamino)-4-chloro-5-trifluoromethyl-pyrimidine (method 12 or 14) are dissolved in 5 ml DMF and combined batchwise with 3.36 g (18.889 mmol) N-bromosuccinimide. This reaction mixture is stirred for 16 h at ambient temperature. Then the solvent is eliminated in vacuo and the residue is purified by column chromatography. The carrier used is C18-RP-silica gel and a gradient is run through which consists of 95% water and 5% acetonitrile at the starting point and consists of 2% water and 98% acetonitrile at the finishing point. 0.1% formic acid are added to both the water and to the acetonitrile.

Yield: 571 mg (1.440 mmol, 46%) MS (ESI): 396/398 (M+H)+

Method 30
2-(4-Acryloylamino-2-methoxy-phenylamino)-4-(2-(2-fluoro-ethyl)-1-methyl-3-oxo-2,3-dihydro-1H-isoindol-4-ylamino)-5-trifluoromethyl-pyrimidine

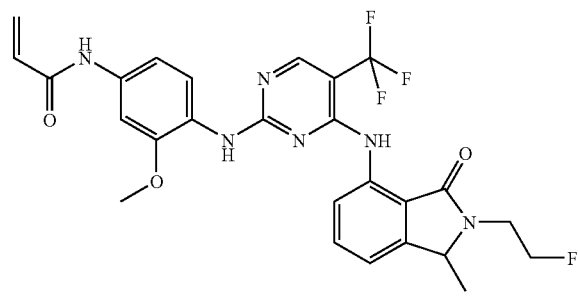

a) 4-amino-2-methoxy-phenylamino)-4-(2-(2-fluoro-ethyl)-1-methyl-3-oxo-2,3-dihydro-1H-isoindol-4-ylamino)-5-trifluoromethyl-pyrimidine 1 g (1.925 mmol) 2-(4-carboxy-2-methoxy-phenylamino)-4-[2-(2-fluoro-ethyl)-1-methyl-3-oxo-2,3-dihydro-1H-isoindol-4-ylamino]-5-trifluoromethyl-pyrimidine (prepared analogously to Example 53) are dissolved in 2 ml of toluene and combined successively with 0.43 ml (2.503 mmol) diisopropylethylamine, with 1.8 ml tert-butanol and with 0.49 ml (2.310 mmol) diphenylphosphorylazide and heated to 80° C. for 18 h. The reaction mixture is cooled, diluted with 100 ml of ethyl acetate and washed twice with 0.5 N sodium hydroxide solution. The organic phase is dried with magnesium sulphate and the solvent is eliminated in vacuo. The residue is taken up in dichloromethane and combined with 4 M dioxanic hydrochloric acid. The mixture is stirred for 72 h at ambient temperature. It is diluted with ethyl acetate and extracted 4 times with 1 N hydrochloric acid. The aqueous phases are combined and extracted once with ethyl acetate. The aqueous phase is made basic with sodium hydroxide solution and extracted three times with ethyl acetate. The organic phases are combined, dried and the solvent is eliminated in vacuo.

Yield: 606 mg (1.236 mmol, 64%) MS (ESI): 491 (M+H)+ b) 2-(4-Acryloylamino-2-methoxy-phenylamino)-4-(2-(2-fluoro-ethyl)-1-methyl-3-oxo-2,3-dihydro-1H-isoindol-4-ylamino)-5-trifluoromethyl-pyrimidine 311 mg (0.634 mmol) 2-(4-amino-2-methoxy-phenylamino)-4-(2-(2-fluoro-ethyl)-1-methyl-3-oxo-2,3-dihydro-1H-isoindol-4-ylamino)-5-trifluoromethyl-pyrimidine are dissolved in 10 ml THF and combined with 115 µl (0.824 mmol) triethylamine and 62 µl (0.761 mmol) acrylic chloride. This mixture is stirred for 1 h at ambient temperature. Then it is diluted with ethyl acetate and extracted three times with water. The organic phase is dried with magnesium sulphate and the solvent is eliminated in vacuo.

Yield: 340 mg (0.625 mmol, 98%) MS (ESI): 545 (M+H)+

The following compounds are prepared analogously to this process:

| | MS (ESI) (M + H)+ | | MS (ESI) (M + H)+ |
|---|---|---|---|
| | 581 | | 659 |
| | 582 | | 611 |

Method 31

Separation of the racemic 7-amino-2-(2-fluoro-ethyl)-3-methyl-2,3-dihydro-isoindol-1-one (method 22) into the two enantiomers The separation is carried out by preparative chromatography under the following conditions:

column: 280×110 mm CHIRALPAK® AD 20 μm

Eluant: 95% acetonitrile/5% isopropanol (v/v)

Flow rate: 570 ml/min

Temperature: ambient temperature

The enantiomer that elutes first is known as enantiomer 1 and in the chemical formula bears the symbol *1:

Enantiomer 1

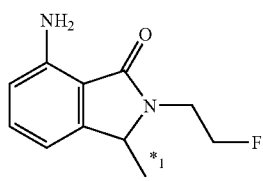

The enantiomer that elutes second is known as enantiomer 2 and in the chemical formula bears the symbol *2:

Enantiomer 2

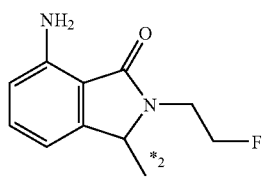

Method 32

7-amino-3-ethyl-indan-1-one

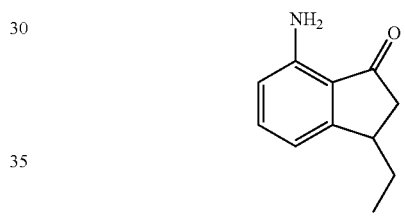

262 mg (1.364 mmol) copper iodide are taken and heated in an argon current. Then the copper iodide is suspended in ether and cooled to −78° C. At this temperature 0.8 ml of a 3 M ethylmagnesium bromide solution (in ether) are added and the mixture is stirred for 10 min and then left to thaw to 0° C. After 15 min stirring at this temperature the mixture is cooled to −78° C. again and 200 mg (0.802 mmol) N-(3-oxo-3H-inden-4-yl)-benzamide, dissolved in 9 ml THF, are added dropwise and the mixture is stirred for 1 h at 0° C. The reaction mixture is diluted with dichloromethane and washed three times with concentrated aqueous ammonia solution. The organic phase is dried with magnesium sulphate and the solvent is eliminated in vacuo. The residue is purified by column chromatography. The carrier used is C18-RP-silica gel and a gradient is run through which consists of 98% water and 2% acetonitrile at the starting point and 2% water and 98% acetonitrile at the finishing point. 0.1% formic acid are added to both the water and to the acetonitrile. The suitable fractions are freeze-dried. This intermediate product is dissolved in 2 ml dioxane and combined with 5 ml concentrated hydrochloric acid. The reaction mixture is refluxed for 24 h with stirring. Then it is diluted with water and extracted three times with dichloromethane. The combined organic phases are again washed with water, dried and the solvent is removed. The residue is purified by column chromatography. The carrier used is silica gel and the eluant used is dichloromethane, to which 5% of a mixture of 90% methanol and 10% saturated aqueous ammonia solution have been added.

Yield: 70 mg (0.399 mmol; 29%) MS (ESI): 176 (M+H)+

The following compounds are prepared analogously to this process:

| MS (ESI) (M + H)+ | | MS (ESI) (M + H)+ | |
|---|---|---|---|
| 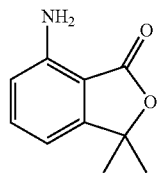 | 162 | | 190 |

| MS (ESI) (M + H)+ | | MS (ESI) (M + H)+ | |
|---|---|---|---|
| | 164 | | 190 |
| | 192 | | 178 |
| | 220 | | |

Method 33

7-amino-3,3-dimethyl-3H-isobenzofuran-1-one 250 mg (0.609 mmol) methyl 2-dibenzylamino-benzoate are combined under argon with 0.609 ml of a 1 M lithium chloride solution (THF). This solution is cooled to—ambient temperature and slowly 0.914 ml (1.827 mmol) of a 2 M isopropyl-magnesium chloride solution are metered in. After stirring for 16 h at this temperature, 45 µl (0.609 mmol) acetone are added dropwise and the mixture is stirred for 4 h at ambient temperature. The reaction solution is combined with sodium hydrogen carbonate solution and extracted three times with dichloromethane. The combined organic phases are dried and the solvent is eliminated in vacuo. The residue is purified by column chromatography. The carrier used is C18-RP-silica gel and a gradient is run through which consists of 95% water and 5% acetonitrile at the starting point and 5% water and 95% acetonitrile at the finishing point. 0.1% formic acid are added to both the water and to the acetonitrile. The suitable fractions are freeze-dried. This intermediate product is dissolved in 50 ml of methanol combined with 10 mg palladium on charcoal and hydrogenated for 20 h at 5 bar hydrogen pressure and ambient temperature. Then the catalyst is filtered off and the solvent is eliminated in vacuo. The residue is purified by column chromatography. The carrier used is C18-RP-silica gel and a gradient is run through which consists of 95% water and 5% acetonitrile at the starting point and consists of 5% water and 95% acetonitrile at the finishing point. 0.1% formic acid are added to both the water and to the acetonitrile. The suitable fractions are freeze-dried.

Yield: 34 mg (0.192 mmol; 32%) MS (ESI): 178 (M+H)+

The following compounds are prepared analogously to this process:

Method 34

7-amino-2-(2-fluoro-ethyl)-3,3-dimethyl-2,3-dihydro-isoindol-1-one

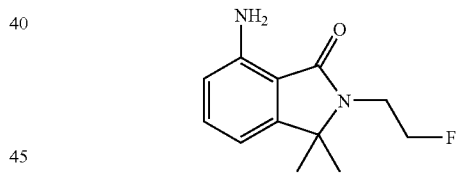

a) methyl 2-(cyano-dimethyl-methyl)-6-nitro-benzoate 3 g (13.625 mmol) methyl 2-cyanomethyl-6-nitro-benzoate (WO 9518097) are dissolved in 20 ml THF combined with 4.33 ml (68.788 mmol) iodomethane and cooled to 0° C. At this temperature 40.87 ml of a 1 M potassium-tert-butoxide solution is slowly added dropwise. The mixture is heated to ambient temperature and stirred for 16 h at this temperature. The reaction mixture is diluted with ethyl acetate and extracted three times with 1 M hydrochloric acid. The combined organic phases are dried and the solvent is eliminated in vacuo.

Yield: 3.11 g (12.535 mmol; 92%)

b) 3,3-dimethyl-7-nitro-2,3-dihydro-isoindol-1-one

Reaction Mixture 1

1 g (4.028 mmol) methyl 2-(cyano-dimethyl-methyl)-6-nitro-benzoate are suspended in 20% ethanolic potassium hydroxide solution and stirred for 24 h at ambient temperature.

Reaction Mixture 2

1.9 g (47.577 mmol) sodium hydroxide are dissolved in 40 ml of water cooled to 0° C. and combined with 0.5 ml (28.899 mmol) bromine. reaction mixture 1 is slowly added dropwise to this solution. After 8 h the same amount of reaction mixture 1 is added again. The mixture is stirred for a further 48 h at RT. Then sodium sulphite solution is added, the mixture is stirred for 20 min and then acidified with potassium hydrogen sulphate solution. It is extracted three times with ethyl acetate. The combined organic phases are dried and the solvent is eliminated in vacuo. The residue is purified by column chromatography. The carrier used is silica gel and the eluant used is a mixture of cyclohexane:ethyl acetate (3:1).

Yield: 67 mg (0.325 mmol, 8%) MS (ESI): 207 (M+H)$^+$ c) 3,3-dimethyl-7-amino-2,3-dihydro-isoindol-1-one 67 mg (0.325 mmol) 3,3-dimethyl-7-nitro-2,3-dihydro-isoindol-1-one are dissolved in 50 ml of methanol and combined with 10 mg palladium on charcoal. The mixture is hydrogenated for 16 h at 4 bar H$_2$ pressure and ambient temperature. Then the catalyst is filtered off and the solvent is eliminated in vacuo.

Yield: 50 mg (0.284 mmol, 93%) MS (ESI): 177 (M+H)$^+$ d) 7-dibenzylamino-3,3-dimethyl-2,3-dihydro-isoindol-1-one 50 mg (0.284 mmol) 3,3-dimethyl-7-amino-2,3-dihydro-isoindol-1-one are dissolved in 0.5 ml DMF and combined with 141 mg (1.021 mmol) potassium carbonate and 10 mg (0.028 mmol) tetrabutylammonium iodide. The mixture is heated to 50° C. and 155 µl (1.277 mmol) benzylbromide are added dropwise thereto. After stirring for 16 h at this temperature the mixture is diluted with ethyl acetate and extracted three times with 1 M hydrochloric acid. The combined organic phases are dried and the solvent is eliminated in vacuo.

Yield: 67 mg (0.188 mmol; 66%) MS (ESI): 357 (M+H)$^+$ e) 7-dibenzylamino-2-(2-fluoro-ethyl)-3,3-dimethyl-2,3-dihydro-isoindol-1-one 67 mg (0.188 mmol) 7-dibenzylamino-3,3-dimethyl-2,3-dihydro-isoindol-1-one are dissolved in 1 ml (7.877 mmol) 1-bromo-2-fluoroethane and combined with 52 mg (0.376 mmol) sodium hydride. After 4 h stirring at ambient temperature the mixture is diluted with ethyl acetate and extracted three times with 1 M hydrochloric acid. The combined organic phases are dried and the solvent is eliminated in vacuo.

Yield: 75 mg (0.188 mmol; 100%) MS (ESI): 403 (M+H)$^+$ f) 7-amino-2-(2-fluoro-ethyl)-3,3-dimethyl-2,3-dihydro-isoindol-1-one 75 mg (0.188 mmol) 7-dibenzylamino-2-(2-fluoro-ethyl)-3,3-dimethyl-2,3-dihydro-isoindol-1-one are dissolved in 50 ml of methanol and combined with 10 mg palladium on charcoal. The mixture is hydrogenated for 16 h at 5 bar H$_2$ pressure and ambient temperature. Then the catalyst is filtered off and the solvent is eliminated in vacuo.

Yield: 36 mg (0.162 mmol, 87%) MS (ESI): 223 (M+H)$^+$

EXAMPLE 1

2-(2-methoxy-4-N-propylcarbamoyl-phenylamino)-4-(3-oxo-2,3-dihydro-1H-isoindol-4-ylamino)-5-trifluoromethyl-pyrimidine

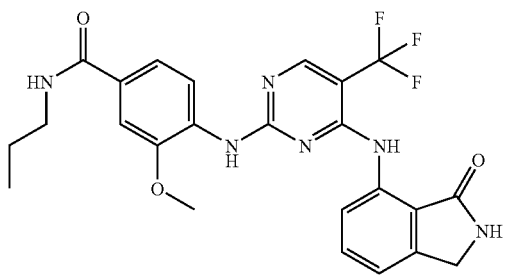

100 mg (0.257 mmol) 2-(2-methoxy-4-propylcarbamoyl-phenylamino)-4-chloro-5-trifluoro-methyl-pyrimidine (method 1) are dissolved in 1 ml N,N-dimethylacetamide and combined with 83 mg (0.565 mmol) 7-amino-2,3-dihydro-isoindol-1-one (method 2). 48 µl of a 4 molar solution of HCl (0.193 mmol) in 1,4-dioxane are metered into this reaction mixture. After two days at 50° C. the solvent is eliminated in vacuo. The crude product is purified by column chromatography. The carrier used is silica gel and the eluant used is dichloromethane, to which 5% of a mixture of 90% methanol and 10% saturated aqueous ammonia solution have been added. The concentrated crude product is again purified by column chromatography. The carrier used is C18-RP-silica gel and a gradient is run through which consists of 80% water and 20% acetonitrile at the starting point and 60% water and 40% acetonitrile aat the finishing point.

Yield: 42 mg (0.084 mmol; 33%) UV max: 318 nm MS (ESI): 501 (M+H)$^+$ $^1$H-NMR: 0.92 (t, 3H), 1.51-1.63 (m, 2H), 3.21-3.29 (m, 2H), 3.86 (s, 3H), 4.37 (s, 2H), 7.14-7.21 (m, 1H), 7.33 (t, 1H), 7.47-7.54 (m, 1H), 7.55-7.60 (m, 1H), 7.73-7.82 (m, 1H), 8.35-8.50 (m, 3H), 8.75 (s, 1H), 9.09 (s, 1H), 10.66 (s, 1H)

EXAMPLES 2-17

The following compounds are prepared by an analogous method as described in Example 1. 2-(2-Methoxy-4-propyl-carbamoyl-phenylamino)-4-chloro-5-trifluoromethylpyrimidine and a corresponding 7-amino-2,3-dihydro-isoindol-1-one derivative (method 2) are used. N-methyl-2-pyrrolidinone or N,N-dimethylacetamide is used as solvent.

| # | A | UV max [nm] | MS (ESI) (M + H)+ |
|---|---|---|---|
| 2 | X₁-isoindolin-1-one, N-methyl | 322 | 515 |
| 3 | X₁-isoindolin-1-one, N-ethyl | 314 | 529 |
| 4 | X₁-isoindolin-1-one, N-isopropyl | 285 | 543 |
| 5 | X₁-isoindolin-1-one, N-cyclohexyl | 286/310 | 583 |
| 6 | X₁-isoindolin-1-one, N-isopentyl | 322 | 571 |
| 7 | X₁-isoindolin-1-one, N-(tetrahydropyran-4-yl) | 285/321 | 585 |
| 8 | X₁-isoindolin-1-one, N-(3-hydroxypropyl) | 285/318 | 559 |
| 9 | X₁-isoindolin-1-one, N-(2-acetamidoethyl) | 285/318 | 586 |
| 10 | X₁-isoindolin-1-one, N-[3-(2-oxopyrrolidin-1-yl)propyl] | 281/316 | 626 |
| 11 | X₁-isoindolin-1-one, N-(2-hydroxyethyl) | 284/316 | 545 |
| 12 | X₁-isoindolin-1-one, N-phenyl | 325 | 577 |
| 13 | X₁-isoindolin-1-one, N-[(1-methylimidazol-2-yl)methyl] | 282/318 | 595 |
| 14 | X₁-isoindolin-1-one, N-(4-hydroxybutyl) | 284/322 | 573 |

-continued

| # | A | UV max [nm] | MS (ESI) (M + H)+ |
|---|---|---|---|
| 15 | X₁ (isoindolinone with 4-hydroxybenzyl) | 286, 306 | 607 |
| 16 | X₁ (isoindolinone with ethylamine) | 325 | |
| 17 | X₁ (isoindolinone with 3-hydroxybenzyl) | 318/282 | 607 |

EXAMPLE 18

2-(2-methoxy-4-N-propylcarbamoyl-phenylamino)-4-(3-oxo-1,3-dihydro-isobenzofuran-4-ylamino)-5-trifluoromethyl-pyrimidine

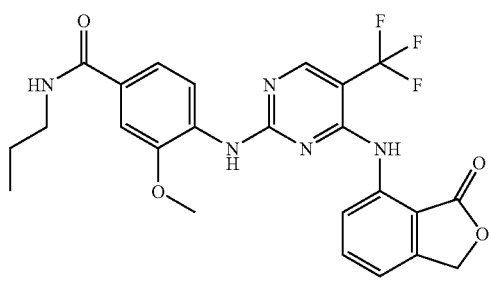

100 mg (0.257 mmol) 2-(2-methoxy-4-propylcarbamoyl-phenylamino)-4-chloro-5-trifluoro-methyl-pyrimidine (method 1) are dissolved in 1 ml N,N-dimethylacetamide and combined with 46 mg (0.308 mmol) 7-amino-3H-isobenzofuran-1-one (Safdar Hayat et al., *Tetrahedron Lett* 2001, 42(9):1647-1649). 48 ìl of a 4 molar solution of HCl (0.193 mmol) in 1,4-dioxane zudosiert metered into this reaction mixture. After 4 days at 50° C. the solvent is eliminated in vacuo. The crude product is purified by column chromatography. The carrier used is silica gel and the eluant used is dichloromethane, to which 4% of a mixture of 90% methanol and 10% saturated aqueous ammonia solution have been added.

Yield: 26 mg (0.051 mmol; 20%) UV max: 322 nm MS (ESI): 502 (M+H)+ ¹H-NMR: 0.92 (t, 3H), 1.51-1.63 (m, 2H), 3.22-3.28 (m, 2H), 3.86 (s, 3H), 5.42 (s, 2H), 7.24-7.30 (m, 1H), 7.44-7.55 (m, 2H), 7.55-7.60 (m, 1H), 7.67-7.78 (m, 1H), 8.38-8.48 (m, 2H), 8.50 (s, 1H), 9.21 (s, 1H), 9.64 (s, 1H)

EXAMPLES 19-37

The following compounds are prepared by analogous methods to those described in Example 1 and Example 18. 2-(2-methoxy-4-propylcarbamoyl-phenylamino)-4-chloro-5-trifluoromethylpyrimidine (method 1) is used. The corresponding aniline derivative is commercially obtainable, known from the literature or is prepared by the processes described in method 2 and 4 to 9. N-methyl-2-pyrrolidinone or N,N-dimethylacetamide is used as solvent.

| # | A | UV max [nm] | MS (ESI) (M + H)+ |
|---|---|---|---|
| 19 | X₁ (isobenzofuranone with ethyl acetate) | 235 | 586 |
| 20 | X₁ (4,4-dimethyl-dihydroisoquinolinone) | 323/226 | 543 |
| 21 | X₁ (N-methyl-phthalazinone) | 325 | 530 |
| 22 | X₁ (quinazolinone) | 262 | 514 |

-continued

[Structure: N-propyl benzamide with methoxy group, linked via NH to pyrimidine bearing CF3 and NH-A]

| # | A | UV max [nm] | MS (ESI) (M + H)+ |
|---|---|---|---|
| 23 | X₁-substituted phthalazinone with N-ethyl (1-oxo-3-ethyl-3,4-dihydrophthalazine) | 320 | 544 |
| 24 | X₁-substituted 2-ethyl-phthalazin-1(2H)-one | 318 | 542 |
| 25 | X₁-substituted 2,3-dihydrophthalazine-1,4-dione | 312 | 530 |
| 26 | X₁-substituted 2,3,4,5-tetrahydro-1H-benzo[c]azepin-1-one | 315 | 529 |
| 27 | X₁-substituted 2-methyl-phthalazin-1(2H)-one | 314 | 528 |
| 28 | X₁-substituted 1,2-dihydro-3H-indazol-3-one | 317 | 502 |
| 29 | X₁-substituted 1-methyl-1,2-dihydro-3H-indazol-3-one | 316 | 516 |

-continued

[Structure: same core as above]

| # | A | UV max [nm] | MS (ESI) (M + H)+ |
|---|---|---|---|
| 30 | X₁-substituted 4-methyl-3,4-dihydroisoquinolin-1(2H)-one | 322 | 529 |
| 31 | X₁-substituted 9H-fluoren-9-one | 255 | 548 |
| 32 | X₁-substituted indan-1-one | 320 | 500 |
| 33 | X₁-substituted 3,4-dihydroisoquinolin-1(2H)-one | 325 | 515 |
| 34 | X₁-substituted 3-hydroxyindan-1-one | 250/286/318 | 516 |
| 35 | X₁-substituted 2-(acetylamino)isoindolin-1-one | 320 | 558 |
| 36 | X₁-substituted 3,4-dihydronaphthalen-1(2H)-one | 316 | 514 |

-continued

| # | A | UV max [nm] | MS (ESI) (M + H)+ |
|---|---|---|---|
| 37 | (X₁-substituted isoindolin-1-one with N-NH-CH₂-C(O)-OH) | | 321 |

EXAMPLE 38

2-(2-methoxy-4-N-propylcarbamoyl-phenylamino)-4-(4-methyl-5-oxo-2,3,4,5-tetrahydro-benzo[f][1,4]oxazepin-6-ylamino)-5-trifluoromethyl-pyrimidine

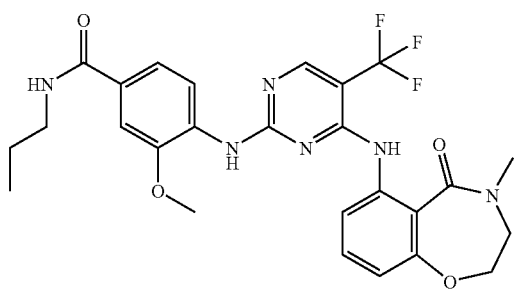

50 mg (0.129 mmol) 2-(2-methoxy-4-propylcarbamoyl-phenylamino)-4-chloro-5-trifluoro-methyl-pyrimidine (method 1) are dissolved in 200 μl 1,4-dioxane and combined with 25 mg (0.13 mmol) 6-amino-4-methyl-3,4-dihydro-2H-benzo[f][1,4]oxazepin-5-one (method 10). 36 μl of a 4 molar solution of HCl (0.144 mmol) in 1,4-dioxane are metered into this reaction mixture. After 4 days at 50° C. the solvent is eliminated in vacuo. The crude product is purified by column chromatography. The carrier used is silica gel and the eluant used is a mixture of dichloromethane and ethyl acetate (1:1).

Yield: 23 mg (0.042 mmol; 33%) UV max: 318 nm MS (ESI): 545 (M+H)+ ¹H-NMR: 0.91 (t, 3H), 1.49-1.61 (m, 2H), 3.09 (s, 3H), 3.20-3.28 (m, 2H), 3.49 (t, 2H), 3.88 (s, 3H), 4.31 (t, 2H), 6.83-6.88 (m, 1H), 7.34-7.45 (m, 2H), 7.50-7.54 (m, 1H), 7.88-8.00 (m, 2H), 8.37-8.44 (m, 2H), 8.62 (s, 1H), 9.97 (s, 1H)

EXAMPLES 39-52

The following compounds are prepared by analogous methods to those described in Example 1 and 18. 2-(2-methoxy-4-propylcarbamoyl-phenylamino)-4-chloro-5-trifluoromethylpyrimidine (method 1) is used. The corresponding aniline derivative is commercially obtainable, known from the literature or is prepared by the processes described in method 10 and 11. N-methyl-2-pyrrolidinone or N,N-dimethylacetamide is used as solvent.

| # | A | UV max [nm] | MS (ESI) (M + H)+ |
|---|---|---|---|
| 39 | (X₁, N-ethyl benzoxazepinone) | 229/279/315 | 559 |
| 40 | (X₁, NH benzoxazepinone) | 282/314 | 545 |
| 41 | (X₁, NH methyl benzoxazepinone) | 282/318 | 587 |
| 42 | (X₁, NH isobutyl benzoxazepinone) | 282/314 | 571 |
| 43 | (X₁, pyrrolidine-fused benzoxazepinone) | 282/318 | 585 |
| 44 | (X₁, NH cyclohexane-fused benzoxazepinone) | 318 | 559 |
| 45 | (X₁, NH gem-dimethyl benzoxazepinone) | 234/320 | 559 |

-continued

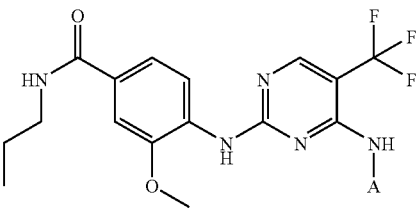

| # | A | UV max [nm] | MS (ESI) (M + H)+ |
|---|---|---|---|
| 46 | 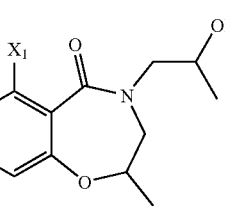 | 282/218 | 603 |
| 47 | 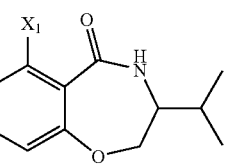 | 278/318 | 531 |
| 48 | 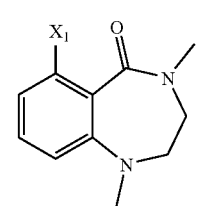 | 286/314 | 573 |
| 49 | 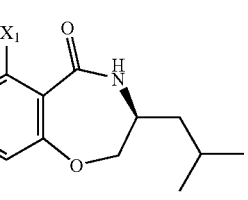 | 274/314 | 558 |
| 50 | 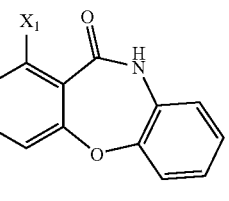 | 318 | 587 |
| 51 |  | 223/282/318 | 579 |

-continued

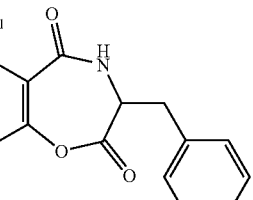

| # | A | UV max [nm] | MS (ESI) (M + H)+ |
|---|---|---|---|
| 52 | 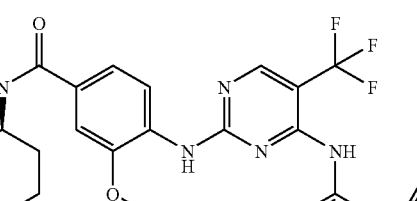 | 318 | 634 |

EXAMPLE 53

2-[2-methoxy-4-(4-morpholin-4-yl-(1,4-trans-cyclohexyl) carbamoyl)-phenylamino]-4-(2-carbamoyl-3-fluoro-phenylamino)-5-trifluoromethyl-pyrimidine 102 mg (0.29 mmol) 2-(4-carboxyamino-2-methoxy-phenylamino)-4-chloro-5-trifluoromethyl-pyrimidine (method 12) are dissolved in 250 µl N-methyl-2-pyrrolidinone and combined with 47 mg (0.319 mmol) 7-amino-indan-1-one (method 8). 15 µl of a 4 M solution of HCl (0.058 mmol) in 1,4-dioxane are metered into this reaction mixture. After 16 h at 90° C. the reaction mixture is stirred into 150 ml of a aqueous 1 N hydrochloric acid. The precipitate is filtered off and dried in vacuo. 100 mg (0.174 mmol) of this precipitate, 150 µl (0.875 mmol) N-ethyldiisopropylamine, 68 mg (0.210 mmol) O-(benzotriazol-1-yl)-N,N,N',N'-tetramethyluronium-tetrafluoroborate and 30 mg (0.163 mmol) trans-4-morpholin-4-yl-cyclohexylamine (method 13) are dissolved in 5 ml N,N-dimethylformamide. After 15 h at ambient temperature the solvent is eliminated in vacuo. The crude product is purified by column chromatography. The carrier used is silica gel and the eluant used is dichloromethane, to which 7% of a mixture of 90% methanol and 10% saturated aqueous ammonia solution have been added.

Yield: 55 mg (0.100 mmol; 57%) UV max: 318 nm MS (ESI): 555 (M+H)+ 1H-NMR: 1.55-1.69 (m, 2H), 1.74-1.84 (m, 2H), 1.91-2.02 (m, 2H), 2.18 (s, 3H), 2.69-2.75 (m, 2H), 2.75-2.84 (m, 2H), 3.03-3.10 (m, 2H), 3.70-3.83 (m, 1H), 3.86 (s, 3H), 7.15-7.21 (m, 1H), 7.36-7.46 (m, 1H), 7.48-7.54 (m, 1H), 7.54-7.58 (m, 1H), 7.71-7.79 (m, 1H), 8.18-8.25 (m, 1H), 8.30-8.45 (m, 1H), 8.48 (s, 1H), 9.16 (s, 1H), 10.59 (s, 1H)

EXAMPLES 54-77

The following compounds are prepared by an analogous method to that described in Example 53. The corresponding aniline is described in method 2, 7, 8, or 9 or known from the literature. The amine used to prepare the amide is commercially obtainable or is described in method 13.

| # | A | $R_3'$ | UV max [nm] | ME (ESI) $(M+H)^+$ |
|---|---|---|---|---|
| 54 | 7-X₁ indan-1-one | X₂ 1-methylpiperidin-4-yl | 318 | 555 |
| 55 | 8-X₁ tetralin-1-one | X₂ 1-methylpiperidin-4-yl | 318 | 569 |
| 56 | 7-X₁ 2-methylisoindolin-1-one | X₂ 1-methylpiperidin-4-yl | 322 | 570 |
| 57 | 7-X₁ 2-methylisoindolin-1-one | X₂ trans-4-morpholinocyclohexyl | 320 | 640 |
| 58 | 7-X₁ isoindolin-1-one | X₂ 1-methylpiperidin-4-yl | 284, 322 | 556 |

-continued

| # | A | R₃' | UV max [nm] | ME (ESI) (M + H)⁺ |
|---|---|---|---|---|
| 59 | 7-X₁-isoindolin-1-one | 4-(morpholin-4-yl)cyclohexyl (X₂) | 282, 318 | 626 |
| 60 | 8-X₁-3-methyl-3,4-dihydrophthalazin-1(2H)-one | 4-(morpholin-4-yl)cyclohexyl (X₂) | 325 | 655 |
| 61 | 8-X₁-3-methyl-3,4-dihydrophthalazin-1(2H)-one | 1-methylpiperidin-4-yl (X₂) | 325 | 585 |
| 62 | 8-X₁-3,4-dihydronaphthalen-1(2H)-one | 4-(morpholin-4-yl)cyclohexyl (X₂) | 254, 286, 318 | 639 |
| 63 | 7-X₁-2,3-dihydro-1H-inden-1-one | 1-benzylpiperidin-4-yl (X₂) | 321 | 631 |

-continued

| # | A | R₃' | UV max [nm] | ME (ESI) (M + H)⁺ |
|---|---|-----|-------------|-------------------|
| 64 | X₁-(8-oxo-1,2,3,4-tetrahydroisoquinolin-NH) | X₂-(1-methylpiperidin-4-yl) | 322 | 570 |
| 65 | X₁-(8-oxo-1,2,3,4-tetrahydroisoquinolin-NH) | X₂-(4-morpholinocyclohexyl) | 322 | 640 |
| 66 | X₁-(3-oxo-2-(acetamido)isoindolin-yl) | X₂-(4-morpholinocyclohexyl) | 322 | 683 |
| 67 | X₁-(3-oxo-2-(acetamido)isoindolin-yl) | X₂-(1-methylpiperidin-4-yl) | 322 | 613 |
| 68 | X₁-(2-ethyl-3-oxoisoindolin-yl) | X₂-(4-morpholinocyclohexyl) | 286, 322 | 654 |

-continued
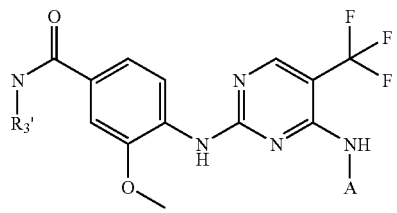
| # | A | R₃' | UV max [nm] | ME (ESI) (M + H)⁺ |
|---|---|---|---|---|
| 69 | X₁-(2-ethyl-isoindolin-1-one) | X₂-(1-methylpiperidin-4-yl) | 286, 322 | 584 |
| 70 | X₁-(isobenzofuran-1(3H)-one) | X₂-(trans-4-morpholinocyclohexyl) | 282, 322 | 627 |
| 71 | X₁-(2-(2-hydroxyethyl)-isoindolin-1-one) | X₂-(trans-4-morpholinocyclohexyl) | 322 | 670 |
| 72 | X₁-(2-(2-hydroxyethyl)-isoindolin-1-one) | X₂-(1-methylpiperidin-4-yl) | 286, 322 | 600 |
| 73 | X₁-(2-(3-hydroxypropyl)-isoindolin-1-one) | X₂-(trans-4-morpholinocyclohexyl) | 322 | 684 |

-continued

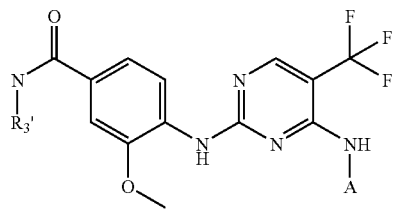

| # | A | R₃' | UV max [nm] | ME (ESI) (M + H)⁺ |
|---|---|-----|-------------|-------------------|
| 74 | X₁-(7-position of 2-(3-hydroxypropyl)isoindolin-1-one) | X₂-(1-methylpiperidin-4-yl) | 286, 322 | 614 |
| 75 | X₁-(7-position of isobenzofuran-1(3H)-one) | X₂-(1-methylpiperidin-4-yl) | 322 | 557 |
| 76 | X₁-(7-position of 2-(2-hydroxybenzyl)isoindolin-1-one) | X₂-(4-morpholinocyclohexyl) | 330 | 732 |
| 77 | X₁-(8-position of 4-methyl-3,4-dihydroisoquinolin-1(2H)-one) | X₂-(4-morpholinocyclohexyl) | 325 | 654 |

EXAMPLES 78-140

The following compounds are prepared by an analogous method to that described in Example 53. 2-(4-Carboxy-2-methoxy-phenylamino)-4-chloro-5-trifluoromethyl-pyrimidine may be prepared according to method 12 or 14. The corresponding aniline is described in the supplements to method 10. The amine used to prepare the amide is commercially obtainable or is described in method 13, in the supplements to method 13, 15 or 25.

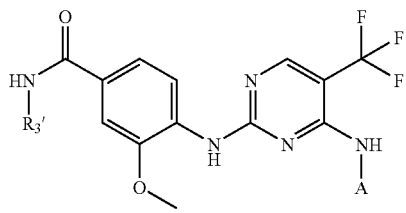
| # | A | R₃' | UV max [nm] | MS (ESI) (M + H)⁺ |
|---|---|---|---|---|
| 78 | | | 318 | 308 |
| 79 | | | 326 | 346 |
| 80 | | | 318 | 706 |
| 81 | | | 318 | 584 |
| 82 | | | 318 | 614 |

-continued

| # | A | R₃' | UV max [nm] | MS (ESI) (M + H)⁺ |
|---|---|-----|-------------|-------------------|
| 83 | (benzyloxymethyl benzoxazepinone with X₁) | (cyclohexyl-morpholine with X₂) | 318 | 776 |
| 84 | (pyrrolidine-fused benzoxazepinone with X₁) | (N-methylpiperidine with X₂) | 318 | 626 |
| 85 | (pyrrolidine-fused benzoxazepinone with X₁) | (cyclohexyl-morpholine with X₂) | 318 | 348 |
| 86 | (pyrrolidine-fused benzoxazepinone with X₁) | (benzyl-morpholine with X₂) | 318 | 718 |
| 87 | (ethyl benzoxazepinone with X₁) | (cyclohexyl-morpholine with X₂) | 318 | 684 |

-continued

| # | A | R₃' | UV max [nm] | MS (ESI) (M + H)⁺ |
|---|---|---|---|---|
| 88 | (3-ethyl-benzoxazepinone with X₁) | (4-(morpholinomethyl)benzyl with X₂) | 318 | 353 |
| 89 | (3-ethyl-benzoxazepinone with X₁) | (4-(morpholinomethyl)phenyl with X₂) | 322 | 346 |
| 90 | (3-hydroxymethyl-benzoxazepinone with X₁) | (4-morpholinocyclohexyl with X₂) | 318 | 686 |
| 91 | (3-benzyl-benzoxazepinone with X₁) | (propyl with X₂) | 310 | 621 |

-continued

| # | A | R₃' | UV max [nm] | MS (ESI) (M + H)⁺ |
|---|---|-----|-------------|-------------------|
| 92 | | | 318 | 746 |
| 93 | | | 318 | 676 |
| 94 | | | 318 | 316 |
| 95 | | | 318 | 696 |

-continued

| # | A | R₃' | UV max [nm] | MS (ESI) (M + H)⁺ |
|---|---|-----|-------------|-------------------|
| 96 | | | 282; 310 | 571 |
| 97 | | | 318 | 614 |
| 98 | | | 318 | 684 |
| 99 | | | 315 | 559 |
| 100 | | | 314 | 621 |

-continued
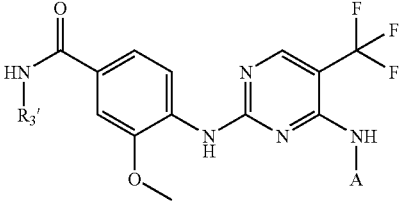
| # | A | R₃' | UV max [nm] | MS (ESI) (M + H)⁺ |
|---|---|-----|-------------|-------------------|
| 101 | 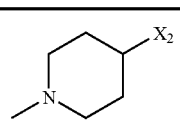 | 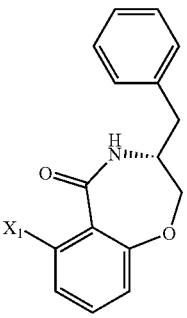 | 314 | 676 |
| 102 | 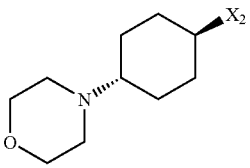 | 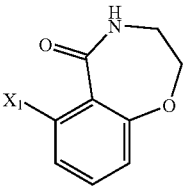 | 318 | 747 |
| 103 | 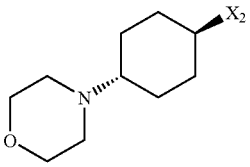 | 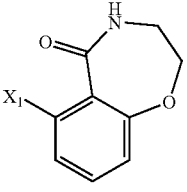 | 318 | 656 |
| 104 | 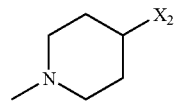 | 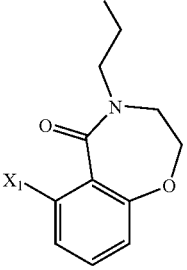 | 318 | 586 |
| 105 | 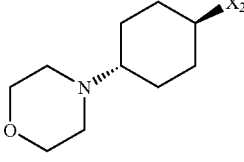 | | 318 | (M |

-continued

| # | A | R₃' | UV max [nm] | MS (ESI) (M + H)⁺ |
|---|---|---|---|---|
| 106 | | | 318 | 730 |
| 107 | | | 322 | 674 |
| 108 | | | 318 | 640 |
| 109 | | | 322 | 640 |
| 110 | | | 282, 318 | 614 |

-continued

| # | A | R₃' | UV max [nm] | MS (ESI) (M + H)⁺ |
|---|---|---|---|---|
| 111 | | | 226, 282, 318 | 640 |
| 112 | | | 318 | 614 |
| 113 | | | | 626 |
| 114 | | | 318 | 640 |
| 115 | | | 318 | 640 |
| 116 | | | 318 | 654 |
| 117 | | | 318 | 668 |

-continued

| # | A | R₃' | UV max [nm] | MS (ESI) (M + H)⁺ |
|---|---|-----|-------------|-------------------|
| 118 | | | 318 | 628 |
| 119 | | | 318 | 600 |
| 120 | | | 318–322 | 614 |
| 121 | | | 318 | 670 |
| 122 | | | 318 | 654 |
| 123 | | | 318 | 626 |

-continued

| # | A | R₃' | UV max [nm] | MS (ESI) (M + H)⁺ |
|---|---|---|---|---|
| 124 | (3,3-dimethyl-benzoxazepinone with X₁) | cyclohexyl-pyrrolidine with X₂ | 282, 318 | 668 |
| 125 | (3,3-dimethyl-benzoxazepinone with X₁) | cyclobutyl-N(methyl)(isopropyl) with X₂ *2" *2' | 282, 318 | 642 |
| 126 | (3,3-dimethyl-benzoxazepinone with X₁) | cyclobutyl-piperazine-propargyl with X₂ *2" *2' | 282, 318 | 693 |
| 127 | (pyrrolidine-fused benzoxazepinone with X₁) | pyrrolidine-cyclohexyl with X₂ | 318 | 680 |
| 128 | (pyrrolidine-fused benzoxazepinone with X₁) | cyclobutyl-N(methyl)(isopropyl) with X₂ *2" *2' | 318 | 654 |
| 129 | (pyrrolidine-fused benzoxazepinone with X₁) | cyclobutyl-piperazine-propargyl with X₂ *2" *2' | 318 | 705 |

-continued

| # | A | R₃' | UV max [nm] | MS (ESI) (M + H)⁺ |
|---|---|---|---|---|
| 130 | | | 226, 282, 318 | 628 |
| 131 | | | 318 | 668 |
| 132 | | | 318-322 | 642 |
| 133 | | | 318 | 693 |
| 134 | | | 318-322 | 642 |
| 135 | | | 318 | 682 |

-continued

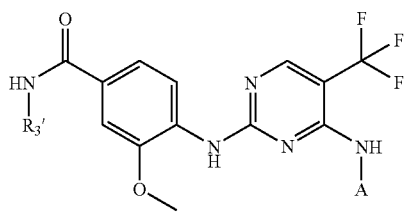

| # | A | R₃' | UV max [nm] | MS (ESI) (M + H)⁺ |
|---|---|-----|-------------|---------------------|
| 136 | | | 318 | 698 |
| 137 | | | 318-322 | 656 |
| 138 | | | 318-322 | 707 |
| 139 | | | 318-322 | 640 |
| 140 | | | 318-322 | 628 |

EXAMPLES 141-166

The following compounds are prepared by an analogous method to that described in Example 53. The preparation of 2-(4-carboxy-phenylamino)-4-chloro-5-trifluoromethyl-pyrimidine is described in method 14. The corresponding aniline is described in method 10. The amine used to prepare the amide is commercially obtainable or is described in method 13, 15 or 25.

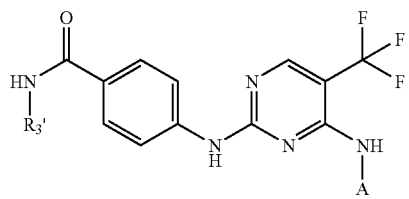
| # | A | R₃' | UV max [nm] | MS (ESI) (M + H)⁺ |
|---|---|---|---|---|
| 141 | | | 302 | 596 |
| 142 | | | 302 | 610 |
| 143 | | | 302 | 596 |
| 144 | | | 302 | 584 |
| 145 | | | 302 | 610 |

-continued
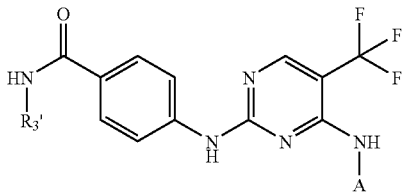
| # | A | R₃' | UV max [nm] | MS (ESI) (M + H)⁺ |
|---|---|---|---|---|
| 146 | 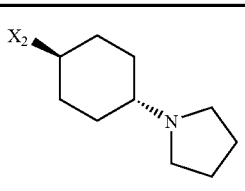 | 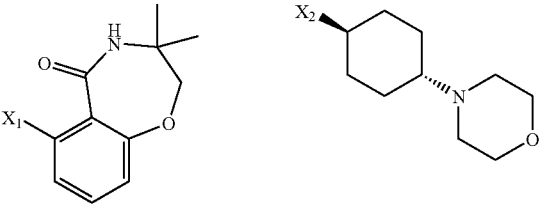 | 302 | 638 |
| 147 | 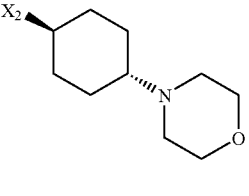 | 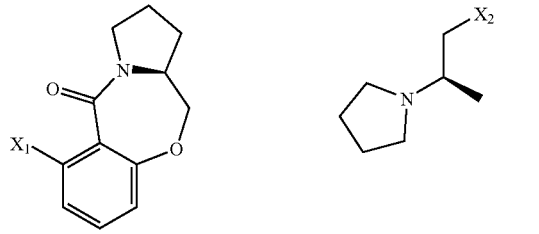 | 298 | 654 |
| 148 | 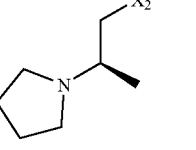 | 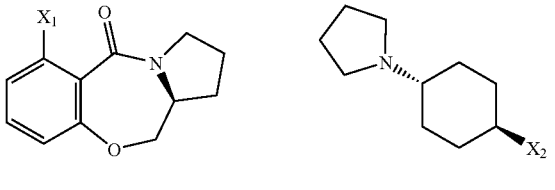 | 302 | 610 |
| 149 | 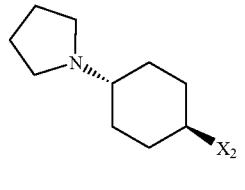 | 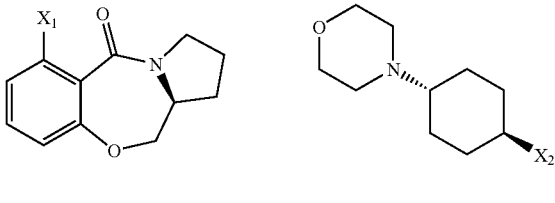 | 302 | 650 |
| 150 | 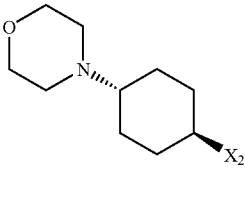 | 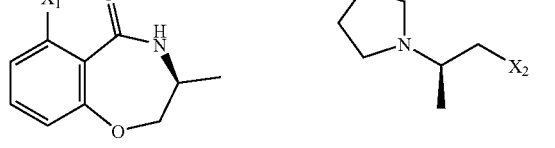 | 298-302 | 666 |
| 151 | 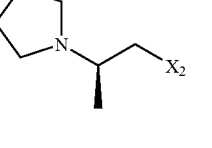 | | 302 | 584 |

-continued
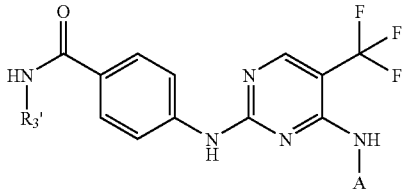
| # | A | R3' | UV max [nm] | MS (ESI) (M + H)+ |
|---|---|---|---|---|
| 152 | 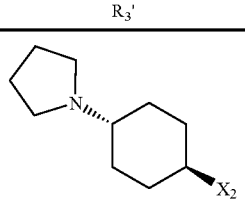 | 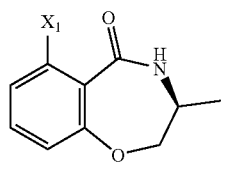 | 302 | 624 |
| 153 | 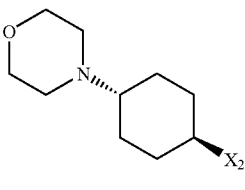 | 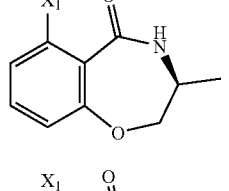 | 298-302 | 640 |
| 154 | 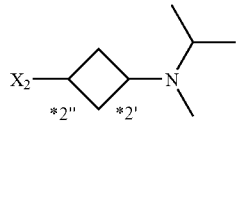 | 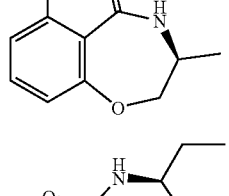 | 302 | 598 |
| 155 | 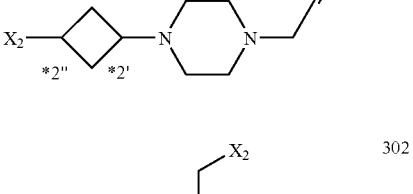 | 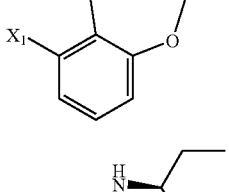 | 298-302 | 649 |
| 156 | 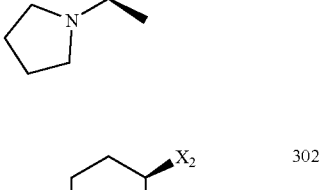 | 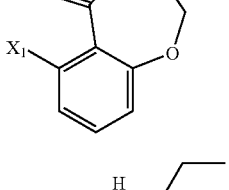 | 302 | 598 |
| 157 | 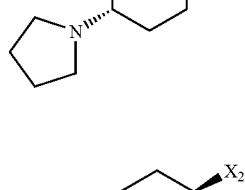 | 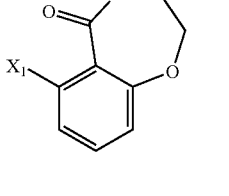 | 302 | 638 |
| 158 | 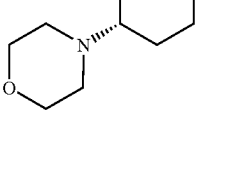 | | 298-302 | 654 |

-continued

| # | A | R₃' | UV max [nm] | MS (ESI) (M + H)⁺ |
|---|---|---|---|---|
| 159 | | | 302 | 612 |
| 160 | | | 302 | 663 |
| 161 | | | 302 | 612 |
| 162 | | | 302 | 652 |
| 163 | | | 298-302 | 668 |
| 164 | | | 302 | 677 |

-continued

| # | A | R3' | UV max [nm] | MS (ESI) (M + H)+ |
|---|---|---|---|---|
| 165 | ![structure] | ![structure] | 302 | 626 |
| 166 | ![structure] | ![structure] | 302 | 624 |

EXAMPLE 167

2-(2-methoxy-4-piperazin-1-yl-phenylamino)-4-(3,3-dimethyl-5-oxo-2,3,4,5-tetrahydro-benzo[f][1,4]oxazepin-6-ylamino)-5-trifluoromethyl-pyrimidine

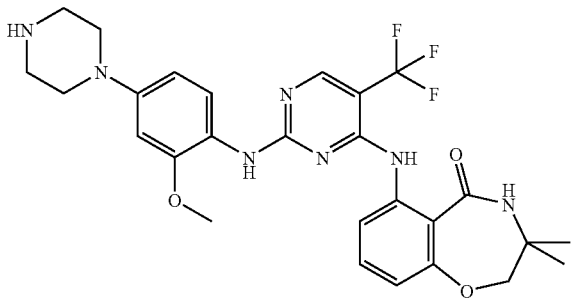

500 mg (0.958 mmol) 2-[4-(4-benzyloxycarbonyl-piperazin-1-yl)-phenylamino]-4-chloro-5-trifluoromethyl-pyrimidine (method 14) are dissolved in 0.5 ml NMP, combined with 198 mg (0.960 mmol) 6-amino-3,3-dimethyl-3,4-dihydro-2H-benzo[f][1,4]oxazepin-5-one (method 10) and with 25 μl (0.1 mmol) dioxanic hydrochloric acid. This reaction mixture is stirred for 1.5 h at 100° C. The solvent is eliminated in vacuo and the residue is purified by column chromatography. The carrier used is C18-RP-silica gel and a gradient is run through which consists of 95% water and 5% acetonitrile at the starting point and consists of 5% water and 95% acetonitrile at the finishing point. 0.1% formic acid are added to both the water and to the acetonitrile.

Yield: 0.59 g (0.86 mmol; 90%)

0.59 g (0.86 mmol) of the above-mentioned intermediate products are dissolved in 50 ml of dimethylformamide and combined with a quantity of distilled water such that there is no precipitation. To this solution are added 60 mg palladium on charcoal and the mixture is hydrogenated at 7 bar $H_2$ pressure and 20° C. for 6 h. The catalyst is filtered off and the solvent is eliminated in vacuo. The residue is purified by column chromatography. The carrier used is C18-RP-silica gel and a gradient is run through which consists at the starting point of 60% water and 40% acetonitrile and at the finishing point of 15% water and 85% acetonitrile. 10 mmol/l ammonium hydrogen carbonate and 20 mmol/l ammonia are dissolved in the water. The suitable fractions are freeze-dried. The residue is dissolved in acetonitrile and combined with 2 ml of a 1 M hydrochloric acid solution. Then the solvent is eliminated in vacuo. The substance is obtained as the dihydrochloride.

Yield: 0.46 g (0.73 mmol; 85%) UV max: 284 nm MS (ESI): 558 (M+H)+ $^1$H-NMR: 1.19 (s, 6H), 3.19-3.28 (m, 4H), 3.41-3.49 (m, 4H), 3.80 (s, 3H), 4.07 (s, 1H), 6.54-6.60 (m, 1H), 6.72-6.76 (m, 1H), 6.83-6.89 (m, 1H), 7.21-7.42 (m, 2H), 7.85-8.20 (m, 1H), 8.33-8.60 (m, 1H), 8.74 (s, 1H), 9.30-9.71 (m, 3H), 12.84 (s, 1H)

EXAMPLE 168

2-(2-methoxy-4-piperazin-1-yl-phenylamino)-4-((S)-4-oxo-2,3,10,10a-tetrahydro-1H,4H-9-oxa-3a-aza-benzo[f]azulen-5-ylamino)-5-trifluoromethyl-pyrimidine

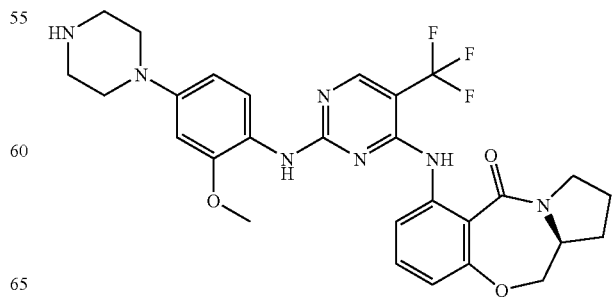

This compound is prepared analogously to Example 167. The aniline used is described in method 10.

Yield: 0.23 g (0.41 mmol; 91%) UV max: 282 nm MS (ESI): 570 (M+H)+ $^1$H-NMR: 1.53-1.71 (m, 1H), 1.79-2.06 (m, 3H), 3.15-3.32 (m, 4H), 3.32-3.55 (m, 5H), 3.58-3.72 (m, 1H), 3.72-3.94 (m, 4H), 4.00-4.23 (m, 2H), 6.48-6.61 (m, 1H), 6.68-6.77 (m, 1H), 6.83-7.00 (m, 1H), 7.19-7.50 (m, 2H), 7.78-8.10 (m, 1H), 8.23-8.60 (m, 1H), 9.18-9.64 (m, 3H), 10.54-10.86 (m, 1H)

EXAMPLE 169

2-[4-(4-ethyl-piperazin-1-yl)-2-methoxy-phenylamino]-4-((S)-4-oxo-2,3,10,10a-tetrahydro-1H.4H-9-oxa-3a-aza-benzo[f]azulen-5-ylamino-5-trifluoromethyl-pyrimidine

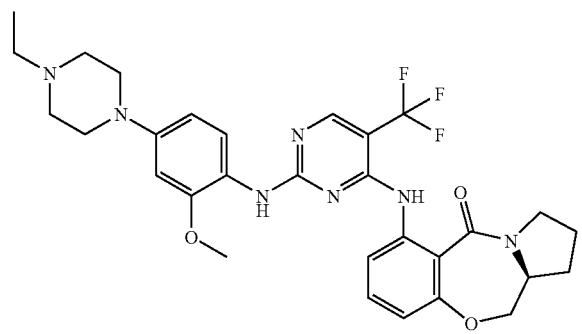

60 mg (0.11 mmol) 2-(2-methoxy-4-piperazin-1-yl-phenylamino)-4-((S)-4-oxo-2,3,10,10a-tetrahydro-1H.4H-9-oxa-3a-aza-benzo[f]azulen-5-ylamino-5-trifluoromethyl-pyrimidine (Example 168) are dissolved in 300 μl dimethylformamide and combined with 12 μl (0.21 mmol) acetaldehyde and 47 mg (0.21 mmol) sodium triacetoxyborohydride. This reaction mixture is stirred at 20° C. for 20 h. The solvent is eliminated in vacuo and the residue is purified by column chromatography. The carrier used is C18-RP-silica gel and a gradient is run through which consists of 95% water and 5% acetonitrile at the starting point and 50% water and 50% acetonitrile at the finishing point. 0.1% formic acid are added to both the water and to the acetonitrile. The suitable fractions are combined with 500 μl of a 1 N hydrochloric acid and freeze-dried. The product is obtained as the dihydrochloride.

Yield: 49 mg (0.074 mmol; 71%) UV max: 282 nm MS (ESI): 598 (M+H)+$^1$H-NMR: 1.23-1.37 (m, 3H), 1.57-1.72 (m, 1H), 1.80-2.06 (m, 3H), 3.02-3.27 (m, 6H), 3.34-3.48 (m, 1H), 3.48-3.71 (m, 3H), 3.71-3.94 (m, 7H), 6.48-6.61 (m, 1H), 6.68-6.79 (m, 1H), 6.84-6.97 (m, 1H), 7.18-7.43 (m, 2H), 7.78-8.08 (m, 1H), 8.26-8.53 (m, 1H), 9.14-9.44 (m, 1H), 10.49-10.74 (m, 1H), 10.80-11.08 (m, 1H)

EXAMPLE 170

2-[4-(4-methyl-piperazin-1-yl)-2-methoxy-phenylamino]-4-((S)-4-oxo-2,3,10,10a-tetrahydro-1H.4H-9-oxa-3a-aza-benzo[f]azulen-5-ylamino-5-trifluoromethyl-pyrimidine

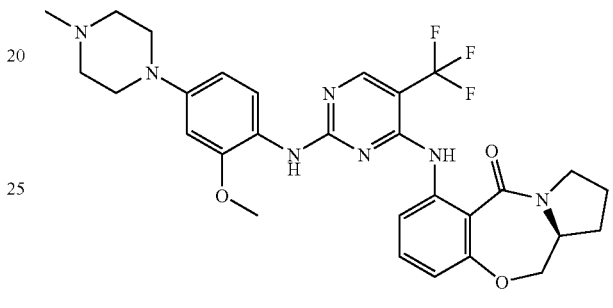

To prepare this compound formaldehyde is used instead of acetaldehyde. Otherwise the method is as in Example 169.

Yield: 16 mg (0.024 mmol; 28%) UV max: 278 nm MS (ESI): 584 (M+H)+$^1$H-NMR: 1.58-1.71 (m, 1H), 1.81-2.06 (m, 3H), 2.78-2.88 (m, 3H), 3.00-3.23 (m, 4H), 4.03-4.21 (m, 2H), 6.48-6.59 (m, 1H), 6.69-6.78 (m, 1H), 6.80-6.91 (m, 1H), 7.17-7.44 (m, 2H), 7.92-8.15 (m, 1H), 8.34 (s, 1H), 8.86-9.04 (m, 1H), 10.38-10.64 (m, 2H)

EXAMPLES 171-180

The following Examples are prepared analogously to Example 169 and 170. The corresponding aniline is described in the supplements to method 10.

| # | A | D | UV max [nm] | MS (ESI) (M + H)+ |
|---|---|---|---|---|
| 171 | ![X1 structure] | X2 | 226, 282 | 572 |

-continued
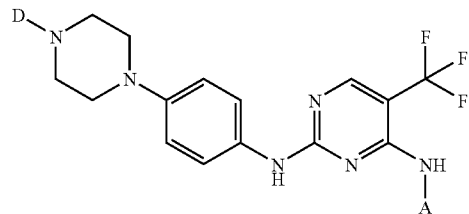
| # | A | D | UV max [nm] | MS (ESI) (M + H)+ |
|---|---|---|---|---|
| 172 | | | 250, 282 | 586 |
| 173 | | | 250, 282 | 596 |
| 174 | | | 250, 282 | 600 |
| 175 | | | 282 | 544 |
| 176 | | | 282 | 558 |
| 177 | | | 218; 282 | 586 |
| 178 | | | 282 | 582 |

-continued

| # | A | D | UV max [nm] | MS (ESI) (M + H)+ |
|---|---|---|---|---|
| 179 | (structure with ethyl, benzoxazepinone, X1) | H—X2 | 226 | 558 |
| 180 | (structure with propyl, benzoxazepinone, X1) | H—X2 | 226 | 572 |

EXAMPLES 181-332

The following compounds are prepared by an analogous process to that described in Example 53. 2-(4-Carboxy-2-methoxy-phenylamino)-4-chloro-5-trifluoromethyl-pyrimidine may be obtained according to method 12 or 14. The corresponding aniline described in method 11. The amine used to prepare the amide is commercially obtainable or described in method 13, 15 and 25.

| # | A | R3' | UV max [nm] | MS (ESI) (M + H)+ |
|---|---|---|---|---|
| 181 | (benzodiazepinedione with benzyl and X1) | (cyclohexyl-morpholine with X2) | 318, 282, 234 | 380 |

-continued
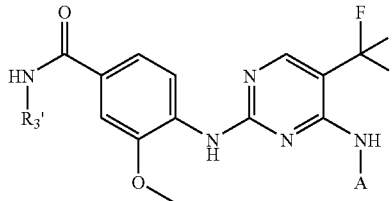
| # | A | R3' | UV max [nm] | MS (ESI) (M + H)+ |
|---|---|---|---|---|
| 182 | 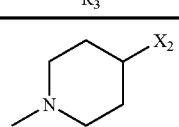 | 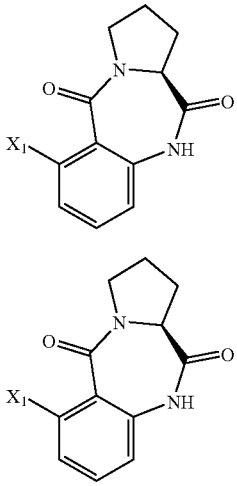 | 238 | 639 |
| 183 | 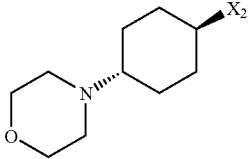 | 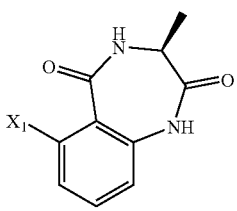 | 234; 318 | 709 |
| 184 | 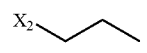 | 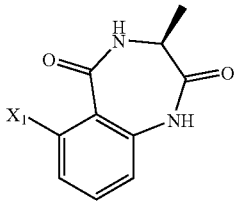 | 318, 282, 248 | 558 |
| 185 | 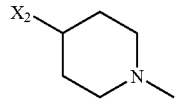 | 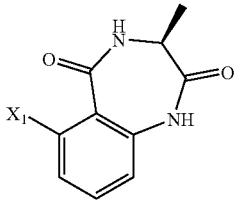 | 318, 280 | 613 |
| 186 | 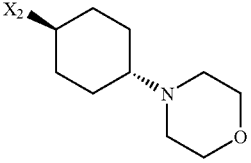 | 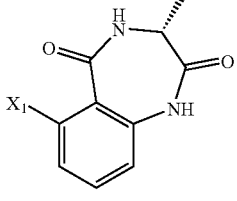 | 316, 282, 234 | 342 |
| 187 | 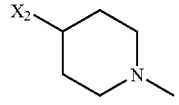 | | 318, 284, 238 | 307 |

-continued
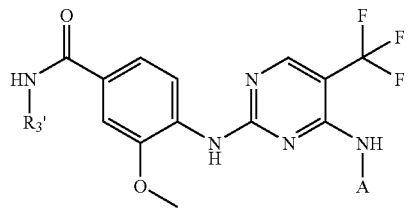
| # | A | R₃' | UV max [nm] | MS (ESI) (M + H)⁺ |
|---|---|-----|-------------|-------------------|
| 188 | | | 318, 282, 242 | 342 |
| 189 | | | 314, 282, 242 | 600 |
| 190 | | | 318, 282, 234 | 328 |
| 191 | | | 318 | 363 |
| 192 | | | 318, 230 | 650 |

-continued

| # | A | R₃' | UV max [nm] | MS (ESI) (M + H)⁺ |
|---|---|---|---|---|
| 193 | benzyl-substituted benzodiazepinedione with X₁ | X₂-propyl | 314 | 634 |
| 194 | benzyl-substituted benzodiazepinedione with X₁ | X₂-(1-methylpiperidin-4-yl) | 318 | 634 |
| 195 | isopropyl-substituted benzodiazepinedione with X₁ | X₂-(4-morpholinocyclohexyl) | 318 | 671 |
| 196 | benzyl-substituted benzodiazepinedione with X₁ | X₂-(4-morpholinocyclohexyl) | 318, 230 | 380 |
| 197 | methyl-substituted benzodiazepinedione with X₁ | X₂-propyl | 314, 282, 250 | 558 |

-continued

| # | A | R₃' | UV max [nm] | MS (ESI) (M + H)⁺ |
|---|---|---|---|---|
| 198 | (benzodiazepinedione with tyrosine-like side chain, X₁) | X₂-(1-methylpiperidin-4-yl) | 319 | 705 |
| 199 | (benzodiazepinedione with tyrosine-like side chain, X₁) | X₂-(4-morpholinocyclohexyl) | 318, 226 | 775 |
| 200 | (benzodiazepinedione with isopropyl side chain, X₁) | X₂-(1-methylpiperidin-4-yl) | 318 | 634 |
| 201 | (benzodiazepinedione with isopropyl side chain, X₁) | X₂-propyl | 314 | 634 |
| 202 | (pyrrolidine-fused benzodiazepinedione, X₁) | X₂-propyl | 230; 318 | 584 |

-continued
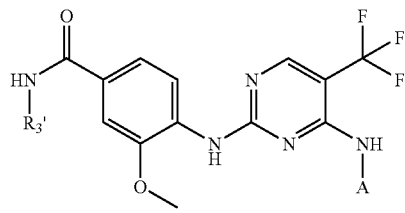
| # | A | R₃' | UV max [nm] | MS (ESI) (M + H)⁺ |
|---|---|---|---|---|
| 203 | | | 317 | 572 |
| 204 | | | 318, 230 | 697 |
| 205 | | | 318, 234 | 544 |
| 206 | | | 318 | 669 |
| 207 | | | 318, 230 | 650 |
| 208 | | | 317 | 627 |

-continued

| # | A | R$_3$' | UV max [nm] | MS (ESI) (M + H)$^+$ |
|---|---|---|---|---|
| 209 | (benzodiazepinedione with X$_1$) | X$_2$-(N-methylpiperidin-4-yl) | 318, 230 | 599 |
| 210 | (benzodiazepinedione with X$_1$ and 4-hydroxybenzyl) | X$_2$-(N-methylpiperidin-4-yl) | 318, 230 | 705 |
| 211 | (pyrrolo-benzodiazepinedione with X$_1$) | (N-ethylpyrrolidin-2-yl)methyl-X$_2$ | 230; 322 | 653 |
| 212 | (pyrrolo-benzodiazepinedione with X$_1$) | morpholino-ethyl-X$_2$ | 230; 322 | 655 |
| 213 | (pyrrolo-benzodiazepinedione with X$_1$) | morpholino-propyl-X$_2$ | 230; 318 | 669 |
| 214 | (benzodiazepinedione with X$_1$ and isobutyl) | X$_2$-propyl | 230, 282, 314 | 634 |

-continued
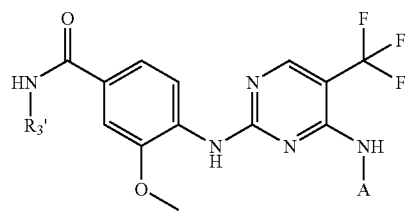
| # | A | R₃' | UV max [nm] | MS (ESI) (M + H)⁺ |
|---|---|---|---|---|
| 215 | | | 318 | 655 |
| 216 | | | 318, 234 | 725 |
| 217 | | | 314, 235 | 586 |
| 218 | | | 318, 230 | 641 |
| 219 | | | 318, 226 | 711 |

-continued

| # | A | R₃' | UV max [nm] | MS (ESI) (M + H)⁺ |
|---|---|---|---|---|
| 220 | [benzodiazepinedione with cyclohexylmethyl substituent, X₁] | X₂–propyl | 318, 230 | 640 |
| 221 | [benzodiazepinedione with cyclohexylmethyl substituent, X₁] | X₂–cyclohexyl–morpholine | 318 | 765 |
| 222 | [pyrrolo-benzodiazepinedione with OH substituent, X₁] | X₂–propyl | 318 | 600 |
| 223 | [benzodiazepinedione with indolylmethyl substituent, X₁] | X₂–propyl | 315 | 673 |
| 224 | [benzodiazepinedione with indolylmethyl substituent, X₁] | X₂–(1-methylpiperidin-4-yl) | 319, 226 | 728 |

-continued
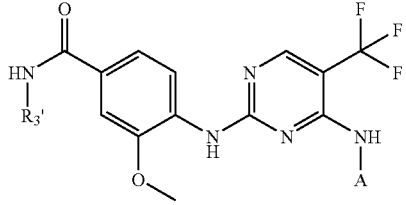
| # | A | R₃' | UV max [nm] | MS (ESI) (M + H)⁺ |
|---|---|---|---|---|
| 225 |  | 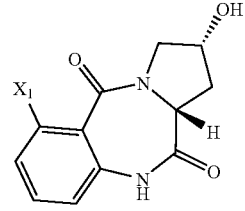 | 318, 226 | 798 |
| 226 | 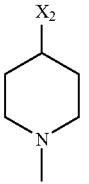 | 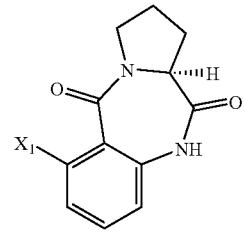 | 318, 234 | 655 |
| 227 | 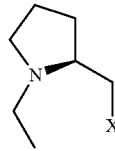 | 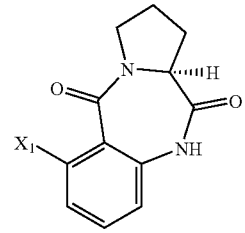 | 230; 322 | 653 |
| 228 | 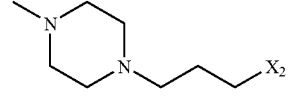 | 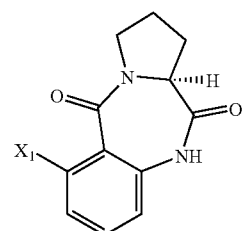 | 230; 318 | 682 |
| 229 | 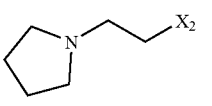 | | 234; 318 | 639 |

-continued
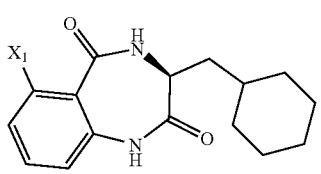
| # | A | R3' | UV max [nm] | MS (ESI) (M + H)+ |
|---|---|---|---|---|
| 230 | 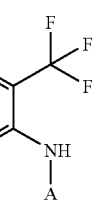 | 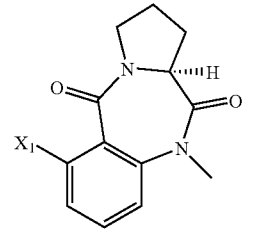 | 318, 226 | 695 |
| 231 | 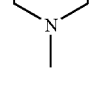 | 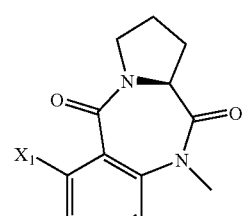 | 234, 282, 318 | 598 |
| 232 | 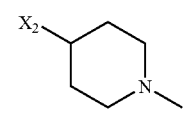 | 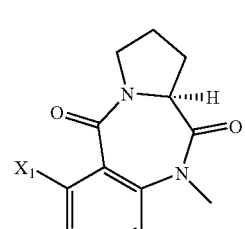 | 230, 282, 318 | 653 |
| 233 | 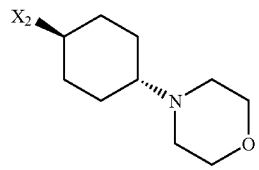 | 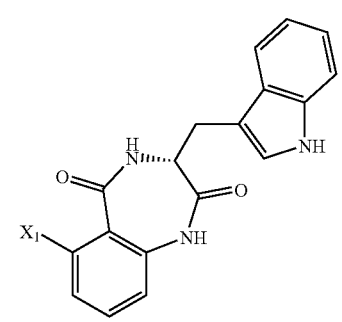 | 234, 282, 318 | 723 |
| 234 | 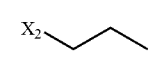 | 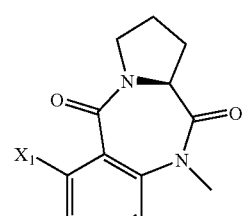 | 318, 222 | 673 |

-continued

| # | A | R₃' | UV max [nm] | MS (ESI) (M + H)⁺ |
|---|---|---|---|---|
| 235 | (pyrrolo-benzodiazepine-dione with OH, X₁) | cyclohexyl-morpholine-X₂ | 318 | 725 |
| 236 | (benzodiazepine-dione with indolylmethyl, X₁) | cyclohexyl-morpholine-X₂ | 318, 282, 226 | 798 |
| 237 | (benzodiazepine-dione with propyl, X₁) | N-methylpiperidine-X₂ | 230; 318 | 641 |
| 238 | (benzodiazepine-dione with propyl, X₁) | morpholine-cyclohexyl-X₂ | 230; 318 | 711 |
| 239 | (benzodiazepine-dione with propyl, X₁) | propyl-X₂ | 234; 318 | 586 |

-continued

| # | A | R₃' | UV max [nm] | MS (ESI) (M + H)⁺ |
|---|---|---|---|---|
| 240 | | | 318, 226 | 745 |
| 241 | | | 322 | 703 |
| 242 | | | 320, 226 | 732 |
| 243 | | | 321, 221 | 694 |
| 244 | | | 230, 282, 318 | 652 |

-continued
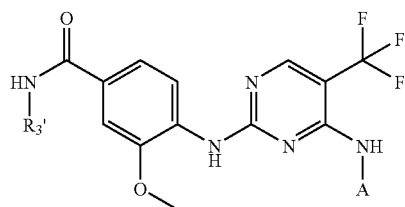
| # | A | R₃' | UV max [nm] | MS (ESI) (M + H)⁺ |
|---|---|---|---|---|
| 245 | | X₂-(1-methylpiperidin-4-yl) | 234, 282, 318 | 707 |
| 246 | | X₂-(4-morpholinocyclohexyl) | 230, 282, 318 | 777 |
| 247 | | X₂-propyl | 230, 282, 318 | 630 |
| 248 | | X₂-(1-methylpiperidin-4-yl) | 234, 282, 318 | 685 |

-continued

| # | A | R₃' | UV max [nm] | MS (ESI) (M + H)⁺ |
|---|---|---|---|---|
| 249 | | | 234, 282, 318 | 755 |
| 250 | | | 230, 282, 318 | 630 |
| 251 | | | 230, 282, 318 | 685 |
| 252 | | | 230, 282, 318 | 755 |

-continued

| # | A | R₃' | UV max [nm] | MS (ESI) (M + H)⁺ |
|---|---|-----|-------------|-------------------|
| 253 | (pyrrolidine-fused benzodiazepinedione with X₁) | 2,2,6,6-tetramethyl-1-methylpiperidin-4-yl-X₂ | 230; 318 | 695 |
| 254 | (3-fluorobenzyl benzodiazepinedione with X₁) | 1-methylpiperidin-4-yl-X₂ | 230; 318 | 70 |
| 255 | (3-fluorobenzyl benzodiazepinedione with X₁) | 4-morpholinocyclohexyl-X₂ | 230; 318 | 389 |
| 256 | (3-fluorobenzyl benzodiazepinedione with X₁) | propyl-X₂ | 230; 318 | 652 |

-continued
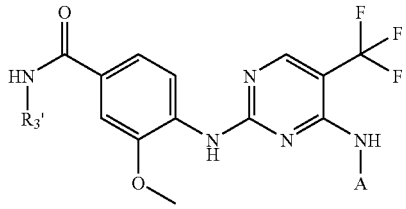
| # | A | R3' | UV max [nm] | MS (ESI) (M + H)+ |
|---|---|---|---|---|
| 257 | 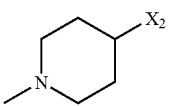 | 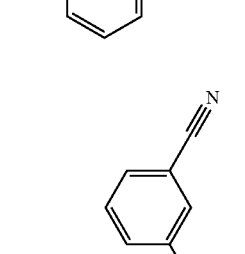 | 230 | 357 |
| 258 | 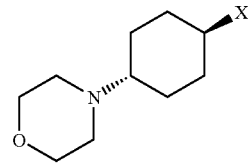 | 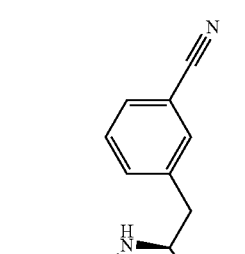 | 230 | 784 |
| 259 | 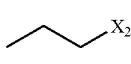 | (propyl-X2) | 230 | 659 |

-continued
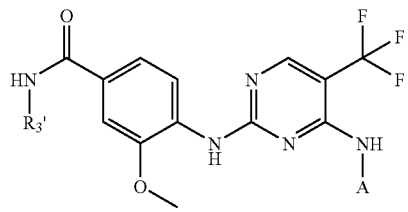
| # | A | R₃' | UV max [nm] | MS (ESI) (M + H)⁺ |
|---|---|---|---|---|
| 260 | | | 319, 230 | 689 |
| 261 | | | 322 | 703 |
| 262 | | | 322 | 705 |
| 263 | | | 320 | 719 |
| 264 | | | 226 | 690 |

-continued

| # | A | R$_3$' | UV max [nm] | MS (ESI) (M + H)$^+$ |
|---|---|---|---|---|
| 265 | | | 226; 318 | 760 |
| 266 | | | 230 | 635 |
| 267 | | | 230; 318 | 381 |
| 268 | | | 318 | 812 |
| 269 | | | 318 | 652 |

-continued
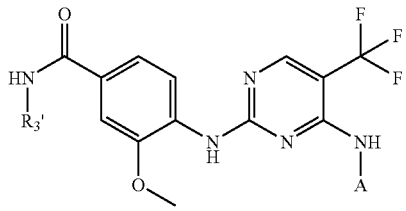
| # | A | R₃' | UV max [nm] | MS (ESI) (M + H)⁺ |
|---|---|---|---|---|
| 270 | 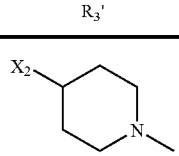 | 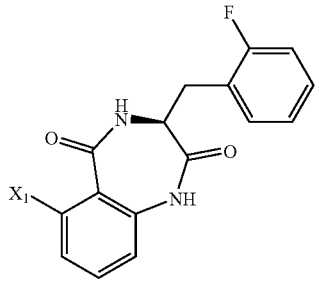 | 318 | 707 |
| 271 | 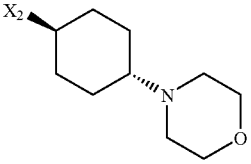 | 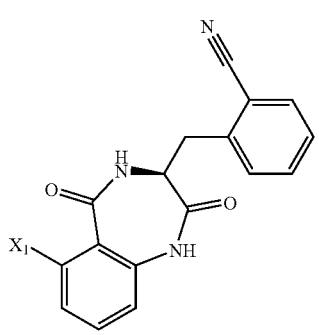 | 318, 226 | 777 |
| 272 | 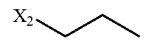 | 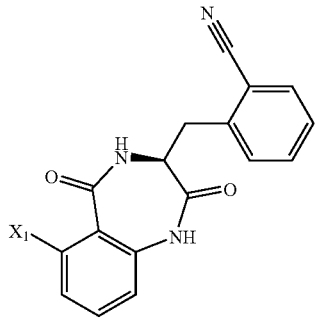 | 318 | 659 |
| 273 | 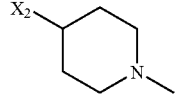 | 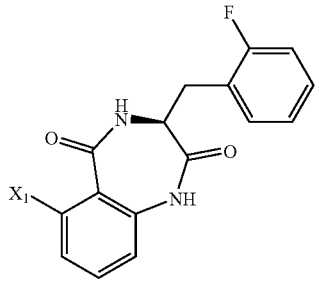 | 318 | 714 |

-continued

| # | A | R₃' | UV max [nm] | MS (ESI) (M + H)⁺ |
|---|---|---|---|---|
| 274 | (S)-3-(4-chlorobenzyl)-8-X₁-2,5-dioxo-2,3,4,5-tetrahydro-1H-benzo[e][1,4]diazepine | X₂-propyl | 315, 239 | 669 |
| 275 | (S)-3-(4-chlorobenzyl)-8-X₁-2,5-dioxo-2,3,4,5-tetrahydro-1H-benzo[e][1,4]diazepine | X₂-(1-methylpiperidin-4-yl) | 319, 222 | 723 |
| 276 | (S)-3-(4-chlorobenzyl)-8-X₁-2,5-dioxo-2,3,4,5-tetrahydro-1H-benzo[e][1,4]diazepine | X₂-(trans-4-morpholinocyclohexyl) | 318, 226 | 793 |
| 277 | (S)-3-phenyl-8-X₁-2,5-dioxo-2,3,4,5-tetrahydro-1H-benzo[e][1,4]diazepine | X₂-propyl | 316 | 620 |
| 278 | (S)-3-phenyl-8-X₁-2,5-dioxo-2,3,4,5-tetrahydro-1H-benzo[e][1,4]diazepine | X₂-(1-methylpiperidin-4-yl) | 318 | 675 |

-continued

| # | A | R₃' | UV max [nm] | MS (ESI) (M + H)⁺ |
|---|---|---|---|---|
| 279 | | | 318, 226 | 745 |
| 280 | | | 317, 226 | 620 |
| 281 | | | 318 | 675 |
| 282 | | | 318, 230 | 745 |

-continued
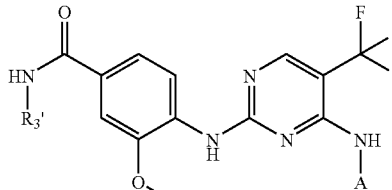
| # | A | R₃' | UV max [nm] | MS (ESI) (M + H)⁺ |
|---|---|---|---|---|
| 283 | 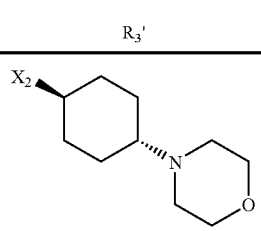 | 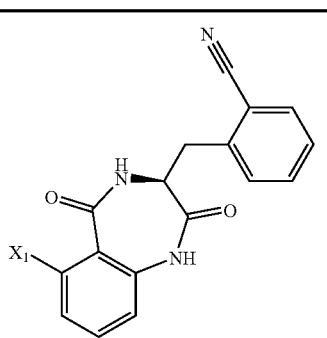 | 318 | 784 |
| 284 | 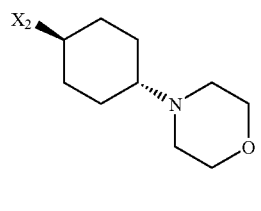 | 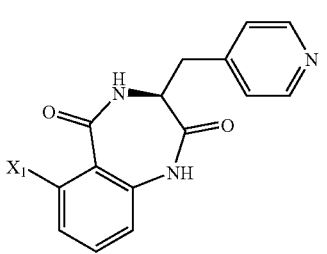 | 318 | 758 |
| 285 | 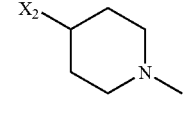 | 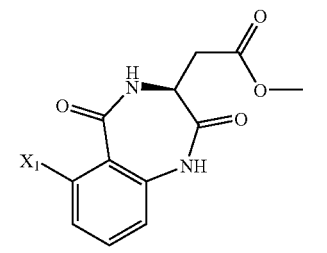 | 318 | 688 |
| 286 | 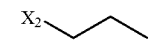 | 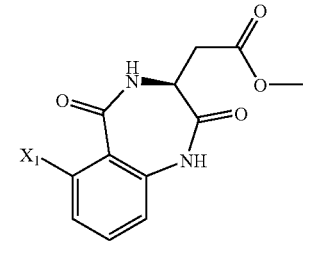 | 238, 282, 314 | 616 |
| 287 | 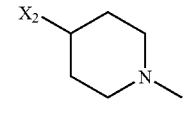 | | 230, 282, 318 | 671 |

-continued

| # | A | R₃' | UV max [nm] | MS (ESI) (M + H)⁺ |
|---|---|---|---|---|
| 288 | (benzodiazepinedione with methyl ester side chain, X₁) | X₂-cyclohexyl-morpholine | 230, 282, 318 | 741 |
| 289 | (benzodiazepinedione with methyl ester side chain, X₁) | X₂-propyl | 234, 282, 318 | 616 |
| 290 | (benzodiazepinedione with methyl ester side chain, X₁) | X₂-N-methylpiperidinyl | 226, 282, 318 | 671 |
| 291 | (benzodiazepinedione with methyl ester side chain, X₁) | X₂-cyclohexyl-morpholine | 234, 282, 318 | 741 |
| 292 | (N-methyl benzodiazepinedione with benzyl side chain, X₁) | X₂-propyl | 234, 282, 318 | 648 |

-continued
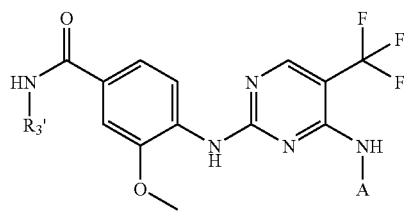
| # | A | R₃' | UV max [nm] | MS (ESI) (M + H)⁺ |
|---|---|---|---|---|
| 293 | | | 230, 282, 318 | 703 |
| 294 | | | 226, 282, 318 | 773 |
| 295 | | | 226, 282, 318 | 893 |
| 296 | | | 226, 282, 318 | 727 |

-continued

| # | A | R₃' | UV max [nm] | MS (ESI) (M + H)⁺ |
|---|---|-----|-------------|-------------------|
| 297 | | | 226, 282, 318 | 754 |
| 298 | | | 230, 282, 318 | 823 |
| 299 | | | 282, 318 | 669 |
| 300 | | | 282, 318 | 613 |
| 301 | | | 282, 318 | 641 |

-continued

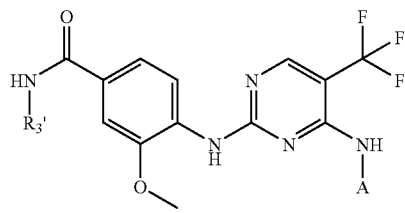

| # | A | R₃' | UV max [nm] | MS (ESI) (M + H)⁺ |
|---|---|---|---|---|
| 302 | (X₁-substituted benzodiazepinedione with spirocyclobutane) | (X₂-CH₂CH₂-pyrrolidine) | 286, 318 | 639 |
| 303 | (X₁-substituted benzodiazepinedione with gem-dimethyl) | (X₂-CH₂CH₂-pyrrolidine) | 286, 318 | 627 |
| 304 | (X₁-substituted benzodiazepinedione with gem-dimethyl) | (X₂-CH₂CH₂CH₂-piperidine) | 286, 318 | 655 |
| 305 | (X₁-substituted benzodiazepinedione with spirocyclobutane) | (X₂-CH₂CH₂CH₂-piperidine) | 286, 318 | 667 |
| 306 | (X₁-substituted benzodiazepinedione with benzyl) | (X₂-CH₂CH₂CH₂-piperidine) | 286, 318 | 717 |
| 307 | (X₁-substituted benzodiazepinedione with benzyl) | (X₂-CH₂CH₂-pyrrolidine) | 286, 318 | 689 |

-continued

| # | A | R₃' | UV max [nm] | MS (ESI) (M + H)⁺ |
|---|---|---|---|---|
| 308 | | | 286, 318 | 665 |
| 309 | | | 230, 286, 318 | 653 |
| 310 | | | 230, 282, 318 | 715 |
| 311 | | | 286, 322 | 695 |
| 312 | | | 234, 286, 318 | 667 |
| 313 | | | 230, 282, 318 | 639 |

-continued
| # | A | R₃' | UV max [nm] | MS (ESI) (M + H)⁺ |
|---|---|---|---|---|
| 314 | | | 230, 282, 318 | 667 |
| 315 | | | 230, 282, 318 | 681 |
| 316 | | | 230, 282, 318 | 695 |
| 317 | | | | 679 |
| 318 | | | 226, 284, 318 | 681 |

-continued
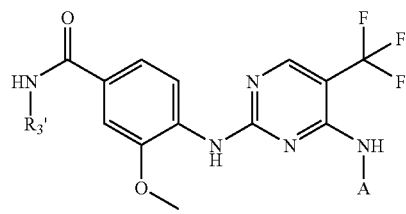
| # | A | R$_3$' | UV max [nm] | MS (ESI) (M + H)$^+$ |
|---|---|---|---|---|
| 319 | | | 230, 284, 318 | 697 |
| 320 | | | 226, 284, 314 | 750 |
| 321 | | | 230, 286, 318 | 669 |
| 322 | | | 230, 282, 318 | 693 |

-continued
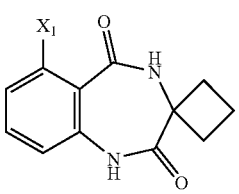
| # | A | R₃' | UV max [nm] | MS (ESI) (M + H)⁺ |
|---|---|-----|-------------|-------------------|
| 323 | 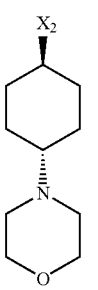 | 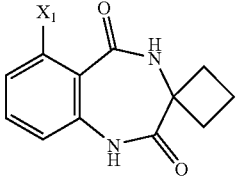 | 230, 282, 314 | 709 |
| 324 | 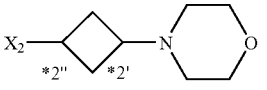 | 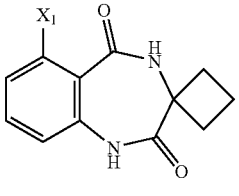 | 230, 286, 314 | 681 |
| 325 | 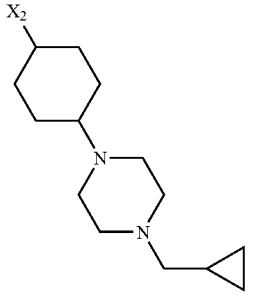 | 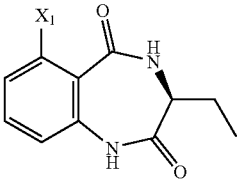 | 226, 286, 314 | 762 |
| 326 | 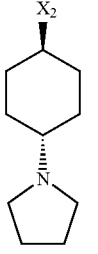 | 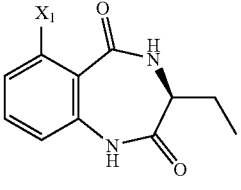 | 230, 282, 318 | 681 |
| 327 | 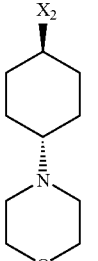 | | 230, 282, 314 | 697 |

-continued
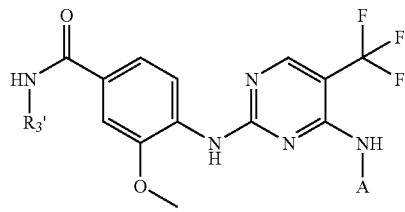
| # | A | R3' | UV max [nm] | MS (ESI) (M + H)+ |
|---|---|-----|-------------|-------------------|
| 328 | 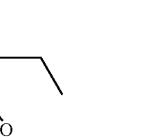 | 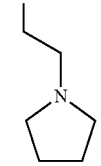 | 234, 282, 318 | 627 |
| 329 | 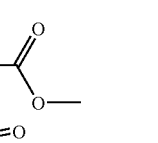 | 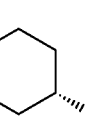 | 226, 282, 318 | 767 |
| 330 |  |  | 226, 282, 318 | 725 |
| 331 | 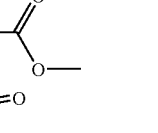 | 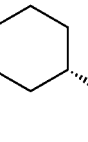 | 230, 286, 318 | 711 |
| 332 | 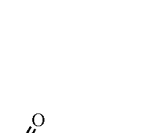 |  | 226, 282, 318 | 671 |

-continued
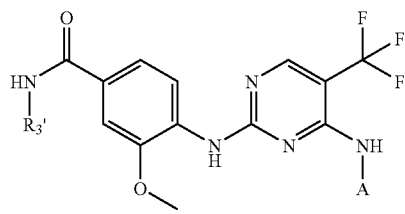
| # | A | R3' | UV max [nm] | MS (ESI) (M + H)+ |
|---|---|---|---|---|
| 333 | | | 234, 282, 314 | 718 |
| 334 | | | 234, 282, 318 | 693 |
| 335 | | | 234, 286, 318 | 653 |
| 336 | | | 284, 318 | 706 |
| 337 | | | 230, 282, 318 | 641 |
| 338 | | | 230, 282, 314 | 667 |

-continued
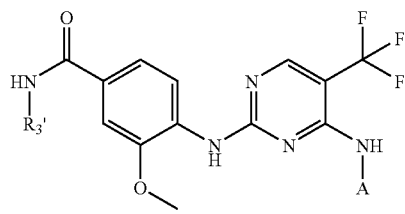
| # | A | R₃' | UV max [nm] | MS (ESI) (M + H)⁺ |
|---|---|---|---|---|
| 339 | | | 283, 318 | 655 |
| 340 | | | 230, 286, 318 | 699 |
| 341 | | | 230, 282, 318 | 750 |
| 342 | | | 230, 282, 318 | 627 |
| 343 | | | 250, 282, 318 | 667 |

-continued

| # | A | R₃' | UV max [nm] | MS (ESI) (M + H)⁺ |
|---|---|---|---|---|
| 344 | | | 230, 282, 318 | 683 |
| 345 | | | 238, 282, 314 | 641 |
| 346 | | | 230, 314 | 692 |
| 347 | | | 282, 318 | 723 |
| 348 | | | 234, 286, 314 | 653 |
| 349 | | | 286, 318 | 667 |

-continued

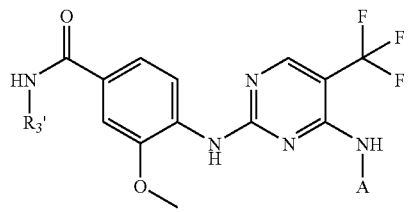

| # | A | R₃' | UV max [nm] | MS (ESI) (M + H)⁺ |
|---|---|---|---|---|
| 350 | ![A350] | ![R350] | 234, 286, 314 | 718 |
| 351 | ![A351] | ![R351] | 230, 286, 318 | 685 |

EXAMPLES 352-372

The following compounds are prepared by an analogous process to that described in Example 53 described, prepared. 2-(4-carboxy-phenylamino)-4-chloro-5-trifluoromethyl-pyrimidine may after method 14 prepared are. The corresponding aniline is in method 11 described. The amine used to prepare the amide is commercially obtainable or is in method 13, 15 or 25 described.

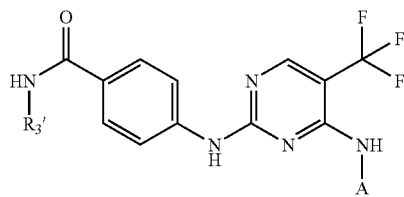

| # | A | R₃' | UV max [nm] | MS (ESI) (M + H)⁺ |
|---|---|---|---|---|
| 352 | ![A352] | ![R352] | 222, 302 | 688 |

-continued
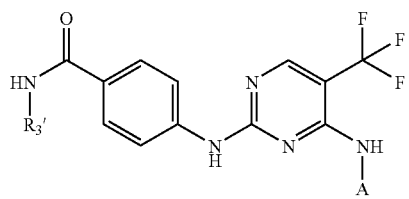
| # | A | R₃' | UV max [nm] | MS (ESI) (M + H)⁺ |
|---|---|---|---|---|
| 353 | | | 246, 298 | 663 |
| 354 | | | 234, 298 | 679 |
| 355 | | | 234, 302 | 623 |
| 356 | | | 298 | 611 |
| 357 | | | 246, 302 | 676 |

-continued
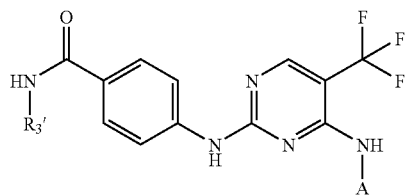
| # | A | R$_3$' | UV max [nm] | MS (ESI) (M + H)$^+$ |
|---|---|---|---|---|
| 358 | | | | 651 |
| 359 | | | | 667 |
| 360 | | | 246, 302 | 611 |
| 361 | | *2″ *2′ | 298 | 662 |
| 362 | | | | 637 |

-continued
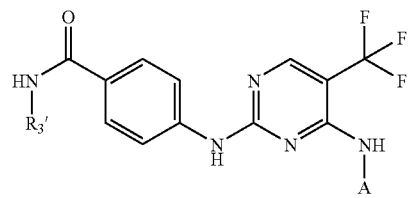
| # | A | R₃' | UV max [nm] | MS (ESI) (M + H)⁺ |
|---|---|-----|-------------|-------------------|
| 363 | | | 234, 298 | 653 |
| 364 | | | 226, 302 | 597 |
| 365 | | | 302 | 637 |
| 366 | | | 246, 302 | 625 |
| 367 | | | 302 | 695 |

-continued

| # | A | R₃' | UV max [nm] | MS (ESI) (M + H)⁺ |
|---|---|---|---|---|
| 368 | | | 302 | 711 |
| 369 | | | 302 | 669 |
| 370 | | | 302 | 720 |
| 371 | | | 300 | 693 |
| 372 | | | 242, 302 | 655 |

EXAMPLES 373-386
The following Examples are prepared analogously to Example 169 and 170 The corresponding aniline is described in method 11.
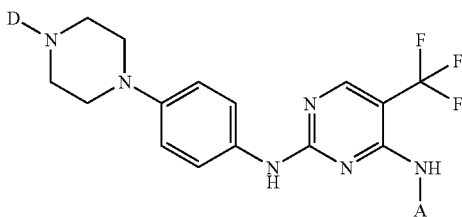
| # | A | D | UV max [nm] | MS (ESI) (M + H)+ |
|---|---|---|---|---|
| 373 | | | 246 | 621 |
| 374 | | | 246 | 611 |
| 375 | | | 234 | 639 |
| 376 | | | 238 | 597 |
| 377 | | | 250 | 599 |
| 378 | | | 250 | 585 |

-continued

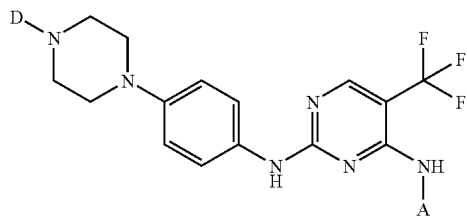

| # | A | D | UV max [nm] | MS (ESI) (M + H)+ |
|---|---|---|---|---|
| 379 | ![A structure with X1, dimethyl benzodiazepinedione] | ![isobutyl-X2] | 250 | 613 |
| 380 | ![A structure with X1, dimethyl benzodiazepinedione] | ![propargyl-X2] | 250 | 609 |
| 381 | ![A structure with X1, pyrrolidine-fused benzodiazepinone] | ![isobutyl-X2] | 246 | 625 |
| 382 | ![A structure with X1, methyl benzodiazepinedione] | ![isobutyl-X2] | 250 | 599 |
| 383 | ![A structure with X1, methyl benzodiazepinedione] | ![ethyl-X2] | 230 | 571 |
| 384 | ![A structure with X1, methyl benzodiazepinedione] | ![propargyl-X2] | 246 | 595 |

-continued

| # | A | D | UV max [nm] | MS (ESI) (M + H)+ |
|---|---|---|---|---|
| 385 | (structure with X₁, benzodiazepinedione with methyl) | (ethyl-X₂) | 250 | 585 |
| 386 | (structure with X₁, benzodiazepinedione with CH₂CO₂Me) | (H-X₂) | 246, 286 | 615 |

EXAMPLES 387-388

The following compounds are prepared by an analogous process to that described in Example 53. 2-(4-Carboxy-2-methoxy-phenylamino)-4-chloro-5-trifluoromethyl-pyrimidine may be prepared according to method 12 or 14. The corresponding aniline is described in method 4 or method 17. The amine used to prepare the amide is commercially obtainable.

| # | A | R₃' | UV max [nm] | MS (ESI) (M + H)+ |
|---|---|---|---|---|
| 387 | (quinazolinone with X₁) | (pyrrolidinyl-ethyl-X₂) | 262, 318 | 569 |
| 388 | (quinazolinone with X₁ and fluoroethyl N-substituent) | (pyrrolidinyl-ethyl-X₂) | 278, 318 | 615 |

EXAMPLES 389-404

The following compounds are prepared by an analogous process to that described in Example 53. 2-(4-Carboxy-2-methoxy-phenylamino)-4-chloro-5-trifluoromethyl-pyrimidine may be prepared according to method 12 or 14. The corresponding aniline is described in method 7, in method 18 or 19. The amine used to prepare the amide is commercially obtainable or is described in method 13.

| # | A | R₃' | UV max [nm] | MS (ESI) (M + H)⁺ |
|---|---|---|---|---|
| 389 | 8-X₁ 4-ethyl dihydroisoquinolinone | 4-morpholinocyclohexyl-X₂ | 284, 322 | 668 |
| 390 | 8-X₁ 4-(3-hydroxypropyl) dihydroisoquinolinone | 4-morpholinocyclohexyl-X₂ | 230, 285, 325 | 698 |
| 391 | 8-X₁ 4-benzyl dihydroisoquinolinone | 4-morpholinocyclohexyl-X₂ | 280, 325 | 730 |
| 392 | 8-X₁ 4-isopropyl dihydroisoquinolinone | 4-morpholinocyclohexyl-X₂ | 230, 285, 325 | 682 |
| 393 | 8-X₁ N-(2-fluoroethyl) dihydroisoquinolinone | (S)-1-ethyl-2-(X₂-methyl)pyrrolidine | 285, 325 | 630 |

-continued

| # | A | R₃' | UV max [nm] | MS (ESI) (M + H)⁺ |
|---|---|-----|-------------|-------------------|
| 394 | 8-X₁-2-(2-fluoroethyl)-3,4-dihydroisoquinolin-1(2H)-one | 4-morpholinocyclohexyl-X₂ | 284, 322 | 686 |
| 395 | 8-X₁-2-(2-fluoroethyl)-3,4-dihydroisoquinolin-1(2H)-one | 2-(pyrrolidin-1-yl)ethyl-X₂ | 285, 325 | 616 |
| 396 | 8-X₁-2-methyl-3,4-dihydroisoquinolin-1(2H)-one | 4-morpholinocyclohexyl-X₂ | 285, 322 | 654 |
| 397 | 8-X₁-2-methyl-3,4-dihydroisoquinolin-1(2H)-one | 2-(pyrrolidin-1-yl)ethyl-X₂ | 285, 325 | 584 |
| 398 | 8-X₁-2-methyl-3,4-dihydroisoquinolin-1(2H)-one | (1-ethylpyrrolidin-2-yl)methyl-X₂ | 285, 325 | 598 |
| 399 | 8-X₁-2,4-dimethyl-3,4-dihydroisoquinolin-1(2H)-one | 4-morpholinocyclohexyl-X₂ | 285, 325 | 668 |

-continued

| # | A | R₃' | UV max [nm] | MS (ESI) (M + H)⁺ |
|---|---|---|---|---|
| 400 | 8-X₁, 2-methyl, 4-methyl-3,4-dihydroisoquinolin-1(2H)-one | 1-(2-X₂-ethyl)pyrrolidine | 285, 325 | 598 |
| 401 | 8-X₁, 2-methyl, 4-methyl-3,4-dihydroisoquinolin-1(2H)-one | (S)-1-ethyl-2-(X₂-methyl)pyrrolidine | 285, 325 | 612 |
| 402 | 8-X₁, 2-(2-fluoroethyl), 4-methyl-3,4-dihydroisoquinolin-1(2H)-one | 4-(4-X₂-cyclohexyl)morpholine | 285, 322 | 700 |
| 403 | 8-X₁, 2-(2-fluoroethyl), 4-methyl-3,4-dihydroisoquinolin-1(2H)-one | 1-(2-X₂-ethyl)pyrrolidine | 285, 322 | 630 |
| 404 | X₁-substituted benzo-naphthyridinone | 4-(4-X₂-cyclohexyl)morpholine | 262 | 688 |

EXAMPLE 405

2-[4-([1,4']bipiperidinyl-4-ylcarbamoyl)-2-methoxy-phenylamino]-4-(2-(2-fluoro-ethyl)-1-methyl-3-oxo-2,3-dihydro-1H-isoindol-4-ylamino)-5-trifluoromethyl-pyrimidine

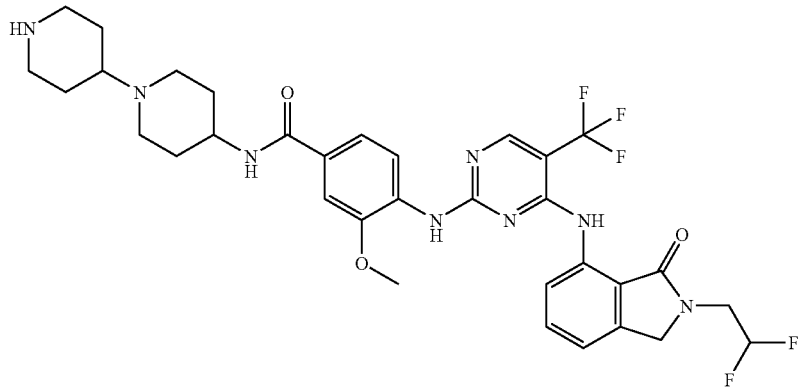

1150 mg (3.308 mmol) 2-(4-carboxy-2-methoxy-phenylamino)-4-chloro-5-trifluoromethyl-pyrimidine (method 12 or 14) are dissolved in 2,5 ml N-methyl-2-pyrrolidinone and combined with 883 mg (4.161 mmol) 7-amino-2-(2,2-difluoro-ethyl)-2,3-dihydro-isoindol-1-one (method 2). 115 μl of a 4 M solution of HCl (0.460 mmol) in 1,4-dioxane are metered into this reaction mixture. After 16 h at 90° C. the reaction mixture is stirred into 150 ml of an aqueous 1 N hydrochloric acid. The precipitate is filtered off and dried in vacuo.

Yield: 1626 mg (3.110 mmol; 94%) MS (ESI): 524 (M+H)$^+$ 100 mg (0.191 mmol) of this precipitate, 240 μl (1.402 mmol) N-ethyldiisopropylamine, 89 mg (0.279 mmol) O-(benzotriazol-1-yl)-N,N,N',N'-tetramethyluronium-tetrafluoroborate and 76 mg (0.267 mmol) tert-butyl 4-amino-[1,4']bipiperidinyl-1'-carboxylate are dissolved in 3 ml N,N-dimethylformamide. After 15 h at 20° C. the solvent is eliminated in vacuo. The residue is taken up in 20 ml dichloromethane and 5 ml of methanol and filtered through aluminium oxide. The aluminium oxide is washed several times with a mixture of dichloromethane and methanol (4:1). The solvent of the combined fractions is eliminated in vacuo. The residue is dissolved in 5 ml dichloromethane and combined with 5 ml trifluoroacetic acid. This mixture is stirred for 3 h at 20° C. and then the solvent is eliminated in vacuo. The crude product is purified by column chromatography. The carrier material used is C18-RP-silica gel and a gradient is run through which consists of 90% water and 10% acetonitrile at the starting point and 5% water and 95% acetonitrile at the finishing point. 0.1% formic acid are added both to the water and to the acetonitrile. The suitable fractions are combined with 500 μl of a 1 N hydrochloric acid and freeze-dried. The product is obtained as the trihydrochloride.

Yield: 42 mg (0.053 mmol; 28%) UV max: 322 nm MS (ESI): 689 (M+H)$^{+1}$H-NMR: 1.92-2.19 (m, 6H), 2.28-2.37 (m, 2H), 2.86-3.00 (m, 2H), 3.07-3.19 (m, 3H), 3.84-4.18 (m, 7H), 4.59 (s, 2H), 6.15-6.47 (m, 1H), 7.23-7.28 (m, 1H), 7.35-7.43 (m, 1H), 7.54-7.64 (m, 2H), 7.75-7.82 (m, 1H), 8.40-8.64 (m, 3H), 8.90-9.01 (m, 1H), 9.10-9.25 (m, 2H), 10.40-10.47 (m, 1H), 10.91-11.27 (m, 1H)

EXAMPLES 406-407

The following compounds are prepared by an analogous process to that described in Example 405.

| # | | UV max [nm] | MS (ESI) (M + H)$^+$ |
|---|---|---|---|
| 406 | (structure shown) | 318 | 606 |

| # | | | UV max [nm] | MS (ESI) (M + H)+ |
|---|---|---|---|---|
| 407 | | | 322, 286 | 606 |

EXAMPLE 408

2-[2-methoxy-4-(1'-methyl-[1,4']bipiperidinyl-4-ylcarbamoyl)-phenylamino]-4-(2-(2-fluoro-ethyl)-1-methyl-3-oxo-2,3-dihydro-1H-isoindol-4-ylamino)-5-trifluoromethyl-pyrimidine

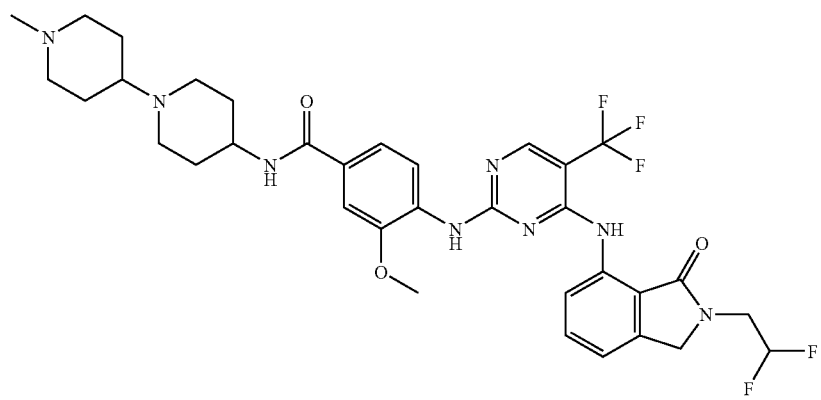

70 mg (0.087 mmol) 2-[4-([1,4']bipiperidinyl-4-ylcarbamoyl)-2-methoxy-phenylamino]4-(2-(2-fluoro-ethyl)-1-methyl-3-oxo-2,3-dihydro-1H-isoindol-4-ylamino)-5-trifluoromethyl-pyrimidine (Example 405) are dissolved in 3 ml of methanol, and combined with 8.5 μl (0.508 mmol) acetic acid and with 8 μl (0.107 mmol) of a 37% aqueous formaldehyde solution. Then at 20° C. 7.0 mg (0.112 mmol) sodium cyanoborohydride are added. This mixture is stirred for 16 h at 20° C. The solvent is eliminated in vacuo and the crude product is purified by column chromatography. The carrier material used is C18-RP-silica gel and a gradient is run through which consists at the starting point of 95% water and 5% acetonitrile and at the finishing point of 5% water and 95% acetonitrile. 0.1% formic acid are added both to the water and to the acetonitrile. The suitable fractions are combined with 500 μl of a 1 N hydrochloric acid and freeze-dried. The product is obtained as the trihydrochloride.

Yield: 18 mg (0.022 mmol; 25%) UV max: 322 nm MS (ESI): 703 (M+H)+

EXAMPLES 409-491

The following compounds are prepared by an analogous process to that described in Example 53. 2-(4-Carboxy-2-methoxy-phenylamino)-4-chloro-5-trifluoromethyl-pyrimidine may be prepared according to method 12 or 14. The corresponding aniline is described in method 2. The amine used to prepare the amide is commercially obtainable or is described in method 13, 20 or 21.

| # | A | R₃' | UV max [nm] | MS (ESI) (M + H)⁺ |
|---|---|---|---|---|
| 409 | | | 285, 320 | 584 |
| 410 | | | 322 | 716 |
| 411 | | | 326 | 703 |
| 412 | | | | 558 |
| 413 | | | 282, 318 | 699 |
| 414 | | | 322, 286 | 668 |

-continued
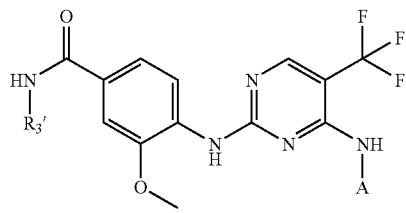
| # | A | R₃' | UV max [nm] | MS (ESI) (M + H)⁺ |
|---|---|---|---|---|
| 415 | | | 322.3 | 724 |
| 416 | | | 322.3 | 362 |
| 417 | | | 322, 286 | 738 |
| 418 | | | 322, 286 | 738 |
| 419 | | | 282, 314 | 738 |

-continued

| # | A | R₃' | UV max [nm] | MS (ESI) (M + H)⁺ |
|---|---|---|---|---|
| 420 | | | 286, 314 | 738 |
| 421 | | | 286, 318 | 700 |
| 422 | | | 286, 322 | 698 |
| 423 | | | 286, 318 | 700 |
| 424 | | | 286, 322 | 712 |
| 425 | | | 286, 322 | 724 |

-continued
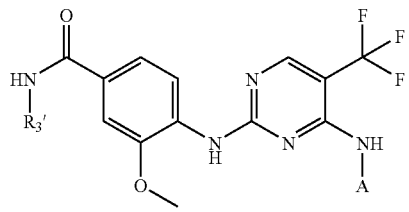
| # | A | R<sub>3</sub>' | UV max [nm] | MS (ESI) (M + H)+ |
|---|---|---|---|---|
| 426 | | | 322, 286 | 672 |
| 427 | | | 282, 322 | 723 |
| 428 | | | 322, 285 | 602 |
| 429 | | | 326.3 | 616 |
| 430 | | | 322, 286 | 616 |
| 431 | | | 318, 286 | 645 |

-continued
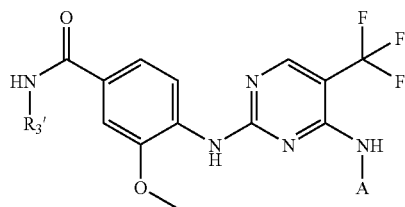
| # | A | R3' | UV max [nm] | MS (ESI) (M + H)+ |
|---|---|-----|-------------|-------------------|
| 432 | X1-(7-isoindolinone-N-CH2CH2F) | X2-CH2CH2CH2-morpholine | 321, 284 | 632 |
| 433 | X1-(7-isoindolinone-N-CH2CH2F) | X2-CH2CH2-morpholine | 322, 286 | 618 |
| 434 | X1-(7-isoindolinone-N-CH2CHF2) | X2-cyclohexyl-morpholine | 318, 282 | 690 |
| 435 | X1-(7-isoindolinone-N-CH2CF3) | X2-cyclohexyl-morpholine | 322, 282 | 708 |
| 436 | X1-(7-isoindolinone-N-CH2CH2CH2F) | X2-cyclohexyl-morpholine | 322, 286 | 686 |

-continued
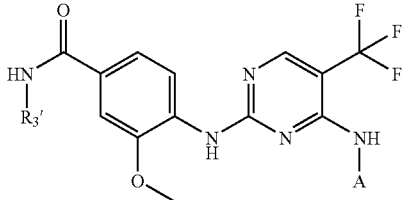
| # | A | R₃' | UV max [nm] | MS (ESI) (M + H)⁺ |
|---|---|---|---|---|
| 437 |  | 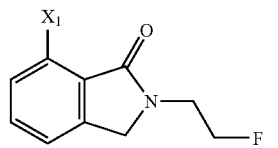 | 322, 284 | 722 |
| 438 | 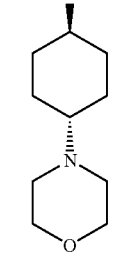 | 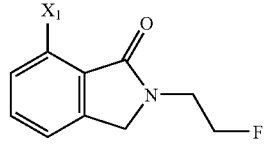 | 322, 282 | 658 |
| 439 | 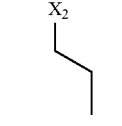 | 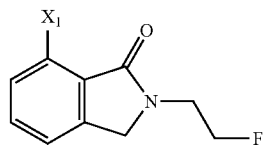 | 322, 285 | 547 |
| 440 | 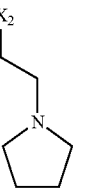 | 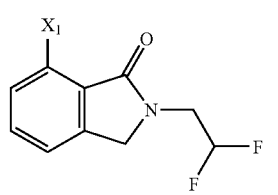 | 322, 286 | 602 |
| 441 | 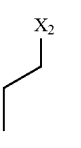 | 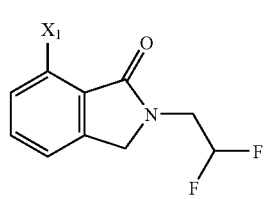 | 286.3 | 565 |
| 442 | 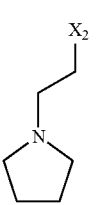 | | 322, 286 | 620 |

-continued

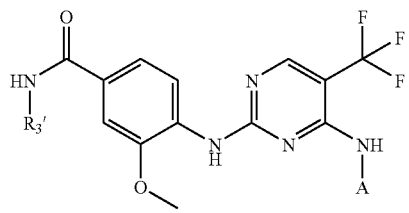

| # | A | R$_3$' | UV max [nm] | MS (ESI) (M + H)$^+$ |
|---|---|---|---|---|
| 443 | X$_1$-(2-(2-fluoroethyl)-isoindolin-1-one) | X$_2$-(trans-cyclohexyl-CH$_2$-morpholine) | 322, 284 | 686 |
| 444 | X$_1$-(2-(2,2-difluoroethyl)-isoindolin-1-one) | X$_2$-CH$_2$-(1-ethylpyrrolidin-2-yl) | 326.3 | 634 |
| 445 | X$_1$-(2-(2,2-difluoroethyl)-isoindolin-1-one) | X$_2$-CH$_2$-(1-ethylpyrrolidin-2-yl) | 326, 286 | 634 |
| 446 | X$_1$-(2-(2,2-difluoroethyl)-isoindolin-1-one) | X$_2$-(1,2,2,6,6-pentamethylpiperidin-4-yl) | 322, 284 | 676 |
| 447 | X$_1$-(2-(2,2-difluoroethyl)-isoindolin-1-one) | X$_2$-(CH$_2$)$_3$-(4-methylpiperazin-1-yl) | 322.3 | 663 |

-continued
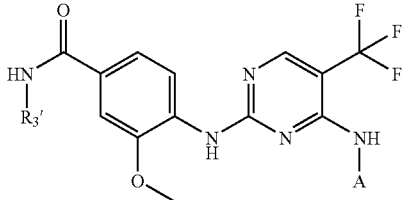
| # | A | R₃' | UV max [nm] | MS (ESI) (M + H)⁺ |
|---|---|---|---|---|
| 448 | 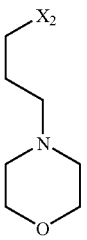 | 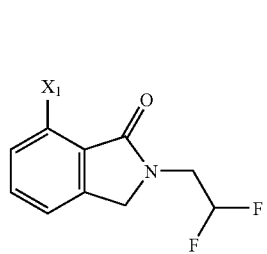 | 325.3 | 650 |
| 449 | 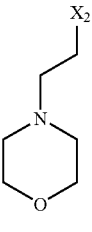 | 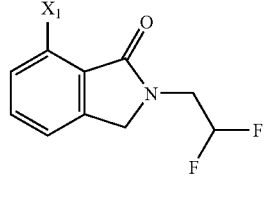 | 325.3 | 635 |
| 450 | 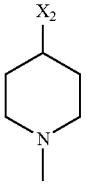 | 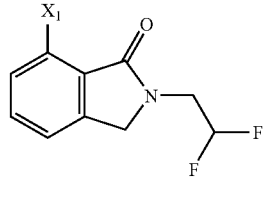 | 322, 282 | 620 |
| 451 | 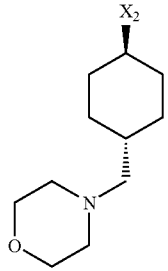 | 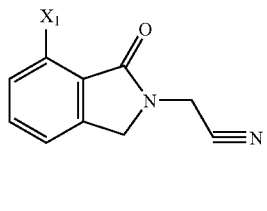 | 322, 282 | 704 |
| 452 | 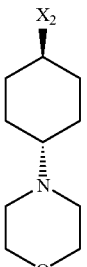 | | 322, 282 | 665 |

-continued
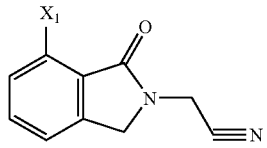
| # | A | R₃' | UV max [nm] | MS (ESI) (M + H)⁺ |
|---|---|-----|-------------|-------------------|
| 453 | 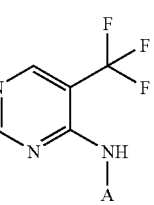 | 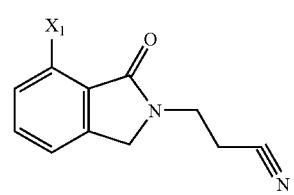 | 326, 282 | 595 |
| 454 | 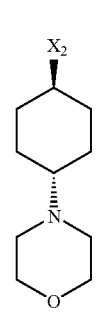 | 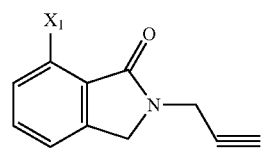 | 322, 284 | 677 |
| 455 | 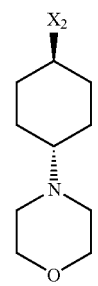 | 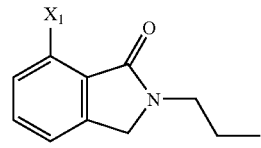 | 322.3 | 664 |
| 456 | 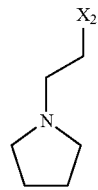 | 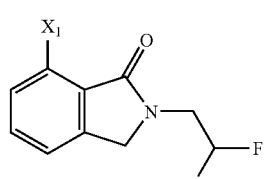 | 326, 286 | 594 |
| 457 | 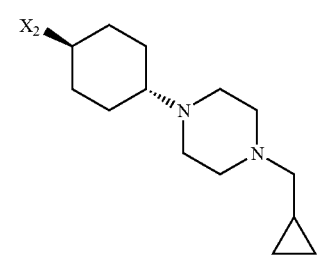 |  | 322, 282 | 743 |

-continued
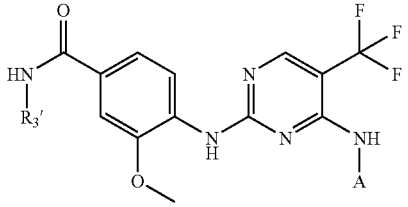
| # | A | R₃' | UV max [nm] | MS (ESI) (M + H)⁺ |
|---|---|-----|-------------|-------------------|
| 458 | 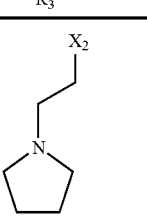 | 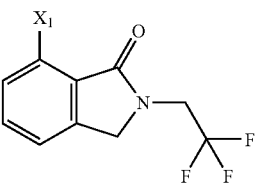 | 326, 286 | 638 |
| 459 | 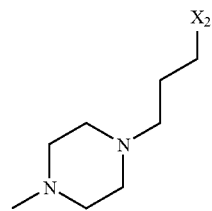 | 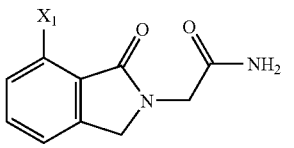 | 326, 283 | 681 |
| 460 | 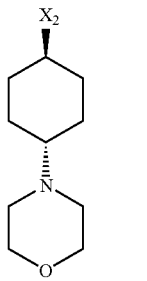 | 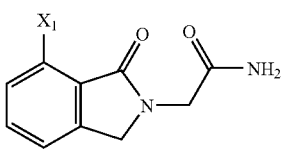 | 318, 284 | 681 |
| 461 | 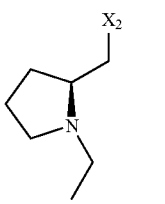 | 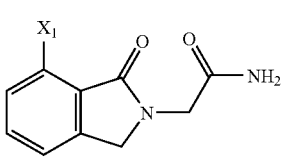 | 318, 286 | 627 |
| 462 | 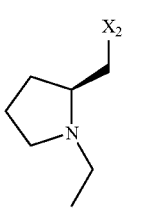 | 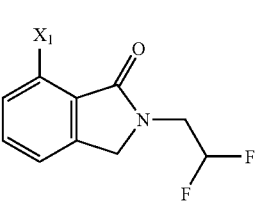 | 322, 286 | 627 |
| 463 | 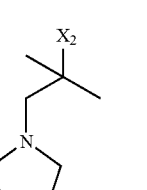 | | 326, 286 | 648 |

-continued
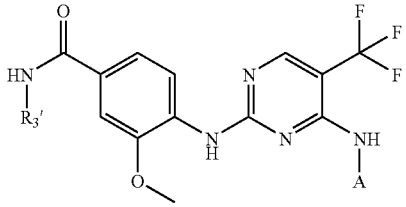
| # | A | R₃' | UV max [nm] | MS (ESI) (M + H)⁺ |
|---|---|-----|-------------|-------------------|
| 464 | 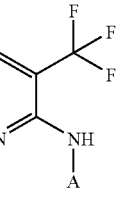 | 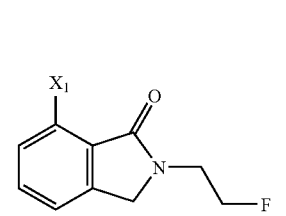 | 322, 286 | 611 |
| 465 | 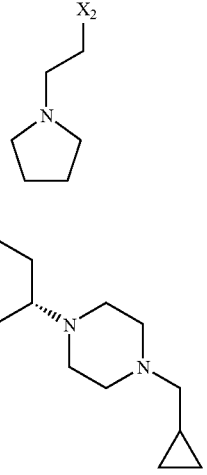 | 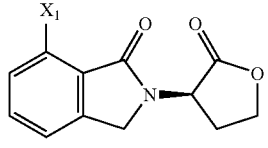 | 322, 286 | 723 |
| 466 | 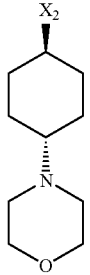 | 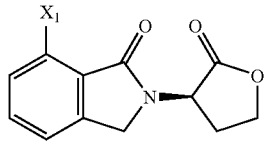 | 322, 282 | 710 |
| 467 | 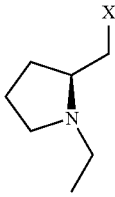 | 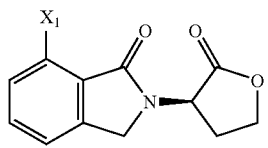 | 326, 286 | 654 |
| 468 | 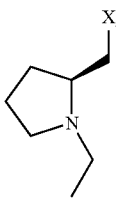 | | 326, 286 | 654 |

-continued
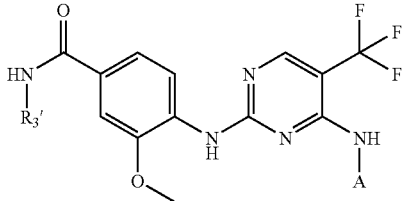
| # | A | R₃' | UV max [nm] | MS (ESI) (M + H)⁺ |
|---|---|---|---|---|
| 469 | 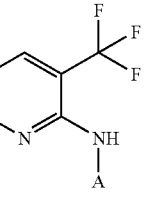 | 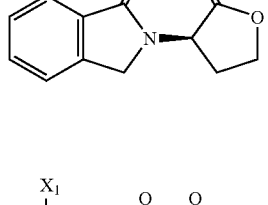 | 322, 284 | 683 |
| 470 | 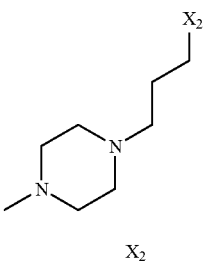 | 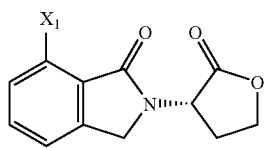 | 326, 286 | 640 |
| 471 | 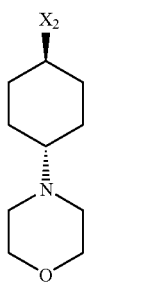 | 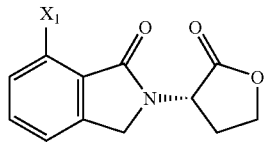 | 318, 283 | 710 |
| 472 | 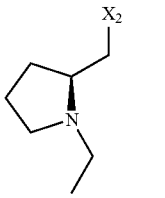 | 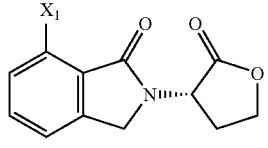 | 326, 286 | 654 |
| 473 | 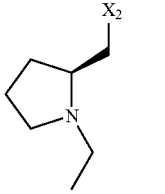 | 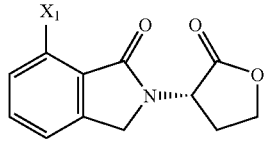 | 326, 286 | 654 |
| 474 | 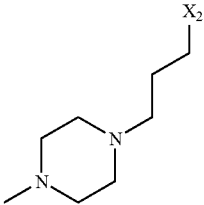 | | 321, 285 | 683 |

-continued
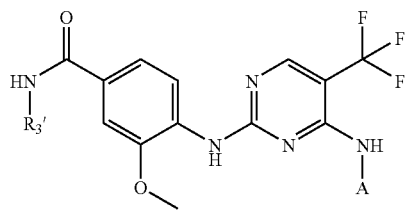
| # | A | R₃' | UV max [nm] | MS (ESI) (M + H)⁺ |
|---|---|-----|-------------|-------------------|
| 475 | X₁-(2-(2-fluoroethyl)isoindolin-1-one) | X₂-CH₂-C(CH₃)₂-CH₂-pyrrolidin-1-yl | 326, 286 | 630 |
| 476 | X₁-(2-isobutylisoindolin-1-one) | X₂-(trans-4-morpholinocyclohexyl) | 322, 286 | 682 |
| 477 | X₁-(2-isobutylisoindolin-1-one) | X₂-CH₂CH₂-pyrrolidin-1-yl | 318, 286 | 612 |
| 478 | X₁-(2-(2,2-difluoroethyl)isoindolin-1-one) | X₂-(piperidin-4-yl) | 318.3 | 606 |
| 479 | X₁-(2-(2,2-difluoroethyl)isoindolin-1-one) | X₂-N(CH₃)₂ | 322, 286 | 566 |
| 480 | X₁-(2-(2,2-difluoroethyl)isoindolin-1-one) | X₂-(4-methylpiperazin-1-yl) | 322, 286 | 621 |

-continued

| # | A | R₃' | UV max [nm] | MS (ESI) (M + H)⁺ |
|---|---|-----|-------------|-------------------|
| 481 | 7-X₁-2-(2,2-difluoroethyl)isoindolin-1-one | 4-methylpiperazin-1-yl-ethyl-X₂ | 318, 286 | 649 |
| 482 | 7-X₁-2-(2,2-difluoroethyl)isoindolin-1-one | (pyrrolidin-2-yl)methyl-X₂ | 322, 286 | 606 |
| 483 | 7-X₁-2-(2,2,2-trifluoroethyl)isoindolin-1-one | (1-ethylpyrrolidin-2-yl)methyl-X₂ | 326, 286 | 652 |
| 484 | 7-X₁-2-(2,2-difluoropropyl)isoindolin-1-one | (1-ethylpyrrolidin-2-yl)methyl-X₂ | 326, 286 | 648 |
| 485 | 7-X₁-2-(2,2-difluoropropyl)isoindolin-1-one | trans-4-morpholinocyclohexyl-X₂ | 322, 284 | 704 |
| 486 | 7-X₁-2-(2,2-difluoropropyl)isoindolin-1-one | 2-(pyrrolidin-1-yl)ethyl-X₂ | 326, 286 | 634 |

-continued
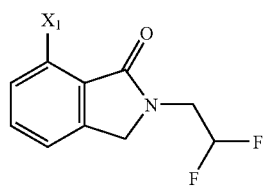
| # | A | R₃' | UV max [nm] | MS (ESI) (M + H)⁺ |
|---|---|---|---|---|
| 487 | 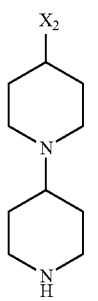 | 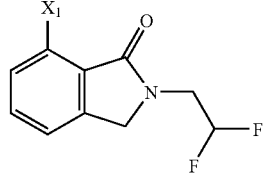 | 322, 285 | 689 |
| 488 | 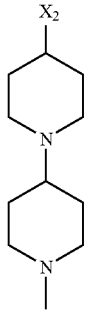 | 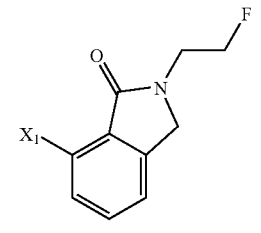 | 322, 285 | 703 |
| 489 | 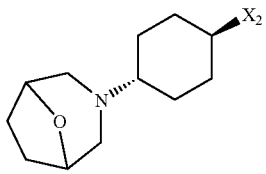 | 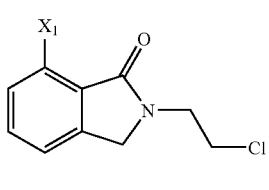 | 322 | 698 |
| 490 | 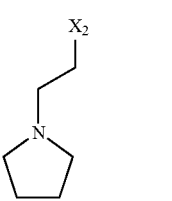 |  | 322, 286 | 619 |

-continued

| # | A | R₃' | UV max [nm] | MS (ESI) (M + H)⁺ |
|---|---|-----|-------------|-------------------|
| 491 | 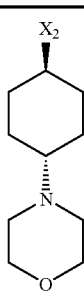 | 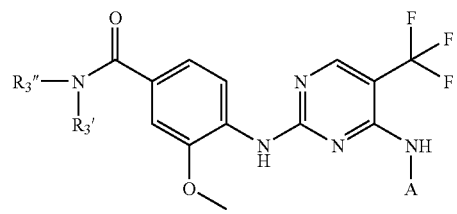 | 322, 286 | 689 |

EXAMPLES 492-621

The following compounds are prepared by an analogous process to that described in Example 53. 2-(4-carboxy-2-methoxy-phenylamino)-4-chloro-5-trifluoromethylpyrimidine may be prepared according to method 12 or 14. The corresponding aniline is described in method 22. The amine used to prepare the amide is commercially obtainable, described in method 13, 15, 20, 21, 23, 24 and 25 or in J. Med. Chem. 2003, 46(5), 702-715.

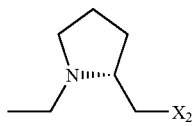

| # | A | R₃' | R₃'' | UV max [nm] | MS (ESI) (M + H)⁺ |
|---|---|-----|------|-------------|-------------------|
| 492 | 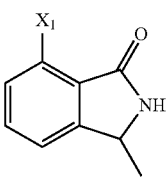 | 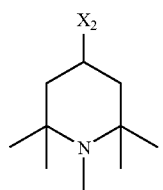 | H | 286, 322 | 584 |
| 493 | 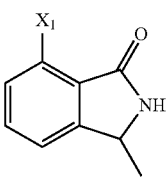 | 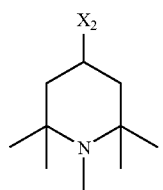 | H | 286, 322 | 826 |

-continued
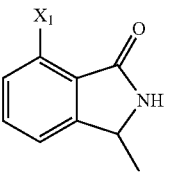
| # | A | R₃' | R₃'' | UV max [nm] | MS (ESI) (M + H)⁺ |
|---|---|---|---|---|---|
| 494 | 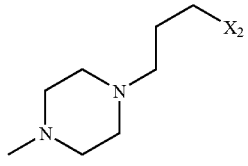 | 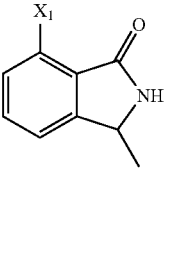 | H | 284, 322 | 613 |
| 495 | 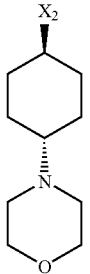 | 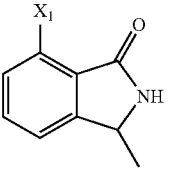 | H | 282, 322 | 640 |
| 496 | 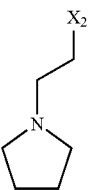 | 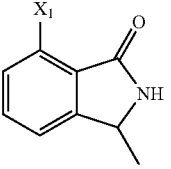 | H | 286, 320 | 570 |
| 497 | 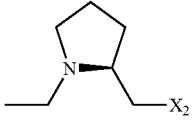 | 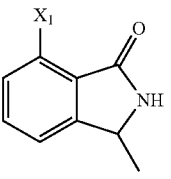 | H | 286, 322 | 584 |
| 498 | 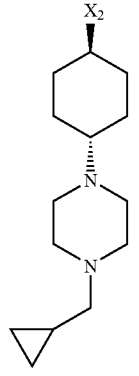 | | H | 282, 322 | 693 |

-continued

| # | A | R₃' | R₃" | UV max [nm] | MS (ESI) (M + H)⁺ |
|---|---|---|---|---|---|
| 499 | X₁-(3-methyl-1-oxoisoindolin-2-yl)ethyl fluoride | X₂-(trans-4-morpholinocyclohexyl) | H | 286, 322 | 686 |
| 500 | X₁-(3-methyl-1-oxoisoindolin-2-yl)ethyl fluoride | X₂-(2-pyrrolidin-1-ylethyl) | H | 286, 326 | 616 |
| 501 | X₁-(3-methyl-1-oxoisoindolin-2-yl)ethyl fluoride | X₂-methyl-(1-ethylpyrrolidin-2-yl) | H | 286, 326 | 630 |
| 502 | X₁-(3-methyl-1-oxoisoindolin-2-yl)-2,2-difluoroethyl | X₂-(trans-4-morpholinocyclohexyl) | H | 282, 325 | 704 |
| 503 | X₁-(3-methyl-1-oxoisoindolin-2-yl)-2,2-difluoroethyl | X₂-(2-pyrrolidin-1-ylethyl) | H | 286, 326 | 634 |

-continued

| # | A | R₃' | R₃" | UV max [nm] | MS (ESI) (M + H)⁺ |
|---|---|---|---|---|---|
| 504 | X₁-(3-methyl-1-oxo-2-(2,2-difluoroethyl)isoindolin-4-yl) | (1-ethylpyrrolidin-2-yl)methyl-X₂ | H | 286, 326 | 648 |
| 505 | X₁-(3-methyl-1-oxo-2-(2-fluoroethyl)isoindolin-4-yl) | trans-4-(8-oxa-3-azabicyclo[3.2.1]octan-3-yl)cyclohexyl-X₂ | H | 286, 322 | 712 |
| 506 | X₁-(3-methyl-1-oxo-2-(2-fluoroethyl)isoindolin-4-yl) | trans-4-(4-(cyclopropylmethyl)piperazin-1-yl)cyclohexyl-X₂ | H | 322, 286 | 739 |
| 507 | X₁-(3-methyl-1-oxo-2-(2-fluoroethyl)isoindolin-4-yl) | 2-(4-methylpiperazin-1-yl)ethyl-X₂ | H | 322, 286 | 645 |
| 508 | X₁-(3-methyl-1-oxo-2-(2-fluoroethyl)isoindolin-4-yl) | 2-morpholinoethyl-X₂ | H | 326, 286 | 632 |

-continued

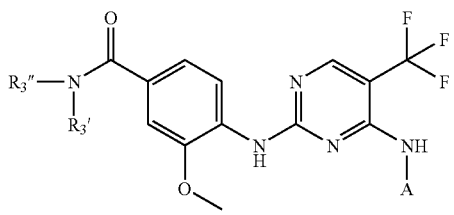

| # | A | R₃' | R₃" | UV max [nm] | MS (ESI) (M + H)⁺ |
|---|---|---|---|---|---|
| 509 | X₁-(3-methyl-2-(2-fluoroethyl)isoindolin-1-one) | X₂-(1,2,2,6,6-pentamethylpiperidin-4-yl) | H | 322, 286 | 672 |
| 510 | X₁-(3-methyl-2-(2-fluoroethyl)isoindolin-1-one) | X₂-(trans-4-(morpholinomethyl)cyclohexyl) | H | 322, 284 | 700 |
| 511 | X₁-(3-methyl-2-(2-fluoroethyl)isoindolin-1-one) | X₂-(1-methylpiperidin-4-yl) | H | 314, 286 | 616 |
| 512 | X₁-(3-methyl-2-(2-fluoroethyl)isoindolin-1-one) | X₂-(trans-4-(pyrrolidin-1-ylmethyl)cyclohexyl) | H | 286, 322 | 684 |
| 513 | X₁-(3-methyl-2-(2-fluoroethyl)isoindolin-1-one) | X₂-(trans-4-(azetidin-1-ylmethyl)cyclohexyl) | H | 286, 322 | 670 |

-continued

| # | A | R₃' | R₃" | UV max [nm] | MS (ESI) (M + H)⁺ |
|---|---|---|---|---|---|
| 514 | | | H | 282, 322 | 658 |
| 515 | | | H | 322, 286 | 632 |
| 516 | | | H | 326, 286 | 628 |
| 517 | | | H | 325, 286 | 628 |
| 518 | | | H | 326, 286 | 659 |
| 519 | | | H | 326 | 699 |

-continued

| # | A | R₃' | R₃" | UV max [nm] | MS (ESI) (M + H)⁺ |
|---|---|---|---|---|---|
| 520 | 1-(2-fluoroethyl)-3-methyl-isoindolin-1-one (X₁) | (1-methylpyrrolidin-3-yl)methyl (X₂) | H | 284, 326 | 616 |
| 521 | 1-(2-fluoroethyl)-3-methyl-isoindolin-1-one (X₁) | (1-methylpiperidin-4-yl)methyl (X₂) | H | 234, 282, 314 | 630 |
| 522 | 1-(2-fluoroethyl)-3-methyl-isoindolin-1-one (X₁) | 2-[(2S)-2-(methoxymethyl)pyrrolidin-1-yl]ethyl (X₂) | H | 326 | 660 |
| 523 | 1-(2-fluoroethyl)-3-methyl-isoindolin-1-one (X₁) | 2-(5-methyl-2,5-diazabicyclo[2.2.1]heptan-2-yl)ethyl (X₂) | H | 326 | 657 |
| 524 | 2-(2-fluoroethyl)-3-methyl-isoindolin-1-one (X₁) | (3R)-1-(2-aminoethyl)piperidin-3-yl (X₂) | H | | 645 |
| 525 | 2-(2-fluoroethyl)-3-methyl-isoindolin-1-one (X₁) | (3R)-1-(cyanomethyl)pyrrolidin-3-yl (X₂) | H | 326 | 627 |

-continued

| # | A | R₃' | R₃" | UV max [nm] | MS (ESI) (M + H)⁺ |
|---|---|---|---|---|---|
| 526 | | | H | 326 | 660 |
| 527 | | | H | 326 | 659 |
| 528 | | | H | 326 | 692 |
| 529 | | | H | 326 | 644 |
| 530 | | | H | 326 | 628 |

-continued
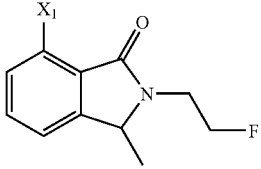
| # | A | R₃' | R₃" | UV max [nm] | MS (ESI) (M + H)⁺ |
|---|---|---|---|---|---|
| 531 | 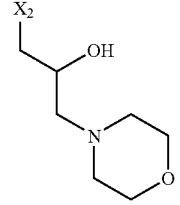 | 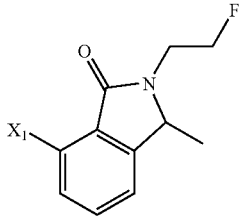 | H | 322 | 662 |
| 532 | 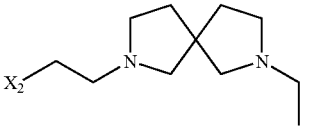 | 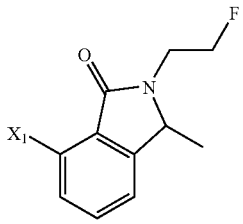 | H | 326 | 699 |
| 533 | 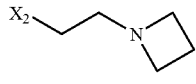 | 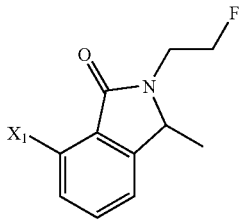 | H | 326 | 602 |
| 534 | 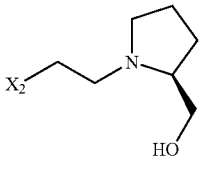 | 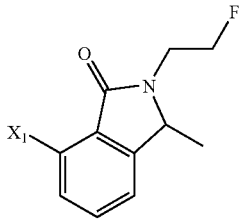 | H | | 646 |
| 535 | 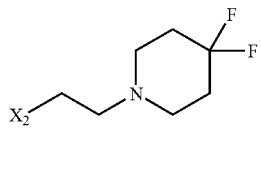 | | H | 326 | 666 |

-continued
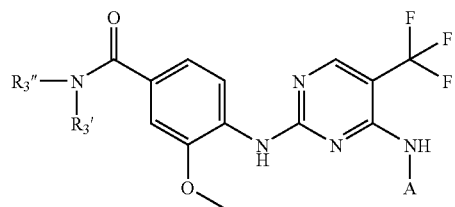
| # | A | R₃' | R₃" | UV max [nm] | MS (ESI) (M + H)⁺ |
|---|---|---|---|---|---|
| 536 | | | H | 326 | 646 |
| 537 | | | H | 326 | — |
| 538 | | | H | 322 | 616 |
| 539 | | | H | 318 | 630 |
| 540 | | | H | 318 | 630 |

-continued
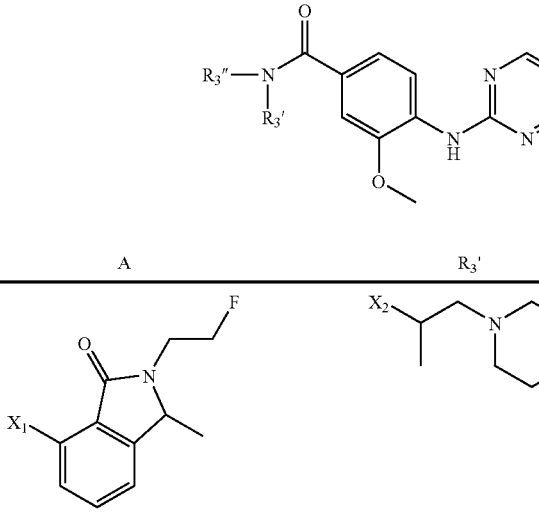
| # | A | R₃' | R₃'' | UV max [nm] | MS (ESI) (M + H)⁺ |
|---|---|---|---|---|---|
| 541 | 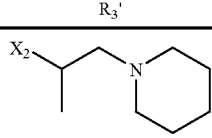 | 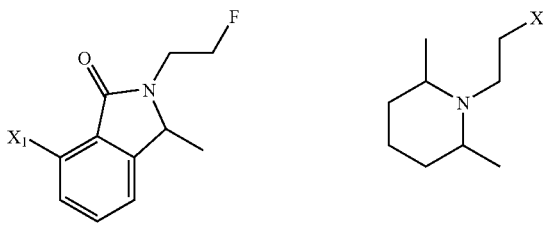 | H | 274 | 644 |
| 542 | 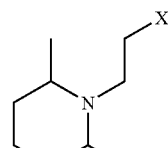 | 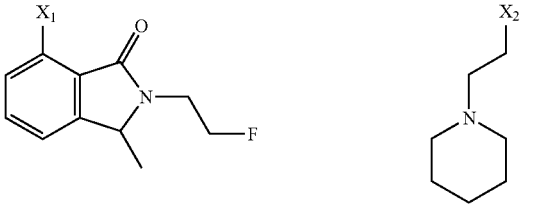 | H | 326 | 658 |
| 543 | 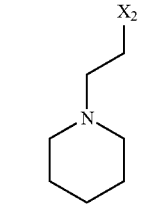 | 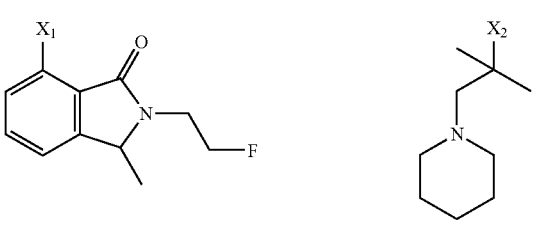 | H | 286, 324 | 630 |
| 544 | 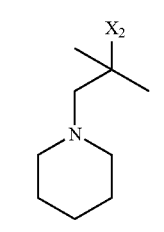 | 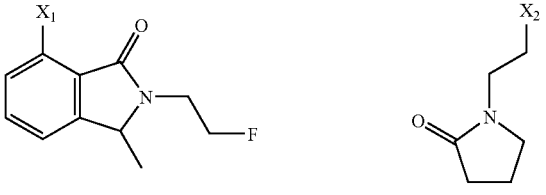 | H | 286, 326 | 658 |
| 545 | 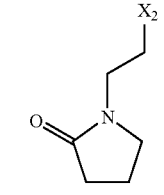 | 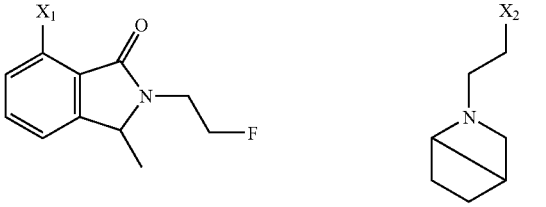 | H | 286, 322 | 630 |
| 546 | 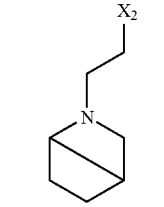 | | H | 286, 326 | 642 |

-continued

| # | A | R₃' | R₃" | UV max [nm] | MS (ESI) (M + H)⁺ |
|---|---|---|---|---|---|
| 547 | X₁-(3-methyl-2-(2-fluoroethyl)isoindolin-1-one) | X₂-CH₂CH₂-NH₂ | H | 286, 322 | 562 |
| 548 | X₁-(3-methyl-2-(2-fluoroethyl)isoindolin-1-one) | X₂-CH₂CH₂-(1-methylpyrrolidin-2-yl) | H | 322-326 | 630 |
| 549 | X₁-(3-methyl-2-(2-fluoroethyl)isoindolin-1-one) | X₂-CH₂-(1-methylpiperidin-2-yl) | H | 326 | 630 |
| 550 | X₁-(3-methyl-2-(2-fluoroethyl)isoindolin-1-one) | X₂-CH₂CH₂-O-CH₂CH₂-OH | H | 286, 322 | 607 |
| 551 | X₁-(3-methyl-2-(2-fluoroethyl)isoindolin-1-one) | X₂-CH₂CH₂-N(iPr)₂ | H | | 646 |
| 552 | X₁-(3-methyl-2-(2-fluoroethyl)isoindolin-1-one) | X₂-CH₂CH₂CH₂-(piperidin-1-yl) | H | | 644 |

-continued

| # | A | R₃' | R₃'' | UV max [nm] | MS (ESI) (M + H)⁺ |
|---|---|---|---|---|---|
| 553 | | | H | 326 | 644 |
| 554 | | | H | 322-326 | 658 |
| 555 | | | H | 322-326 | 658 |
| 556 | | | H | 286, 326 | 658 |
| 557 | | | H | 322-326 | 642 |
| 558 | | | H | 322-326 | 642 |

-continued
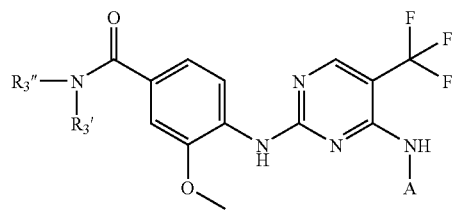
| # | A | R₃' | R₃" | UV max [nm] | MS (ESI) (M + H)⁺ |
|---|---|---|---|---|---|
| 559 | | | H | 286, 322 | 656 |
| 560 | | | H | 286, 322 | 656 |
| 561 | | | H | 286, 322 | 671 |
| 562 | | | H | 286, 322 | 671 |

-continued
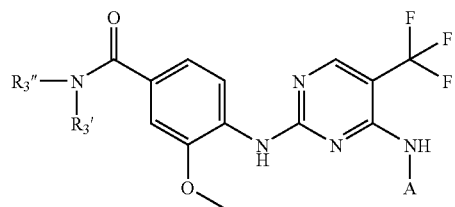
| # | A | R3' | R3" | UV max [nm] | MS (ESI) (M + H)+ |
|---|---|---|---|---|---|
| 563 | | | H | 318 | 685 |
| 564 | | | H | 322-326 | 685 |
| 565 | | | H | 322-326 | 754 |
| 566 | | | H | 322-326 | 672 |
| 567 | | | H | 322 | 711 |

-continued
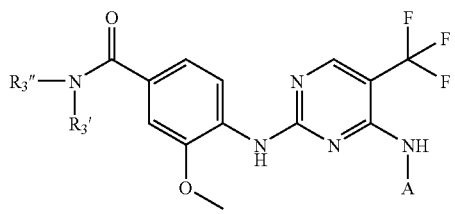
| # | A | R₃' | R₃" | UV max [nm] | MS (ESI) (M + H)⁺ |
|---|---|---|---|---|---|
| 568 | | | H | 322-326 | 711 |
| 569 | | | H | 326 | 624 |
| 570 | | | H | 326 | 645 |
| 571 | | | H | 322-326 | 650 |
| 572 | | | H | 286, 326 | 684 |

-continued

| # | A | R₃' | R₃" | UV max [nm] | MS (ESI) (M + H)⁺ |
|---|---|---|---|---|---|
| 573 | (2-(2-fluoroethyl)-3-methyl-isoindolin-1-one, X₁) | (cyclobutyl-N(Me)-cyclohexyl, X₂) | H | 286, 326 | 684 |
| 574 | (2-(2-fluoroethyl)-3-methyl-isoindolin-1-one, X₁) | (1,4-diethyl-1,4-diazepan-6-yl, X₂) | H | 326 | 673 |
| 575 | (2-(2-fluoroethyl)-3-methyl-isoindolin-1-one, X₁) | (3-(pyrrolidin-1-ylmethyl)cyclohexylmethyl, X₂) | H | 322 | 698 |
| 576 | (2-(2-fluoroethyl)-3-methyl-isoindolin-1-one, X₁) | (3-morpholinopropyl, X₂) | H | 326, 286 | 646 |
| 577 | (2-(2-fluoroethyl)-3-methyl-isoindolin-1-one, X₁) | (4-(pyrrolidin-1-ylmethyl)cyclohexyl, X₂) | H | 286, 322 | 684 |

-continued

| # | A | R₃' | R₃'' | UV max [nm] | MS (ESI) (M + H)⁺ |
|---|---|---|---|---|---|
| 578 | | | H | 282, 322 | 658 |
| 579 | | | H | 322, 286 | 617 |
| 580 | | | H | 326, 286 | 644 |
| 581 | | | H | 326, 286 | 590 |
| 582 | | | H | 286, 326 | 673 |
| 583 | | | H | 326, 285 | 652 |

-continued
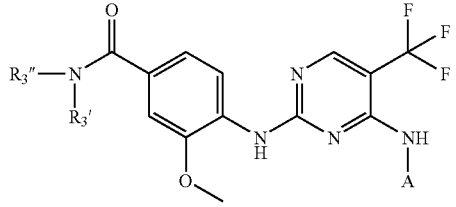
| # | A | R3' | R3'' | UV max [nm] | MS (ESI) (M + H)+ |
|---|---|---|---|---|---|
| 584 | 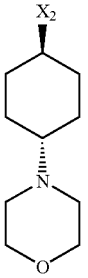 | 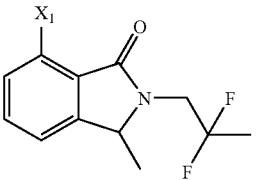 | H | 326, 282 | 722 |
| 585 | 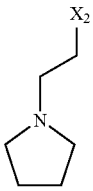 | 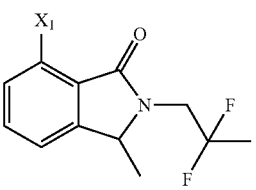 | H | 326, 286 | 648 |
| 586 | 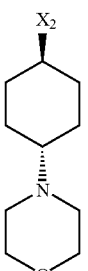 | 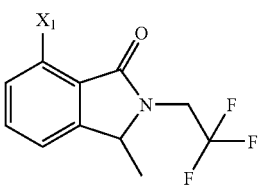 | H | 326, 285 | 718 |
| 587 | 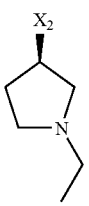 | 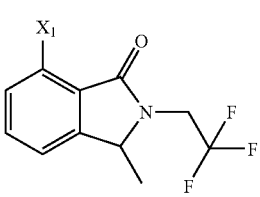 | H | 326, 286 | 652 |
| 588 | 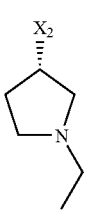 | | H | 326, 284 | 652 |

-continued
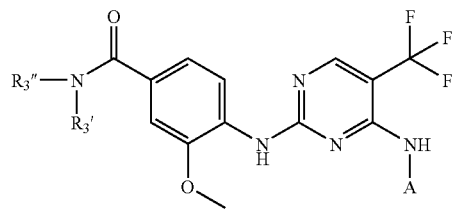
| # | A | R₃' | R₃" | UV max [nm] | MS (ESI) (M + H)⁺ |
|---|---|---|---|---|---|
| 589 | | | H | 325, 283 | 681 |
| 590 | | | H | 325.3 | 652 |
| 591 | | | H | 326.3 | 666 |
| 592 | | | H | 325, 283 | 666 |
| 593 | | | H | 325.3 | 648 |
| 594 | | | H | 325, 284 | 648 |

-continued

| # | A | R$_3$' | R$_3$" | UV max [nm] | MS (ESI) (M + H)$^+$ |
|---|---|---|---|---|---|
| 595 | X$_1$-(3-methyl-2,2-difluoropropyl isoindolinone) | X$_2$-CH$_2$CH$_2$-(4-methylpiperazin-1-yl) | H | 325, 284 | 677 |
| 596 | X$_1$-(3-methyl-2,2-difluoropropyl isoindolinone) | X$_2$-(1-methylpiperidin-4-yl) | H | 325, 284 | 648 |
| 597 | X$_1$-(3-methyl-2,2-difluoropropyl isoindolinone) | X$_2$-CH$_2$-(1-ethylpyrrolidin-2-yl) | H | 326, 285 | 662 |
| 598 | X$_1$-(3-methyl-2,2-difluoropropyl isoindolinone) | X$_2$-CH$_2$-(1-methylpiperidin-4-yl) | H | 325, 284 | 662 |
| 599 | X$_1$-(3-methyl-2,2,2-trifluoroethyl isoindolinone) | X$_2$-(1-(pyrrolidin-1-ylmethyl)piperidin-4-yl) | H | 326, 282 | 720 |
| 600 | X$_1$-(3-methyl-2-fluoroethyl isoindolinone) | X$_2$-CH$_2$CH$_2$-NH$_2$ | -X$_2$ | 314, 283 | 576 |

-continued

| # | A | R₃' | R₃" | UV max [nm] | MS (ESI) (M + H)⁺ |
|---|---|---|---|---|---|
| 601 | X₁-(3-methyl-2-(2-fluoroethyl)isoindolinone) | X₂-(trans-4-(2,6-dimethylmorpholin-4-yl)cyclohexyl) | H | 322, 286 | 714 |
| 602 | X₁-(3-methyl-2-(2-fluoroethyl)isoindolinone) | X₂-(trans-4-(pyrrolidin-1-yl)cyclohexyl) | H | 286, 322 | 670 |
| 603 | X₁-(3-methyl-2-(2-hydroxyethyl)isoindolinone) | X₂-(2-(pyrrolidin-1-yl)ethyl) | H | 324, 285 | 614 |
| 604 | X₁-(3-methyl-2-(2-hydroxyethyl)isoindolinone) | X₂-(trans-4-morpholinocyclohexyl) | H | 324, 284 | 684 |
| 605 | X₁-(3-methyl-2-(2-methoxyethyl)isoindolinone) | X₂-(2-(pyrrolidin-1-yl)ethyl) | H | 324, 285 | 628 |

-continued

| # | A | R₃' | R₃'' | UV max [nm] | MS (ESI) (M + H)⁺ |
|---|---|---|---|---|---|
| 606 | X₁-(7-position of 2-(2-methoxyethyl)-3-methylisoindolin-1-one) | trans-4-(morpholin-4-yl)cyclohexyl-X₂ | H | 324, 284 | 698 |
| 607 | X₁-(7-position of 2-(2-fluoroethyl)-3-methylisoindolin-1-one) | 3-(pyrrolidin-1-yl)propyl-X₂ | H | 285, 322 | 630 |
| 608 | X₁-(7-position of 2-(2-fluoroethyl)-3-methylisoindolin-1-one) | (S)-2-aminopropyl-X₂ | H | 325, 284 | 576 |
| 609 | X₁-(7-position of 2-(2-fluoroethyl)-3-methylisoindolin-1-one) | (R)-2-aminopropyl-X₂ | H | 325, 284 | 576 |
| 610 | X₁-(7-position of 2-(2-fluoroethyl)-3-methylisoindolin-1-one) | 2-(4-methyl-1,4-diazepan-1-yl)ethyl-X₂ | H | 326, 286 | 659 |
| 611 | X₁-(7-position of 2-(2-fluoroethyl)-3-methylisoindolin-1-one) | 2-(1,4-oxazepan-4-yl)ethyl-X₂ | H | 326, 286 | 646 |

-continued

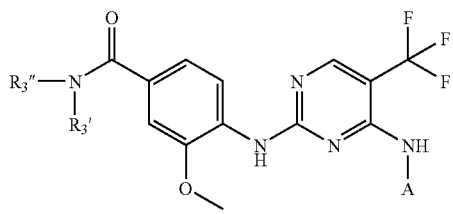

| # | A | R3' | R3" | UV max [nm] | MS (ESI) (M + H)+ |
|---|---|---|---|---|---|
| 612 | 2-(2-fluoroethyl)-3-methyl-isoindolin-1-one with X1 | pyrrolidine-CH(CH3)-CH2-X2 | H | 325, 285 | 630 |
| 613 | 2-(2-fluoroethyl)-3-methyl-isoindolin-1-one with X1 | pyrrolidine-CH(CH3)-CH2-X2 | H | 325, 284 | 630 |
| 614 | 2-(2-fluoroethyl)-3-methyl-isoindolin-1-one with X1 | H2N-C(CH3)2-CH2-X2 | H | 325, 285 | 590 |
| 615 | 2-(2-fluoroethyl)-3-methyl-isoindolin-1-one with X1 | pyrrolidinyl-CH2-cyclopropyl-X2 | H | 285, 325 | 642 |
| 616 | 2-(2-fluoroethyl)-3-methyl-isoindolin-1-one with X1 | cyclopentyl-pyrrolidine-CH2-X2 | H | 325, 285 | 670 |
| 617 | 2-(2-fluoroethyl)-3-methyl-isoindolin-1-one with X1 | cyclopentyl-piperidine-CH2-X2 | H | 326, 286 | 684 |

-continued

| # | A | R$_3'$ | R$_3''$ | UV max [nm] | MS (ESI) (M + H)$^+$ |
|---|---|---|---|---|---|
| 618 | (isoindolinone with X$_1$, N-CH$_2$CH$_2$F, methyl) | (isopropyl-CH$_2$-X$_2$ with pyrrolidine) | H | 326, 286 | 658 |
| 619 | (isoindolinone with X$_1$, N-CH$_2$CH$_2$F, methyl) | (cyclohexyl-CH$_2$-X$_2$ with pyrrolidine) | H | 285, 324 | 684 |
| 620 | (isoindolinone with X$_1$, N-CH$_2$CH$_2$F, methyl) | (isopropyl-CH$_2$-X$_2$ with pyrrolidine) | H | 326, 286 | 658 |
| 621 | (isoindolinone with X$_1$, N-CH$_2$CH$_2$F, methyl) | (cyclohexyl-CH$_2$-X$_2$ with OH) | H | 280, 320 | 631 |

EXAMPLE 622

2-(2-methoxy-4-[2-(2-pyrrolidin-1-yl-ethylcarbamoyl)-ethylamino]-phenylamino)-4-(2-(2-fluoro-ethyl)-1-methyl-3-oxo-2,3-dihydro-1H-isoindol-4-ylamino)-5-trifluoromethyl-pyrimidine 73 mg (0.193 mmol) 3-(4-amino-3-methoxy-phenylamino)-N-(2-pyrrolidin-1-yl-ethyl)-propionamide hydrochloride (method 28) are dissolved in 3 ml 2-butanol and combined with 50 mg (0.129 mmol) 2-chloro-4-(2-(2-fluor-ethyl)-1-methyl-3-oxo-2,3-dihydro-1H-isoindol-4-ylamino)-5-trifluoromethyl-pyrimidine (method 26). This

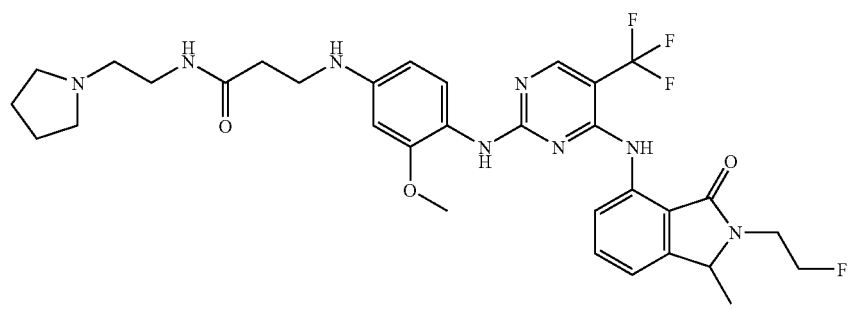

reaction mixture is stirred for 16 h at 100° C. The solvent is eliminated in vacuo and the residue is purified by column chromatography. The carrier material used is C18-RP-silica gel and a gradient is run through which consists at the starting point of 90% water and 10% acetonitrile and at the finishing point of 55% water and 45% acetonitrile. 0.1% formic acid are added both to the water and to the acetonitrile. The suitable fractions are combined with 500 µl of a 1 M aqueous hydrochloric acid and freeze-dried. The product is obtained as the dihydrochloride.

Yield: 33 mg (0.045 mmol; 35%) UV max: 314 nm MS (ESI): 659 (M+H)$^{+1}$H-NMR: 1.35-1.48 (m, 3H), 1.64-1.78 (m, 4H), 2.37-2.46 (m, 2H), 3.48-3.75 (m, 4H), 3.97-4.14 (m, 1H), 4.50-4.78 (m, 3H), 5.55-5.71 (m, 1H), 6.14-6.42 (m, 2H), 6.96-7.32 (m, 3H), 7.86-7.98 (m, 1H), 8.32 (s, 1H), 8.84 (s, 1H), 10.41 (s, 1H)

EXAMPLE 623

2-(2-fluoro-ethyl)-7-(2-{4-[4-(2-hydroxy-ethyl)-1H-imidazol-2-yl]-2-methoxy-phenylamine}-4-(2-(2-fluoro-ethyl)-1-methyl-3-oxo-2,3-dihydro-1H-isoindol-4-ylamino)-5-trifluoromethyl-pyrimidine

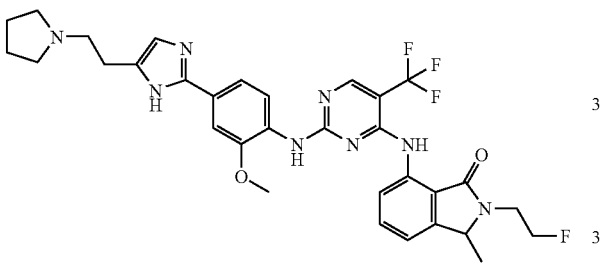

0.07 g (0.3 mmol) 2-[2-(4-amino-3-methoxy-phenyl)-1H-imidazol-4-yl]-ethanol (method 27) are suspended in 2 ml dioxane and brought into solution in the ultrasound bath at 50° C. 0.8 ml (3.20 mmol) 4 N dioxanic hydrochloric acid are added. The dioxane is eliminated in vacuo, combined with 0.096 g (0,247 mmol) 7-(2-chloro-5-trifluoromethyl-pyrimidine-4-ylamine)-2-(2-fluoro-ethyl)-3-methyl-2,3-dihydro-isoindol-1-one and suspended in butanol. The mixture is stirred for 16 h at 100° C. The crude product is purified by column chromatography. The carrier material used is C18-RP-silica gel. A gradient is run through which consists at the starting point of 75% water and 25% acetonitrile and at the finishing point of 30% water and 70% acetonitrile. 0.1% ammonia is added to the water. 23 mg of this intermediate product and 0.018 g (0.094 mmol) p-toluenesulphonyl chloride are suspended in 0.9 ml of tetrahydrofuran and 0.02 ml (0.139 mmol) triethylamine and combined with 0.007 g (0.057 mmol) 4-dimethylamino-pyridine. This reaction mixture is stirred for 16 h at 20° C. Then it is combined with 0.36 ml (5.064 mmol) pyrrolidine and stirred for 16 h at 60° C. The crude product is purified by column chromatography. The carrier material used is C18-RP-silica gel. A gradient is run through which consists of 90% water and 10% acetonitrile at the starting point and of 60% water and 40% acetonitrile at the finishing point. 0.1% formic acid is added to the water.

Yield: 7 mg (0.011 mmol, 28%) MS (ESI): 639 (M+H)$^{+UV}$ max: 330 nm NMR: 1.42-1.46 (m, 3H), 1.78-2.08 (m, 6H), 2.29 (s, 1H), 3.95-4.16 (m, 4H), 4.52-4.78 (m, 3H), 7.09-7.13 (m, 1H), 7.24-7.28 (m, 1H), 7.46-7.50 (m, 1H), 7.52-7.58 (m, 2H), 7.64-7.67 (m, 1H), 7.82-7.88 (m, 1H), 8.02-8.13 (m, 2H), 8.50-8.60 (m, 2H), 9.20-9.23 (m, 1H), 10.52-10,82 (m, 2H).

EXAMPLES 624-638

The following compounds are prepared by an analogous process to that described in Example 622 or 623. The corresponding aniline is described in method 27 and 28.

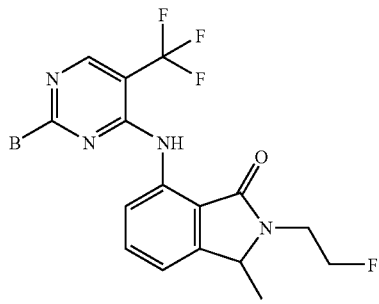

| # | B | UV max [nm] | MS (ESI) (M + H)⁺ |
|---|---|---|---|
| 624 | 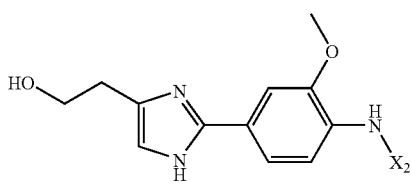 | 290, 326 | 586 |

-continued
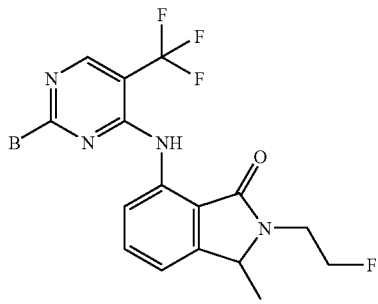
| # | B | UV max [nm] | MS (ESI) (M + H)+ |
|---|---|---|---|
| 625 | 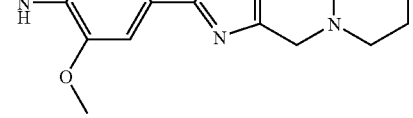 | 290, 330 | 654 |
| 626 | 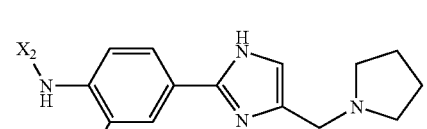 | 290, 326 | 625 |
| 627 |  | 326 | 512 |
| 628 | 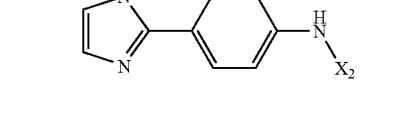 | 314 | 685 |
| 629 | 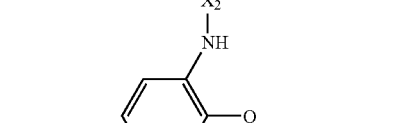 | 290, 314 | 659 |

-continued
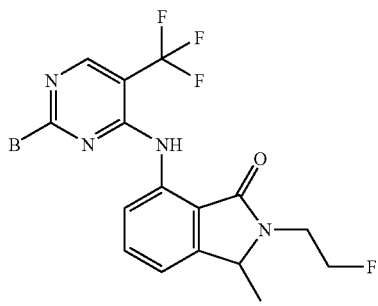
| # | B | UV max [nm] | MS (ESI) (M + H)+ |
|---|---|---|---|
| 630 | | | 659 |
| 631 | | 278 | 592 |
| 632 | | 314 | 592 |
| 633 | | 314 | 588 |
| 634 | | 314 | 602 |

-continued
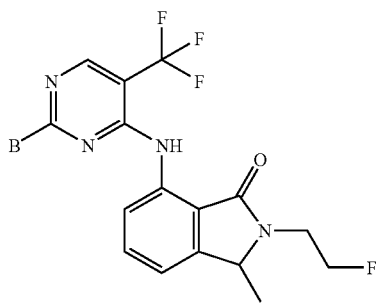
| # | B | UV max [nm] | MS (ESI) (M + H)+ |
|---|---|---|---|
| 635 | 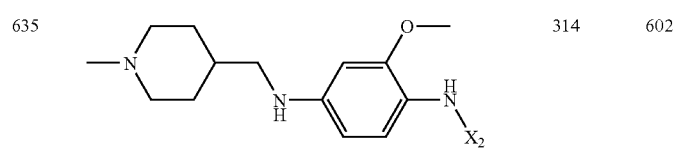 | 314 | 602 |
| 636 | 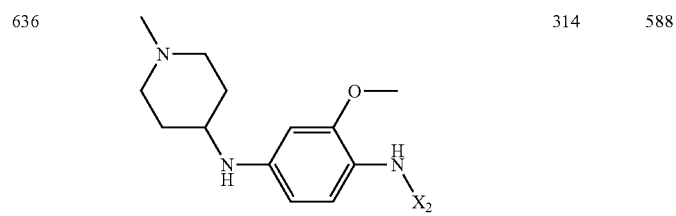 | 314 | 588 |
| 637 | 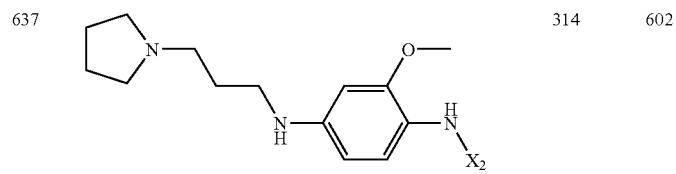 | 314 | 602 |
| 638 | 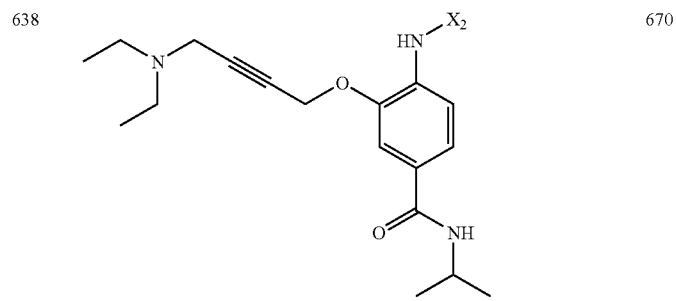 | | 670 |

EXAMPLE 639

2-(4-(4-isopropyl-[1,4]diazepin-1-yl)-2-methoxy-phenylamino)-4-(2-(2-fluoro-ethyl)-1-methyl-3-oxo-2,3-dihydro-1H-isoindol-4-ylamino)-5-trifluoromethyl-pyrimidine

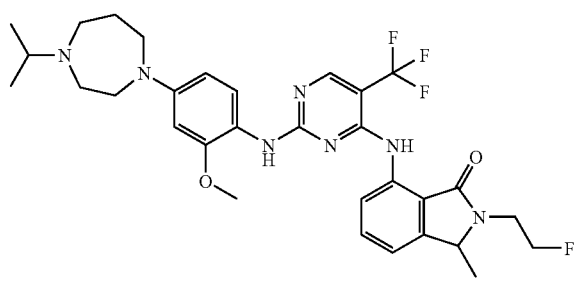

50 mg (0.087 mmol) 2-(4-(4-[1,4]diazepan-1-yl)-2-methoxy-phenylamino)-4-(2-(2-fluoro-ethyl)-1-methyl-3-oxo-2,3-dihydro-1H-isoindol-4-ylamino)-5-trifluoromethyl-pyrimidine (method from Example 622, aniline from method 28) are dissolved in 0.5 ml dimethylacetamide and combined with 13 µl (0.174 mmol) acetone. 37 mg (0.175 mmol) sodium triacetoxyborohydride are added to this reaction mixture. After 16 h at 20° C. the solvent is eliminated in vacuo. The residue is purified by column chromatography. The carrier material used is C18-RP-silica gel and within 15 min a gradient is run through which consists of 95% water and 5% acetonitrile at the starting point and 5% water and 95% acetonitrile at the finishing point. 0.1% formic acid are added both to the water and to the acetonitrile. The suitable fractions are combined with 500 µl of a 1 M aqueous hydrochloric acid and freeze-dried. The product is obtained as the dihydrochloride.

Yield: 51 mg (0.074 mmol; 85%) UV max: 314 nm MS (ESI): 616 (M+H)$^+$ $^1$H-NMR: 1.23-1.35 (m, 6H), 1.35-1.51 (m, 3H), 2.16-2.29 (m, 1H), 2.95-3.05 (m, 1H), 3.12-3.23 (m, 1H), 3.42-3.66 (m, 6H), 3.78 (s, 3H), 3.83-4.00 (m, 2H), 4.00-4.16 (m, 1H), 4.50-4.79 (m, 3H), 6.32-6.63 (m, 2H), 7.08-8.59 (m, 4H), 9.24-9.76 (m, 1H), 10.67 (s, 2H)

EXAMPLES 640-648

The following compounds are prepared by an analogous process to that described in Example 639.

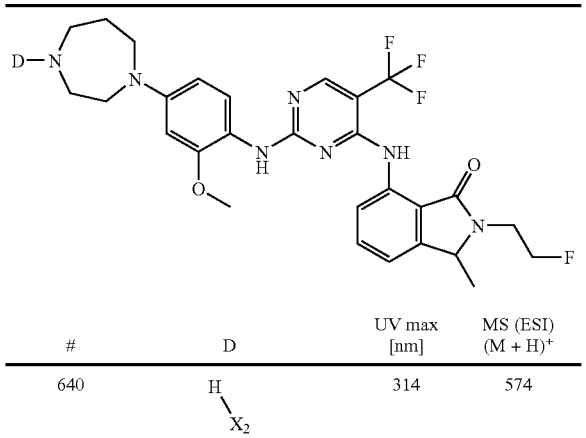

| # | D | UV max [nm] | MS (ESI) (M + H)$^+$ |
|---|---|---|---|
| 640 | H–X$_2$ | 314 | 574 |

-continued

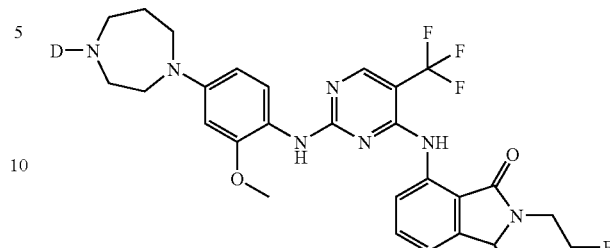

| # | D | UV max [nm] | MS (ESI) (M + H)$^+$ |
|---|---|---|---|
| 641 | cyclopropyl-CH$_2$–X$_2$ | 310-314 | 628 |
| 642 | CH$_3$CH$_2$–X$_2$ | 310-314 | 602 |
| 643 | (CH$_3$)$_2$CH–X$_2$ | 310-314 | 630 |
| 644 | —N(piperidyl)-CH$_2$–X$_2$ | 314 | 671 |
| 645 | HO–CH$_2$CH$_2$–X$_2$ | 310-314 | 618 |
| 646 | tetrahydropyran-4-yl–X$_2$ | 314 | 658 |
| 647 | (CH$_3$)$_2$CH–X$_2$ | 314 | 588 |

EXAMPLES 648-659

The following compounds are prepared by an analogous process to that described in Example 639. For the reductive amination 2-(2-methoxy-4-piperazin-1-yl-phenylamino)-4-(2-(2-fluoro-ethyl)-1-methyl-3-oxo-2,3-dihydro-1H-isoindol-4-ylamino)-5-trifluoromethyl-pyrimidine is used. The aniline for preparing this compound is described in method 28.

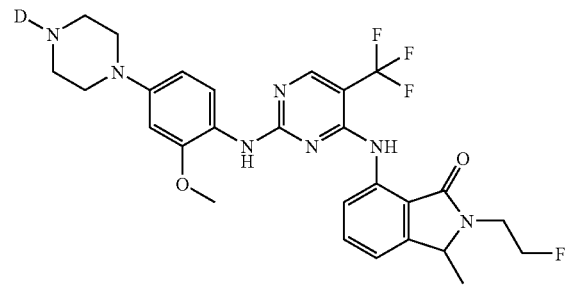

| # | D | UV max [nm] | MS (ESI) (M + H)+ |
|---|---|---|---|
| 648 | Me₂N–CH₂CH₂–X₂ | 286, 314 | 631 |
| 649 | H₂N–CH₂CH₂–X₂ | 286, 314 | 603 |
| 650 | 4-piperidinyl (HN) –X₂ | 282, 314 | 643 |
| 651 | 1-methyl-azepan-4-yl –X₂ | 282, 314 | 671 |
| 652 | X₂–CH₂–(4-piperidinyl NH) | 286, 314 | 657 |
| 653 | cyclopropyl-CH(CH₃)–X₂ | 282, 314 | 628 |

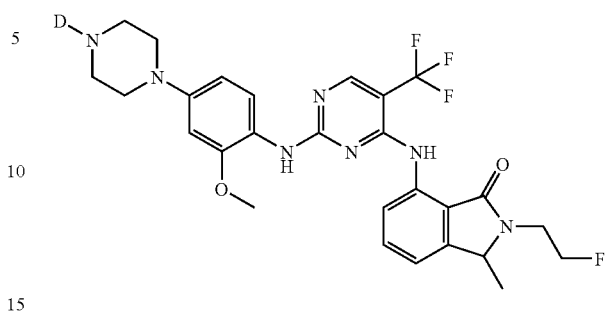

| # | D | UV max [nm] | MS (ESI) (M + H)+ |
|---|---|---|---|
| 654 | 1-methyl-piperidin-4-yl –X₂ | 286, 314 | 657 |
| 655 | 1-ethyl-piperidin-3-yl –X₂ | 286, 314 | 671 |
| 656 | cyclopropyl-CH₂–X₂ | 282, 314 | 614 |
| 657 | H–X₂ | 282, 314 | 560 |
| 658 | X₂–C(O)–O–CH₂–phenyl | 234, 283, 314 | 694 |
| 659 | CH₃–X₂ | 286, 314 | 574 |

EXAMPLES 660-666

The following compounds are prepared by an analogous process to that described in Example 53. 2-(4-Carboxy-2-bromo-phenylamino)-4-chloro-5-trifluoromethyl-pyrimidine may be prepared according to method 29. The corresponding aniline is described in method 22. The amine used to prepare the amide is commercially obtainable or described in method 13.

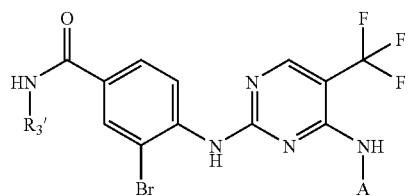
| # | A | R₃' | UV max [nm] | MS (ESI) (M + H)⁺ |
|---|---|---|---|---|
| 660 | | | 314 | 678/680 |
| 661 | | | 314 | 626/628 |
| 662 | | | 314 | 626/628 |
| 663 | | | 286 | 609/611 |
| 664 | | | 314 | 734/736 |

-continued

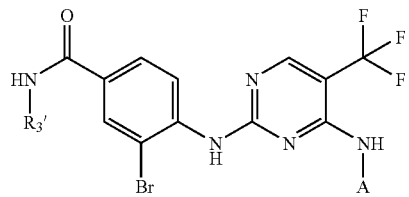

| # | A | R₃' | UV max [nm] | MS (ESI) (M + H)⁺ |
|---|---|---|---|---|
| 665 | (isoindolinone with N-CH₂CH₂F, methyl) | X₂-CH₂CH₂-N(piperazine)N-CH₃ | 314 | 693/695 |
| 666 | (isoindolinone with N-CH₂CH₂F, methyl) | X₂-CH₂-(4-piperidinyl)-N-CH₃ | 286 | 678/680 |

EXAMPLES 667-681

The following compounds are prepared by an analogous process to that described in Example 53. 2-(4-Carboxy-phenylamino)-4-chloro-5-trifluoromethyl-pyrimidine may be prepared according to method 14. The corresponding aniline is described in method 22. The amine used to prepare the amide is commercially obtainable or described in method 13. In addition, the group R₃' may be synthesised analogously to Example 639 by reductive amination. An amine is used which has another protected amino function in the side chain. The protective group used may be a tert-butoxycarbonyl, benzyloxycarbonyl or benzyl group. This protective group is cleaved by a procedure familiar to the skilled man and reductive amination (analogously to Example 639) or alkylation (analogously to method 34 or WO2004052857) are the last steps in this sequence.

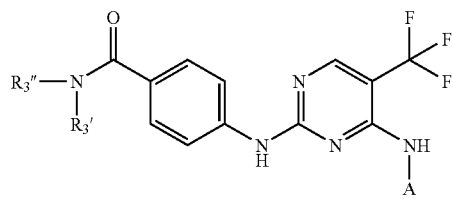

| # | A | R₃' | R₃" | UV max [nm] | MS (ESI) (M + H)⁺ |
|---|---|---|---|---|---|
| 667 | (isoindolinone with N-CH₂CH₂F, methyl) | X₂-(4-piperidinyl)-N-CH₃ | H | 314 | 586 |

-continued

| # | A | R$_3'$ | R$_3''$ | UV max [nm] | MS (ESI) (M + H)$^+$ |
|---|---|---|---|---|---|
| 668 | 3-methyl-2-(2-fluoroethyl)-1-oxoisoindoline, X$_1$ | (1-methylpyrrolidin-3-yl)methyl, X$_2$ | H | 314 | 586 |
| 669 | 3-methyl-2-(2-fluoroethyl)-1-oxoisoindoline, X$_1$ | 2-(pyrrolidin-1-yl)ethyl, X$_2$ | H | 314 | 586 |
| 670 | 3-methyl-2-(2-fluoroethyl)-1-oxoisoindoline, X$_1$ | 1,2,2,6,6-pentamethylpiperidin-4-yl, X$_2$ | H | 314 | 642 |
| 671 | 3-methyl-2-(2-fluoroethyl)-1-oxoisoindoline, X$_1$ | 1-(2-hydroxyethyl)piperidin-4-yl, X$_2$ | H | 314 | 616 |
| 672 | 3-methyl-2-(2-fluoroethyl)-1-oxoisoindoline, X$_1$ | (1-methylpiperidin-4-yl)methyl, X$_2$ | H | 290 | 600 |

-continued

| # | A | R₃' | R₃" | UV max [nm] | MS (ESI) (M + H)⁺ |
|---|---|---|---|---|---|
| 673 | 1-methyl-7-X₁-2-(2-fluoroethyl)isoindolin-3-one | X₂-cyclohexyl-piperazinyl-CH₂-cyclopropyl | H | 290 | 709 |
| 674 | 1-methyl-7-X₁-2-(2-fluoroethyl)isoindolin-3-one | X₂-CH₂-(1-ethylpyrrolidin-2-yl) | H | 314 | 600 |
| 675 | 1-methyl-7-X₁-2-(2-fluoroethyl)isoindolin-3-one | X₂-(1-ethylpyrrolidin-3-yl) | H | 314 | 586 |
| 676 | 1-methyl-7-X₁-2-(2-fluoroethyl)isoindolin-3-one | X₂-CH₂CH₂-N(CH₃)₂ | X₂-CH₃ | 286 | 574 |
| 677 | 1-methyl-7-X₁-2-(2-fluoroethyl)isoindolin-3-one | X₂-(4-methylpiperazin-1-yl) | H | 286 | 572 |

-continued
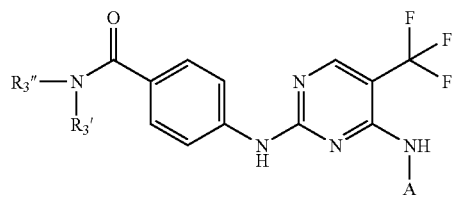
| # | A | R₃' | R₃" | UV max [nm] | MS (ESI) (M + H)⁺ |
|---|---|-----|-----|-------------|-------------------|
| 678 | | | H | 290 | 682 |
| 679 | | | H | 314 | 642 |
| 680 | | | H | 290 | 656 |
| 681 | | | H | 314 | 615 |

EXAMPLE 682

2-(2-methoxy-4-[3-(4-methyl-piperazin-1-yl)-propionylamino]-phenylamino)-4-(2-(2-fluoro-ethyl)-1-methyl-3-oxo-2,3-dihydro-1H-isoindol-4-ylamino)-5-trifluoromethyl-pyrimidine

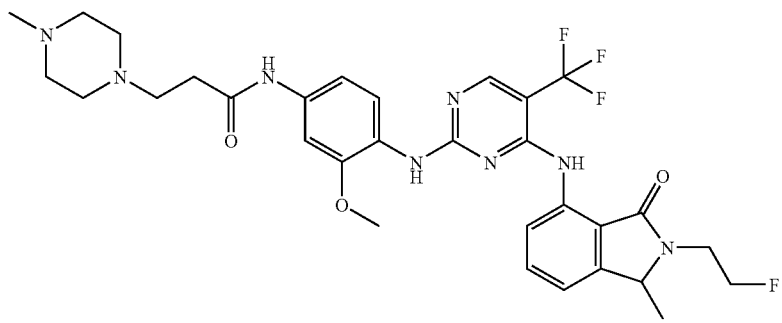

63 mg (0.116 mmol) 2-(4-acryloylamino-2-methoxy-phenylamino)-4-(2-(2-fluoro-ethyl)-1-methyl-3-oxo-2,3-dihydro-1H-isoindol-4-ylamino)-5-trifluoromethyl-pyrimidine (method 30) are dissolved in 1 ml of methanol and combined with 70 mg (0.699 mmol) N-methyl-piperazine. After stirring for 48 h at 20° C. the solvent is eliminated in vacuo. The residue is purified by column chromatography. The carrier material used is C18-RP-silica gel and a gradient is run through within 20 min which consists of 95% water and 5% acetonitrile at the starting point and of 2% water and 98% acetonitrile at the finishing point. 0.1% formic acid are added both to the water and to the acetonitrile. The suitable fractions are combined with 500 µl of a 1 M aqueous hydrochloric acid and freeze-dried. The product is obtained as the dihydrochloride.

Yield: 58 mg (0.081 mmol; 70%) UV max: 282 nm MS (ESI): 645 (M+H)$^{+1}$H-NMR: 1.42 (d, 3H), 2.18 (s, 3H), 2.29-2.43 (m, 4H), 2.65-2.70 (m, 2H), 3.50-3.62 (m, 1H), 3.72 (s, 3H), 4.00-4.12 (m, 1H), 4.52-4.76 (m, 3H), 7.12-7.17 (m, 1H), 7.12-7.42 (m 4H), 7.51 (s, 1H), 8.17 (s, 1H), 8.38 (s, 1H), 9.08 (s, 1H), 10.18 (s, 1H), 10.46 (s, 1H)

EXAMPLES 683-692

The following compounds are prepared by an analogous process to that described in Example 682.

| # | E | UV max [nm] | MS (ESI) (M + H)+ |
|---|---|---|---|
| 683 | X₂–N(CH₂CH₂N(CH₃)₂)(CH₂CH₃) | 282 | 661 |
| 684 | X₂–N(piperidin-4-yl)–N(CH₃)₂ | 282 | 673 |
| 685 | X₂–N(piperidin-4-yl)CH₂CH₂N(CH₃)₂ | 282 | 701 |
| 686 | X₂–N(4-methylpiperazin-1-yl) | 282 | 645 |
| 687 | X₂–N(piperidin-4-yl)NH-cyclopropyl | 282 | 685 |
| 688 | X₂–N(pyrrolidin-1-yl) | 282 | 616 |

-continued

| # | E | UV max [nm] | MS (ESI) (M + H)+ |
|---|---|---|---|
| 689 | X₂–N(piperidin-4-yl)-piperidin-1-yl | 282 | 713 |
| 690 | X₂–N(piperidin-1-yl) | 282 | 630 |
| 691 | X₂–N(morpholin-4-yl) | 282 | 632 |
| 692 | X₂–N(azetidin-1-yl) | 282 | 602 |

EXAMPLES 693-704

The following compounds are prepared by an analogous process to that described in Example 682. 2-(4-(2-Bromo-acetylamino)-2-methoxy-phenylamino)-4-(2-(2-fluoro-ethyl)-1-methyl-3-oxo-2,3-dihydro-1H-isoindol-4-ylamino)-5-trifluoromethyl-pyrimidine or 2-(4-(2-bromo-acetylamino)-2-bromo-phenylamino)-4-(2-(2-fluoro-ethyl)-1-methyl-3-oxo-2,3-dihydro-1H-isoindol-4-ylamino)-5-trifluoromethyl-pyrimidine or 2-[5-(2-bromo-acetylamino)-pyridin-2-ylamino]-4-(2-(2-fluoro-ethyl)-1-methyl-3-oxo-2,3-dihydro-1H-isoindol-4-ylamino)-5-trifluoromethyl-pyrimidine, which are described in method 30, are used as educt for the nucleophilic substitution.

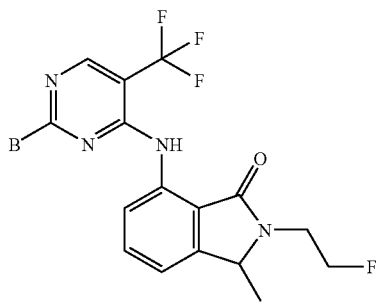
| # | B | UV max [nm] | MS (ESI) (M + H)+ |
|---|---|---|---|
| 693 | | 282 | 685 |
| 694 | | 282 | 685 |
| 695 | | 314 | 659 |
| 696 | | 282 | 645 |
| 697 | | 282 | 644 |

-continued
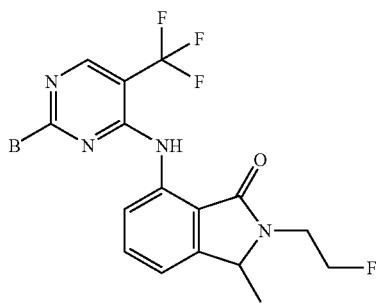
| # | B | UV max [nm] | MS (ESI) (M + H)$^+$ |
|---|---|---|---|
| 698 | | 282 | 618 |
| 699 | | 282 | 602 |
| 700 | | 282 | 687 |
| 701 | | 322 | 573 |

-continued

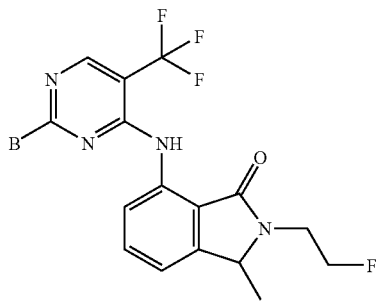

| # | B | UV max [nm] | MS (ESI) (M + H)+ |
|---|---|---|---|
| 702 | (dimethylamino-piperidinyl-acetamido-pyridinyl-X₁) | 322 | 630 |
| 703 | (pyrrolidinyl-acetamido-bromophenyl-X₁) | 222 | 650 |
| 704 | (dimethylamino-piperidinyl-acetamido-bromophenyl-X₁) | 278 | 707 |

EXAMPLE 705

2-(2-methoxy-4-[3-(3-pyrrolidin-1-yl-ethyl)-ureido]-phenylamino)-4-(2-(2-fluoro-ethyl)-1-methyl-3-oxo-2,3-dihydro-1H-isoindol-4-ylamino)-5-trifluoromethyl-pyrimidine 70 mg (0.135 mmol) 2-(4-carboxy-2-methoxy-phenylamino)-4-(2-(2-fluoro-ethyl)-1-methyl-3-oxo-2,3-dihydro-1H-isoindol-4-ylamino)-5-trifluoromethyl-pyrimidine (analogously to Example 53) are dissolved in 2 ml of toluene and combined with 190 μl (1.348 mmol) triethylamine and 60 μl (0.270 mmol) diphenylphosphorylazide. This reaction

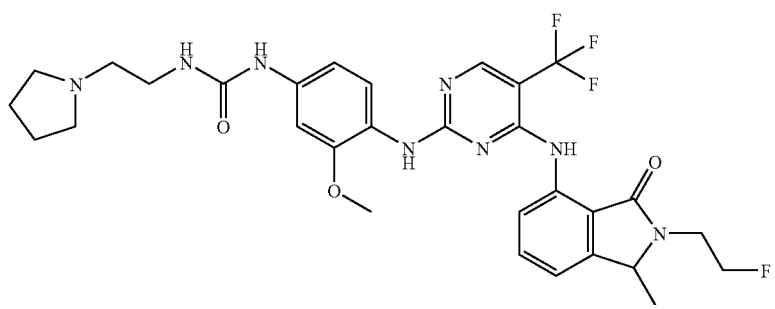

mixture is stirred for 48 h at 20° C. Then the temperature of the suspension is adjusted to 95° C. for 2 h, whereupon a clear brown solution is formed. Then 31 mg (0.270 mmol) 1-(2-aminoethyl)-pyrrolidine are added and the mixture is again stirred for 1 h at 95° C. The solvent is eliminated in vacuo. The residue is purified by column chromatography. The carrier used is C18-RP-silica gel and within 15 min a gradient is run through which consists of 95% water and 5% acetonitrile at the starting point and consists of 2% water and 98% acetonitrile at the finishing point. 0.1% formic acid are added to both the water and to the acetonitrile. The suitable fractions are made basic with 5 M sodium hydroxide solution and extracted 4 times with 50 ml dichloromethane. The combined organic phases are dried and the solvent is eliminated in vacuo.

Yield: 42 mg (0.067 mmol; 50%) UV max: 282 nm MS (ESI): 631 (M+H)$^{+1}$H-NMR: 1.42-1.48 (m, 3H), 1.69-1.79 (m, 4H), 3.22-3.28 (m, 2H), 3.49-3.62 (m, 1H), 3.70 (s, 3H), 3.99-4.12 (m, 1H), 4.53-4.76 (m, 3H), 6.17 (s, 1H), 6.84-6.91 (m, 1H), 7.15-7.33 (m, 3H), 7.40 (s, 1H), 8.36 (s, 1H), 8.76 (s, 1H), 9.01 (s, 1H), 10.44 (s, 1H)

EXAMPLE 706

2-(2-methoxy-4-ureido-phenylamino)-4-(2-(2-fluoro-ethyl)-1-methyl-3-oxo-2,3-dihydro-1H-isoindol-4-ylamino)-5-trifluoromethyl-pyrimidine

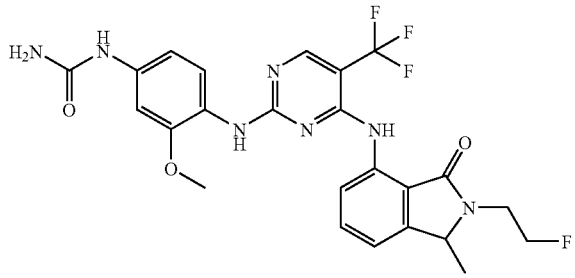

This compound is prepared analogously to Example 705.
UV max: 282/314 nm MS (ESI): 534 (M+H)$^{+1}$H-NMR: 1.42 (d, 3H), 3.48-3.64 (m, 1H), 3.69 (s, 3H), 3.98-4.13 (m, 1H), 4.50-4.77 (m, 3H), 5.89 (s, 2H), 6.94 (d, 1H), 7.16-7.30 (m, 2H), 7.36 (s, 1H), 8.33-8.41 (m, 2H), 8.38 (s, 1H), 8.73 (s, 1H), 9.00 (s, 1H), 10.44 (s, 1H)

EXAMPLE 707

2-(2-methoxy-4-[(1-methyl-piperidin-4-carbonyl)-amino]-phenylamino)-4-(2-(2-fluoro-ethyl)-1-methyl-3-oxo-2,3-dihydro-1H-isoindol-4-ylamino)-5-trifluoromethyl-pyrimidine

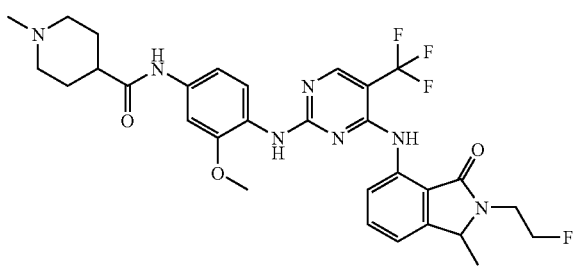

Starting from 2-(4-amino-2-methoxy-phenylamino)-4-(2-(2-fluoro-ethyl)-1-methyl-3-oxo-2,3-dihydro-1H-isoindol-4-ylamino)-5-trifluoromethyl-pyrimidine (method 30) the above-mentioned product is prepared using an amide linking method familiar to the skilled man (cf. also Example 53 or 1032). The substance is obtained as a free base.

UV max: 282 nm MS (ESI): 616 (M+H)$^{+1}$H-NMR (400 MHz, CDCl$_3$): 1.51 (d, 3H), 2.25-2.32 (m, 1H), 2.36 (s, 3H), 3.00-3.07 (m, 2H), 3.53-3.65 (m, 1H), 3.92 (s, 3H), 4.13-4.27 (m, 1H), 4.56-4.77 (m, 3H), 6.84 (d, 1H), 7.07 (d, 1H), 7.44 (s, 1H), 7.47-7.54 (m, 1H), 7.57 (s, 1H), 7.62 (s, 1H), 8.16-8.24 (m, 1H), 8.39 (s, 1H), 8.60-8.68 (m, 1H), 10.42 (s, 1H)

EXAMPLES 708-795

Using an analogous method to that described in Example 53 a primary amine which has another protected amino function in the side chain is coupled to 2-(4-carboxy-2-methoxy-phenylamino)-4-[2-(2-fluoro-ethyl)-1-methyl-3-oxo-2,3-dihydro-1H-isoindol-4-ylamino]-5-trifluoromethyl-pyrimidine. The protective group used may be a tert-butoxycarbonyl, benzyloxycarbonyl or benzyl group. This protective group is cleaved using a procedure familiar to the skilled man and reductive amination (analogously to Example 639) or alkylation (analogously to method 34 or WO2004052857) are the final steps in this sequence.

| # | R$_3'$ | UV max [nm] | MS (ESI) (M + H)$^+$ |
|---|---|---|---|
| 708 | benzyl-piperidinyl-methyl (X$_2$) | 285, 322 | 706 |
| 709 | pyrrolidinyl-methyl-cyclopropyl (X$_2$) | 285, 322 | 656 |
| 710 | N-methyl-piperidinyl-methyl (X$_2$) | 285, 322 | 630 |

-continued
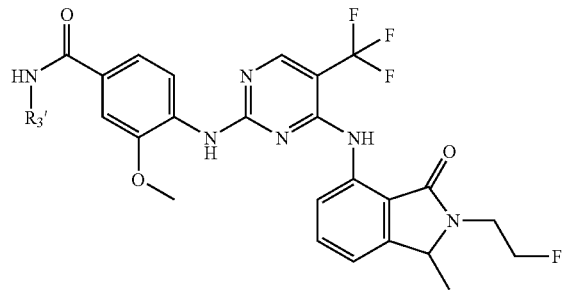
| # | R₃' | UV max [nm] | MS (ESI) (M + H)⁺ |
|---|---|---|---|
| 711 | 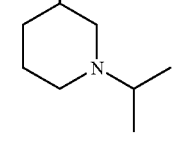 | 322, 286 | 644 |
| 712 | 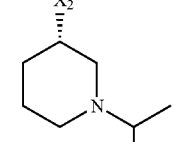 | 325, 286 | 699 |
| 713 | 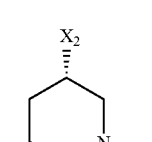 | 282, 318 | 644 |
| 714 | 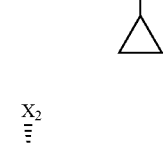 | 326 | 685 |
| 715 | 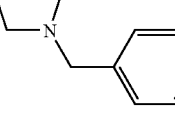 | 326 | 658 |
| 716 | 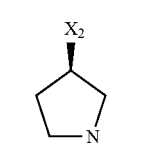 | 326 | 699 |
| 717 |  | 326 | 630 |
-continued
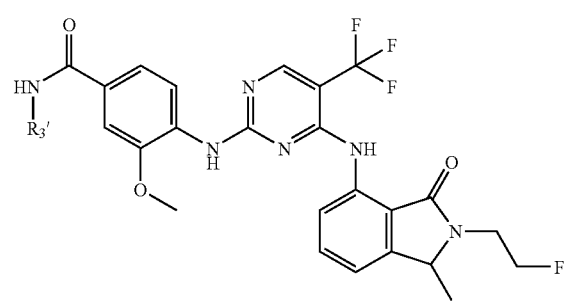
| # | R₃' | UV max [nm] | MS (ESI) (M + H)⁺ |
|---|---|---|---|
| 718 |  | 326 | 644 |
| 719 | | 322 | 644 |
| 720 | | 326 | 656 |
| 721 | | 326 | 678 |
| 722 | | 314 | 630 |

-continued

| # | R₃' | UV max [nm] | MS (ESI) (M + H)⁺ |
|---|---|---|---|
| 723 | (S)-3-(cyanomethyl)piperidin-1-yl (X₂) | 322 | 641 |
| 724 | octahydropyrrolo[3,4-c]pyrrole with cyclopropylmethyl (X₂-ethyl) | 326 | 712 |
| 725 | (S)-1-(cyclopropylmethyl)pyrrolidin-3-yl (X₂) | 326 | 642 |
| 726 | (R)-1-(cyclopropylmethyl)pyrrolidin-3-yl (X₂) | 322 | 642 |
| 727 | (S)-1-(tetrahydro-2H-pyran-4-yl)pyrrolidin-3-yl (X₂) | 318 | 672 |

-continued

| # | R₃' | UV max [nm] | MS (ESI) (M + H)⁺ |
|---|---|---|---|
| 728 | (S)-1-(tetrahydro-2H-pyran-4-yl)piperidin-3-yl (X₂) | 301 | 686 |
| 729 | (S)-pyrrolidin-3-yl (X₂) | 326 | 588 |
| 730 | (S)-1-cyclobutylpyrrolidin-3-yl (X₂) | 326 | 642 |
| 731 | (S)-1-cyclopentylpiperidin-3-yl (X₂) | 326 | 670 |
| 732 | (S)-1-cyclobutylpyrrolidin-3-yl (X₂) | 326 | 642 |
| 733 | 1-methylazepan-4-yl (X₂) | 326 | 630 |

353

-continued

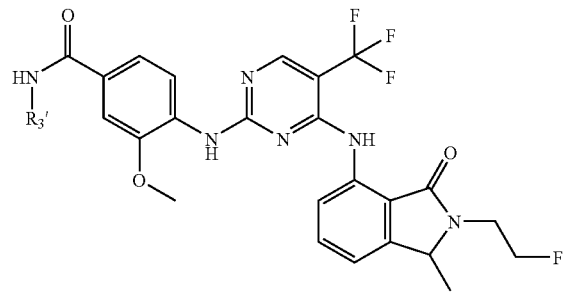

| # | R3' | UV max [nm] | MS (ESI) (M + H)+ |
|---|---|---|---|
| 734 | (piperidinyl-N-methylpiperidine, X2) | 326 | 699 |
| 735 | (N-methylpiperidine, X2) | 310 | 616 |
| 736 | (N-cyclopentylpyrrolidine, X2) | 326 | 656 |
| 737 | (N-propylpyrrolidine, X2) | 322 | 630 |
| 738 | (N-cyclopentylpyrrolidine, X2) | 326 | 656 |

354

-continued

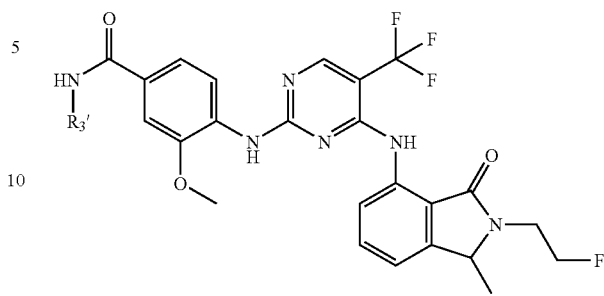

| # | R3' | UV max [nm] | MS (ESI) (M + H)+ |
|---|---|---|---|
| 739 | (N-cyclobutylpiperidine, X2) | 326 | 656 |
| 740 | (N-(2,2-difluoroethyl)pyrrolidine, X2) | 266 | 652 |
| 741 | (N-cyclobutylazetidine, X2) | 326 | 629 |
| 742 | (N-methylpiperidinyl azetidine, X2) | 326 | 671 |
| 743 | (N-ethylpiperidine, X2) | 326 | 630 |
| 744 | (N-cyclopentylazetidine, X2) | 326 | 642 |
| 745 | (N-ethylazetidine, X2) | 326 | 602 |
| 746 | (N-cyclopropylmethylazetidine, X2) | 326 | 628 |

-continued

| # | R3' | UV max [nm] | MS (ESI) (M + H)+ |
|---|---|---|---|
| 747 | X2-azetidine-N-iPr | 326 | 616 |
| 748 | X2-piperidin-3-yl NH | 326 | 602 |
| 749 | X2-pyrrolidin-3-yl N-CH2CHF2 | 322 | 652 |
| 750 | X2-piperidin-4-yl N-CH2CH2OH | 326 | 646 |
| 751 | X2-pyrrolidin-3-yl N-(tetrahydropyran-4-yl) | 326 | 672 |
| 752 | X2-pyrrolidin-3-yl N-Et | 326 | 616 |

-continued

| # | R3' | UV max [nm] | MS (ESI) (M + H)+ |
|---|---|---|---|
| 753 | X2-pyrrolidin-3-yl N-Et | 326 | 616 |
| 754 | X2-pyrrolidin-3-yl N-(1-methylpiperidin-4-yl) | 326 | 685 |
| 755 | X2-CH2-piperidin-4-yl NH | 322 | 616 |
| 756 | X2-CH2-piperidin-4-yl N-(1-methylpiperidin-4-yl) | 318 | 713 |
| 757 | X2-CH2-azetidin-3-yl NH | 286, 322 | 588 |
| 758 | X2-CH2-pyrrolidin-3-yl NH | 226, 286, 322 | 602 |
| 759 | X2-CH2-pyrrolidin-3-yl N-CH2-cyclopropyl | 322-326 | 656 |

357
-continued
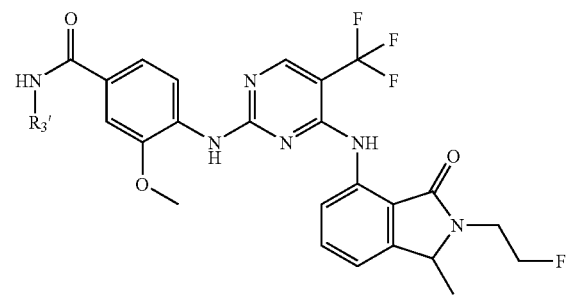
| # | R3' | UV max [nm] | MS (ESI) (M + H)+ |
|---|---|---|---|
| 760 | 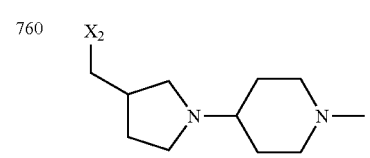 | 322-326 | 699 |
| 761 | 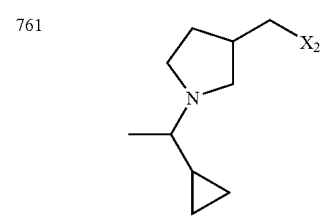 | 322-326 | 670 |
| 762 | 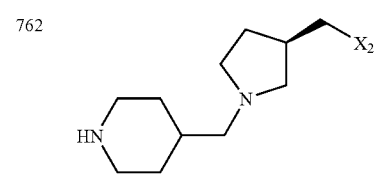 | 322-326 | 699 |
| 763 | 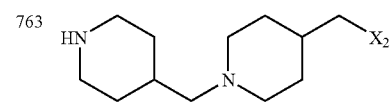 | 322 | 713 |
| 764 | 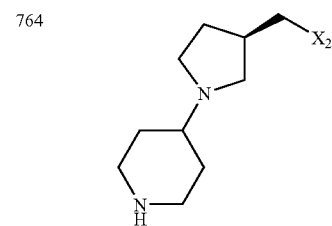 | 326 | 685 |
| 765 | 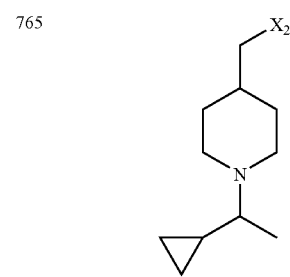 | 322 | 684 |
358
-continued
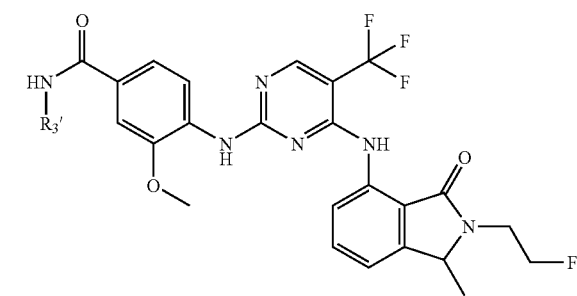
| # | R3' | UV max [nm] | MS (ESI) (M + H)+ |
|---|---|---|---|
| 766 | 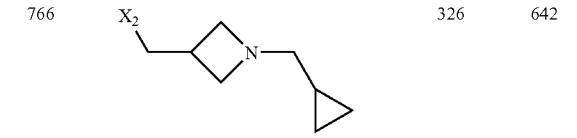 | 326 | 642 |
| 767 | 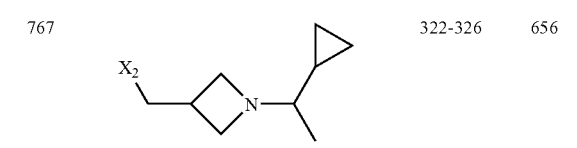 | 322-326 | 656 |
| 768 | 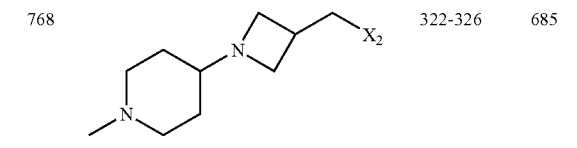 | 322-326 | 685 |
| 769 | 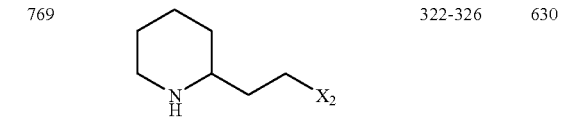 | 322-326 | 630 |
| 770 | 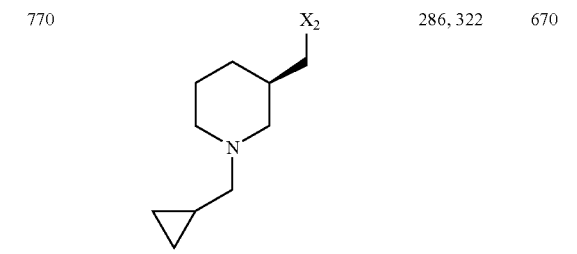 | 286, 322 | 670 |
| 771 | 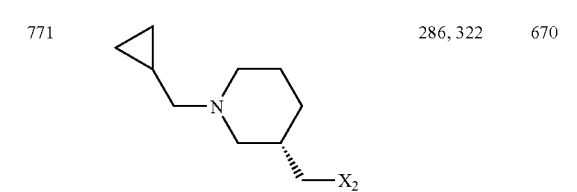 | 286, 322 | 670 |
| 772 | 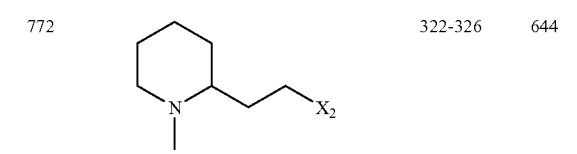 | 322-326 | 644 |

-continued
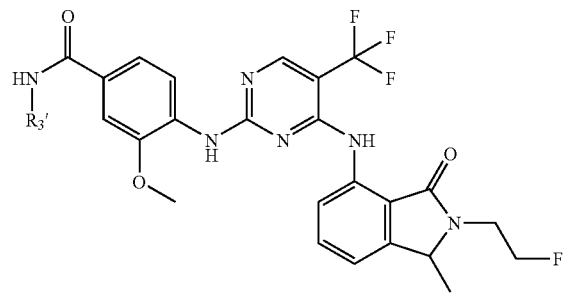
| # | R3' | UV max [nm] | MS (ESI) (M + H)+ |
|---|---|---|---|
| 773 | 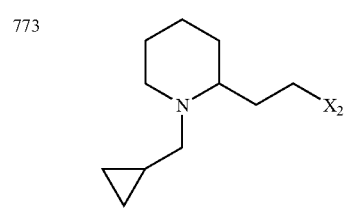 | 322 | 684 |
| 774 | 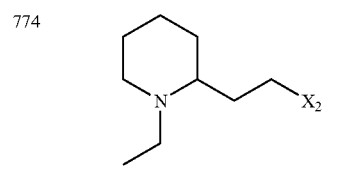 | 322-326 | 658 |
| 775 | 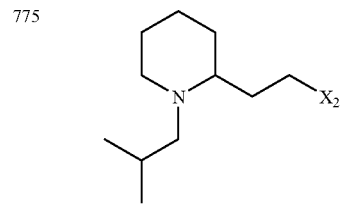 | 322 | 686 |
| 776 | 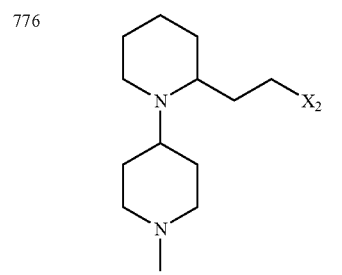 | 322-326 | 727 |
| 777 | 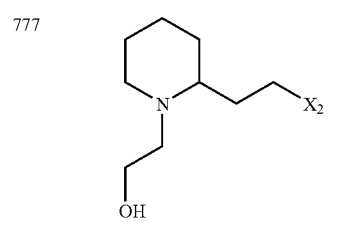 | 322-326 | 674 |
-continued
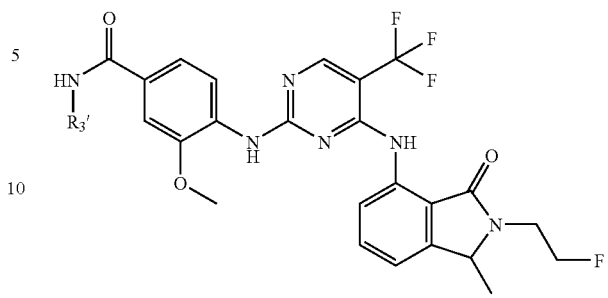
| # | R3' | UV max [nm] | MS (ESI) (M + H)+ |
|---|---|---|---|
| 778 | 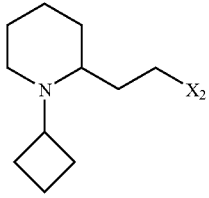 | 322-326 | 684 |
| 796 | 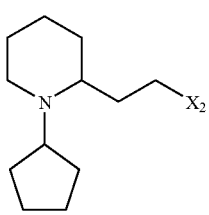 | 322-326 | 698 |
| 780 | 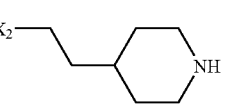 | 286, 322 | 630 |
| 781 | 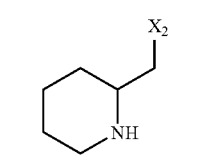 | 282, 314 | 616 |
| 782 | 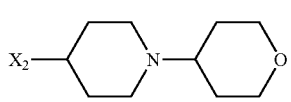 | 322, 286 | 686 |
| 783 | 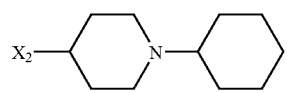 | 326 | 684 |
| 784 | 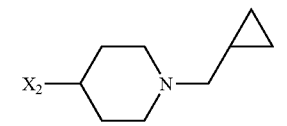 | 324, 286 | 656 |
| 785 | 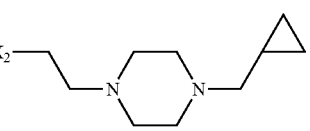 | 326, 286 | 685 |
| 786 |  | 322, 286 | 715 |

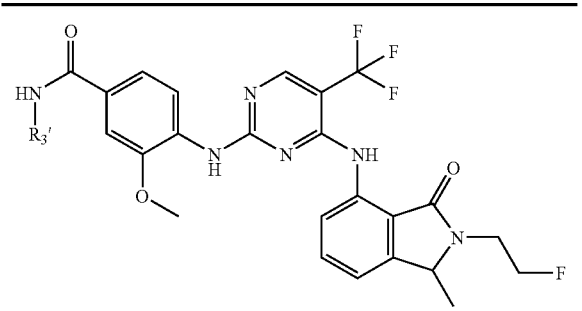

| # | R$_3$' | UV max [nm] | MS (ESI) (M + H)$^+$ |
|---|---|---|---|
| 787 | 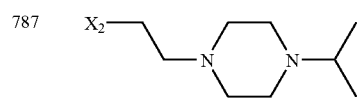 | 322, 286 | 673 |
| 788 | 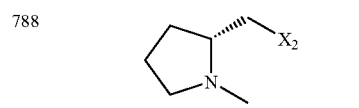 | 285, 322 | 616 |
| 789 | 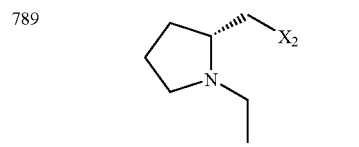 | 285, 322 | 630 |
| 790 | 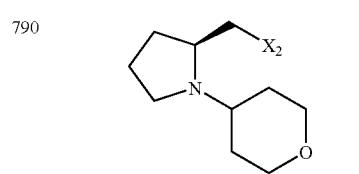 | 285, 322 | 686 |
| 791 | 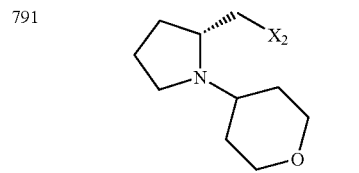 | 285, 322 | 686 |
| 792 | 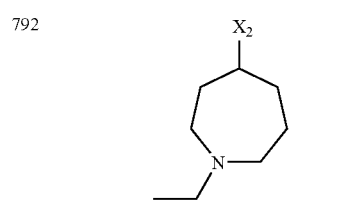 | 326 | 644 |
| 793 | 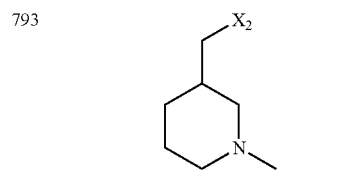 | 322 | 630 |

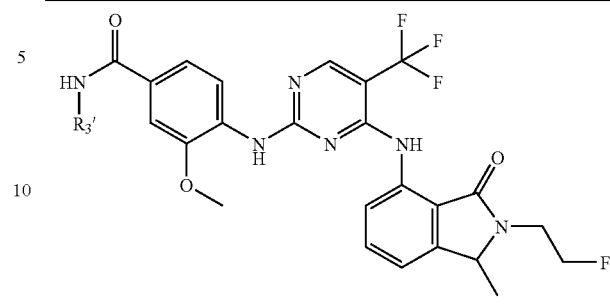

| # | R$_3$' | UV max [nm] | MS (ESI) (M + H)$^+$ |
|---|---|---|---|
| 794 | 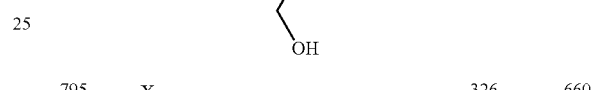 | 326 | 631 |
| 795 | 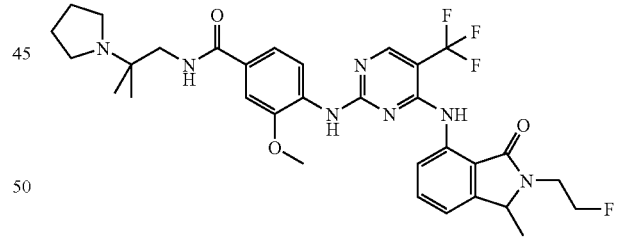 | 326 | 660 |

EXAMPLE 796

2-[2-methoxy-4-(2-methyl-2-pyrrolidin-1-yl-propylcarbamoyl)-phenylamino]-4-(2-(2-fluoro-ethyl)-1-methyl-3-oxo-2,3-dihydro-1H-isoindol-4-ylamino)-5-trifluoromethyl-pyrimidine 200 mg (0.385 mmol) 2-(4-carboxy-2-methoxy-phenylamino)-4-[2-(2-fluoro-ethyl)-1-methyl-3-oxo-2,3-dihydro-1H-isoindol-4-ylamino]-5-trifluoromethyl-pyrimidine (analogously to Example 53) are dissolved in 1 ml of dimethylformamide cooled to 0° C. and combined with 520 µl (3.038 mmol) diisopropylethylamine and 160 mg (0.498 mmol) O-(benzotriazol-1-yl)-N,N,N',N'-tetramethyluronium-tetrafluoroborate. This solution is slowly added dropwise after 10 min to 56 µl (0.539 mmol) 1,2-diamino-2-methylpropane, which is dissolved in 300 µl dimethylformamide. The reaction mixture is stirred for 24 h at 20° C. and then the solvent is eliminated in vacuo. The residue is purified by column chromatography. The carrier used is C18-RP-silica gel and within 15 min a gradient is run through which consists at the starting point of 90% water and 10% acetonitrile and at the finishing point of 50% water and 50% acetonitrile. 0.1% formic acid are added to both the water and to the acetonitrile. The suitable fractions are freeze-dried. This intermediate product is combined with 70 mg (0.515 mmol) potassium carbonate and with 84 mg (0.506 mmol) potassium iodide and suspended in 2 ml acetonitrile. 20 µl (0.170 mmol) 1,4-dibromobutane are added to this mixture and it is stirred under reflux conditions for 16 h. Then the solvents are solvent eliminated in vacuo and the residue is purified by column chromatography. The carrier used is C18-RP-silica gel and within 15 min a gradient is run through which consists at the starting point of 90% water and 10% acetonitrile and at the finishing point of 50% water and 50% acetonitrile. 0.1% formic acid are added to both the water and to the acetonitrile. The suitable fractions are combined with 0.5 ml 1 N hydrochloric acid and freeze-dried. The product is obtained as the dihydrochloride.

Yield: 20-mg (0.032 mmol, 8%) UV max: 325 nm MS (ESI): 644 (M+H)$^+$ $^1$H-NMR (400 MHz): 1.30-1.47 (m, 9H), 1.85-2.01 (m, 4H), 3.20-3.31 (m, 2H), 3.91 (s, 3H), 3.99-4.15 (m, 1H), 4.51-4.78 (m, 3H), 7.23-7.29 (m, 1H), 7.39-7.47 (m, 1H), 7.63-7.69 (m, 1H), 7.73-7.77 (m, 1H), 7.79-7.87 (m, 1H), 8.40-8.59 (m, 2H), 8.75-8.82 (m, 1H), 9.16-9.21 (m, 1H), 10.50-10.63 (m, 2H)

EXAMPLES 797-806

The following compounds are prepared by an analogous method to that described in Example 796:

| # | R$_3$' | UV max [nm] | MS (ESI) (M + H)$^+$ |
|---|---|---|---|
| 797 | pyrrolidine-CH$_2$-cyclopropyl-X$_2$ | 285, 325 | 642 |
| 798 | cyclopropyl(CH$_2$-pyrrolidine)-X$_2$ | 284, 325 | 642 |
| 799 | pyrrolidine-C(CH$_3$)$_2$-CH$_2$-X$_2$ | 325, 285 | 644 |
| 800 | piperidine-CH(CH$_3$)-CH$_2$-X$_2$ | 325, 285 | 644 |
| 801 | piperidine-CH(CH$_3$)-CH$_2$-X$_2$ | 325, 285 | 644 |
| 802 | pyrrolidine-CH$_2$-cyclopropyl-CH$_2$-X$_2$ | 325, 285 | 656 |
| 803 | X$_2$-C(CH$_3$)$_2$-CH$_2$-piperidine | 325, 285 | 658 |
| 804 | pyrrolidine-CH$_2$-C(CH$_3$)$_2$-CH$_2$-X$_2$ | 325, 284 | 658 |
| 805 | X$_2$-CH$_2$-cyclopropyl-CH$_2$-piperidine | 326, 286 | 670 |
| 806 | X$_2$-cyclohexyl-pyrrolidine | 324, 285 | 670 |

EXAMPLES 807-821
The following compounds are prepared by an analogous process to that described in Example 53. The corresponding aniline is described in method 31. The amine used to prepare the amide is commercially obtainable or is described in method 13, 21 or in method 25.
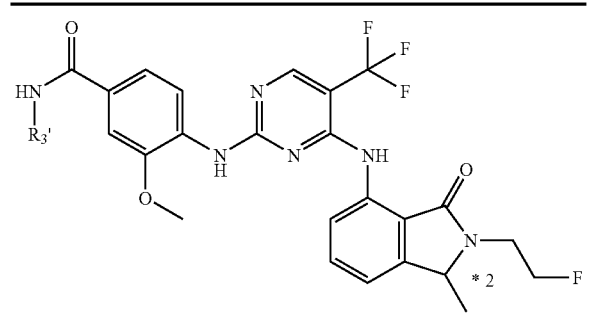
| # | R3' | UV max [nm] | MS (ESI) (M + H)+ |
|---|---|---|---|
| 807 | 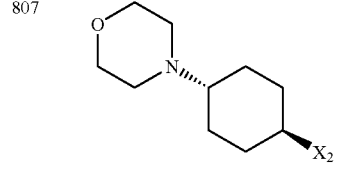 | 286, 322 | 686 |
| 808 | 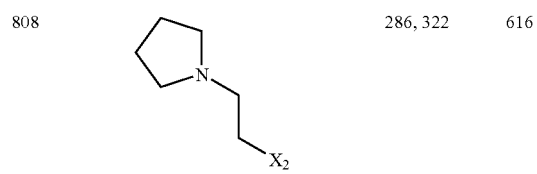 | 286, 322 | 616 |
| 809 | 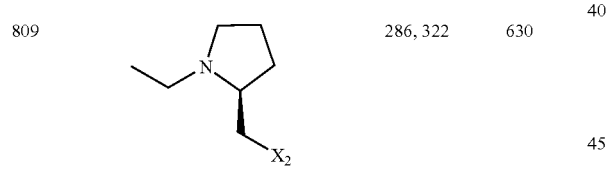 | 286, 322 | 630 |
| 810 | 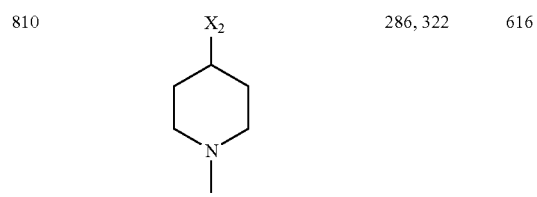 | 286, 322 | 616 |
| 811 | 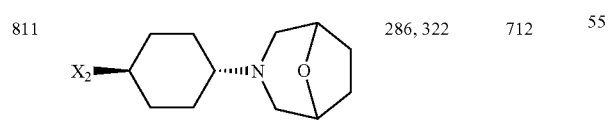 | 286, 322 | 712 |
| 812 | 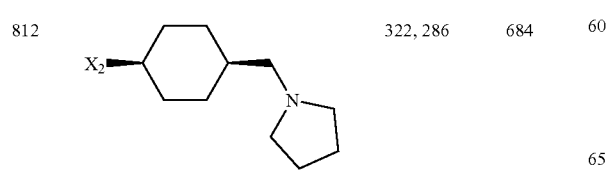 | 322, 286 | 684 |
-continued
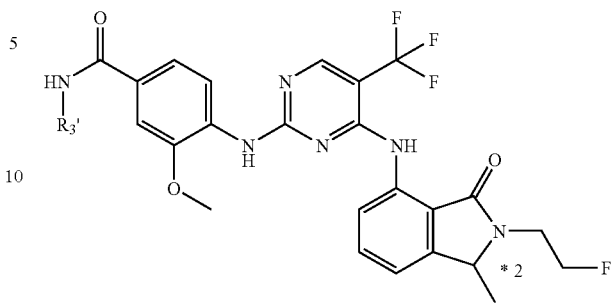
| # | R3' | UV max [nm] | MS (ESI) (M + H)+ |
|---|---|---|---|
| 813 | 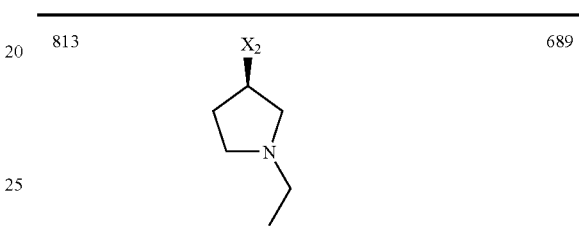 |  | 689 |
| 814 | 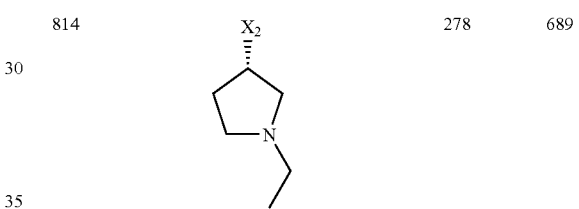 | 278 | 689 |
| 815 | 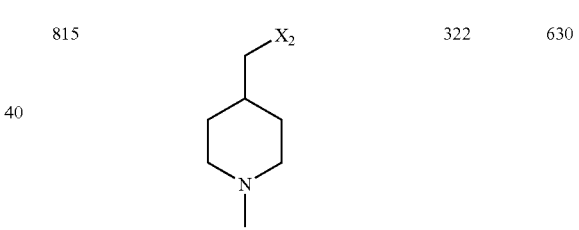 | 322 | 630 |
| 816 | 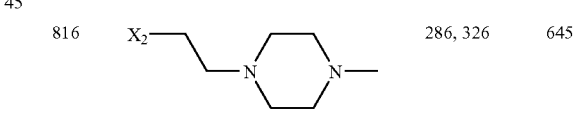 | 286, 326 | 645 |
| 817 | 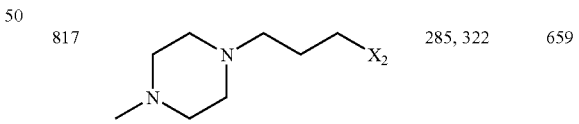 | 285, 322 | 659 |
| 818 | 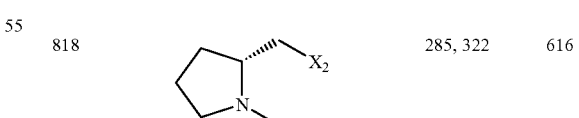 | 285, 322 | 616 |
| 819 | 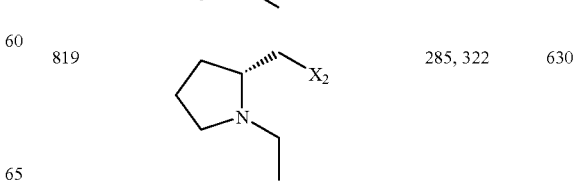 | 285, 322 | 630 |

-continued
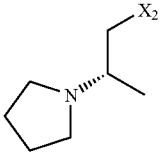
| # | R₃' | UV max [nm] | MS (ESI) (M + H)⁺ |
|---|-----|-------------|-------------------|
| 820 | 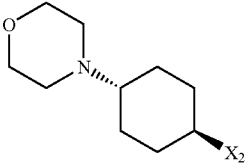 | | 630 |
| 821 | 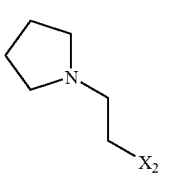 | 322, 286 | 630 |
-continued
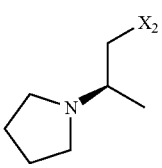
| # | R₃' | UV max [nm] | MS (ESI) (M + H)⁺ |
|---|-----|-------------|-------------------|
EXAMPLES 822-885
The following compounds are prepared by an analogous process to that described in Example 53. The corresponding aniline is described in method 31. The amine used to prepare the amide is commercially obtainable, described in method 13, 15, 20, 21, 23, 24 and 25 or in J. Med. Chem. 2003, 46(5), 702-715.
| # | R₃' | UV max [nm] | MS (ESI) (M + H)⁺ |
|---|-----|-------------|-------------------|
| 822 | | 286, 322 | 686 |
| 823 | | 325, 284 | 616 |

-continued
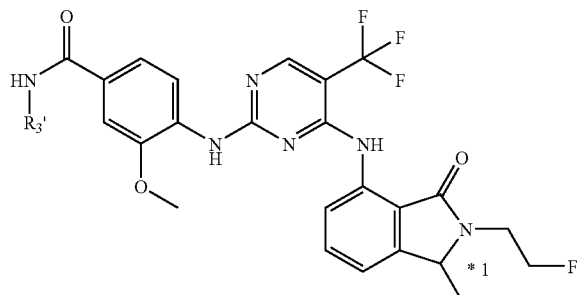
| # | R₃' | UV max [nm] | MS (ESI) (M + H)⁺ |
|---|---|---|---|
| 824 | | 286, 326 | 630 |
| 825 | | 286, 322 | 616 |
| 826 | | 286, 318 | 712 |
| 827 | | 286, 322 | 684 |
| 828 | | 326 | 645 |
| 829 | | 316 | 689 |

-continued
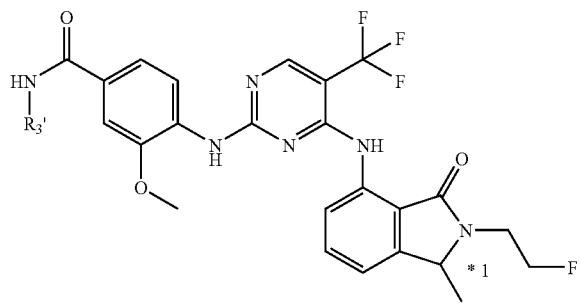
| # | R₃' | UV max [nm] | MS (ESI) (M + H)⁺ |
|---|---|---|---|
| 830 | (1-ethylpyrrolidin-3-yl), X₂ attached | 322 | 689 |
| 831 | azepan-4-yl, X₂ attached | | 616 |
| 832 | 1-(pyrrolidin-1-yl)propan-2-yl, X₂ attached | 318 | 630 |
| 833 | pyrrolidin-3-yl, X₂ attached | 326 | 588 |
| 834 | (1-methylpiperidin-4-yl)methyl, X₂ attached | 322 | 630 |
| 835 | 2-(piperidin-1-yl)ethyl, X₂ attached | 286, 322 | 630 |
| 836 | 3-morpholinocyclobutyl, X₂ attached (*2', *2") | | 658 |

-continued
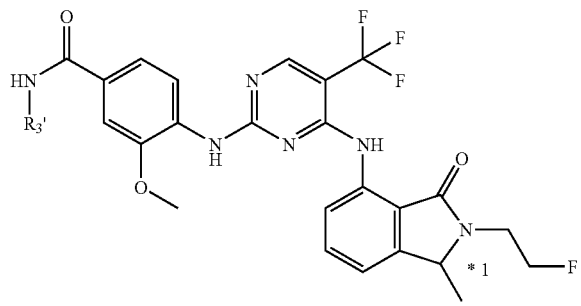
| # | R₃' | UV max [nm] | MS (ESI) (M + H)⁺ |
|---|---|---|---|
| 837 | pyrrolidin-3-ylmethyl-X₂ | 322-326 | 602 |
| 838 | piperidin-3-ylmethyl-X₂ | 322-326 | 616 |
| 839 | piperidin-3-ylmethyl-X₂ | 322 | 616 |
| 840 | 1-methylpyrrolidin-3-ylmethyl-X₂ | 322-326 | 616 |
| 841 | 1-methylpiperidin-3-ylmethyl-X₂ | 322-326 | 630 |
| 842 | 1-methylpiperidin-3-ylmethyl-X₂ | 322-326 | 630 |
| 843 | 3-(piperidin-1-yl)propyl-X₂ | 286, 322 | 644 |
| 844 | X₂-cyclobutyl-pyrrolidin-1-yl (*2', *2") | 286, 322 | 642 |

-continued
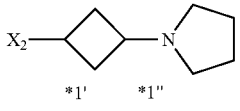
| # | R3' | UV max [nm] | MS (ESI) (M + H)+ |
|---|---|---|---|
| 845 | 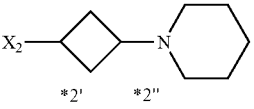 | 286, 322 | 642 |
| 846 | 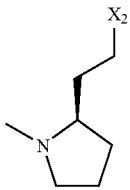 | 286, 322 | 656 |
| 847 | 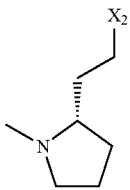 | 282, 318 | 630 |
| 848 | 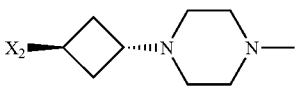 | 282, 322 | 630 |
| 849 | 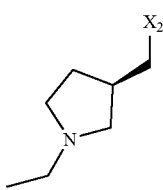 | 286, 318 | 671 |
| 850 | 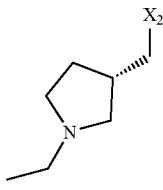 | 286, 322 | 630 |
| 851 | 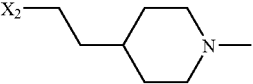 | 286, 322 | 630 |
| 852 | | 286, 322 | 644 |

-continued
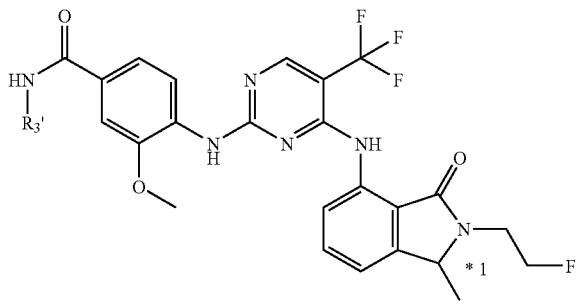
| # | R₃' | UV max [nm] | MS (ESI) (M + H)⁺ |
|---|---|---|---|
| 853 | X₂–⬜–N(piperidine)–OH  *1' *1" | 322-326 | 672 |
| 854 | X₂–⬜–N(piperidine)–OH  *2' *2" | 322 | 672 |
| 855 | X₂–⬜–N(piperidine)–N(pyrrolidine)  *2' *2" | 286, 322 | 725 |
| 856 | X₂–⬜–N(piperidine)–N(pyrrolidine)  *1' *1" | 286, 322 | 725 |
| 857 | X₂–⬜–N(diazepane)–N-Me  *2' *2" | 322-326 | 685 |
| 858 | X₂–⬜–N(Me)–CH₂–(N-Me piperidine)  *1' *1" | 286, 322 | 713 |
| 859 | X₂–⬜–N(Me)–CH₂–(N-Me piperidine)  *2' *2" | 286, 322 | 713 |
| 860 | X₂–⬜–N(Me)(iPr)  *1' *1" | 286, 322 | 644 |
| 861 | X₂–⬜–N(Me)(iPr)  *2' *2" | 286, 322 | 644 |

-continued
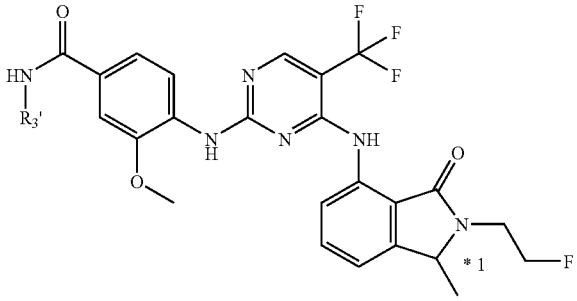
| # | R₃' | UV max [nm] | MS (ESI) (M + H)⁺ |
|---|---|---|---|
| 862 | 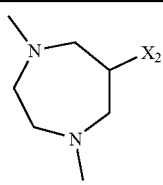 | 318-322 | 645 |
| 863 | 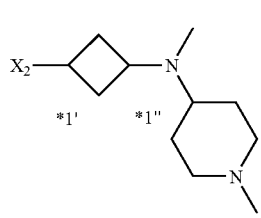 | 286, 322 | 658 |
| 864 | 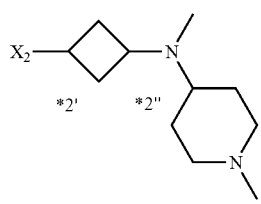 | 286, 322 | 699 |
| 865 | 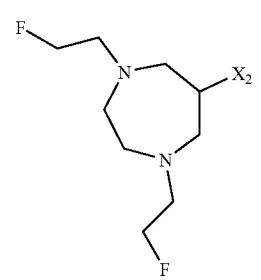 | 286, 322 | 699 |
| 866 | 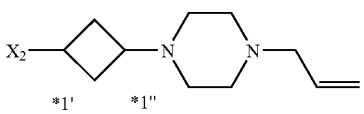 | 326 | 709 |
| 867 |  | 322 | 697 |

-continued

| # | R₃' | UV max [nm] | MS (ESI) (M + H)⁺ |
|---|---|---|---|
| 868 | X₂—(cyclobutyl *2')—(piperazine *2")—CH₂CH=CH₂ | 322 | 697 |
| 869 | X₂—(cyclobutyl *1')—(piperazine *1")—CH₂C≡CH | 318 | 695 |
| 870 | X₂—(pyridyl)—CH₂—(piperidine) | 290.3 | 693 |
| 871 | X₂—(cyclobutyl *2')—(piperazine *2")—CH₂C≡CH | 322 | 695 |
| 872 | X₂—(cyclobutyl *2')—(piperazine *2")—CH₂CH₂CF₃ | 286, 322 | 753 |
| 873 | X₂—(cyclobutyl *2')—N(CH₃)—(cyclopropyl) *2" | 286, 326 | 642 |
| 874 | X₂—CH₂CH₂—(piperazine)—CH₃ | 286, 322 | 645 |
| 875 | X₂—CH₂CH₂CH₂—(piperazine)—N—CH₃ | 322, 286 | 659 |

-continued
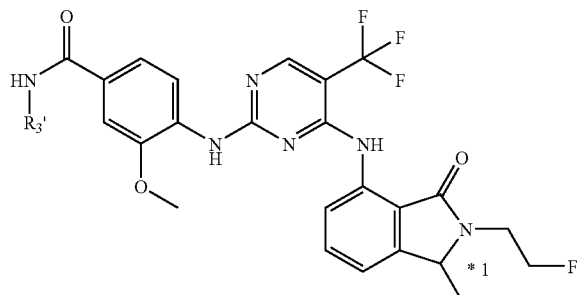
| # | R₃' | UV max [nm] | MS (ESI) (M + H)⁺ |
|---|---|---|---|
| 876 | 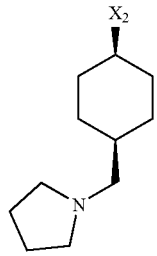 | 282, 322 | 684 |
| 877 | 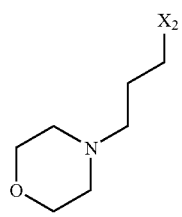 | 324, 284 | 646 |
| 878 | 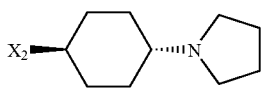 | 286, 322 | 670 |
| 879 | 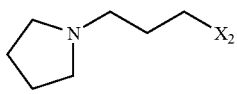 | 325, 284 | 630 |
| 880 | 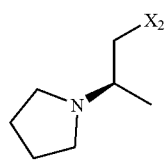 | 322, 286 | 630 |

-continued
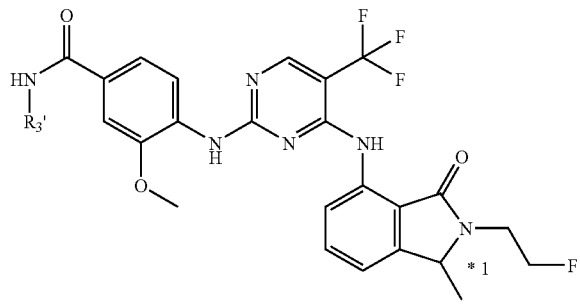
| # | R3' | UV max [nm] | MS (ESI) (M + H)+ |
|---|---|---|---|
| 881 | | 322, 286 | 684 |
| 882 | | 325, 286 | 670 |
| 883 | | 322, 286 | 646 |
| 884 | | 326, 286 | 644 |
| 885 | | 325, 285 | 630 |

EXAMPLES 886-891
The following compounds are prepared by an analogous process to that described in Example 622 or 623. The corresponding aniline is described in method 27 or 28.
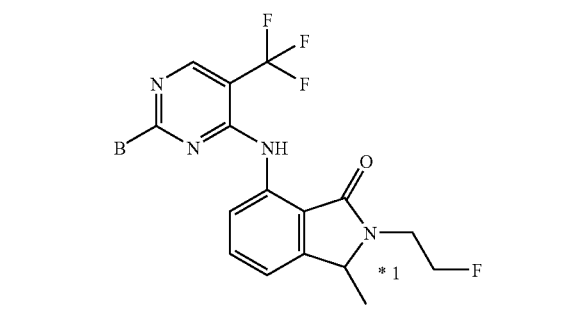
| # | B | UV max [nm] | MS (ESI) (M + H)+ |
|---|---|---|---|
| 886 | 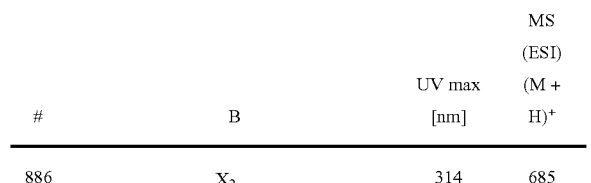 | 314 | 685 |
| 887 | 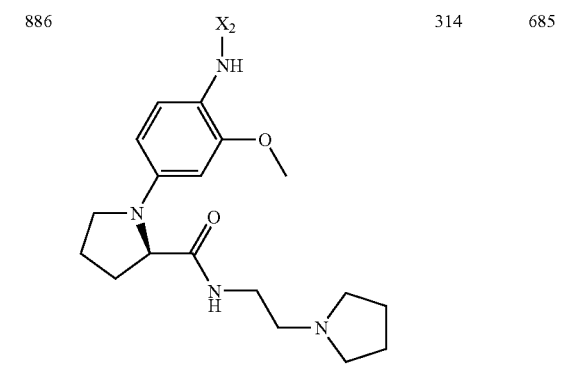 | 314 | 685 |
-continued
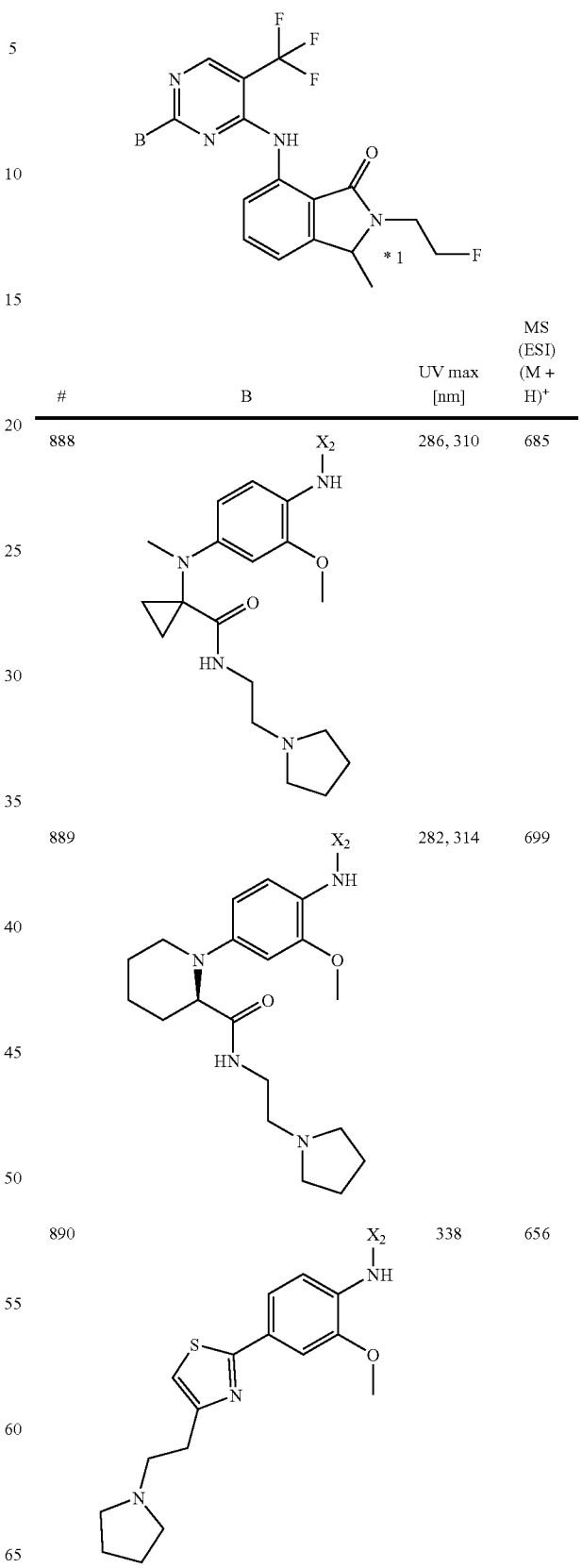
| # | B | UV max [nm] | MS (ESI) (M + H)+ |
|---|---|---|---|
| 888 | | 286, 310 | 685 |
| 889 | | 282, 314 | 699 |
| 890 | | 338 | 656 |

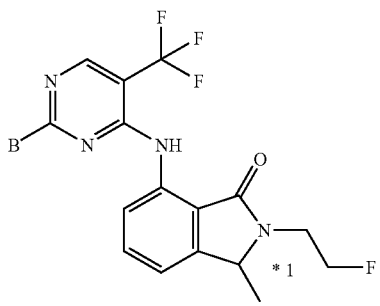

| # | B | UV max [nm] | MS (ESI) (M + H)+ |
|---|---|---|---|
| 891 | | 314 | 588 |

EXAMPLES 892-894

The following compounds are prepared by an analogous process to that described in Example 53. 2-(4-carboxy-2-bromo-phenylamino)-4-chloro-5-trifluoromethyl-pyrimidine is described in method 29. The corresponding aniline is described in method 31. The amine used to prepare the amide is commercially obtainable.

| # | R₃' | UV max [nm] | MS (ESI) (M + H)+ |
|---|---|---|---|
| 892 | | 314 | 665 |
| 893 | | 270 | 665 |

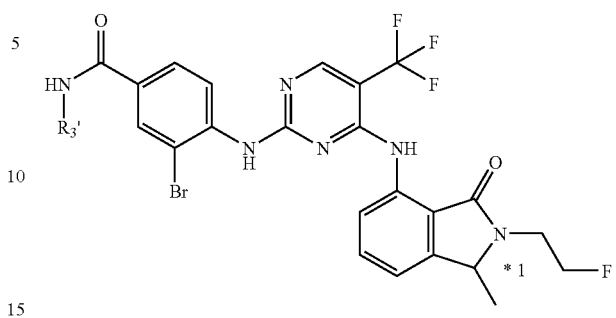

| # | R₃' | UV max [nm] | MS (ESI) (M + H)+ |
|---|---|---|---|
| 894 | | 270 | 680 |

EXAMPLE 895

2-(2-methoxy-4-[(1-methyl-piperidin-4-carbonyl)-amino]-phenylamino)-4-(2-(2-fluoro-ethyl)-1-methyl-3-oxo-2,3-dihydro-1H-isoindol-4-ylamino)-5-trifluoromethyl-pyrimidine Enantiomer 1

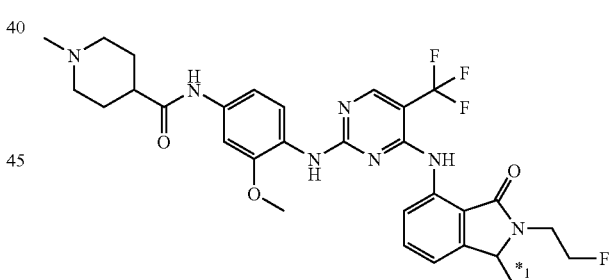

Starting from 2-(4-amino-2-methoxy-phenylamino)-4-(2-(2-fluoro-ethyl)-1-methyl-3-oxo-2,3-dihydro-1H-isoindol-4-ylamino)-5-trifluoromethyl-pyrimidine enantiomer 1 (analogously to method 30) the above-mentioned product is prepared by an amide linking method familiar to the skilled man (cf. also Example 1032). It is obtained as the dihydrochloride.

UV max 310 nm MS (ESI): 616 (M+H)+ ¹H-NMR (500 MHz): 1.42 (d, 3H), 1.69-1.77 (m, 2H), 1.77-1.84 (m, 2H), 1.94-2.03 (m, 2H), 2.23 (s, 3H), 2.29-2.38 (m, 1H), 2.86-2.93 (m, 2H), 3.72 (s, 3H), 4.00-4.12 (m, 1H), 4.52-4.75 (m, 3H), 7.16 (d, 3H), 7.18-7.24 (m, 1H), 7.32-7.41 (m, 1H), 7.57 (s, 1H), 8.18 (s, 1H), 8.38 (s, 1H), 9.07 (s, 1H), 9.95 (s, 1H), 10.46 (s, 1H)

EXAMPLE 896

2-(2-methoxy-4-(2-pyrrolidin-1-yl-acetylamino)-phenylamino)-4-(2-(2-fluoro-ethyl)-1-methyl-3-oxo-2,3-dihydro-1H-isoindol-4-ylamino)-5-trifluoromethyl-pyrimidine Enantiomer 1

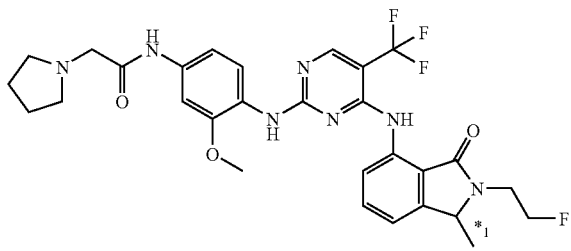

Starting from 2-(4-amino-2-methoxy-phenylamino)-4-(2-(2-fluoro-ethyl)-1-methyl-3-oxo-2,3-dihydro-1H-isoindol-4-ylamino)-5-trifluoromethyl-pyrimidine Enantiomer 1 (analogously to method 30) the above-mentioned product is prepared by an amide linking method familiar to the skilled man (cf. also Example 1032). It is obtained as the dihydrochloride.

UV max: 282 nm MS (ESI): 602 (M+H)$^+$ $^1$H-NMR (500 MHz): 1.43 (d, 3H), 1.87-2.00 (m, 2H), 2.00-2.10 (m, 2H), 3.12-3.22 (m, 2H), 3.74 (s, 3H), 4.00-4.13 (m, 1H), 4.28-4.32 (m, 2H), 4.53-4.76 (m, 3H), 7.19-7.49 (m, 4H), 7.51 (s, 1H), 8.41 (s, 1H), 9.26 (s, 1H), 10.20-10.31 (m, 1H), 10.54 (s, 1H), 10.86 (s, 1H)

EXAMPLES 897-952

Using a method analogous to that described in Example 53 a primary amine which has another protected amino function in the side chain is coupled to 2-(4-carboxy-2-methoxy-phenylamino)-4-[2-(2-fluoro-ethyl)-1-methyl-3-oxo-2,3-dihydro-1H-isoindol-4-ylamino]-5-trifluoromethyl-pyrimidine Enantiomer 1. The protective group used may be a tert-butoxycarbonyl, benzyloxycarbonyl or benzyl group. This protective group is cleaved using a procedure familiar to the skilled man and reductive amination (analogously to Example 639) or alkylation (analogously to method 34 or WO2004052857) are the final steps in this sequence.

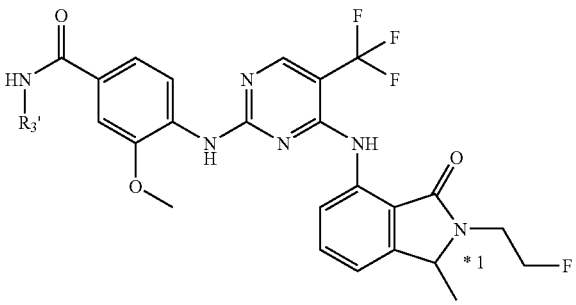

| # | R$_3$' | UV max [nm] | MS (ESI) (M + H)$^+$ |
|---|---|---|---|
| 897 | ![X2-pyrrolidine-tetrahydropyran] | | 672 |
| 898 | ![X2-piperidine-isopropyl] | 322 | 644 |

-continued

| # | R₃' | UV max [nm] | MS (ESI) (M + H)⁺ |
|---|---|---|---|
| 899 | X₂—(S)-pyrrolidin-3-yl, N-isopropyl | 326 | 630 |
| 900 | X₂—piperidin-4-yl, N-ethyl | 326 | 630 |
| 901 | X₂—azepan-4-yl, N-ethyl | 322 | 644 |
| 902 | X₂—piperidin-3-yl, N-cyclopropyl | 322 | 642 |
| 903 | X₂—azepan-4-yl, N-isopropyl | 322 | 658 |
| 904 | X₂—piperidin-4-yl, N-cyclopropyl | 326 | 615 |

-continued

[Structure: benzamide with HN-R3', methoxy, linked via NH to pyrimidine bearing CF3 and NH to methyl-isoindolin-1-one with N-CH2CH2F, marked *1]

| # | R3' | UV max [nm] | MS (ESI) (M + H)+ |
|---|---|---|---|
| 905 | X2-(1-cyclopropyl-azepan-4-yl) | 322 | 656 |
| 906 | X2-(1-isobutyl-piperidin-3-yl) | 326 | 658 |
| 907 | X2-(1-propyl-piperidin-3-yl) | 326 | 644 |
| 908 | X2-(1-isopropyl-piperidin-3-yl) | 322 | 644 |
| 909 | X2-(1-cyclopentyl-piperidin-3-yl) | 322 | 670 |
| 910 | X2-(1-(tetrahydropyran-4-yl)-piperidin-3-yl) | 306 | 686 |

-continued

| # | R₃' | UV max [nm] | MS (ESI) (M + H)⁺ |
|---|-----|-------------|-------------------|
| 911 | (3-ethylpiperidin-3-yl) | 326 | 630 |
| 912 | (1-(2,2-difluoroethyl)piperidin-3-yl) | | 666 |
| 913 | ((1-(cyclopropylmethyl)pyrrolidin-3-yl)methyl) | 286, 322 | 656 |
| 914 | ((1-(cyclopropylmethyl)pyrrolidin-3-yl)methyl) | 286, 322 | 656 |
| 915 | (2-(1-(cyclopropylmethyl)pyrrolidin-2-yl)ethyl) | 286, 318 | 670 |
| 916 | (2-(1'-methyl-[1,3'-bipiperidin]-2-yl)ethyl) | 286, 322 | 713 |

-continued

| # | R₃' | UV max [nm] | MS (ESI) (M + H)⁺ |
|---|---|---|---|
| 917 | (2-(1-(cyclopropylmethyl)pyrrolidin-2-yl)ethyl)-X₂ | 286, 322 | 670 |
| 918 | (2-(1-(1-methylpiperidin-4-yl)pyrrolidin-2-yl)ethyl)-X₂ | 286.3 | 713 |
| 919 | ((1-(cyclopropylmethyl)azetidin-3-yl)methyl)-X₂ | 286, 322 | 642 |
| 920 | (2-(1-isobutylpyrrolidin-2-yl)ethyl)-X₂ | 286, 322 | 672 |
| 921 | (2-(1-isobutylpyrrolidin-2-yl)ethyl)-X₂ | 286, 322 | 672 |
| 922 | (2-(1-ethylpyrrolidin-2-yl)ethyl)-X₂ | 286, 322 | 644 |

-continued
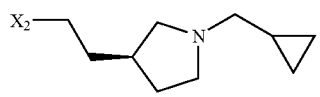
| # | R3' | UV max [nm] | MS (ESI) (M + H)+ |
|---|---|---|---|
| 923 | 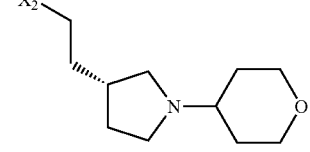 | 286, 322 | 670 |
| 924 | 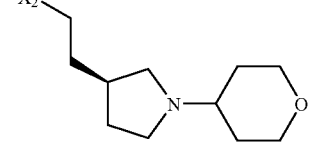 | 286, 322 | 700 |
| 925 | 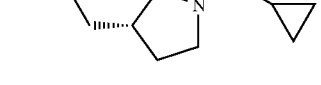 | 286, 322 | 700 |
| 926 | 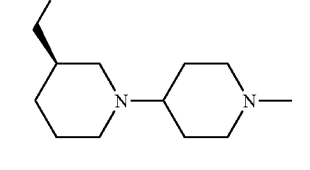 | 286, 322 | 670 |
| 927 | 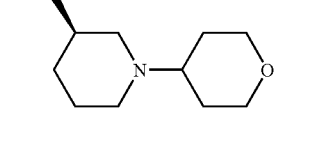 | 326 | 713 |
| 928 | 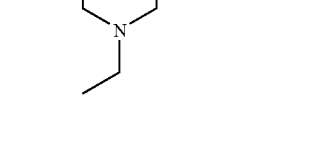 | 322-326 | 700 |
| 929 | | 322-326 | 644 |

-continued
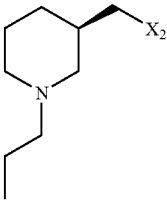
| # | R3' | UV max [nm] | MS (ESI) (M + H)+ |
|---|---|---|---|
| 930 | 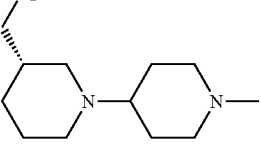 | 322 | 658 |
| 931 | 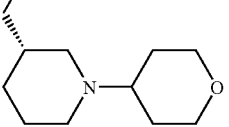 | 322-326 | 713 |
| 932 | 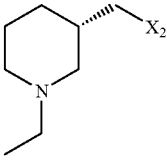 | 322 | 700 |
| 933 | 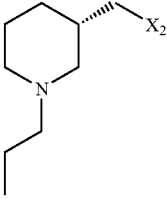 | 322-326 | 644 |
| 934 | 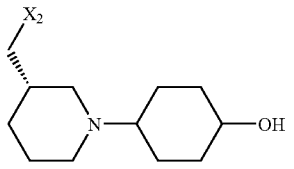 | 322 | 658 |
| 935 | | 322-326 | 714 |

-continued
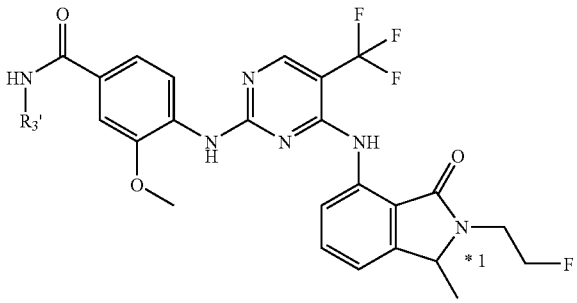
| # | R₃' | UV max [nm] | MS (ESI) (M + H)⁺ |
|---|---|---|---|
| 936 | 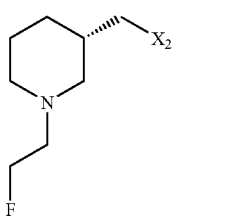 | 322 | 714 |
| 937 | 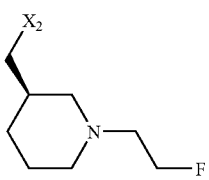 | 322 | 662 |
| 938 | 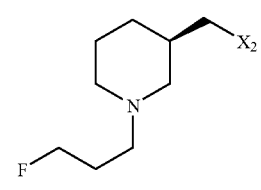 | 322-326 | 662 |
| 939 | 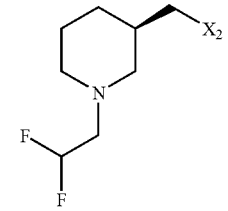 | | 676 |
| 940 | 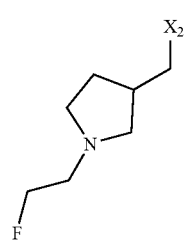 | 322-326 | 680 |
| 941 | | 286, 322 | 648 |

-continued

| # | R₃' | UV max [nm] | MS (ESI) (M + H)⁺ |
|---|---|---|---|
| 942 | (X₂-CH₂-[2-(1-(2-fluoroethyl)pyrrolidinyl)]) | 230, 286, 318 | 662 |
| 943 | X₂-CH₂CH₂-[4-(1-propargylpiperidinyl)] | 284, 324 | 668 |
| 944 | X₂-CH₂CH₂-[4-(1-allylpiperidinyl)] | 282, 322 | 670 |
| 945 | X₂-CH₂CH₂-[4-(1-(pent-2-ynyl)piperidinyl)] | 282, 322 | 696 |
| 946 | X₂-CH₂-[3-(1-allylpyrrolidinyl)] | 228, 284, 322 | 642 |
| 947 | X₂-CH₂CH₂-[4-(1-isopropylpiperidinyl)] | 226, 286, 322 | 672 |
| 948 | X₂-CH₂-[3-(1-isopropylpyrrolidinyl)] | 286, 322 | 644 |
| 949 | X₂-[4-(1-isopropylpiperidinyl)] | 324, 284 | 644 |
| 950 | (1-methylpyrrolidin-2-yl)-CH₂-X₂ | 285, 322 | 616 |

-continued
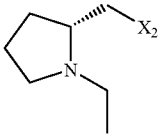
| # | R₃' | UV max [nm] | MS (ESI) (M + H)⁺ |
|---|---|---|---|
| 951 | 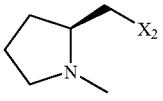 | 285, 325 | 630 |
| 952 | 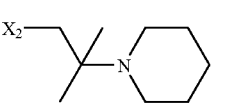 | 285, 325 | 616 |
EXAMPLES 953-958
The following compounds are prepared by a method analogous to that described in Example 796:
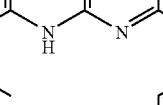
| # | R₃' | UV max [nm] | MS (ESI) (M + H)⁺ |
|---|---|---|---|
| 953 | 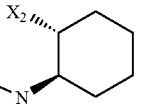 | 326, 286 | 658 |
| 954 | 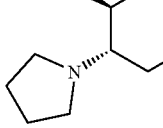 | 325, 285 | 670 |
-continued
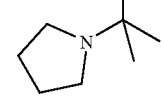
| # | R₃' | UV max [nm] | MS (ESI) (M + H)⁺ |
|---|---|---|---|
| 955 | | 325, 285 | 670 |
| 956 | | 325, 284 | 644 |
| 957 | | 325, 284 | 658 |

-continued

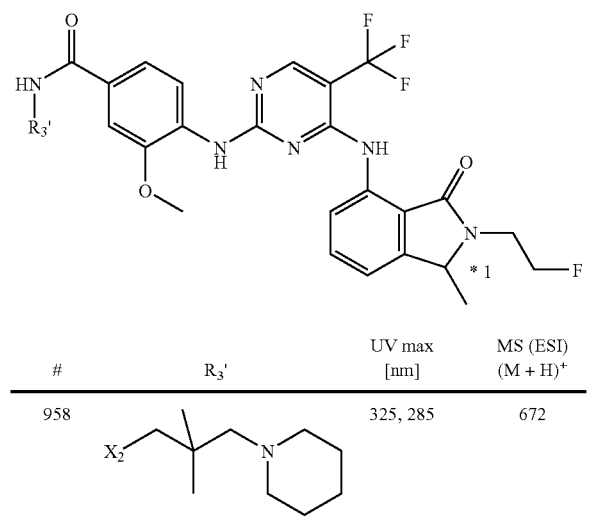

| # | R3' | UV max [nm] | MS (ESI) (M + H)+ |
|---|---|---|---|
| 958 | X2 (2,2-dimethyl-3-piperidin-1-yl-propyl) | 325, 285 | 672 |

EXAMPLE 959

2-(2-methoxy-4-(2-pyrrolidin-1-yl-ethylcarbamoyl)-phenylamino)-4-(2-(2-fluoro-ethyl)-1-ethyl-3-oxo-2,3-dihydro-1H-isoindol-4-ylamino)-5-trifluoromethyl-pyrimidine

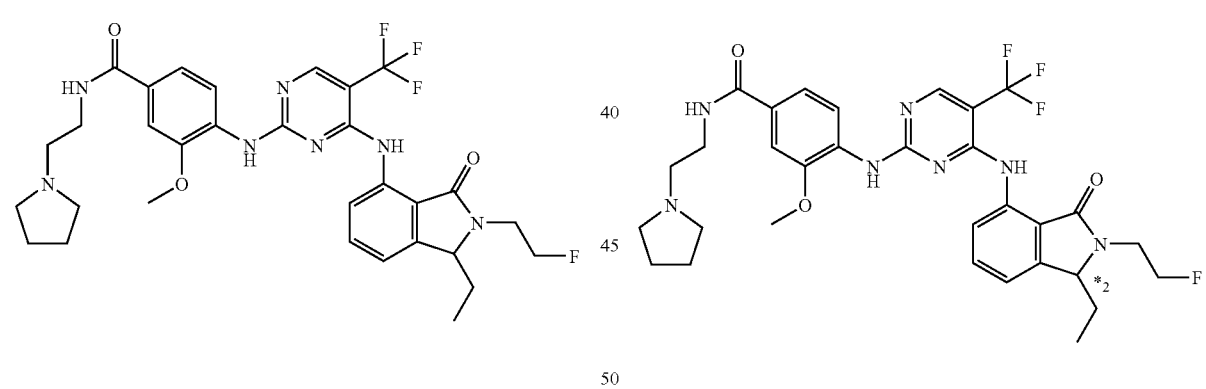

The racemic synthesis of the above-mentioned compound is carried out using by a method analogous to that described in Example 53. The corresponding aniline is described in method 22. The two enantiomers are isolated by preparative chromatography:

column: 250×4.6 mm CHIRALPAK ADH®
eluant: 25 ethanol/75 methanol (v/v) (0.03% triethylamine is added to each solvent)
flow rate: 0.5 ml/min
temperature: 20° C.

The enantiomer that elutes first is referred to as Enantiomer 1 and bears the symbol *1 in the chemical formula.

Enantiomer 1

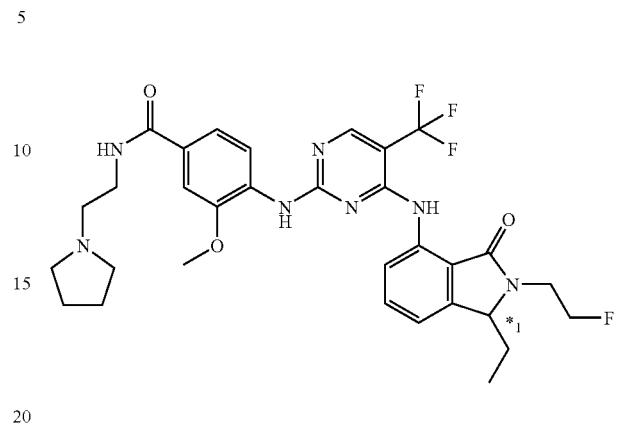

retention time: 9.96 min

The enantiomer that elutes second is referred to as Enantiomer 2 and bears the symbol *2 in the chemical formula.

Enantiomer 2 retention time: 12.60 min

EXAMPLES 960-976

The following compounds are prepared by an analogous method to that described in Example 53. The corresponding aniline is described in method 22. The amine used to prepare the amide is commercially obtainable or is described in method 13.

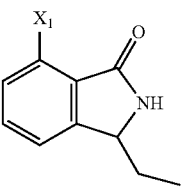
| # | A | R3' | UV max [nm] | MS (ESI) (M + H)+ |
|---|---|---|---|---|
| 960 | 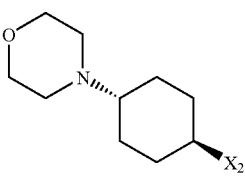 | 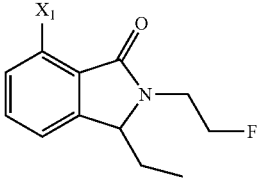 | 280, 320 | 654 |
| 961 | 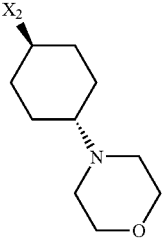 | 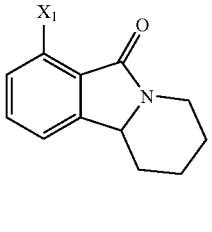 | 282, 318 | |
| 962 | 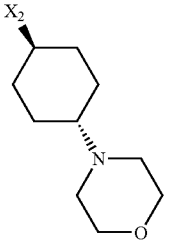 | 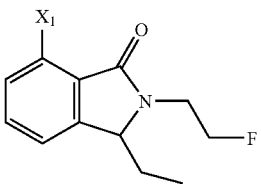 | 286, 322 | 680 |
| 963 | 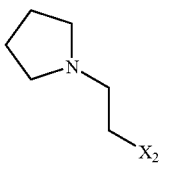 | 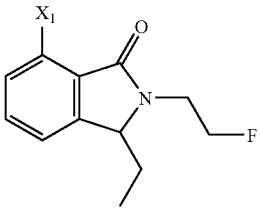 | 286, 326 | 630 |
| 964 | 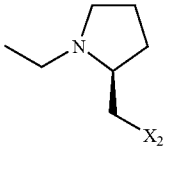 | 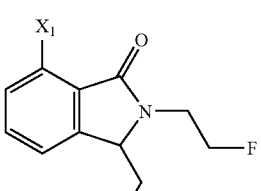 | 286, 326 | 644 |
| 965 | 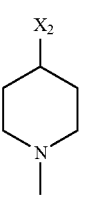 | | 286, 326 | 630 |

-continued

| # | A | R₃' | UV max [nm] | MS (ESI) (M + H)⁺ |
|---|---|---|---|---|
| 966 | 7-X₁, 3-ethyl, 2-(2-fluoroethyl)isoindolin-1-one | X₂-CH₂CH₂-(4-methylpiperazin-1-yl) | 286, 326 | 659 |
| 967 | 7-X₁, 3-ethyl, 2-(2-fluoroethyl)isoindolin-1-one | X₂-CH₂-(1-methylpyrrolidin-3-yl) | 286, 326 | 630 |
| 968 | 7-X₁, 3-ethyl, 2-(2-fluoroethyl)isoindolin-1-one | X₂-CH₂-(1-methylpiperidin-4-yl) | 286, 322 | 644 |
| 969 | 7-X₁, 3-propyl, 2-(2-fluoroethyl)isoindolin-1-one | X₂-(1-methylpiperidin-4-yl) | 286, 326 | 644 |
| 970 | 7-X₁, 3-propyl, 2-(2-fluoroethyl)isoindolin-1-one | pyrrolidin-1-yl-CH₂CH₂-X₂ | 286, 326 | 644 |

-continued
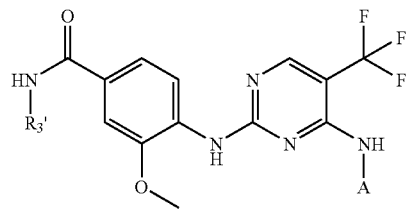
| # | A | R₃' | UV max [nm] | MS (ESI) (M + H)⁺ |
|---|---|-----|-------------|-------------------|
| 971 | | | 286, 326 | 714 |
| 972 | | | 286, 322 | 632 |
| 973 | | | 286, 326 | 646 |
| 974 | | | 286, 326 | 660 |
| 975 | | | 282, 326 | 685 |

-continued
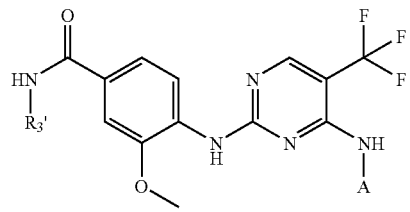
| # | A | R₃' | UV max [nm] | MS (ESI) (M + H)⁺ |
|---|---|-----|-------------|-------------------|
| 976 | 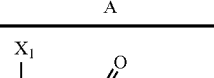 | 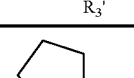 | 282, 326 | 659 |
EXAMPLES 977-980
The following compounds are prepared by an analogous method to that described in Example 53. The corresponding aniline is described in method 6. The amine used to prepare the amide is described in method 13.
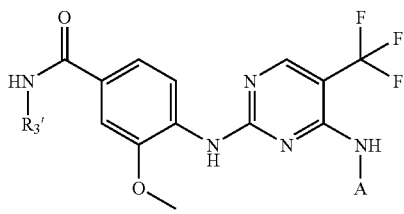
| # | A | R₃' | UV max [nm] | MS (ESI) (M + H)⁺ |
|---|---|-----|-------------|-------------------|
| 977 | | | 234, 282, 318 | 655 |
| 978 | | | 226, 282, 318 | 655 |
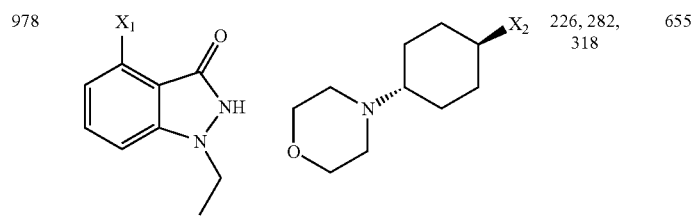

-continued
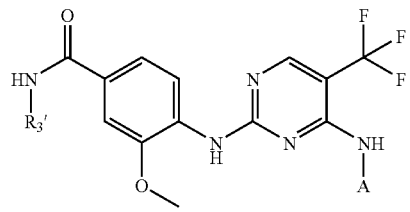
| # | A | R₃' | UV max [nm] | MS (ESI) (M + H)⁺ |
|---|---|-----|-------------|-------------------|
| 979 | | | 222, 282, 318 | 641 |
| 980 | | | 230, 282, 671 | 671 |
EXAMPLES 981-999
The following compounds are prepared by an analogous method to that described in Example 53. The corresponding aniline is described in method 32. The amine used to prepare the amide is commercially obtainable or described in method 13.
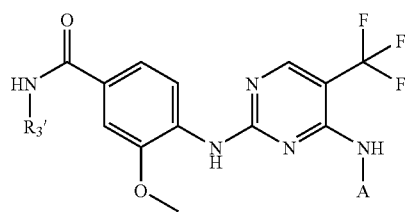
| # | A | R₃' | UV max [nm] | MS (ESI) (M + H)⁺ |
|---|---|-----|-------------|-------------------|
| 981 | | | 318 | 612 |

-continued
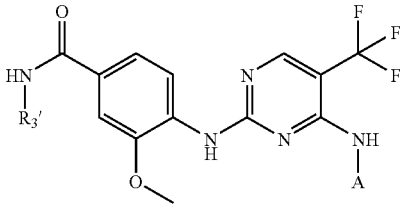
| # | A | R₃' | UV max [nm] | MS (ESI) (M + H)⁺ |
|---|---|---|---|---|
| 982 | 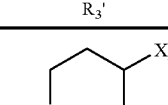 | 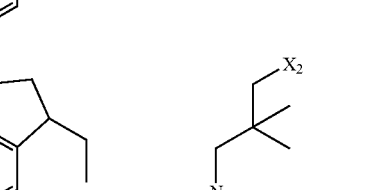 | 318 | 583 |
| 983 | 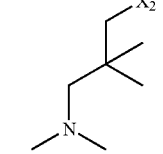 | 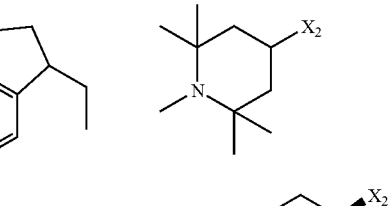 | 322 | 599 |
| 984 | 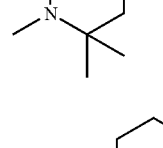 | 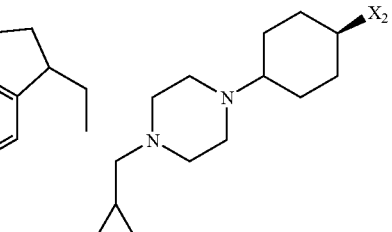 | | 639 |
| 985 | 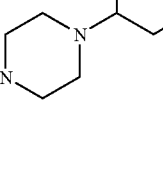 | 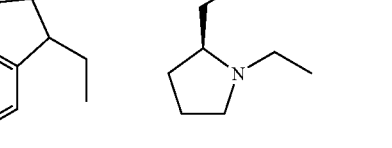 | 286 | 706 |
| 986 | 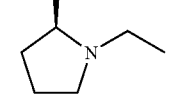 | 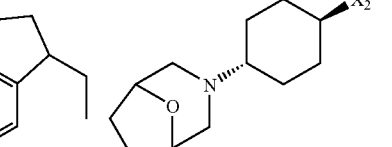 | 322 | 597 |
| 987 | 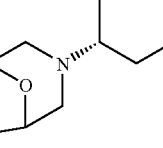 | 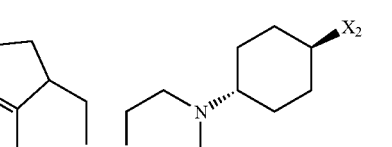 | 318 | 679 |
| 988 | 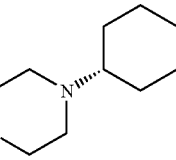 |  | 286 | 653 |

-continued

| # | A | R₃' | UV max [nm] | MS (ESI) (M + H)⁺ |
|---|---|-----|-------------|-------------------|
| 989 | X₁-(3-propyl-indan-1-one) | X₂-CH₂-(1-ethyl-pyrrolidin-2-yl) | 322 | 611 |
| 990 | X₁-(3-methyl-indan-1-one) | X₂-CH₂-(1-ethyl-pyrrolidin-2-yl) | 322 | 583 |
| 991 | X₁-(3-methyl-indan-1-one) | X₂-(1,2,2,6,6-pentamethyl-piperidin-4-yl) | 318 | 625 |
| 992 | X₁-(3-propyl-indan-1-one) | X₂-(1-methyl-piperidin-4-yl) | 318 | 597 |
| 993 | X₁-(3-methyl-indan-1-one) | X₂-CH₂CH₂-(4-methyl-piperazin-1-yl) | 318 | 598 |
| 994 | X₁-(3-methyl-indan-1-one) | X₂-(1-methyl-piperidin-4-yl) | 318 | 569 |

-continued

| # | A | R₃' | UV max [nm] | MS (ESI) (M + H)⁺ |
|---|---|-----|-------------|-------------------|
| 995 | | | 322 | 585 |
| 996 | | | 286 | 639 |
| 997 | | | 318 | 626 |
| 998 | | | 318 | 599 |
| 999 | | | 318 | 318 |

EXAMPLES 1000-1024
The following compounds are prepared by an analogous method to that described in Example 53. The corresponding aniline is described in method 33. The amine used to prepare the amide is commercially obtainable or described in method 13 or 21.
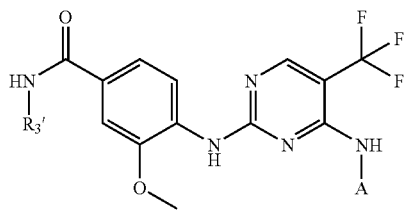
| # | A | R₃' | UV max [nm] | MS (ESI) (M + H)⁺ |
|---|---|-----|-------------|-------------------|
| 1000 | | | 282, 322 | 614 |
| 1001 | | | 282, 322 | 841 |
| 1002 | | | 282, 326 | 571 |
| 1003 | | | 280, 322 | 655 |
| 1004 | | | 280, 325 | 655 |

-continued

| # | A | R₃' | UV max [nm] | MS (ESI) (M + H)⁺ |
|---|---|---|---|---|
| 1005 | (X₁-phthalide-isopropyl) | (morpholine-cyclohexyl-X₂) | 280, 322 | 669 |
| 1006 | (X₁-phthalide-isopropyl) | (pyrrolidine-ethyl-X₂) | 280, 325 | 599 |
| 1007 | (X₁-phthalide-isopropyl) | (N-ethyl-pyrrolidine-methyl-X₂) | 282, 327 | 613 |
| 1008 | (X₁-methyl-phthalide-isobutyl) | (morpholine-cyclohexyl-X₂) | 280, 322 | 697 |
| 1009 | (X₁-methyl-phthalide-isobutyl) | (pyrrolidine-ethyl-X₂) | 282, 325 | 627 |
| 1010 | (X₁-methyl-phthalide-isobutyl) | (N-ethyl-pyrrolidine-methyl-X₂) | 283, 328 | 641 |

-continued

| # | A | R₃' | UV max [nm] | MS (ESI) (M + H)⁺ |
|---|---|---|---|---|
| 1011 | 3-ethyl-7-X₁-isobenzofuran-1(3H)-one | 2-(pyrrolidin-1-yl)ethyl-X₂ | 280, 325 | 585 |
| 1012 | 3-ethyl-7-X₁-isobenzofuran-1(3H)-one | (1-ethylpyrrolidin-2-yl)methyl-X₂ | 280, 325 | 599 |
| 1013 | 3,3-dimethyl-7-X₁-isobenzofuran-1(3H)-one | 2-(pyrrolidin-1-yl)ethyl-X₂ | 326, 283 | 585 |
| 1014 | 3,3-dimethyl-7-X₁-isobenzofuran-1(3H)-one | (1-ethylpyrrolidin-2-yl)methyl-X₂ | 282, 327 | 599 |
| 1015 | 7-X₁-spiro[isobenzofuran-1(3H),1'-cyclobutan]-3-one | 2-(pyrrolidin-1-yl)ethyl-X₂ | 322-326 | 597 |
| 1016 | 7-X₁-spiro[isobenzofuran-1(3H),1'-cyclobutan]-3-one | 2-(piperidin-1-yl)ethyl-X₂ | 326 | 611 |

-continued
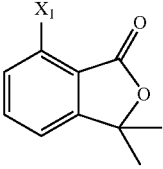
| # | A | R₃' | UV max [nm] | MS (ESI) (M + H)⁺ |
|---|---|---|---|---|
| 1017 | 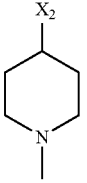 | 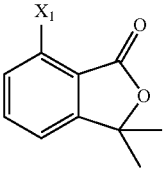 | 280, 325 | 585 |
| 1018 | 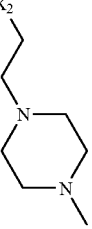 | 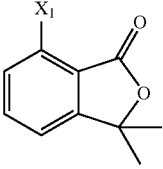 | 280, 325 | 614 |
| 1019 | 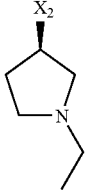 | 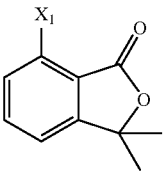 | 280, 325 | 585 |
| 1020 | 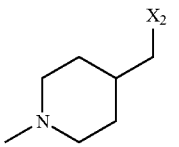 | 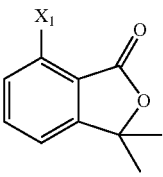 | 280, 322 | 599 |
| 1021 | 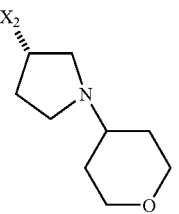 | 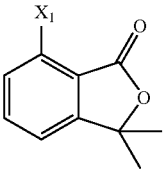 | 280, 325 | 641 |
| 1022 | 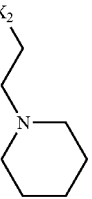 |  | 280, 325 | 599 |

-continued
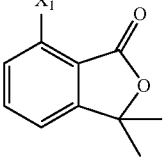
| # | A | R₃' | UV max [nm] | MS (ESI) (M + H)⁺ |
|---|---|-----|-------------|-------------------|
| 1023 | 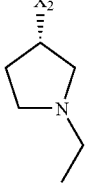 X₁ | 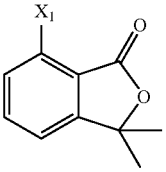 X₂ | 280, 325 | 585 |
| 1024 | 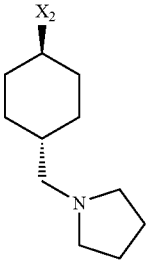 X₁ | 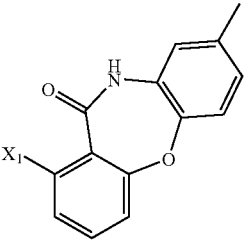 X₂ | 280, 322 | 653 |
EXAMPLES 1025-1032
The following compounds are prepared by an analogous method to that described in Example 53. The corresponding aniline is described in method 10. The amine used to prepare the amide is commercially obtainable or described in method 13.
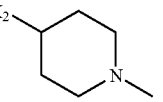
| # | A | R₃' | UV max [nm] | MS (ESI) (M + H)⁺ |
|---|---|-----|-------------|-------------------|
| 1025 | (structure with X₁) | X₂-(1-methylpiperidin-4-yl) | 318 | 648 |

-continued

| # | A | R₃' | UV max [nm] | MS (ESI) (M + H)⁺ |
|---|---|---|---|---|
| 1026 | | | 318 | 359 |
| 1027 | | | 322 | 662 |
| 1028 | | | 322 | 662 |
| 1029 | | | 322 | 664 |
| 1030 | | | 226, 318 | 678 |

-continued

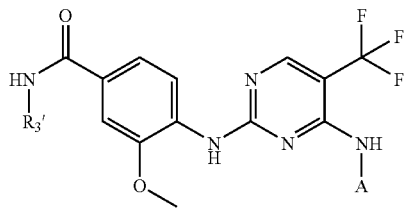

| # | A | R₃' | UV max [nm] | MS (ESI) (M + H)⁺ |
|---|---|---|---|---|
| 1031 | ![A structure] | ![R3' structure] | 226, 318 | 691 |
| 1032 | ![A structure] | ![R3' structure] | 322 | 648 |

EXAMPLES 1033-1035

The following compounds are prepared by an analogous method to that described in Example 53. The corresponding aniline is described in method 2. The amine used to prepare the amide is described in method 13.

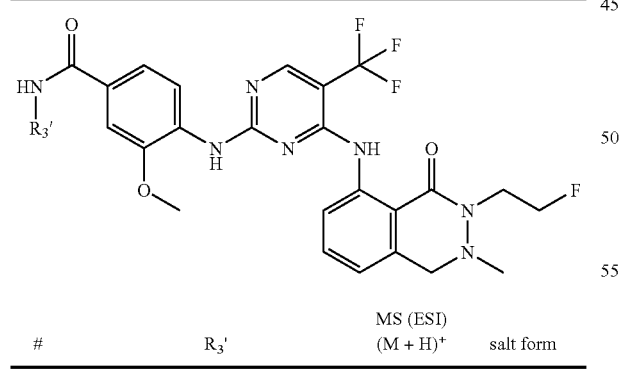

| # | R₃' | MS (ESI) (M + H)⁺ | salt form |
|---|---|---|---|
| 1033 | ![R3' structure] | 701 | base |

-continued

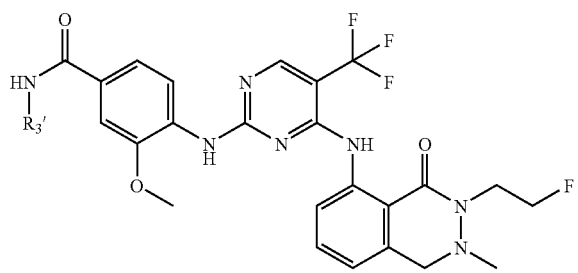

| # | R₃' | MS (ESI) (M + H)⁺ | salt form |
|---|---|---|---|
| 1034 | ![R3' structure] | 645 | formate |
| 1035 | 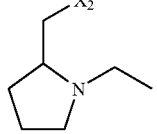 | 631 | formate |

EXAMPLE 1036

2-(2-methoxy-4-(2-pyrrolidin-1-yl-ethylcarbamoyl)-phenalamino)-4-(2-(2-fluoro-ethyl)-1,1-dimethyl-3-oxo-2,3-dihydro-1H-isoindol-4-ylamino)-5-trifluoromethyl-pyrimidine

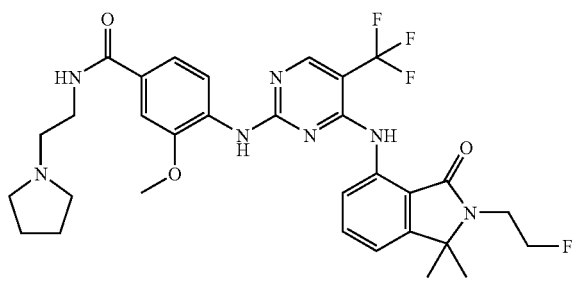

The above-mentioned compound is prepared by a method analogous to that described in Example 53. The corresponding aniline is described in method 34. The amine used to prepare the amide is commercially obtainable. The substance is obtained as the dihydrochloride.

UV max: 326, 286 nm MS (ESI): 630 (M+H)$^+$ $^1$H-NMR (400 MHz): 1.44-1.50 (m, 6H), 1.84-1.95 (m, 2H), 1.98-2.07 (m, 2H), 3.02-3.12 (m, 2H), 3.62-3.70 (m, 4H), 3.71-3.76 (m, 1H), 3.77-3.81 (m, 1H), 3.89 (s, 3H), 4.57-4.61 (m, 1H), 4.69-4.73 (m, 1H), 7.27-7.31 (m, 1H), 7.39-7.45 (m, 1H), 7.55-7.59 (m, 1H), 7.63-7.66 (m, 1H), 7.84-7.88 (m, 1H), 8.44-8.55 (m, 2H), 8.77-8.82 (m, 1H), 9.11-9.15 (m, 1H), 9.91-10.03 (m, 1H), 10.51-10.55 (m, 1H)

EXAMPLE 1037

2-(2-methoxy-4-[2-(4-methyl-piperazin-1-yl)-ethylcarbamoyl]-phenylamino)-4-(2-(2-fluoro-ethyl)-3-oxo-2,3-dihydro-1H-isoindol-4-ylamino)-5-acetyl-pyrimidine 50 mg (0.104 mmol) 2-(4-carboxy-2-methoxy-phenylamino)-4-(2-(2-fluoro-ethyl)-3-oxo-2,3-dihydro-1H-isoindol-4-ylamino)-5-acetyl-pyrimidine (prepared by an analogous process to that described in Example 622 or 623) are dissolved in 0.5 ml of dimethylformamide and combined with 72 µl (0.520 mmol) and 34 mg (0.104 mmol) O-(benzotriazol-1-yl)-N,N,N',N'-tetramethyluronium-tetrafluoroborate. After stirring for 20 min at 20° C., 23 mg (0.156 mmol) 2-(4-methylpiperazin-1-yl)-ethylamine are added. The reaction is completed after 2 h at 20° C. Then the solvent is eliminated in vacuo and the residue is purified by column chromatography. The carrier used is C18-RP-silica gel and a gradient is run through within 20 min which consists of 95% water and 5% acetonitrile at the starting point and consists of 5% water and 95% acetonitrile at the finishing point. 0.1% formic acid are added to both the water and to the acetonitrile. The suitable fractions are combined with 500 µl of a 1 M aqueous hydrochloric acid and freeze-dried. The product is obtained as the trihydrochloride.

UV max: 326 nm MS (ESI): 605 (M+H)$^+$ $^1$H-NMR (500 MHz): 2.53-2.58 (m, 3H), 2.80-2.92 (m, 3H), 3.62-3.88 (m, 9H), 3.88-4.01 (m, 4H), 4.54 (s, 2H), 4.58-4.66 (m, 1H), 4.69-4.77 (m, 1H), 7.14-7.32 (m, 1H), 7.32-7.50 (m, 1H), 7.50-7.59 (m, 1H), 7.63-7.75 (m, 1H), 7.78-8.01 (m, 1H), 8.29-8.60 (m, 1H), 8.73-8.99 (m, 2H), 9.03-9.18 (m, 1H), 12.31-12.41 (m, 1H)

EXAMPLES 1038-1060

The following compounds are prepared by an analogous method to that described in Example 1037. The aniline used is described in method 28.

The amine used to prepare the amide is commercially obtainable or described in method 13.

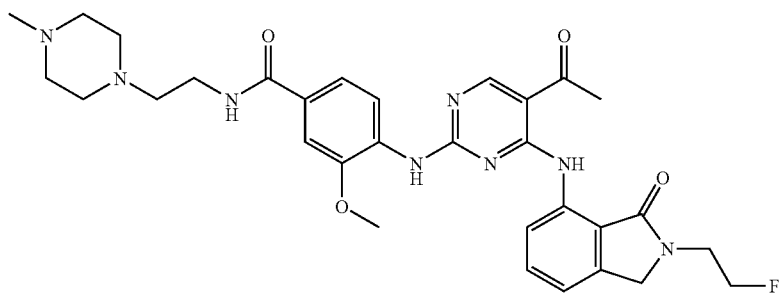

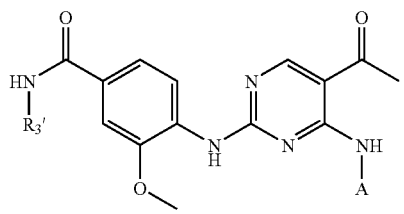
| # | A | R3' | UV max [nm] | MS (ESI) (M + H)+ |
|---|---|---|---|---|
| 1038 | | | 326 | 660 |
| 1039 | | | 326 | 646 |
| 1040 | | | 328 | 576 |
| 1041 | | | 318 | 672 |
| 1042 | | | 326 | 605 |

-continued

| # | A | R₃' | UV max [nm] | MS (ESI) (M + H)⁺ |
|---|---|---|---|---|
| 1043 | | | 330 | 590 |
| 1044 | | | 318 | 663 |
| 1045 | | | 330 | 604 |
| 1046 | | | 326 | 686 |
| 1047 | | | 326 | 604 |

-continued

| # | A | R₃' | UV max [nm] | MS (ESI) (M + H)⁺ |
|---|---|---|---|---|
| 1048 | | | 330 | 590 |
| 1049 | | | 326 | 713 |
| 1050 | | | 330 | 590 |
| 1051 | | | 250 | 614 |
| 1052 | | | 334-338 | 600 |
| 1053 | | | 334-338 | 614 |

-continued

| # | A | R₃' | UV max [nm] | MS (ESI) (M + H)⁺ |
|---|---|---|---|---|
| 1054 | | | 338 | 600 |
| 1055 | | | 338 | 670 |
| 1056 | | | 334 | 696 |
| 1057 | | | 330 | 622 |
| 1058 | | | 327 | 340 |
| 1059 | | | 330 | 608 |

-continued
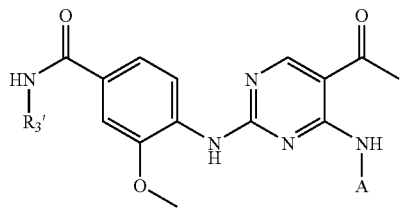
| # | A | R₃' | UV max [nm] | MS (ESI) (M + H)⁺ |
|---|---|---|---|---|
| 1060 | 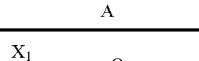 | 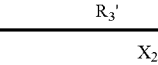 | 330 | 632 |
EXAMPLES 1061-1069
The following compounds are prepared by an analogous method to that described in Example 622 or 623. The corresponding aniline is described in method 28.
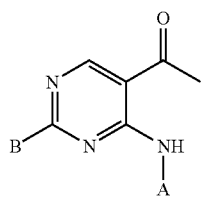
| # | A | B | UV max [nm] | MS (ESI) (M + H)⁺ |
|---|---|---|---|---|
| 1061 | 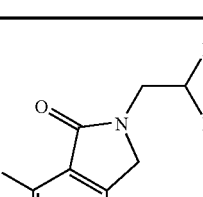 | 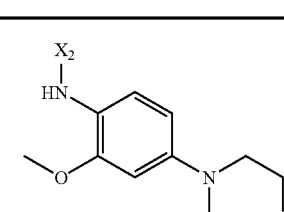 | 254, 316 | 552 |
| 1062 | | | 254, 314 | 548 |

-continued
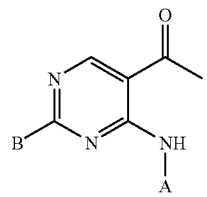
| # | A | B | UV max [nm] | MS (ESI) (M + H)+ |
|---|---|---|---|---|
| 1063 | | | 250 | 598 |
| 1064 | | | 254, 318 | 588 |
| 1065 | | | 250 | 518 |

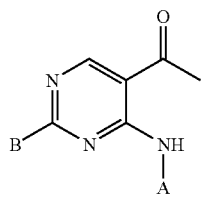
| # | A | B | UV max [nm] | MS (ESI) (M + H)+ |
|---|---|---|---|---|
| 1066 | | | 252, 318 | 606 |
| 1067 | | | 250, 310 | 566 |
| 1068 | | | 254, 318 | 552 |
| 1069 | | | 262; 314-318 | 566 |

EXAMPLES 1070-1071

The following compounds are prepared by an analogous method to that described in Example 622 or 623 and 53. The corresponding aniline is described in method 28. The amine used to prepare the amide is commercially obtainable or described in method 13.

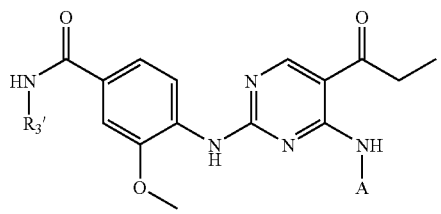

| # | A | R₃' | UV max [nm] | MS (ESI) (M + H)⁺ |
|---|---|---|---|---|
| 1070 | (isoindolinone with X₁ and CH₂CHF₂) | X₂-CH₂CH₂-pyrrolidine | 330 | 608 |
| 1071 | (isoindolinone with X₁ and CH₂CHF₂) | X₂-cyclohexyl-morpholine | 330 | 678 |

EXAMPLES 1072-1085

The following compounds are prepared by an analogous method to that described in Example 1037. The corresponding aniline is described in method 28. The amine used to prepare the amide is commercially obtainable or described in method 13.

| # | Z | R3' | UV max [nm] | MS (ESI) (M + H)+ |
|---|---|---|---|---|
| 1072 | I | X2—(4-(1-methylpiperidinyl)) | 285, 320 | 674 |
| 1073 | NO2 | X2—(4-morpholinylcyclohexyl) | 326 | 663 |
| 1074 | Br | X2—CH2CH2-pyrrolidinyl | 306 | 596 |
| 1075 | NO2 | X2—(4-(1-methylpiperidinyl)) | 326 | 593 |
| 1076 | Br | X2—(4-(1-methylpiperidinyl)) | 262 | 596 |
| 1077 | NO2 | X2—CH2CH2-pyrrolidinyl | 326 | 593 |
| 1078 | Cl | X2—(4-morpholinylcyclohexyl) | 318 | 652 |
| 1079 | Cl | X2—CH2CH2-pyrrolidinyl | 325 | 582 |
| 1080 | Cl | X2—(4-(1-methylpiperidinyl)) | 319 | 582 |
| 1081 | Br | X2—(4-morpholinylcyclohexyl) | 302 | 666 |
| 1082 | Br | X2—CH2CH2-pyrrolidinyl | 322 | 626 |
| 1083 | Br | X2—(4-(1-methylpiperidinyl)) | 318 | 626 |
| 1084 | CF3 | X2—CH2CH2-pyrrolidinyl | 286, 318 | 612 |
| 1085 | C≡CH | X1—I (H) | 280, 325 | 572 |

Biological Properties

As demonstrated by DNA staining followed by FACS analysis, the inhibition of proliferation brought about by the compounds according to the invention is mediated above all by the arrest of the cells in the G2/M phase of the cell cycle. The cells arrest, depending on the type of cell used, for a specific length of time in this cell cycle phase before programmed cell death is initiated. An arrest in the G2/M phase of the cell cycle may be initiated e.g. by the inhibition of specific cell cycle kinases. On the basis of their biological properties the compounds of general formula I according to the invention, their isomers and the physiologically acceptable salts thereof are suitable for treating diseases characterised by excessive or anomalous cell proliferation.

Such diseases include for example: viral infections (e.g. HIV and Kaposi's sarcoma); inflammatory and autoimmune diseases (e.g. colitis, arthritis, Alzheimer's disease, glomerulonephritis and wound healing); bacterial, fungal and/or parasitic infections; leukaemias, lymphomas and solid tmours; skin diseases (e.g. psoriasis); bone diseases; cardiovascular diseases (e.g. restenosis and hypertrophy). They are also useful for protecting proliferating cells (e.g. hair, intestinal, blood and progenitor cells) from DNA damage caused by radiation, UV treatment and/or cytostatic treatment (Davis et al., 2001). The new compounds may be used for the prevention, short- or long-term treatment of the above-mentioned diseases, also in combination with other active substances used for the same indications, e.g. cytostatics, steroids or antibodies.

The activity of the compounds according to the invention on various kinases, for example on serine-threonine kinase PLK-1, was determined by in vitro kinase assays with recombinantly produced protein. In this assay the compounds exhibit a good to very good effect on PLK1, i.e. for example an IC50 value of less than 1 μmol/L, usually less than 0.1 μmol/L.

Example PLK-1 Kinaseassay

Recombinant human PLK1 enzyme linked to GST at its N-terminal end is isolated from insect cells infected with baculovirus (Sf21). Purification is carried out by affinity chromatography on glutathione sepharose columns.

$4 \times 10^7$ Sf21 cells (*Spodoptera frugiperda*) in 200 ml of Sf-900 II Serum free insect cell medium (Life Technologies) are seeded in a spinner flask. After 72 hours' incubation at 27° C. and 70 rpm, $1 \times 10^8$ Sf21 cells are seeded in a total of 180 ml medium in a new spinner flask. After another 24 hours, 20 ml of recombinant Baculovirus stock suspension are added and the cells are cultivated for 72 hours at 27° C. at 70 rpm. 3 hours before harvesting, okadaic acid is added (Calbiochem, final concentration 0.1 μM) and the suspension is incubated further. The cell number is determined, the cells are removed by centrifuging (5 minutes, 4° C., 800 rpm) and washed 1× with PBS (8 g NaCl/l, 0.2 g KCl/l, 1.44 g $Na_2HPO_4$/l, 0.24 g $KH_2PO_4$/l). After centrifuging again the pellet is flash-frozen in liquid nitrogen. Then the pellet is quickly thawed and resuspended in ice-cold lysing buffer (50 mM HEPES pH 7.5, 10 mM $MgCl_2$, 1 mM DTT, 5 μg/ml leupeptin, 5 μg/ml aprotinin, 100 μM NaF, 100 μM PMSF, 10 mM β-glycerolphosphate, 0.1 mM $Na_3VO_4$, 30 mM 4-nitrophenylphosphate) to give $1 \times 10^8$ cells/17.5 ml. The cells are lysed for 30 minutes on ice. After removal of the cell debris by centrifugation (4000 rpm, 5 minutes) the clear supernatant is combined with glutathione sepharose beads (1 ml resuspended and washed beads per 50 ml of supernatant) and the mixture is incubated for 30 minutes at 4° C. on a rotating board. Then the beads are washed with lysing buffer and the recombinant protein is eluted from the beads with 1 ml eluting buffer/ml resuspended beads (eluting buffer: 100 mM Tris/HCl pH=8.0, 120 mM-NaCl, 20 mM reduced glutathione-(Sigma-G-4251), 10 mM $MgCl_2$, 1 mM DTT). The protein concentration is determined by Bradford Assay.

Assay

The following components are combined in a well of a 96-well round-bottomed dish (Greiner bio-one, PS Microtitre plate No. 650101):

10 μl of the compound to be tested in variable concentrations (e.g. beginning at 300 μM, and dilution to 1:3) in 6% DMSO, 0.5 mg/ml casein (Sigma C-5890), 60 mM β-glycerophosphate, 25 mM MOPS pH=7.0, 5 mM EGTA, 15 mM $MgCl_2$, 1 mM DTT 20 μl substrate solution (25 mM MOPS pH=7.0, 15 mM $MgCl_2$, 1 mM DTT, 2.5 mM EGTA, 30 mM β-glycerophosphate, 0.25 mg/ml casein)

20 μl enzyme dilution (1:100 dilution of the enzyme stock in 25 mM MOPS pH=7.0, 15 mM $MgCl_2$, 1 mM DTT)

10 μl ATP solution (45 μM ATP with $1.11 \times 10^6$ Bq/ml gamma-P33-ATP).

The reaction is started by adding the ATP solution and continued for 45 minutes at 30° C. with gentle shaking (650 rpm on an IKA Schüttler MTS2). The reaction is stopped by the addition of 125 μl of ice-cold 5% TCA per well and incubated on ice for at least 30 minutes. The precipitate is transferred by harvesting onto filter plates (96-well microtitre filter plate: UniFilter-96, GF/B; Packard; No. 6005177), then washed four times with 1% TCA and dried at 60° C. After the addition of 35 μl scintillation solution (Ready-Safe; Beckmann) per well the plate is sealed shut with sealing tape and the amount of P33 precipitated is measured with the Wallac Betacounter. The measured data are evaluated using the standard Graphpad software (Levenburg-Marquard Algorhythmus).

The anti-proliferative activity of the compounds according to the invention is determined in the cytotoxicity test on cultivated human tumour cells and/or in a FACS analysis, for example on HeLa S3 cells. In both test methods the compounds exhibit good to very good activity, i.e. for example an EC50 value in the HeLa S3 cytotoxicity test of less than 5 μmol/L, generally less than 1 μmol/L.

Measurement of Cytotoxicity on Cultivated Human Tumour Cells

To measure cytotoxicity on cultivated human tumour cells, cells of cervical carcinoma tumour cell line HeLa S3 (obtained from American Type Culture Collection (ATCC)) are cultivated in Ham's F12 Medium (Life Technologies) and 10% foetal calf serum (Life Technologies) and harvested in the log growth phase. Then the HeLa S3 cells are placed in 96-well plates (Costar) at a density of 1000 cells per well and incubated overnight in an incubator (at 37° C. and 5% CO2), while on each plate 6 wells are filled with medium alone (3 wells as the medium control, 3 wells for incubation with reduced AlamarBlue reagent). The active substances are added to the cells in various concentrations (dissolved in DMSO; DMSO final concentration: 0.1%) (in each case as a triple measurement). After 72 hours incubation 20 μl AlamarBlue reagent (AccuMed International) are added to each well, and the cells are incubated for a further 5-7 hours. As a control, 20 μl reduced AlamarBlue reagent is added to each of 3 wells (AlamarBlue reagent, which is autoclaved for 30 min). After incubation the colour change of the AlamarBlue reagent in the individual wells is determined in a Perkin Elmer fluorescence spectrophotometer (excitation 530 nm, emission 590 nm, slits 15, integrate time 0.1). The amount of AlamarBlue reagent reacted represents the metabolic activity of the cells. The relative cell activity is calculated as a percentage of the control (HeLa S3 cells without inhibitor) and the active substance concentration which inhibits the cell activity by 50% (IC50) is derived. The values are calculated from the average of three individual measurements—with correction of the dummy value (medium control).

FACS Analysis

Propidium iodide (PI) binds stoichiometrically to double-stranded DNA, and is thus suitable for determining the proportion of cells in the G1, S, and G2/M phase of the cell cycle on the basis of the cellular DNA content. Cells in the G0 and G1 phase have a diploid DNA content (2N), whereas cells in the G2 or mitosis phase have a 4N DNA content.

For PI staining, for example, $\times 10^6$ HeLa S3 cells are seeded onto a 75 cm2 cell culture flask, and after 24 h either 0.1% DMSO is added as control or the substance is added in various concentrations (in 0.1% DMSO). The cells are incubated for 24 h with the substance or with DMSO before the cells are washed 2× with PBS and then detached with trypsin/EDTA. The cells are centrifuged (1000 rpm, 5 min, 4° C.), and the cell pellet is washed 2× with PBS before the cells are resuspended in 0.1 ml PBS. Then the cells are fixed with 80% ethanol for 16 hours at 4° C. or alternatively for 2 hours at −20° C. The fixed cells are centrifuged (1000 rpm, 5 min, 4° C.), washed with PBS and then centrifuged again. The cell pellet is resuspended in 2 ml 0.25% Triton X-100 in PBS, and incubated on ice for 5 min before 5 ml PBS are added and the mixture is centrifuged again. The cell pellet is resuspended in 350 µl PI staining solution (0.1 mg/ml RNase A (Sigma, No. R-4875), 10 µg/ml prodium iodide (Sigma, No. P-4864) in 1×PBS). The cells are incubated for 20 min in the dark with the staining buffer before being transferred into sample measuring containers for the FACS scan. The DNA measurement is carried out in a Becton Dickinson FACS Analyzer, with an argon laser (500 mW, emission 488 nm), and the DNA Cell Quest Programme (BD). The logarithmic PI fluorescence is determined with a band-pass filter (BP 585/42). The cell populations in the individual cell cycle phases are quantified using the ModFit LT Programme made by Becton Dickinson.

The compounds according to the invention are also tested accordingly for other tumour cells. For example, these compounds are effective on carcinomas of all kinds of tissue (e.g. breast (MCF7); colon (HCT116), head and neck (FaDu), lung (NCI-H460), pancreas (BxPC-3), prostate (DU145)), sarcomas (e.g. SK-UT-1B), leukaemias and lymphomas (e.g. HL-60; Jurkat, THP-1) and other tumours (e.g. melanomas (BRO), gliomas (U-87MG)) and could be used for such indications. This is evidence of the broad applicability of the compounds according to the invention for the treatment of all kinds of tumour types. The compounds of general formula (I) may be used on their own or in conjunction with other active substances according to the invention, optionally also in conjunction with other pharmacologically active substances.

Suitable preparations include for example tablets, capsules, suppositories, solutions, particularly solutions for injection (s.c., i.v., i.m.) and infussion, elixirs, emulsions or dispersible powders. The content of the pharmaceutically active compound(s) should be in the range from 0.1 to 90 wt.-%, preferably 0.5 to 50 wt.-% of the composition as a whole, i.e. in amounts which are sufficient to achieve the dosage range specified below. The doses specified may, if necessary, be given several times a day.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number or layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving-aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose) emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral or transdermal route, most preferably by oral route. For oral administration the tablets may, of course contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

The dosage for intravenous use is from 1-1000 mg per hour, preferably between 5 and 500 mg per hour.

However, it may sometimes be necessary to depart from the amounts specified, depending on the body weight, the route of administration, the individual response to the drug, the nature of its formulation and the time or interval over which the drug is administered. Thus, in some cases it may be sufficient to use less than the minimum dose given above, whereas in other cases the upper limit may have to be exceeded. When administering large amounts it may be advisable to divide them up into a number of smaller doses spread over the day.

The formulation examples which follow illustrate the present invention without restricting its scope:

Examples of Pharmaceutical Formulations

A) Tablets

| | per tablet |
|---|---|
| active substance | 100 mg |
| lactose | 140 mg |
| corn starch | 240 mg |
| polyvinylpyrrolidone | 15 mg |
| magnesium stearate | 5 mg |
| | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

B) Tablets

| | per tablet |
|---|---|
| active substance | 80 mg |
| lactose | 55 mg |
| corn starch | 190 mg |
| microcrystalline cellulose | 35 mg |
| polyvinylpyrrolidone | 15 mg |
| sodium-carboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodiumcarboxymethyl starch and the magnesium stearate are added and mixed in and the mixture is compressed to form tablets of a suitable size.

C) Ampoule solution

| active substance | 50 mg |
|---|---|
| sodium chloride | 50 mg |
| water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

The invention claimed is:

1. A compound of the following formula (1):

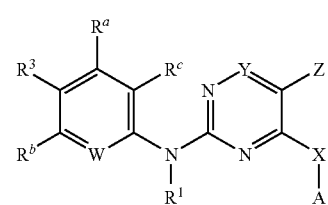

(1)

wherein

W denotes N or C—$R^2$,

X denotes —$NR^{1a}$, O or S,

Y denotes CH,

Z denotes —$CF_3$;

A is selected from one of the following formulas (i), (ii) and (iii):

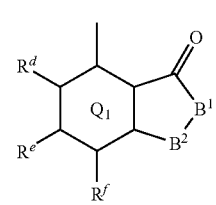

(i)

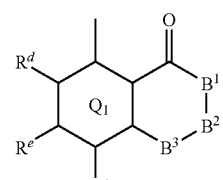

(ii)

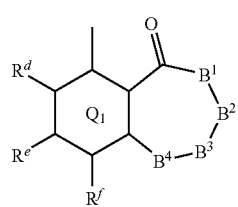

(iii)

$Q_1$ denotes that (i), (ii) and (iii) are mono- or bicyclic aryl;

$B^1$, $B^2$, $B^3$ and $B^4$ each independently of one another denote C—$R^gR^h$, N—$R^i$, O or S;

$R^1$ and $R^{1a}$ each independently of one another denote hydrogen or methyl;

$R^2$ denotes one of hydrogen, halogen, —$OR^4$, —C(=O)$R^4$, —C(=O)$NR^4R^5$, —$NR^4R^5$, —$NR^4C(=O)R^5$, —$NR^4SO_2R^5$, —N=$CR^4R^5$, —C=$NR^i$, —$SR^4$, —$SOR^4$, —$SO_2R^4$, —$SO_2NR^4R^5$, pseudohalogen, and a mono- or polysubstituted group selected from the group consisting of $C_{1-6}$alkyl, $C_{2-6}$alkenyl, $C_{2-6}$alkynyl, $C_{3-6}$-cycloalkyl, aryl, heterocyclyl and heteroaryl, wherein the substituent(s) of the mono- or polysubstituted group are identical or different and are selected from the group consisting of halogen, —$NO_2$, —$OR^4$, —C(=O)$R^4$, —C(=O)$OR^4$, —C(=O)$NR^4R^5$, —$NR^4R^5$, —$NR^4C(=O)R^5$, —$NR^4C(=O)OR^5$, —$NR^4C(=O)NR^5R^6$, —$NR^4SO_2R^5$, —N=$CR^4R^5$,—

SR⁴, —SOR⁴, —SO₂R⁴, —SO₂NR⁴R⁵, —NR⁴SO₂NR⁵R⁶, —OSO₂NR⁵R⁶ and pseudohalogen;

Rᵃ, Rᵇ, Rᶜ, Rᵈ, Rᵉ, Rᶠ, Rᵍ and Rʰ each independently of one another denote a group selected from the group consisting of hydrogen, halogen, =O, —NO₂, —OR⁴, —C(=O)R⁴, —C(=O)OR⁴, —C(=O)NR⁴R⁵, —NR⁴R⁵, —NR⁴C(=O)R⁵, —NR⁴C(=O)OR⁵, —NR⁴C(=O)NR⁵R⁶, —NR⁴SO₂R⁵, —N=CR⁴R⁵, —C=NRⁱ, —SR⁴, —SOR⁴, —SO₂R⁴, —SO₂NR⁴R⁵, —NR⁴SO₂NR⁵R⁶, —OSO₂NR⁵R⁶, pseudohalogen, and an unsubstituted or mono- or polysubstituted group selected from the group consisting of $C_{1-6}$-alkyl, $C_{2-6}$-alkenyl, $C_{2-6}$-alkynyl, $C_{3-6}$-cycloalkyl, aryl, heterocyclyl and heteroaryl, wherein the substituent(s) of the mono- or polysubstituted group are identical or different and are selected from the group consisting of halogen, R⁸, —NO₂, —OR⁴, —C(=O)R⁴, —C(=O)OR⁴, —C(=O)NR⁴R⁵, —NR⁴R⁵, —NR⁴C(=O)R⁵, —NR⁴C(=O)OR⁵, —NR⁴C(=O)NR⁵R⁶, —NR⁴SO₂R⁵, —N=CR⁴R⁵, —SR⁴, —SOR⁴, —SO₂R⁴, —SO₂NR⁴R⁵, —NR⁴SO₂NR⁵R⁶, —OSO₂NR⁵R⁶ and pseudohalogen; wherein Rᵍ and Rʰ are optionally located at the same or at adjacent C atoms and are attached in any combination to a common saturated or partially unsaturated 3-5-membered alkyl bridge which contains one to two heteroatoms;

Rⁱ denotes a group selected from the group consisting of hydrogen, —OR⁴, —C(=O)R⁴, —C(=O)OR⁴, —C(=O)NR⁴R⁵, —NR⁴R⁵, —NR⁴C(=O)R⁵, —NR⁴C(=O)OR⁵, —NR⁴C(=O)NR⁵R⁶, —NR⁴SO₂R⁵, —N=CR⁴R⁵, —SR⁴, —SOR⁴, —SO₂R⁴, —SO₂NR⁴R⁵, —NR⁴SO₂NR⁵R⁶, —OSO₂NR⁵R⁶, pseudohalogen and an unsubstituted or substituted mono- or polysubstituted group selected from the group consisting of $C_{1-6}$alkyl, $C_{2-6}$alkenyl, $C_{2-6}$alkynyl, $C_{3-6}$cycloalkyl, aryl, heterocyclyl and heteroaryl, wherein the substituent(s) of the mono- or polysubstituted group are identical or different and are selected from the group consisting of halogen, R⁸, —NO₂, —OR⁴, —C(=O)R⁴, —C(=O)OR⁴, —C(=O)NR⁴R⁵, —NR⁴R⁵, —NR⁴C(=O)R⁵, —NR⁴C(=O)OR⁵, —NR4C(=O)NR⁵R⁶, —NR⁴SO₂R⁵, —N=CR⁴R⁵, —SR⁴, —SOR⁴, —SO₂R⁴, —SO₂NR⁴R⁵, —NR⁴SO₂NR⁵R⁶, —OSO₂NR⁵R⁶ and pseudohalogen; wherein the Rⁱ groups located at adjacent N atoms are optionally joined together or Rⁱ with Rᵍ or Rʰ located at adjacent C atoms are optionally attached in any combination to a common saturated or partially unsaturated 3-5-membered alkyl bridge which contains one to two heteroatoms;

R³ is selected from the following formulas (iv)-(x):

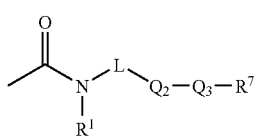
(iv)

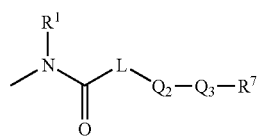
(v)

-continued

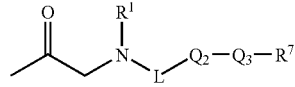
(vi)

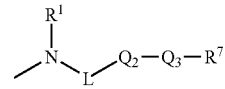
(vii)

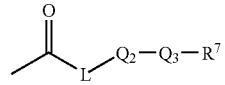
(viii)

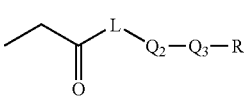
(ix)

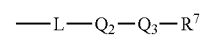
(x)

R⁴, R⁵ and R⁶ each independently of one another denote hydrogen or an unsubstituted or mono- or polysubstituted group selected from the group consisting of $C_{1-5}$-alkyl, $C_{2-5}$alkenyl, $C_{2-5}$alkynyl, $C_{3-10}$cycloalkyl, aryl, heterocyclyl and heteroaryl, wherein the substituent(s) of the mono- or polysubstituted group are identical or different and are selected from the group consisting of $C_{3-10}$-cycloalkyl, aryl, heterocyclyl, heteroaryl, halogen, —NO₂, —OR⁸, —C(=O)R⁸, —C(=O)OR⁸, —C(=O)NR⁸R⁹, —NR⁸R⁹, —NR⁸C(=O)R⁹, —NR⁸C(=O)OR⁹, —NR⁸C(=O)NR⁹R¹⁰, —NR⁸C(=O)ONR⁹R¹⁰, —NR⁸SO₂R⁹, —N=CR⁸R⁹, —SR⁸, —SOR⁸, —SO₂R⁸, —SO₂NR⁸R⁹, —NR⁸SO₂NR⁹R¹⁰, —OSO₂NR⁸R⁹ and pseudohalogen;

L denotes a bond or an unsubstituted or mono- or polysubstituted group selected from the group consisting of $C_{1-16}$-alkyl, $C_{2-16}$-alkenyl, $C_{2-16}$-alkynyl, $C_{3-10}$-cycloalkyl, aryl, heterocyclyl and heteroaryl,wherein the substituent(s) of the mono- or polysubstituted group are identical or different and are selected from the group consisting of halogen, —NO₂, —OR⁸, —C(=O)R⁸, —C(=O)OR⁸, —C(=O)NR⁸R⁹, —NR⁸R⁹, —NR⁸C(=O)R⁹, —NR⁸C(=O)OR⁹, —NR⁸C(=O)NR⁹R¹⁰, —NR⁸C(=O)ONR⁹R¹⁰, —NR⁸SO₂R⁹, —N=CR⁸R⁹, —SR⁸, —SOR⁸, —SO₂R⁸, —SO₂NR⁸R⁹, —NR⁸SO₂NR⁹R¹⁰, —OSO₂NR⁸R⁹ and pseudohalogen;

Q₂ and Q₃ each independently of one another denote a bond or an unsubstituted or mono- or polysubstituted group selected from the group consisting of $C_{1-16}$-alkyl, $C_{2-16}$-alkenyl, $C_{2-16}$-alkynyl, $C_{3-10}$-cycloalkyl, aryl, heterocyclyl and heteroaryl, wherein the substituent(s) of the mono- or polysubstituted group are identical or different and are selected from the group consisting of halogen, —NO₂, —OR⁸, —C(=O)R⁸, —C(=O)OR⁸, —C(=O)NR⁸R⁹, —NR⁸R⁹, —NR⁸C(=O)R⁹, —NR⁸C(=O)OR⁹, —NR⁸C(=O)NR⁹R¹⁰, —NR⁸C(=O)ONR⁹R¹⁰, —NR⁸SO₂R⁹, —N=CR⁸R⁹, —SR⁸, —SOR⁸, —SO₂R⁸, —SO₂NR⁸R⁹, —NR⁸SO₂NR⁹R¹⁰, —OSO₂NR⁸R⁹ and pseudohalogen;

R⁷ denotes hydrogen or an unsubstituted or mono- or polysubstituted group selected from the group consisting of $C_{1-16}$-alkyl, $C_{2-16}$-alkenyl, $C_{2-16}$-alkynyl, $C_{3-10}$-cycloalkyl, aryl, heterocyclyl and heteroaryl, wherein the substituent(s) of the mono- or polysubstituted group are identical or different and are selected from the group consisting of halogen, $NO_2$, $-OR^8$, $-C(=O)R^8$, $-C(=O)OR^8$, $-C(=O)NR^8R^9$, $-NR^8R^9$, $-NR^8COR^9$, $-NR^8C(=O)OR^9$, $-NR^8C(=O)NR^9R^{10}$, $-NR^8C(=O)ONR^9R^{10}$, $-NR^8SO_2R^9$, $-N=CR^8R^9$, $-SR^8$, $-SOR^8$, $-SO_2R^8$, $-SO_2NR^8R^9$, $-NR^8SO_2NR^9R^{10}$, $-OSO_2NR^8R^9$ and pseudohalogen; and $R^8$, $R^9$ and $R^{10}$ each independently of one another denote hydrogen or a substituted or unsubstituted group selected from the group consisting of $C_{1-8}$-alkyl, $C_{2-8}$-alkenyl, $C_{2-8}$-alkynyl, $C_{3-10}$-cycloalkyl, aryl, heterocyclyl and heteroaryl, wherein the substituent(s) of the substituted group are identical or different and are selected from the group consisting of halogen, methyl, ethyl, amino, methylamino, dimethylamino, $-OH$ and pseudohalogen;

or a pharmacologically acceptable acid addition salt thereof.

2. The compound according to claim 1, wherein:
W denotes $C-R^2$.

3. The compound according to claim 1, wherein:
X denotes $-NR^{1a}$ or oxygen;
$R^1$ and $R^{1a}$ denote hydrogen; and
$R^3$ denotes one of the following formulas (iv) and (x):

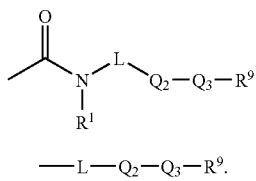

(iv)

$-L-Q_2-Q_3-R^9$.

(x)

4. The compound according to claim 1, wherein:
Y denotes CH; and
$Q_1$ denotes monocyclic aryl compounds.

5. The compound according to claim 1, wherein:
$R^c$ denotes a group selected from the group consisting of hydrogen, $-F$, $-Cl$, methyl and ethyl.

6. The compound according to claim 1, wherein:
$R^a$ and $R^b$ each independently of one another denote one of hydrogen, fluorine and a mono- or polysubstituted group selected from the group consisting of $C_{1-2}$alkyl, $C_2$alkenyl, $C_2$alkynyl, $C_{3-6}$cycloalkyl, aryl, heterocyclyl and heteroaryl, wherein the substituent(s) of the mono- or polysubstituted group are identical or different and are selected from the group consisting of hydrogen, halogen, $-NO_2$, $-OR^4$, $-C(=O)R^4$, $-C(=O)OR^4$, $-C(=O)NR^4R^5$, $-NR^4R^5$, $-NR^4C(=O)R^5$, $-NR^4C(=O)R^6$, $-NR^4C(=O)OR^5$, $-NR^4C(=O)NR^5R^6$, $-NR^4SO_2R^5$, $-N=CR^4R^5$, $-SR^4$, $-SOR^5$, $-SO_2R^4$, $-SO_2NR^4R^5$, $-NR^4$, $-SO_2NR^4R^5$, $-OSO_2NR^4R^5$ and pseudohalogen.

7. The compound according to claim 1, wherein:
$R^a$ and $R^b$ each independently of one another denote hydrogen or fluorine.

8. A pharmaceutical composition comprising the compound of claim 1, or a pharmaceutically active salt thereof, and an excipient or a carrier, wherein the composition has an antiproliferative activity, a selective, kinase-inhibiting mechanism of activity, or a PLK-inhibiting mechanism of activity.

9. A method of preparing a pharmaceutical composition, comprising:
forming a compound of the following formula (1):

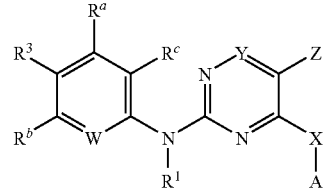

(1)

wherein
W denotes N or $C-R^2$,
X denotes $-NR^{1a}$, O or S,
Y denotes CH,
Z denotes $-CF_3$;
A is selected from one of the following formulas (i), (ii) and (iii):

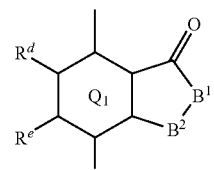

(i)

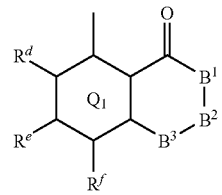

(ii)

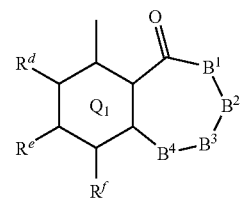

(iii)

$Q_1$ denotes that (i), (ii) and (iii) are mono- or bicyclic aryl;
$B^1$, $B^2$, $B^3$ and $B^4$ each independently denote $C-R^gR^h$, $N-R^i$, O or S;
$R^1$ and $R^{1a}$ each independently denote hydrogen or methyl;
$R^2$ denotes one of hydrogen, halogen, $-OR^4$, $-C(=O)R^4$, $-C(=O)NR^4R^5$, $-NR^4R^5$, $-NR^4C(=O)R^5$, $-NR^4SO_2R^5$, $-N=CR^4R^5$, $-C=NR^i$, $-SR^4$, $-SOR^4$, $-SO_2R^4$, $-SO_2NR^4R^5$, pseudohalogen, and a mono- or polysubstituted group selected from the group consisting of $C_{1-6}$alkyl, $C_{2-6}$alkenyl, $C_{2-6}$alkynyl, $C_{3-6}$-cycloalkyl, aryl, heterocyclyl and heteroaryl, wherein the substituent(s) of the mono- or polysubstituted group are identical or different and are selected from the group consisting of halogen, $-NO_2$, $-OR^4$, $-C(=O)R^4$, $-C(=O)OR^4$, $-C(=O)NR^4R^5$, $-NR^4R^5$, $-NR^4C(=O)R^5$, $-NR^4C(=O)OR^5$, $-NR^4C(=O)NR^5R^6$, $-NR^4SO_2R^5$, $-N=CR^4R^5$, —SR⁴, —SOR⁴, —SO₂R⁴, —SO₂NR⁴R⁵, —NR⁴SO₂NR⁵R⁶, —OSO₂NR⁵R⁶ and pseudohalogen;

Rᵃ, Rᵇ, Rᶜ, Rᵈ, Rᵉ, Rᶠ, Rᵍ and Rʰ each independently of one another denote a group selected from the group consisting of hydrogen, halogen, =O, —NO₂, —OR⁴, —C(=O)R⁴, —C(=O)OR⁴, —C(=O)NR⁴R⁵, —NR⁴R⁵, —NR⁴C(=O)R⁵, —NR⁴C(=O)OR⁵, —NR⁴C(=O)NR⁵R⁶, —NR⁴SO₂R⁵, —N=CR⁴R⁵, —C=NRⁱ, —SR⁴, —SOR⁴, —SO₂R⁴, —SO₂NR⁴R⁵, —NR⁴SO₂NR⁵R⁶, —OSO₂NR⁵R⁶, pseudohalogen, and an unsubstituted or mono- or polysubstituted group selected from the group consisting of C₁₋₆-alkyl, C₂₋₆-alkenyl, C₂₋₆-alkynyl, C₃₋₆-cycloalkyl, aryl, heterocyclyl and heteroaryl, wherein the substituent(s) of the mono- or polysubstituted group are identical or different and are selected from the group consisting of halogen, R⁸, —NO₂, —OR⁴, —C(=O)R⁴, —C(=O)OR⁴, —C(=O)NR⁴R⁵, —NR⁴R⁵, —NR⁴C(=O)R⁵, —NR⁴C(=O)OR⁵, —NR⁴C(=O)NR⁵R⁶, —NR⁴SO₂R⁵, —N=CR⁴R⁵, —SR⁴, —SOR⁴, —SO₂R⁴, —SO₂NR⁴R⁵, —NR⁴SO₂NR⁵R⁶, —OSO₂NR⁵R⁶ and pseudohalogen; wherein Rᵍ and Rʰ are optionally located at the same or at adjacent C atoms and are attached in any combination to a common saturated or partially unsaturated 3-5-membered alkyl bridge which contains one to two heteroatoms;

Rⁱ denotes a group selected from the group consisting of hydrogen, —OR⁴, —C(=O)R⁴, —C(=O)OR⁴, —C(=O)NR⁴R⁵, —NR⁴R⁵, —NR⁴C(=O)R⁵, —NR⁴C(=O)OR⁵, —NR⁴C(=O)NR⁵R⁶, —NR⁴SO₂R⁵, —N=CR⁴R⁵, —SR⁴, —SOR⁴, —SO₂R⁴, —SO₂NR⁴R⁵, —NR⁴SO₂NR⁵R⁶, —OSO₂NR⁵R⁶, pseudohalogen and an unsubstituted or substituted mono- or polysubstituted group selected from the group consisting of C₁₋₆alkyl, C₂₋₆alkenyl, C₂₋₆alkynyl, C₃₋₆cycloalkyl, aryl, heterocyclyl and heteroaryl, wherein the substituent(s) of the mono- or polysubstituted group are identical or different and are selected from the group consisting of halogen, R⁸, —NO₂, —OR⁴, —C(=O)R⁴, —C(=O)OR⁴, —C(=O)NR⁴R⁵, —NR⁴R⁵, —NR⁴C(=O)R⁵, —NR⁴C(=O)OR⁵, —NR4C(=O)NR⁵R⁶, —NR⁴SO₂R⁵, —N=CR⁴R⁵, —SR⁴, —SOR⁴, —SO₂R⁴, —SO₂NR⁴R⁵, —NR⁴SO₂NR⁵R⁶, —OSO₂NR⁵R⁶ and pseudohalogen; wherein the Rⁱ groups located at adjacent N atoms are optionally joined together or Rⁱ with Rᵍ or Rʰ located at adjacent C atoms are optionally attached in any combination to a common saturated or partially unsaturated 3-5-membered alkyl bridge which contains one to two heteroatoms;

R³ is selected from the following formulas (iv)-(x):

(iv)

(v)

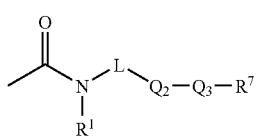

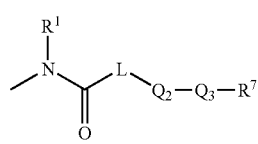

-continued

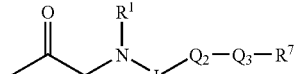
(vi)

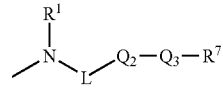
(vii)

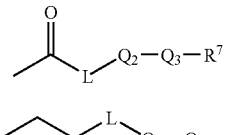
(viii)

(ix)

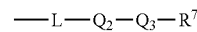
(x)

—L—Q₂—Q₃—R⁷

R⁴, R⁵ and R⁶ each independently of one another denote hydrogen or an unsubstituted or mono- or polysubstituted group selected from the group consisting of C₁₋₅-alkyl, C₂₋₅alkenyl, C₂₋₅alkynyl, C₃₋₁₀cycloalkyl, aryl, heterocyclyl and heteroaryl, wherein the substituent(s) of the mono- or polysubstituted group are identical or different and are selected from the group consisting of C₃₋₁₀-cycloalkyl, aryl, heterocyclyl, heteroaryl, halogen, —NO₂, —OR⁸, —C(=O)R⁸, —C(=O)OR⁸, —C(=O)NR⁸R⁹, —NR⁸R⁹, —NR⁸C(=O)R⁹, —NR⁸C(=O)OR⁹, —NR⁸C(=O)NR⁹R¹⁰, —NR⁸C(=O)ONR⁹R¹⁰, —NR⁸SO₂R⁹, —N=CR⁸R⁹, —SR⁸, —SOR⁸, —SO₂R⁸, —SO₂NR⁸R⁹, —NR⁸SO₂NR⁹R¹⁰, —OSO₂NR⁸R⁹ and pseudohalogen;

L denotes a bond or an unsubstituted or mono- or polysubstituted group selected from the group consisting of C₁₋₁₆alkyl, C₂₋₁₆alkenyl, C₂₋₁₆alkynyl, C₃₋₁₀cycloalkyl, aryl, heterocyclyl and heteroaryl, wherein the substituent(s) of the mono- or polysubstituted group are identical or different and are selected from the group consisting of halogen, —NO₂, —OR⁸, —C(=O)R⁸, —C(=O)OR⁸, —C(=O)NR⁸R⁹, —NR⁸R⁹, —NR⁸C(=O)R⁹, —NR⁸C(=O)OR⁹, —NR⁸C(=O)NR⁹R¹⁰, —NR⁸C(=O)ONR⁹R¹⁰, —NR⁸SO₂R⁹, —N=CR⁸R⁹, —SR⁸, —SOR⁸, —SO₂R⁸, —SO₂NR⁸R⁹, —NR⁸SO₂NR⁹R¹⁰, —OSO₂NR⁸R⁹ and pseudohalogen;

Q₂ and Q₃ each independently of one another denote a bond or an unsubstituted or mono- or polysubstituted group selected from the group consisting of C₁₋₁₆alkyl, C₂₋₁₆alkenyl, C₂₋₁₆-alkynyl, C₃₋₁₀cycloalkyl, aryl, heterocyclyl and heteroaryl, wherein the substituent(s) of the mono- or polysubstituted group are identical or different and are selected from the group consisting of halogen, —NO₂, —OR⁸, —C(=O)R⁸, —C(=O)OR⁸, —C(=O)NR⁸R⁹, —NR⁸R⁹, —NR⁸C(=O)R⁹, —NR⁸C(=O)OR⁹, —NR⁸C(=O)NR⁹R¹⁰, —NR⁸C(=O)ONR⁹R¹⁰, —NR⁸SO₂R⁹, —N=CR⁸R⁹, —SR⁸, —SOR⁸, —SO₂R⁸, —SO₂NR⁸R⁹, —NR⁸SO₂NR⁹R¹⁰, —OSO₂NR⁸R⁹ and pseudohalogen;

R⁷ hydrogen or an unsubstituted or mono- or polysubstituted group selected from the group consisting of C₁₋₁₆alkyl, C₂₋₁₆alkenyl, C₂₋₁₆alkynyl, C₃₋₁₀cycloalkyl, aryl, heterocyclyl and heteroaryl, wherein the substituent(s) of the mono- or polysubstituted group are identical or different and are selected from the group consisting of halogen, $NO_2$, $-OR^8$, $-C(=O)R^8$, $C(=O)OR^8$, $-C(=O)NR^8R^9$, $-NR^8R^9$, $-NR^8COR^9$, $-NR^8C(=O)OR^9$, $-NR^8C(=O)NR^9R^{10}$, $-NR^8C(=O)ONR^9R^{10}$, $-NR^8SO_2R^9$, $-N=CR^8R^9$, $-SR^8$, $-SOR^8$, $-SO_2R^8$, $-SO_2NR^8R^9$, $-NR^8SO_2NR^9R^{10}$, $-OSO_2NR^8R^9$ and pseudohalogen; and $R^8$, $R^9$ and $R^{10}$ each independently of one another denote hydrogen or a substituted or unsubstituted group selected from the group consisting of $C_{1-8}$-alkyl, $C_{2-8}$-alkenyl, $C_{2-8}$-alkynyl, $C_{3-10}$-cycloalkyl, aryl, heterocyclyl and heteroaryl, wherein the substituent(s) of the substituted group are identical or different and are selected from the group consisting of halogen, methyl, ethyl, amino, methylamino, dimethylamino, —OH and pseudohalogen;

or a pharmacologically acceptable acid addition salt thereof and combining the compound with at least one cytostatic or cytotoxic active substance.

10. The pharmaceutical composition of claim 8, further comprising a cytostatic or cytotoxic active substance.

11. A compound of the following formula (1):

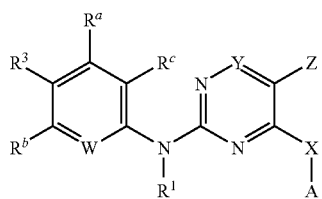

(1)

wherein

W denotes N or $C-R^2$,

X denotes O or S,

Y denotes CH,

Z denotes one of hydrogen, halogen, $-NO_2$, $C_{1-3}$alkyl, $C_{2-3}$alkenyl, $C_{2-3}$alkynyl, halogen-$C_{1-3}$alkyl, $-C(=O)H$, $-C(=O)-C_{1-3}$alkyl, $-C(=O)-C_{2-3}$alkenyl, $-C(=O)-C_{2-3}$alkynyl, $-C(=O)C_{1-3}$alkyl-halogen and pseudohalogen;

A is selected from one of the following formulas (i), (ii) and (iii):

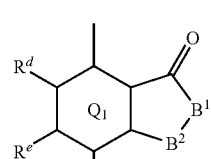

(i)

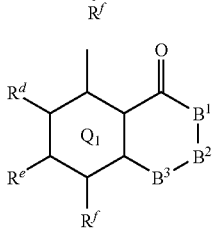

(ii)

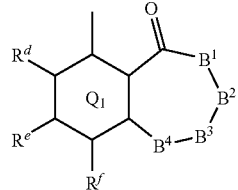

(iii)

with the proviso that when A is (i), Z is not halogen;

$Q_1$ denotes that (i), (ii) and (iii) are mono- or bicyclic aryl;

$B^1$, $B^2$, $B^3$ and $B^4$ each independently of one another denote $C-R^gR^h$, $-N-R^i$, O or S;

$R^1$ and $R^{1a}$ each independently of one another denote hydrogen or methyl;

$R^2$ denotes one of hydrogen, halogen, $-OR^4$, $-C(=O)R^4$, $-C(=O)NR^4R^5$, $-NR^4R^5$, $-NR^4C(=O)R^5$, $-NR^4SO_2R^5$, $-N=CR^4R^5$, $-C=NR^i$, $-SR^4$, $-SOR^4$, $-SO_2R^4$, $-SO_2NR^4R^5$, pseudohalogen, and a mono- or polysubstituted group selected from the group consisting of $C_{1-6}$alkyl, $C_{2-6}$alkenyl, $C_{2-6}$alkynyl, $C_{3-6}$-cycloalkyl, aryl, heterocyclyl and heteroaryl, wherein the substituent(s) of the mono- or polysubstituted group are identical or different and are selected from the group consisting of halogen, $-NO_2$, $-OR^4$, $-C(=O)R^4$, $-C(=O)OR^4$, $-C(=O)NR^4R^5$, $-NR^4R^5$, $-NR^4C(=O)R^5$, $-NR^4C(=O)OR^5$, $-NR^4C(=O)NR^5R^6$, $-NR^4SO_2R^5$, $-N=CR^4R^5$, $-SR^4$, $-SOR^4$, $-SO_2R^4$, $-SO_2NR^4R^5$, $-NR^4SO_2NR^5R^6$, $-OSO_2NR^5R^6$ and pseudohalogen;

$R^a$, $R^b$, $R^c$, $R^d$, $R^e$, $R^f$, $R^g$ and $R^h$ each independently of one another denote a group selected from the group consisting of hydrogen, halogen, =O, $-NO_2$, $-OR^4$, $-C(=O)R^4$, $-C(=O)OR^4$, $-C(=O)NR^4R^5$, $-NR^4R^5$, $-NR^4C(=O)R^5$, $-NR^4C(=O)OR^5$, $-NR^4C(=O)NR^5R^6$, $-NR^4SO_2R^5$, $-N=CR^4R^5$, $-C=NR^i$, $-SR^4$, $-SOR^4$, $-SO_2R^4$, $-SO_2NR^4R^5$, $-NR^4SO_2NR^5R^6$, $-OSO_2NR^5R^6$, pseudohalogen, and an unsubstituted or mono- or polysubstituted group selected from the group consisting of $C_{1-6}$-alkyl, $C_{2-6}$-alkenyl, $C_{2-6}$-alkynyl, $C_{3-6}$-cycloalkyl, aryl, heterocyclyl and heteroaryl, wherein the substituent(s) of the mono- or polysubstituted group are identical or different and are selected from the group consisting of halogen, $R^8$, $-NO_2$, $-OR^4$, $-C(=O)R^4$, $-C(=O)OR^4$, $-C(=O)NR^4R^5$, $-NR^4R^5$, $-NR^4C(=O)R^5$, $-NR^4C(=O)OR^5$, $-NR^4C(=O)NR^5R^6$, $-NR^4SO_2R^5$, $-N=CR^4R^5$, $-SR^4$, $-SOR^4$, $-SO_2R^4$, $-SO_2NR^4R^5$, $-NR^4SO_2NR^5R^6$, $-OSO_2NR^5R^6$ and pseudohalogen; wherein $R^g$ and $R^h$ are optionally located at the same or at adjacent C atoms and are attached in any combination to a common saturated or partially unsaturated 3-5-membered alkyl bridge which contains one to two heteroatoms;

$R^i$ denotes a group selected from the group consisting of hydrogen, $-OR^4$, $-C(=O)R^4$, $-C(=O)OR^4$, $-C(=O)NR^4R^5$, $-NR^4R^5$, $-NR^4C(=O)R^5$, $-NR^4C(=O)OR^5$, $-NR^4C(=O)NR^5R^6$, $-NR^4SO_2R^5$, $-N=CR^4R^5$, $-SR^4$, $-SOR^4$, $-SO_2R^4$, $-SO_2NR^4R^5$, $-NR^4SO_2NR^5R^6$, $-OSO_2NR^5R^6$, pseudohalogen and an unsubstituted or substituted mono- or polysubstituted group selected from the group consisting of $C_{1-6}$alkyl, $C_{2-6}$alkenyl, $C_{2-6}$alkynyl, $C_{3-6}$cycloalkyl, aryl, heterocyclyl and heteroaryl, wherein the substituent(s) of the mono- or polysubstituted group are identical or different and are selected from the group consisting of halogen, $R^8$, —$NO_2$, —$OR^4$, —$C(=O)R^4$, —$C(=O)OR^4$, —$C(=O)NR^4R^5$, —$NR^4R^5$, —$NR^4C(=O)R^5$, —$NR^4C(=O)OR^5$, —$NR^4C(=O)NR^5R^6$, —$NR^4SO_2R^5$, —$N=CR^4R^5$, —$SR^4$, —$SOR^4$, —$SO_2R^4$, —$SO_2NR^4R^5$, —$NR^4SO_2NR^5R^6$, —$OSO_2NR^5R^6$ and pseudohalogen; wherein the $R^i$ groups located at adjacent N atoms are optionally joined together or $R^i$ with $R^g$ or $R^h$ located at adjacent C atoms are optionally attached in any combination to a common saturated or partially unsaturated 3-5-membered alkyl bridge which contains one to two hetero atoms;

$R^3$ is selected from the following formulas (iv) (x):

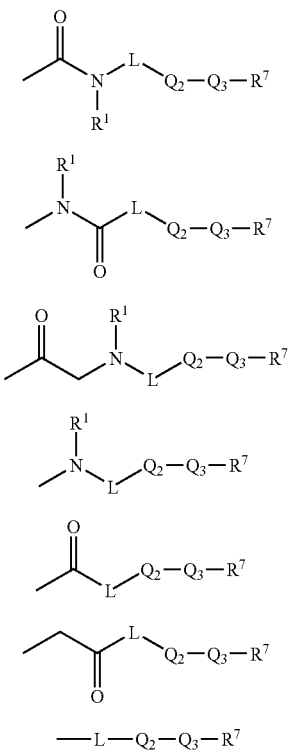

(iv)

(v)

(vi)

(vii)

(viii)

(ix)

(x) —L—$Q_2$—$Q_3$—$R^7$ $R^4$, $R^5$ and $R^6$ each independently of one another denote hydrogen or an unsubstituted or mono- or polysubstituted group selected from the group consisting of $C_{1-5}$-alkyl, $C_{2-5}$alkenyl, $C_{2-5}$alkynyl, $C_{3-10}$-cycloalkyl, aryl, heterocyclyl and heteroaryl, wherein the substituent(s) of the mono- or polysubstituted group are identical or different and are selected from the group consisting of $C_{3-10}$cycloalkyl, aryl, heterocyclyl, heteroaryl, halogen, —$NO_2$, —$OR^8$, —$C(=O)R^8$, —$C(=O)OR^8$, —$C(=O)NR^8R^9$, —$NR^8R^9$, —$NR^8C(=O)R^9$, —$NR^8C(=O)OR^9$, —$NR^8C(=O)NR^9R^{10}$, —$NR^8C(=O)ONR^9R^{10}$, —$NR^8SO_2R^9$, —$N=CR^8R^9$, —$SR^8$, —$SOR^8$, —$SO_2R^8$, —$SO_2NR^8R^9$, —$NR^8SO_2NR^9R^{10}$, —$OSO_2NR^8R^9$ and pseudohalogen;

L denotes a bond or an unsubstituted or mono- or polysubstituted group selected from the group consisting of $C_{1-16}$-alkyl, $C_{2-16}$-alkenyl, $C_{2-16}$-alkynyl, $C_{3-10}$-cycloalkyl, aryl, heterocyclyl and heteroaryl, wherein the substituent(s) of the mono- or polysubstituted group are identical or different and are selected from the group consisting of halogen, —$NO_2$, —$OR^8$, —$C(=O)R^8$, —$C(=O)OR^8$, —$C(=O)NR^8R^9$, —$NR^8R^9$, —$NR^8C(=O)R^9$, —$NR^8C(=O)OR^9$, —$NR^8C(=O)NR^9R^{10}$, —$NR^8C(=O)ONR^9R^{10}$, —$NR^8SO_2R^9$, —$N=CR^8R^9$, —$SR^8$, —$SOR^8$, —$SO_2R^8$, —$SO_2NR^8R^9$, —$NR^8SO_2NR^9R^{10}$, —$OSO_2NR^8R^9$ and pseudohalogen;

$Q_2$ and $Q_3$ each independently of one another denote a bond or an unsubstituted or mono—or polysubstituted group selected from the group consisting of $C_{1-16}$-alkyl, $C_{2-16}$-alkenyl, $C_{2-16}$-alkynyl, $C_{3-10}$-cycloalkyl, aryl, heterocyclyl and heteroaryl, wherein the substituent(s) of the mono- or polysubstituted group are identical or different and are selected from the group consisting of halogen, —$NO_2$, —$OR^8$, —$C(=O)R^8$, —$C(=O)OR^8$, —$C(=O)NR^8R^9$, —$NR^8R^9$, —$NR^8C(=O)R^9$, —$NR^8C(=O)OR^9$, —$NR^8C(=O)NR^9R^{10}$, —$NR^8C(=O)ONR^9R^{10}$, —$NR^8SO_2R^9$, —$N=CR^8R^9$, —$SR^8$, —$SOR^8$, —$SO_2R^8$, —$SO_2NR^8R^9$, —$NR^8SO_2NR^9R^{10}$, —$OSO_2NR^8R^9$ and pseudohalogen;

$R^7$ hydrogen or an unsubstituted or mono- or polysubstituted group selected from the group consisting of $C_{1-16}$-alkyl, $C_{2-16}$-alkenyl, $C_{2-16}$-alkynyl, $C_{3-10}$-cycloalkyl, aryl, heterocyclyl and heteroaryl, wherein the substituent(s) of the mono- or polysubstituted group are identical or different and are selected from the group consisting of halogen, $NO_2$, —$OR^8$, —$C(=O)R^8$, —$C(=O)OR^8$, —$C(=O)NR^8R^9$, —$NR^8R^9$, —$NR^8COR^9$, —$NR^8C(=O)OR^9$, —$NR^8C(=O)NR^9R^{10}$, —$NR^8C(=O)ONR^9R^{10}$, —$NR^8SO_2R^9$, —$N=CR^8R^9$, —$SR^8$, —$SOR^8$, —$SO_2R^8$, —$SO_2NR^8R^9$, —$NR^8SO_2NR^9R^{10}$, —$OSO_2NR^8R^9$ and pseudohalogen; and $R^8$, $R^9$ and $R^{10}$ each independently of one another denote hydrogen or a substituted or unsubstituted group selected from the group consisting of $C_{1-8}$-alkyl, $C_{2-8}$-alkenyl, $C_{2-8}$-alkynyl, $C_{3-10}$-cycloalkyl, aryl, heterocyclyl and heteroaryl, wherein the substituent(s) of the substituted group are identical or different and are selected from the group consisting of halogen, methyl, ethyl, amino, methylamino, dimethylamino, —OH and pseudohalogen;

or a pharmacologically acceptable acid addition salt thereof.

* * * * *